United States Patent
Ejima et al.

(10) Patent No.: US 6,573,377 B1
(45) Date of Patent: Jun. 3, 2003

(54) PYRAZOLE DERIVATIVES AND SALTS THEREOF

(75) Inventors: Akio Ejima, Tokyo (JP); Satoru Ohsuki, Tokyo (JP); Hitoshi Ohki, Tokyo (JP); Hiroyuki Naito, Tokyo (JP); Chie Makino, Tokyo (JP)

(73) Assignee: Daiichi Pharmaceuticals Co., Ltd., Tokyo (JP)

( * ) Notice: Subject to any disclaimer, the term of this patent is extended or adjusted under 35 U.S.C. 154(b) by 0 days.

(21) Appl. No.: 09/744,428
(22) PCT Filed: Jul. 23, 1999
(86) PCT No.: PCT/JP99/03962
§ 371 (c)(1), (2), (4) Date: Jan. 24, 2001
(87) PCT Pub. No.: WO00/05230
PCT Pub. Date: Feb. 3, 2000

(30) Foreign Application Priority Data

Jul. 24, 1998 (JP) ............................................. 10-208807
Sep. 29, 1998 (JP) ........................................... 10-274459

(51) Int. Cl.⁷ ..................... C07D 403/14; C07D 413/14; C07D 401/14; C07D 403/04; C07D 471/04
(52) U.S. Cl. ....................... 544/122; 544/123; 544/238; 544/295; 544/296; 544/321; 544/324; 544/331
(58) Field of Search ................................ 544/122, 123, 544/238, 295, 296, 321, 324, 331

(56) References Cited

U.S. PATENT DOCUMENTS 5,852,019 A * 12/1998 Ejima et al. ................. 514/252

FOREIGN PATENT DOCUMENTS

JP 9-48776 2/1997 ......... C07D/403/04
WO WO 98/32739 7/1998 ......... C07D/231/12

OTHER PUBLICATIONS

Arya et al. (J. Pharm. Sci. (1969), 58(4), 432–40). Abstract.*
FR 1510315 (Jan. 19, 1968) Abstract.*

* cited by examiner

*Primary Examiner*—Bruck Kifle
(74) *Attorney, Agent, or Firm*—Sughrue Mion, PLLC

(57) ABSTRACT

This invention provides compounds having antitumor effect, namely a compound represented by the following formula (I) or (Ia) having various substituents in which G and $G^1$ are condensed tricyclic heterocyclic rings or salts thereof, and a compound represented by the following formula (Ib) having various substituents or salts thereof.

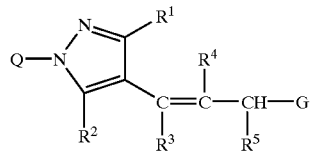

(I)

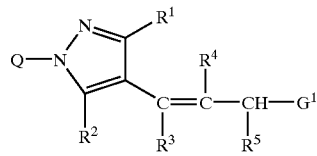

(Ia)

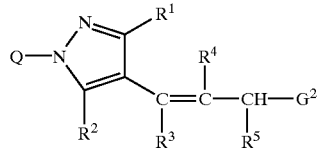

(Ib)

35 Claims, No Drawings

PYRAZOLE DERIVATIVES AND SALTS THEREOF

This application is a §371 of PCT/JP 99/03962, filed on Jul. 23, 1999.

TECHNICAL FIELD

This invention relates to a novel compound having a chemical structure which is different from those of the conventionally used antitumor agents, to an antitumor agent which contains the compound as its active ingredient and to a highly effective antitumor agent capable of showing its efficacy even against 5-FU drug resistant tumors.

BACKGROUND ART

Though a number of 5-FU drugs are currently used as antitumor agents which can be orally administered, it cannot be said that their effects are sufficient, and there are tumors which show resistance against 5-FU drugs, so that concern has been directed toward the development of a drug which has more higher effects and shows its efficacy even against 5-FU drug resistant tumors. In this connection, antitumor effects of pyrazole derivatives related to this invention are described in JP-A-9-48776 (the term "JP-A" as used herein means an "unexamined published Japanese patent application") and WO 98/32739. This invention is to provide pyrazole derivatives having a novel structure in which a condensed tricyclic heterocyclic ring is substituted, and this invention is also to provide novel compounds in which novel substituents are introduced into the pyrimidinyl group of JP-A-9-48776 and the cycloalkyl group, phenyl group, monocyclic heterocyclic ring group and the like of WO 98/32739.

It is to provide a highly effective antitumor agent which has a novel chemical structure different from that of the conventional antitumor agents and shows its efficacy even against 5-FU drug resistant tumors.

DISCLOSURE OF THE INVENTION

As a result of intensive investigations, the present inventors have found that a pyrazole derivative having a novel structure shows its efficacy even against 5-FU drug resistant tumors and has strong antitumor effects.

This invention has been accomplished by founding that this compound also exerts its effect upon P-glycoprotein expression multi-drug resistant strains which are causing clinical problems.

This invention relates to a compound represented by formula (I):

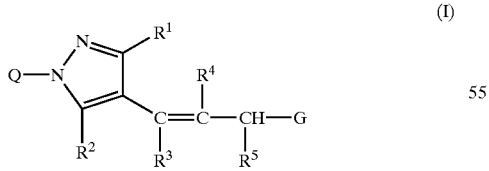

(I)

[in the formula,

R$^1$ represents a hydrogen atom, a halogen atom, a hydroxyl group, an alkoxyl group, an amino group, an alkylamino group, an aryl group or an alkyl group, wherein the alkyl group may have a substituent selected from a halogen atom, an amino group, an alkylamino group, a hydroxyl group, an alkoxyl group, a thiol group and an alkylthio group;

R$^2$ represents a hydrogen atom, a halogen atom, a hydroxyl group, an alkoxyl group, an amino group, an alkylamino group, an aryl group, an alkyl group or a cycloalkyl group, wherein the alkyl group and the cycloalkyl group may have a substituent selected from a halogen atom, an amino group, an alkylamino group, a hydroxyl group, an alkoxyl group, a thiol group and an alkylthio group;

R$^3$ represents a hydrogen atom, a halogen atom, an alkoxyl group, an amino group, an alkylamino group, an aryl group or an alkyl group, wherein the alkyl group may have a substituent selected from a halogen atom, an amino group, an alkylamino group, a hydroxyl group, an alkoxyl group, a thiol group and an alkylthio group;

R$^4$ represents a hydrogen atom, a halogen atom, an alkoxyl group, an amino group, an alkylamino group, an aryl group or an alkyl group, wherein the alkyl group may have a substituent selected from a halogen atom, an amino group, an alkylamino group, a hydroxyl group, an alkoxyl group, a thiol group or an alkylthio group;

R$^5$ represents a hydrogen atom, an alkyl group, an alkenyl group, an alkynyl group, an aryl group or an arylalkyl group, wherein the alkyl group may have a substituent selected from a halogen atom, an amino group, an alkylamino group, a hydroxyl group, an alkoxyl group, a thiol group and an alkylthio group;

Q represents an amidino group, a cycloalkyl group, a phenyl group or a monocyclic heterocyclic ring group, wherein these amidino group, cycloalkyl group, phenyl group and monocyclic heterocyclic ring group may have one or more substituents selected from the group consisting of an alkyl group (which may be substituted by a halogen atom, an amino group, an alkylamino group, a hydroxyl group, an alkoxyl group, a thiol group or an alkylthio group), a halogen atom, a hydroxyl group, an alkoxyl group, an alkoxylalkoxyl group, an amino group, an alkylamino group, an acylamino group, an alkylaminoalkylamino group, a nitro group, a cyano group, a carbamoyl group, a thiol group, an alkylthio group, an arylthio group, an alkylsulfinyl group, an arylsulfinyl group, an alkylsulfonyl group, an arylsulfonyl group, an aminosulfonyl group, an alkylaminosulfonyl group, an arylaminosulfonyl group and an aryl group; and G represents a condensed tricyclic heterocyclic ring, wherein the condensed tricyclic heterocyclic ring may have one or more substituents selected from the group consisting of an alkyl group (which may be substituted by a halogen atom, an amino group, an alkylamino group, a hydroxyl group, an alkoxyl group, a thiol group or an alkylthio group), a halogen atom, a hydroxyl group, an alkoxyl group, a thiol group, an alkylthio group, an amino group, an alkylamino group, an acylamino group, a nitro group, a cyano group, a carbamoyl group and an aryl group, the condensed tricyclic heterocyclic ring may have an epoxy group, and the condensed tricyclic heterocyclic ring may also have a carbonyl, group as a constituent element of the ring] or a salt thereof (with the proviso that, in this compound and a salt thereof, a compound [in which G is a condensed tricyclic heterocyclic ring, and a saturated or unsaturated hydrocarbon ring or heterocyclic ring of the condensed ring can be represented by a saturated hydrocarbon ring or saturated heterocyclic ring having no substituent (excluding a case in which Q is a pyrimidinyl group and binds at the 2-position)] and a salt thereof are excluded).

This invention also provides a compound represented by formula (Ia):

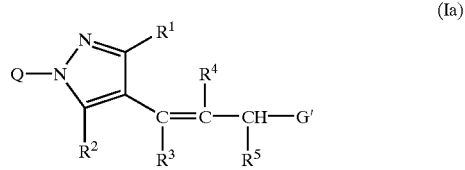

(Ia)

[in the formula, $R^1$, $R^2$, $R^3$, $R^4$, $R^5$ and Q are as defined in the foregoing, and $G^1$ represents a condensed tricyclic heterocyclic group wherein the condensed tricyclic heterocyclic group comprises a nitrogen-containing heterocyclic ring, a saturated or unsaturated hydrocarbon ring or heterocyclic ring, and a benzene ring, wherein the nitrogen-containing heterocyclic ring constituting the condense tricyclic heterocyclic ring may have one or more substituents selected from the group consisting of an alkyl group (which may be substituted by a halogen atom, an amino group, an alkylamino group, a hydroxyl group, an alkoxyl group, a thiol group or an alkylthio group), a halogen atom, a hydroxyl group, an alkoxyl group, a thiol group, an alkylthio group, an amino group an alkylamino group, an acylamino group, a nitro group, a cyano group, a carbamoyl group and an aryl group, and the nitrogen containing heterocyclic ring may contain a carbonyl group as a constituent element of the ring, the saturated or unsaturated hydrocarbon ring or heterocyclic ring constituting the condensed tricyclic heterocyclic ring may have one or more substituents selected from the group consisting of an alkyl group (which may be substituted by a halogen atom, an amino group, an alkylamino group, a hydroxyl group, an alkoxyl group, a thiol group or an alkylthio group), an halogen atom, a hydroxyl group, an alkoxyl group, thiol group, an alkylthio group, an amino group, an alkylamino group, an acylamino group, a nitro group, a cyano group, a carbamoyl group and an aryl group, it may have an epoxy group between ring-forming two atoms, and the saturated or unsaturated hydrocarbon ring or heterocyclic ring may contain a carbonyl group as a constituent element of the ring, and the benzene ring constituting the condensed tricyclic heterocyclic ring may have one or more substituents selected from the group consisting of an alkyl group (which may be substituted by a halogen atom, an amino group, an alkylamino group, a hydroxyl group, an alkoxyl group, a thiol group or an alkylthio group), a halogen atom, a hydroxyl group, an alkoxyl group a thiol group, an alkylthio group, an amino group, an alkylamino group, an acylamino group, a nitro group, a cyano group, a carbamoyl group and an aryl group] or a salt thereof (with the proviso that, in this compound and a salt thereof, a compound [in which $G^1$ is a condensed tricyclic heterocyclic ring, and a saturated or unsaturated hydrocarbon ring or heterocyclic ring of the condensed ring can be represented by a saturated hydrocarbon ring or saturated heterocyclic ring having no substituen (excluding a case in which Q is a pyrimidinyl group and binds at the 2-position)] and a salt thereof are excluded).

Among compounds represented by the aforementioned formula (I) or (Ia), a compound in which Q is a pyrimidinyl group and binds to the pyrazole ring at the 2-position and a salt thereof are preferable.

Also, among compounds represented by the aforementioned formula (I) or (Ia), a compound in which the saturated or unsaturated hydrocarbon ring or heterocyclic ring which constitutes the condensed tricyclic heterocyclic ring has a substituent and a salt thereof are preferable.

This invention also relates to a compound represented by formula (Ib):

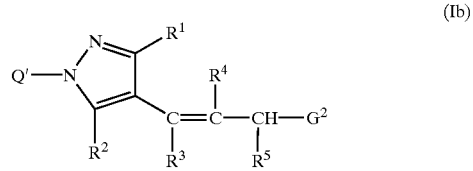

(Ib)

{in the formula, $R^1$, $R^2$, $R^3$, $R^4$ and $R^5$ are as defined in the foregoing, $G^2$ represents a group —$Z^1$—$Z^2$

[wherein $Z^1$ represents a nitrogen-containing saturated heterocyclic ring structure represented by

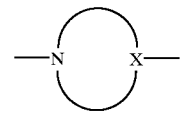

(X is a nitrogen atom or CH), which may contain a ketone moiety, and the ring may have one or more groups as substituents selected from the group consisting of an alkyl group (which may be substituted by a halogen atom, an amino group, an alkylamino group, a hydroxyl group, an alkoxyl group, a thiol group or an alkylthio group), a halogen atom, a hydroxyl group, an alkoxyl group, an amino group, an alkylamino group and an aryl group, and $Z^2$ represents a phenyl group or a heterocyclic ring group, and these phenyl group an d heterocyclic ring group may have one or more substituents selected from the group consisting of an alkyl group (which may be substituted by a halogen atom, an amino group, an alkylamino group, a hydroxyl group, an alkoxyl group, a thiol group or an alkylthio group) a halogen atom, a hydroxyl group, an alkoxyl group, a thiol group, an alkylthio group an amino group, an alkylamino group, an acylamino group, a nitro group, a cyano group, a carbamoyl group and an aryl group]

or represents a condensed tricyclic heterocyclic ring group wherein the condensed tricyclic heterocyclic ring group may have one or more substituents selected from the group consisting of an alkyl group (which may be substituted by a halogen atom, an amino group, an alkylamino group, a hydroxyl group, an alkoxyl group, a thiol group or an alkylthio group), a halogen atom, a hydroxyl group, an alkoxyl group, a thiol group, an alkylthio group, an amino group, an alkylamino group, an acylamino group, a nitro group, a cyano group, a carbamoyl group and an aryl group, the condensed tricyclic heterocyclic ring group may have an epoxy group, and the condensed tricyclic heterocyclic ring may contain a carbonyl group as a constituent element of the ring, and $Q^1$ represents a cycloalkyl group, a phenyl group or a monocyclic heterocyclic ring group, and these cycloalkyl group, phenyl group and monocyclic heterocyclic ring group may have at least one group selected from the following (A) and one or more groups selected from (B) as substituents, (A) an alkyl group having a substituent (the substituent of alkyl group is a group selected from a trialkylammonio group, a cyano group, an ureido group, an alkylureido group, an amidino group, a guanidino group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group and an arylsulfamoyl group, and it may further have at least one group selected from these groups), a group —$R^{71}$—$R^7$ [$R^7$ represents a monocyclic nitrogen-containing heterocyclic ring group or a cycloalkyl group, $R^{71}$ represents single bond or an alkylene group having from 1 to 3 carbon atoms, and $R^7$ and $R^{71}$ (excluding the case of single bond) may each independently have one or more substituents selected from the group consisting of an alkyl group (which may have one or more substituents selected from the group consisting of a halogen atom, a hydroxyl group, an amino group, an alkylamino group, a trialkylammonio group, a cyano group, an ureido group, an alkylureidol group, an amidino group, a guanidino group, an alkoxyl group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a thiol group and an alkylthio group), a halogen atom, a hydroxyl group, an amino group, an alkylamino group, a trialkylammonio group, a cyano group, an ureido group, an alkylureido group, an amidino group, a guanidino group, an alkoxyl group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a thiol group and an alkylthio group], a group —$R^{72}$—$R^{73}$—$R^{74}$—$R^7$ [$R^7$ represents a monocyclic nitrogen-containing heterocyclic ring group or a cycloalkyl group, each of $R^{72}$ and $R^{74}$ independently represents single bond or an alkylene group having from 1 to 3 carbon atoms, $R^{73}$ represents an oxygen atom or a sulfur atom, and $R^7$, $R^{72}$ (excluding the case of single bond) and $R^{74}$ (excluding the case of single bond) may each independently have one or more substituents selected from the group consisting of an alkyl group (which may have one or more substituents selected from the group consisting of a halogen atom, a hydroxyl group, an amino group, an alkylamino group, a trialkylammonio group, a cyano group, an ureido group, an alkylureido group, an amidino group, a guanidino group, an alkoxyl group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a thiol group and an alkylthio group), a halogen atom, a hydroxyl group, an amino group, an alkylamino group, a trialkylammonio group, a cyano group, an ureido group, an alkylureido group, an amidino group, a guanidino group, an alkoxyl group, a hydroxyalkoxyl group, analkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a thiol group and an alkylthio group], a group —$R^{72}$—$NR^{75}$—$R^{74}$—$R^8$ [$R^{72}$ and $R^{74}$ each independently represents single bond or an alkylene group having from 1 to 3 carbon atoms, $R^{75}$ represents an alkyl group (which may have one or more substituents selected from the group consisting of a halogen atom, a hydroxyl group, an amino group, an alkylamino group, a trialkylammonio group, a cyano group, an ureido group, an alkylureido group, an amidino group, a guanidino group, an alkoxyl group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a thiol group and an alkylthio group), a hydrogen atom, a hydroxyl group, an alkoxyl group or —$R^{74}$—$R^8$ and $R^8$ represents an alkylsulfonyl group, an arylsulfonyl group, aminocyclic nitrogen-containing heterocyclic ring group or a cycloalkyl group, wherein $R^8$ (excluding the case of alkylsulfonyl group and arylsulfonyl group), $R^{72}$ (excluding the case of single bond) and $R^{74}$ (excluding the case of single bond) may each independently have one or more substituents selected from the group consisting of an alkyl group (which may have one or more substituents selected from the group consisting of a halogen atom, a hydroxyl group, an amino group, an alkylamino group, a trialkylammonio group, a cyano group, an ureido group, an alkylureido group, an amidino group, a guanidino group, an alkoxyl group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a thiol group and an alkylthio group), a halogen atom, a hydroxyl group, an amino group, an alkylamino group, a trialkylammonio group, a cyano group, an ureido group, an alkylureido group, an amidino group, a guanidino group, an alkoxyl group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a thiol group and an alkylthio group], a group —$R^{81}$—$R^{82}$—$R^9$ [$R^{81}$ represents single bond or an alkylene group having from 1 to 3 carbon atoms, $R^{82}$ represents an oxygen atom or a sulfur atom, wherein $R^{81}$ (excluding the case of single bond) may have one or more substituents selected from the group consisting of alkyl group (which may have one or more substituents selected from the group consisting of a halogen atom, a hydroxyl group, an amino group, an alkylamino group, a trialkylammonio group, a cyano group, an ureido group, an alkylureido group, an amidino group, a guanidino group, an alkoxyl group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a thiol group and an alkylthio group), a halogen atom, a hydroxyl group, an amino group, an alkylamino group, a trialkylammonio group, a cyano group, an ureido group, an alkylureido group, an amidino group, a guanidino group, an alkoxyl group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a thiol group and an alkylthio group, and $R^9$ represents an alkyl group having a substituent, wherein the substituent of alkyl group is selected from the group consisting of a halogen atom, a hydroxyl group, an amino group, an alkylamino group, a trialkylammonio group, a cyano group, an ureido group, an alkylureido group, an amidino group, a guanidino group, an alkoxyl group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a thiol group and an alkylthio group, and it may further have at least one group selected from these groups], or a group —$R^{81}$—$NR^{83}$—$R^9$ [$R^{81}$ represents single bond or an alkylene group having from 1 to 3 carbon atoms, wherein $R^{81}$ (excluding the case of single bond) may have one or more substituents selected from the group consisting of an alkyl group (which may have one or more substituents selected from the group consisting of a halogen atom, a hydroxyl group, an amino group, an alkylamino group, a trialkylammonio group, a cyano group, an ureido group, an alkylureido group, an amidino group, a guanidino group, an alkoxyl group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a thiol group and an alkylthio group), a halogen atom, a hydroxyl group, an amino group, an alkylamino group, a trialkylammonio group, a cyano group, an ureido group, an alkylureido group, an amidino group, a guanidino group, an alkoxyl group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a thiol group and an alkylthio group, $R^{83}$ represents an alkyl group (which may have one or more substituents selected from the group consisting of a halogen atom, a hydroxyl group, an amino group, an alkylamino group, a trialkylammonio group, a cyano group, an ureido group, an alkylureido group, an amidino group, a guanidino group, an alkoxyl group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a thiol group and an alkylthio group), a hydrogen atom, a hydroxyl group or an alkoxyl group, and $R^9$ represents an alkyl group having a substituent, wherein the substituent of alkyl group is selected from the group consisting of a halogen atom, a hydroxyl group, an amino group, an alkylamino group, a trialkylammonio group, a cyano group, an ureido group, an alkylureido group, an amidino group, a guanidino group, an alkoxyl group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a thiol group and an alkylthio group, and it may further have at least one group selected from these groups (with the proviso that a case in which $R^{81}$ is single bond, $R^{83}$ is a hydrogen atom and $R^9$ is an alkylamino group is excluded)], (B) alkyl group (which may be substituted by a halogen atom, an amino group, an alkylamino group, a hydroxyl group, an alkoxyl group, a thiol group or an alkylthio group), a halogen atom, a hydroxyl group, an alkoxyl group, an alkoxylalkoxyl group, an amino group, an alkylamino group, an acylamino group, an alkylaminoalkylamino group, a nitro group, a cyano group, a carbamoyl group, a thiol group, an alkylthio group, an arylthio group, an alkylsulfinyl group, an arylsulfinyl group, an alkylsulfonyl group, an arylsulfonyl group, an aminosulfonyl group, an alkylaminosulfonyl group, an arylaminosulfonyl group or an aryl group} or a salt thereof.

In this connection, those in which the double bond moiety of alkenyl group is either in cis form or trans form are included in the compounds of this invention represented by the formula (I), (Ia) or (Ib).

Also, these compounds of this invention include optional stereoisomers.

Next, the terms as used herein are described.

The "cis (form)" means a case in which $R^3$ and $R^4$ are bonded on the same side based on the double bond, and the "trans (form)" means a case in which $R^3$ and $R^4$ are bonded on the opposite sides based on the double bond.

The "hydroxyl group" may be protected with a protective group.

The "amino group" may be protected with a protective group.

Unless otherwise noted, the "alkyl group", "alkenyl group" and "alkynyl group" may be either straight chain or branched chain, and a group having from 1 (2 in the case of alkenyl group and alkynyl group) to 6 carbon atoms is desirable.

Alkyl moiety of the "alkoxyl group" has preferably from 1 to 6 carbon atoms.

The "aryl group" means a monovalent group formed by removing one hydrogen atom from an aromatic hydrocarbon nucleus, e.g., phenyl, tolyl, biphenylyl, naphthyl and the like.

Amino group of the "aminoalkyl group" may be bonded to any position of an alkyl group. Also, the alkyl group has preferably from 1 to 6 carbon atoms.

The "alkylamino group" means a group in which amino group is substituted by one alkyl group or amino group is substituted by two alkyl groups (the two alkyl groups may be the same or different from each other). Also, the alkyl group has preferably from 1 to 6 carbon atoms.

The "alkylureido group" means a group in which ureido group is substituted by one alkyl group or ureido group is substituted by two alkyl groups (the two alkyl groups may be the same or different from each other). Also, the alkyl group has preferably from 1 to 6 carbon atoms.

The "acyl group" means a group in which hydrogen atom, an alkyl group or an aryl group is bonded to carbonyl group (—CO—), e.g., formyl, acetyl, propanoyl, benzoyl and the like. In this case, a group having from 1 to 6 carbon atoms is desirable as the alkyl group to be bonded, and phenyl group is desirable as the aryl group to be bonded.

The "heterocyclic ring group" means a group derived from a monocyclic or bicyclic saturated or unsaturated heterocyclic ring compound, and it contains one or more of at least one kind of atom selected from the group consisting of oxygen atom, nitrogen atom and sulfur atom as a constituent atom of the ring. For example, groups derived from aziridine, azetidine, pyrrole, furan, thiophene, pyrrolidine, tetrahydrofuran, tetrahydrothiophene, imidazole, pyrazole, imidazolidine, pyrazolidine, oxazole, thiazole, oxadiazole, thiadiazole, pyridine, dihydropyridine, tetrahydropyran, piperidine, pyridazine, pyrimidine, pyrazine, triazine, piperazine, dioxane, pyran, morpholine, thiomorpholine and the like monocyclic heterocyclic ring compounds can be exemplified as the monocyclic heterocyclic ring group. Groups derived from benzofuran, indolizine, benzothiophene, indole, naphthyridine, quinoxaline, quinazoline, chroman and the like bicyclic heterocyclic ring compounds can be exemplified as the bicyclic heterocyclic ring group.

The "nitrogen-containing heterocyclic ring" means a saturated or unsaturated heterocyclic ring which necessarily contains one nitrogen atom as a constituent atom of the heterocyclic ring, and it may further contain one or more of at least one atom selected from the group consisting of oxygen atom, nitrogen atom and sulfur atom as constituent atoms, e.g., aziridine, azetidine, pyrrolidine, imidazolidine, pyrazolidine, piperidine, piperazine, homopiperazine, tetrahydropyridine, morpholine, thiomorpholine, pyridine, pyridazine, pyrimidine, pyrazine, triazine and the like.

The "nitrogen-containing heterocyclic ring group" means a group derived from the above "nitrogen-containing heterocyclic ring".

The "nitrogen-containing saturated heterocyclic ring" means a saturated group among the above "nitrogen-containing heterocyclic ring".

The "condensed tricyclic heterocyclic ring group" means a condensed ring group composed of three rings containing at least one heterocyclic ring. As the condensed tricyclic heterocyclic ring group, a group derived from an ortho condensation compound is desirable. The ortho condensation means a structure in which two rings constituting a polycyclic compound have only two common atoms, and one or more common planes and common atoms two times the number of common planes are present in such a type of compound.

The "single bond" means a simple bond; for example, when $R^{71}$ of —$R^{71}$—$R^7$ is single bond, $R^{71}$ does not substantially exist and the entire structure becomes —$R^7$.

When described herein as "has a substituent" or "may have a substituent", binding position of the substituent is not particularly limited.

Next, each substituent of the compound represented by the formula (I), (Ia) or (Ib) (to be referred also as "compound (I), (Ia) or (Ib) of this invention" hereinafter, the same is applied to other formulae) is described.

$R^1$ is preferably a hydrogen atom, a halogen atom, a hydroxyl group, an alkoxyl group, an amino group, a phenyl group or an alkyl group, and the alkyl group may have an amino group, an alkylamino group, a hydroxyl group, an alkoxyl group, a thiol group or an alkylthio group as a substituent.

$R^2$ is preferably a hydroxyl group, an alkoxyl group, an amino group, an alkyl group or a cycloalkyl group, and the alkyl group and cycloalkyl group may have a halogen atom, an amino group, an alkylamino group, a hydroxyl group, an alkoxyl group, a thiol group or an alkylthio group as a substituent.

$R^3$ is preferably a hydrogen atom or an alkyl group, and the alkyl group may have an amino group, an alkylamino group, a hydroxyl group, an alkoxyl group, a thiol group or an alkylthio group as a substituent.

$R^4$ is preferably a hydrogen atom or an alkyl group, and the alkyl group may have an amino group, an alkylamino group, a hydroxyl group, an alkoxyl group, a thiol group or an alkylthio group as a substituent.

$R^5$ is preferably a hydrogen atom or an alkyl group, and the alkyl group may have an amino group, an alkylamino group, a hydroxyl group, an alkoxyl group, a thiol group or an alkylthio group as a substituent.

G represents a condensed tricyclic heterocyclic ring group. Though it should not particularly be limited, a group composed of a nitrogen-containing heterocyclic ring, a saturated or unsaturated hydrocarbon ring or heterocyclic ring and benzene ring is desirable as the condensed tricyclic heterocyclic ring group.

Also, G may or may not have a substituent but preferably have a substituent.

Regarding the condensed tricyclic heterocyclic ring group G, constituent elements of $G^1$ of the compound (Ia) of this invention are limited to a nitrogen-containing heterocyclic ring, a saturated or unsaturated hydrocarbon ring or heterocyclic ring and benzene ring.

The nitrogen-containing heterocyclic ring which constitutes $G^1$ may or may not have a substituent but preferably have a substituent. Those which will be described later can be exemplified as such a substituent.

Next, $G^2$ of the compound (Ib) of this invention is described.

In the case of the group —$Z^1$—$Z^2$, the nitrogen-containing saturated heterocyclic ring structure $Z^1$ represented by formula:

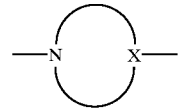

(in the formula, X represents a nitrogen atom or CH) is preferably a group which has a size of five- or six-membered ring, and a group derived from piperazine or piperidine is particularly desirable.

Regarding the heterocyclic ring group of $Z^2$, a monocyclic group having a size of five- or six-membered ring is preferable, and an unsaturated one is more preferable. Illustratively, a pyridyl group, a pyridazyl group, a pyrazyl group, a pyrimidyl group or a triazyl group is desirable.

A phenyrl group or a pyrimidinyl group is desirable as $Z^2$. The phenyl group and pyrimidinyl group may have a substituent, and a case having the same or different two substituents selected from the group consisting of a halogen atom, a hydroxyl group, a cyano group and an alkyl group (which may be substituted by a halogen atom, an amino group, an alkylamino group, a hydroxyl group, an alkoxyl group, a thiol group or an alkylthio group) is desirable.

As the $Z^2$, a phenyl group having the same or different two substituents selected from the group consisting of a halogen atom, a hydroxyl group, a cyano group and an alkyl group (which may be substituted by a halogen atom, an amino group, an alkylamino group, a hydroxyl group, an alkoxyl group, a thiol group or an alkylthio group) is most desirable.

When $G^2$ is a condensed tricyclic heterocyclic ring group, a group composed of a nitrogen-containing heterocyclic ring, a saturated or unsaturated hydrocarbon ring or heterocyclic ring and benzene ring is desirable as the condensed tricyclic heterocyclic ring group.

It is desirable that the condensed tricyclic heterocyclic ring group of G, $G^1$ or $G^2$ has the nitrogen atom of a nitrogen-containing heterocyclic ring which constitutes the condensed tricyclic heterocyclic ring group, as a free valency.

As the nitrogen-containing heterocyclic ring which constitutes the condensed tricyclic heterocyclic ring group of G, $G^1$ or $G^2$ a size of six-membered ring is desirable, illustratively, piperazine, piperidine and tetrahydropyridine are desirable. In addition, those in which the piperazine, piperidine and tetrahydropyridine rings contain carbonyl group as a constituent element can also be cited as preferable examples.

As the saturated or unsaturated hydrocarbon ring or heterocyclic ring which constitutes the condensed tricyclic heterocyclic ring group of G, $G^1$ or $G^2$, a size of from five- to seven-membered ring is desirable, and a six-membered ring is particularly desirable. In addition, those which contain carbonyl group as a constituent element of the rings can also be cited as preferable examples.

As illustrative structure of the condensed tricyclic heterocyclic ring group of G, $G^1$ or $G^2$, a ring represented by

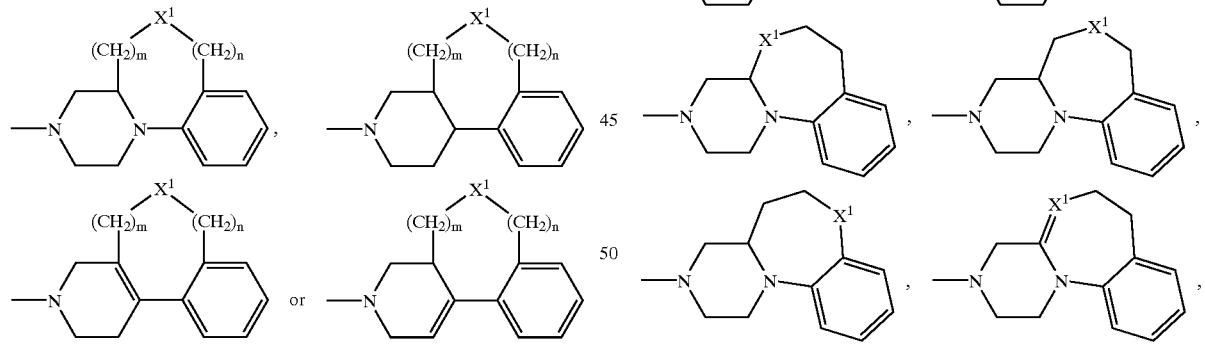

wherein $X^1$ represents an oxygen atom, a sulfur atom, NH, $CH_2$ or C=O, each of m and n is independently 0 or an integer of 1 or 2, and the partial structure represented by

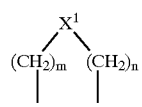

may form an unsaturated ring by containing a double bond, wherein $X^1$ becomes N or CH when the carbon atoms adjacent to $X^1$ form a double bond) is desirable.

Regarding the structure represented by

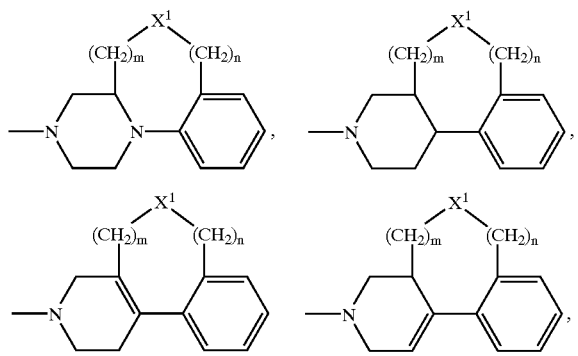

the following can be cited as its illustrative examples.

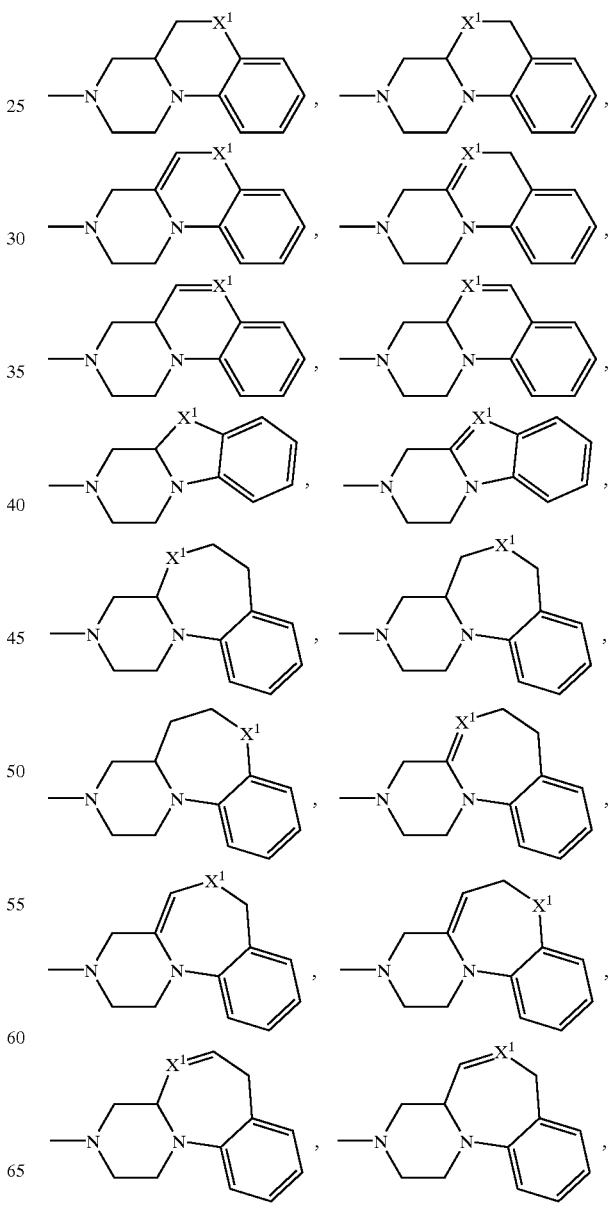

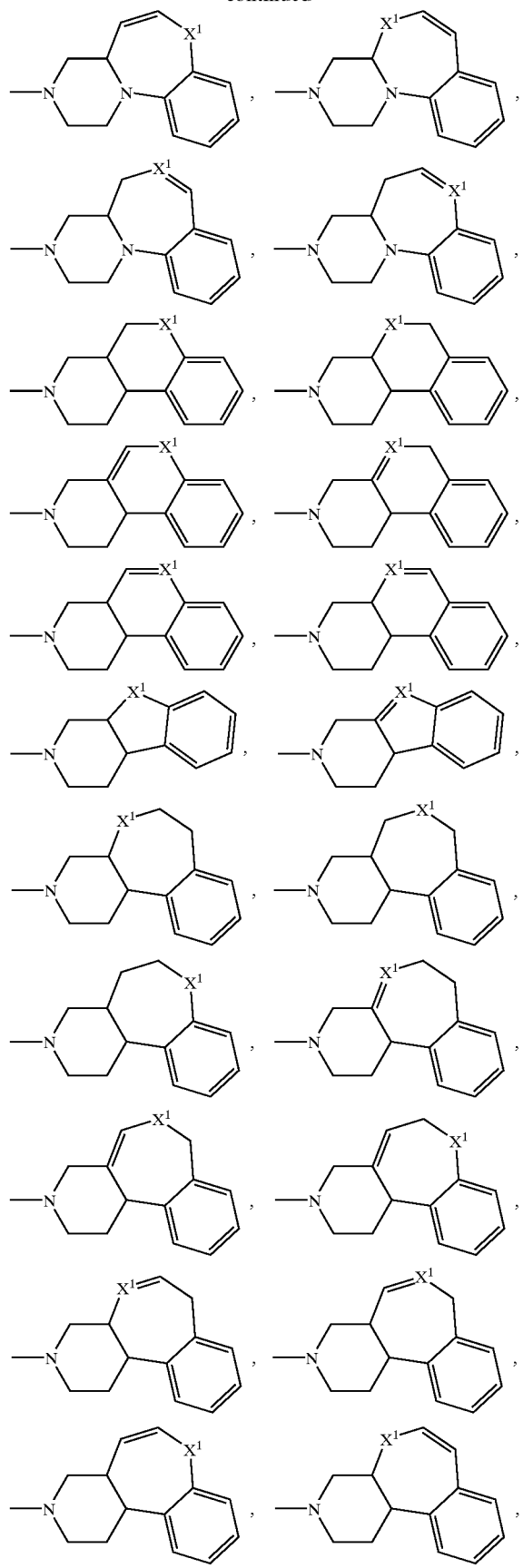
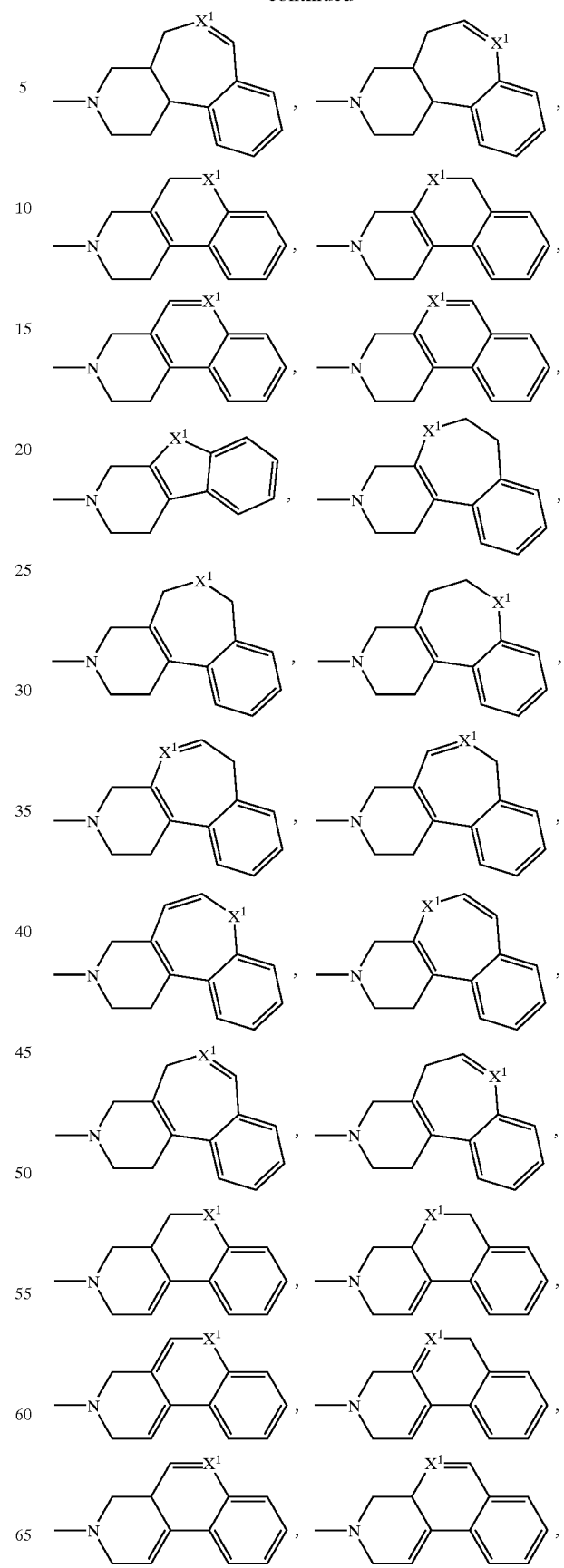

-continued

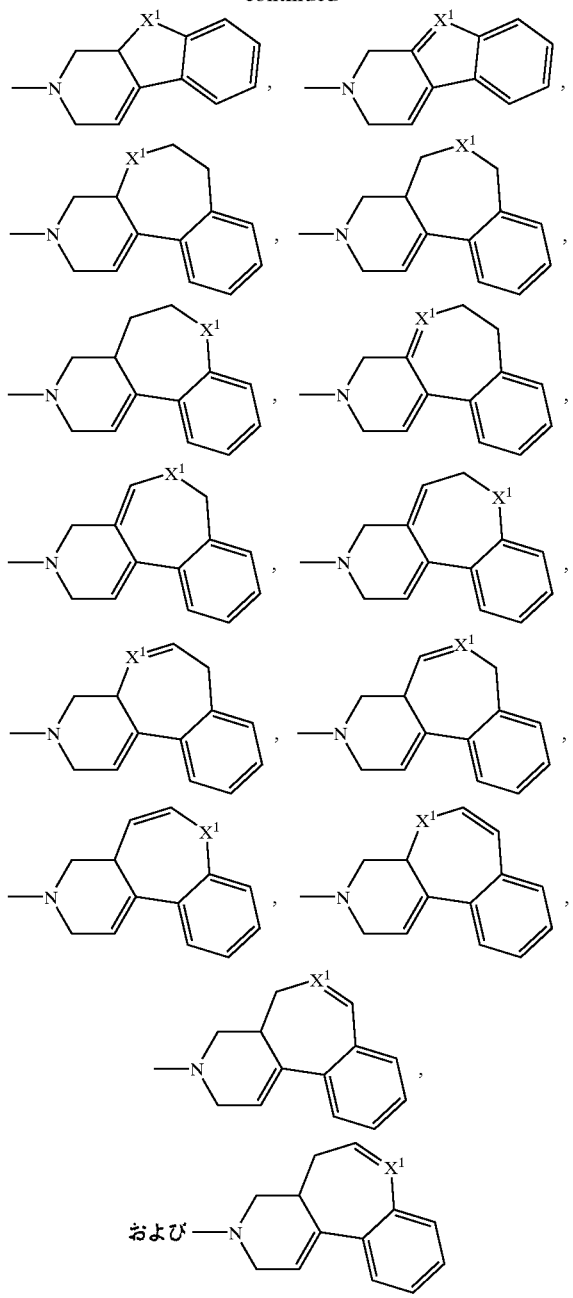

Among these illustrative examples, the following structures are desirable.

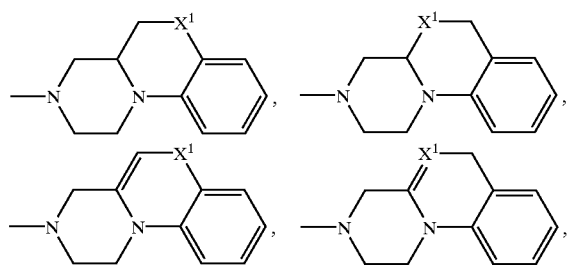

-continued

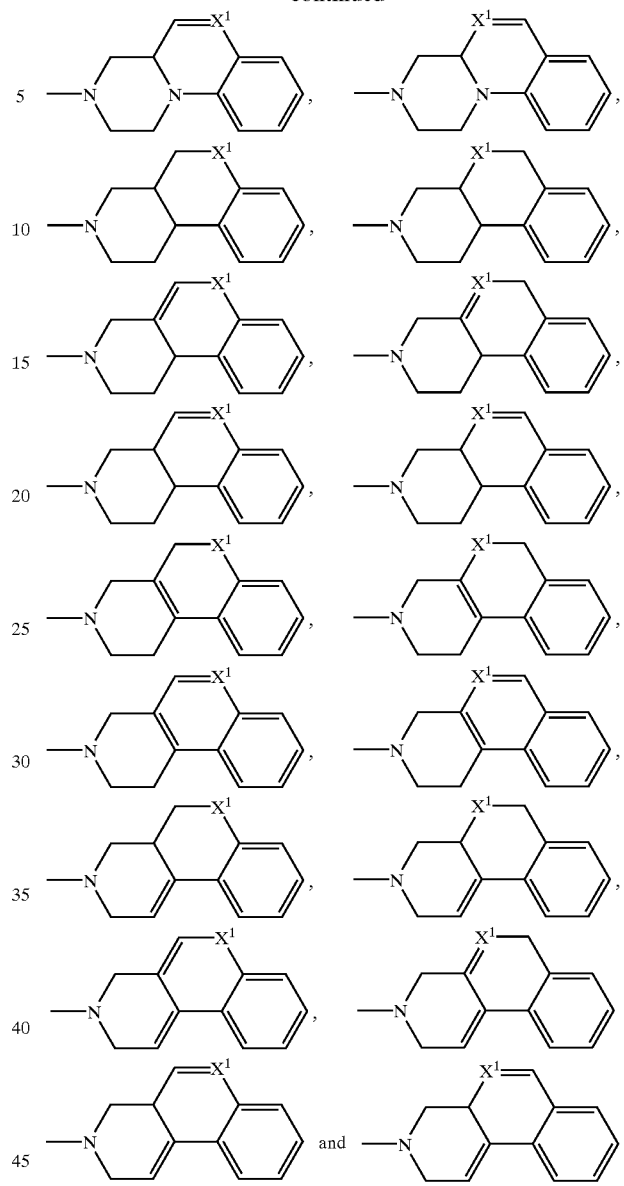

As the substituent of the nitrogen-containing heterocyclic ring moiety which constitutes the condensed tricyclic heterocyclic ring group of G, $G^1$ or $G^2$, an alkyl group (which may be substituted by a halogen atom, an amino group, an alkylamino group, a hydroxyl group, an alkoxyl group, a thiol group or an alkylthio group), a hydroxyl group, an alkoxyl group and an amino group are desirable.

As the substituent of the saturated or unsaturated hydrocarbon ring moiety or heterocyclic ring moiety which constitutes the condensed tricyclic heterocyclic ring group of G, $G^1$ or $G^2$, an alkyl group (which may be substituted by an amino group, an alkylamino group, a hydroxyl group or an alkoxyl group), a hydroxyl group, an alkoxyl group, an amino group and an alkylamino group are desirable.

In addition, a case having an epoxy group between the ring-forming two carbon atoms is also desirable.

As the substituent of the benzene ring which constitutes the condensed tricyclic heterocyclic ring group of G, $G^1$ or $G^2$, an alkyl group (which may be substituted by an amino group, an alkylamino group, a hydroxyl group or an alkoxyl group), a halogen atom, a hydroxyl group, an alkoxyl group, an amino group, an alkylamino group and a cyano group are desirable.

Regarding m and n, a case in which the total of m and n becomes 0, 1 or 2 is desirable, and a case in which it becomes 1 is particularly desirable.

Q or $Q^1$ is preferably a monocyclic heterocyclic ring group.

The monocyclic heterocyclic ring group of Q or $Q^1$ is preferably an unsaturated group, more preferably a group having a size of five- or six-membered ring.

Most preferred as the monocyclic heterocyclic ring group of Q or $Q^1$ is a nitrogen-containing heterocyclic ring group which is an unsaturated monocyclic heterocyclic ring group having a size of five- or six-membered ring and containing at least one nitrogen atom as a constituent atom of the heterocyclic ring and, illustratively, those which are derived from pyridine, pyrimidine, pyridazine, pyrazine and triazine are desirable. However, when Q is pyrimidine, a compound and salts thereof, in which G or $G^1$ is a condensed tricyclic heterocyclic ring and a saturated or unsaturated hydrocarbon ring or heterocyclic ring of the condensed ring can be represented by a saturated hydrocarbon ring or saturated heterocyclic ring having no a substituent (excluding a case in which Q is a pyrimidinyl group and binds at the 2-position), are excluded from the compound (I) and (Ia) of this invention.

$Q^1$ always has at least one substituent selected from (A) and may also have a substituent selected from (B). Among (B), an alkyl group, an amino group, an alkylamino group, a hydroxyl group or an alkoxyl group is desirable, and the alkyl group may have one or more substituents selected from the group consisting of a halogen atom, a hydroxyl group, an amino group, an alkylamino group, a trialkylammonio group, a cyano group, an ureido group, an alkylureido group, an amidino group, a guanidino group, an alkoxyl group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a thiol group and an alkylthio group.

As the compound (I), (Ia) or (Ib) of this invention, its trans form (a case in which $R^3$ and $R^4$ are bonded on the opposite sides based on the double bond) is desirable.

The compound (I) of this invention can be produced by various methods, and a typical production example is shown below.

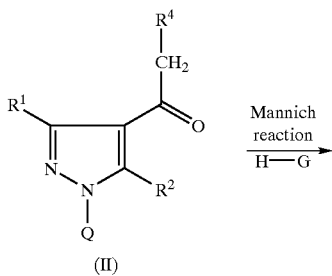

(II)

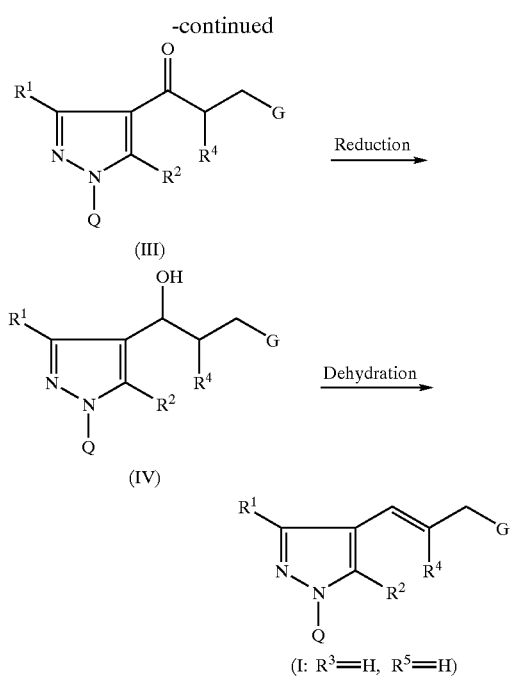

($R^1$, $R^2$, $R^4$, Q and G are as defined in the foregoing.)

That is, the compound (I) of interest can be obtained by reducing a compound (III) obtained by subjecting a compound (II) and a basic compound H-G to Mannich reaction, thereby converting it into a compound (IV), and subsequently dehydrating the product.

Each reaction is described in detail. Mannich reaction:

The compound (III) can be obtained by treating the compound (II) and basic compound H-G in a solvent in the presence of a condensing agent. It is desirable to use the basic compound H-G as its hydrochloride, hydrobromide or the like salt.

As the condensing agent, p-formaldehyde, formaldehyde and the like can be exemplified.

Examples of the solvent to be used include methanol, ethanol, propanol or the like alcohol solvent, N,N-dimethylformaide, acetamide, dimethylacetamide or the like amide solvent, chloroform, dichloromethane, carbon tetrachloride or the like halogenated hydrocarbon solvent, diethyl ether, tetrahydrofuran, dioxane or the like ether solvent and benzene, toluene, xylene or the like aromatic hydrocarbon solvent. A mixed solvent thereof may also be used.

The reaction temperature may be generally within the range of from −20° C. to 150° C., preferably within the range of from 0° C. to 100° C.

The reaction period may be generally within the range of from 5 minutes to 120 hours, preferably within the range of from 30 minutes to 72 hours.

Reduction Reaction

The corresponding compound (IV) can be obtained by reducing the compound (III).

The reduction can be carried out by a method generally used in this field. For example, a method in which the compound is treated in the presence of a reducing agent or a method in which hydrogenation is carried out in the presence of a catalyst can be cited.

Example s of the reducing agent include boron hydride compounds and aluminum hydride compounds, such as sodium borohydride, sodium cyanoborohydride and lithium aluminum hydride. Also, palladium, Raney nickel, platinum oxide and the like can be exemplified as the catalyst.

The solvent to be used is optionally selected depending on the reducing agent, and its examples include methanol, ethanol, propanol or the like alcohol solvent, N,N-dimethylformamide, acetamide, dimethylacetamide or the like amide solvent, chloroform, dichloromethane, carbon tetrachloride or the like halogenated hydrocarbon solvent, diethyl ether, tetrahydrofuran, dioxane or the like ether solvent and benzene, toluene, xylene or the like aromatic hydrocarbon solvent. A mixed solvent there of may also be used.

The reaction temperature may be generally within the range of from −20° C. to 150° C., preferably within the range of from 0° C. to 100° C.

The reaction period may be generally within the range of from 5 minutes to 72 hours, preferably within the range of from 10 minutes to 24 hours.

Dehydration Reaction

The compound (I) of interest can be obtained by subjecting the compound (IV) to dehydration reaction.

The dehydration can be carried out by a method generally used in this field, and a method in which heating is carried out in the presence of an acid can be exemplified.

The acid which can be used in this method may be either an organic acid or an inorganic acid. Hydrochloric acid, sulfuric acid, hydrobromic acid, potassium hydrogensulfate and the like can be exemplified as the inorganic acid, and p-toluenesulfnic acid, methanesulfonic acid, oxalic acid and the like can be exemplified as the organic acid. The inorganic acid is prefer ably used. Also, alumina may be used.

The reaction may be carried out using a solvent, and its examples include N,N-dimethylformamide, acetamide, dimethylacetamide or the like amide solvent, chloroform, dichloromethane, carbon tetrachloride or the like halogenated hydrocarbon solvent, diethyl ether, tetrahydrofuran, dioxane or the like ether solvent and benzene, toluene, xylene or the like aromatic hydrocarbon solvent. A mixed solvent thereof may also be used.

The reaction temperature may be generally within the range of from −20° C. to 150° C., preferably within the range of from 0° C. to 100° C.

The reaction period may be generally within the range of from 5 minutes to 72 hours, preferably within the range of from 10 minutes to 24 hours.

A compound in which $R^3$ is a hydrogen atom and the alkenyl group moiety is trans form can be synthesized by the synthesis method shown in the above, and a compound in which $R^3$ is an alkyl group and a compound in which the alkenyl group moiety is cis form can be synthesized by the following method.

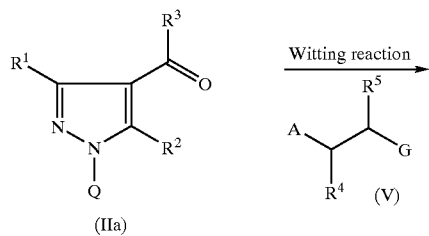

(IIa)

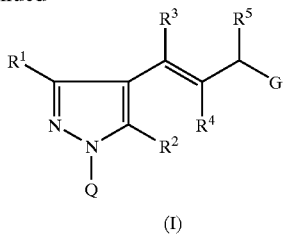

(I)

(A represents a chlorine atom, a bromine atom or an iodine atom, and $R^1$, $R^2$, $R^3$, $R^4$, $R^5$, Q and G are as defined in the foregoing.)

That is, a compound represented by the formula (I) can be obtained by subjecting a compound (IIa) and a compound (V) to Witting reaction.

The production method shown by the above drawing is described in detail.

The compound (I) can be obtained by allowing the compound (V) to react with a tertiary phosphine in a solvent, treating the thus obtained phosphonium salt with a base in a solvent and then adding the compound (IIa).

As the tertiary phosphine to be used, triphenylphosphine, tri-n-butylphosphine and the like can be exemplified.

Examples of the base include n-butyl lithium, phenyl lithium, sodium hydride, potassium t-butoxide, sodium ethoxide and 1,8-diazabicyclo[5.4.0]undec-7-ene (DBU).

Examples of the solvent which can be used include diethyl ether, tetrahydrofuran, dioxane or the like ether solvent, benzene, toluene, xylene or the like aromatic hydrocarbon solvent, methanol, ethanol, propanol or the like alcohol solvent, N,N-dimethylformamide, acetamide, dimethylacetamide or the like amide solvent and chloroform, dichloromethane, carbon tetrachloride or the like halogenated hydrocarbon solvent. A mixed solvent thereof may also be used.

The reaction temperature may be generally within the range of from 30° C. to 150° C., preferably within the range of from 50° C. to 100° C.

The reaction period may be generally within the range of from 5 minutes to 72 hours, preferably within the range of from 10 minutes to 24 hours.

According to the aforementioned production method of the compound (I) of this invention, a compound (Ia) of this invention can be produced in the same manner by the use of the basic compound H-G and compound (V), in which $G^1$ is substituted instead of G. Also, a compound (Ib) of this invention can be produced in the same manner as the case of the aforementioned compound (I) of this invention, by the use of the compound (II) and compound (IIa), in which Q is changed to $Q^1$, and the basic compound H-C and compound (V), in which $G^2$ is substituted instead of G.

The compound (II) and compound (IIa) and the basic compound H-C and compound (V) , as the material compounds, are known compounds or compounds which can be easily synthesized in accordance with known methods described, for example, in JP-A-9-48776, JP-B-54-17760 (the term "JP-B" as used herein means an "examined Japanese patent publication"), JP-B-50-5198, JP-A-8-269057, JP-A-6-279442, JP-W-9-504789 (the term "JP-W" as used herein means an "unexamined published Japanese international patent application"), JP-A-50-58234, JP-A-52-83397, JP-B-46-33032, *Indian Journal of Chemistry,* vol. 13, p. 462 (1975), *Indian Journal of Chemistry,* Sect. B, 25B (12), pp. 1231–1233 (1986), *Indian Journal of Chemistry,* Sect. B, 17B (3), pp. 244–245 (1979), *Journal of Medicinal*

Chemistry, vol. 13, p. 516 (1970), Indian Journal of Chemistry, vol. 7, p. 833 (1969), Helvetica Hemica Acta, vol. 20, p. 1388 (1937), WO 98/00134, WO 98/00401, U.S. Pat. No. 4,367,335, German Patent No. 1901262, Swiss Patent No. 500213 and the like, or by methods which can be generally used by those skilled in the art with reference to these documents.

In addition, the compound (I) of interest can also be obtained in the following manner via an allylation and then via a reductive amination or a substitution reaction. Also, the compound (Ia) of this invention can be produced in the same manner as the case of the aforementioned compound (I) of this invention by the use of the basic compound H-G in which G is replaced by $G^1$, and the compound (Ib) of this invention can be produced in the same manner as the case of the aforementioned compound (I) of this invention by the use of the compound (IIa) in which Q is changed to $Q^1$ and the basic compound H-G in which $G^2$ is substituted instead of G.

basic compound H-G are subjected to reductive amination, deprotected as occasion demand and then subjected to dehydration reaction, thereby obtaining the compound (I). Alternatively, it is possible to obtain the compound (X) by subjecting the compound (VIII) to a reduction reaction or allowing it to react with an alkyl metal compound, thereby converting it into a compound (IX), further converting its hydroxyl group into a leaving group and then carrying out substitution reaction with a basic compound H-G.

Each reaction step is described.

Addition Reaction

The compound (VI) can be obtained by, in a solvent, allowing the compound (IIa) to react with an appropriate allyl metal compound or to undergo addition reaction with an allyl silane in the presence of a Lewis acid (titanium tetrachloride or the like).

Examples of the allyl metal compound which can be used in the reaction include allyl lithium, allyl magnesium halide and allyl tin compound.

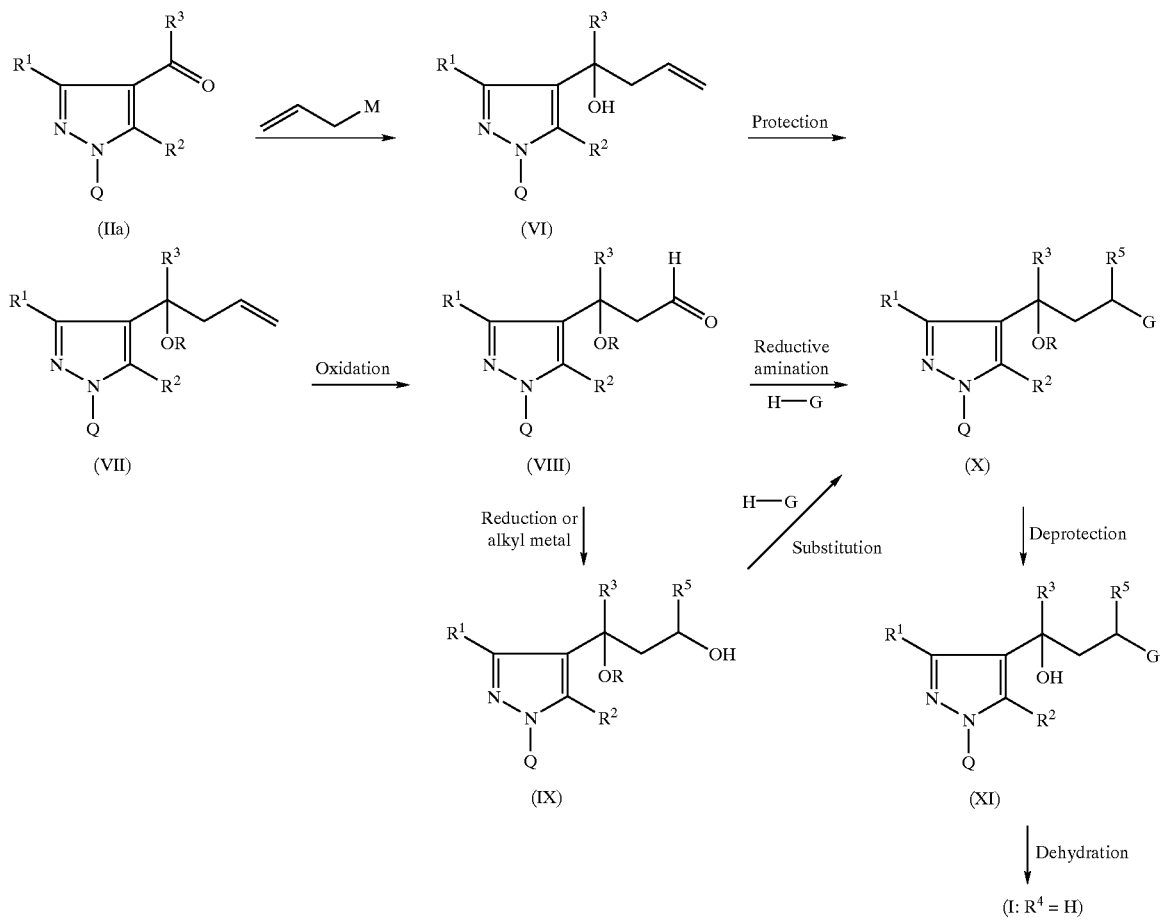

(M represents a metal such as an alkali metal, an alkaline earth metal, tin, zinc or nickel, R represents a protective group of the hydroxyl group, and $R^1$, $R^2$, $R^3$, $R^5$, Q and G are as defined in the foregoing.)

That is, the hydroxyl group of a compound (VI) obtained by allowing the compound (IIa) to react with an appropriate allyl metal compound or to undergo addition reaction with an allyl silane in the presence of a Lewis acid is protected to obtain a compound (VII) which is then oxidized to obtain a compound (VIII). The thus obtained compound (VIII) and a Examples of the allyl silane which can be used in the reaction include allyltrialkylsilane, allyltriarylsilane and the like.

Examples of the Lewis acid which can be used in the reaction include titanium tetrachloride and the like.

Examples of the solvent which can be used in the reaction include diethyl ether, tetrahydrofuran, dioxane or the like ether solvent and hexane, pentane, benzene, toluene, xylene or the like hydrocarbon solvent, or a mixed solvent thereof.

In this connection, when an allyl tin compound is used, water or a hydrous ether solvent may also be used.

The reaction temperature may be generally within the range of from −78 to 100° C., preferably within the range of from −78 to 70° C.

The reaction period may be generally within the range of from 5 minutes to 120 hours, preferably within the range of from 30 minutes to 48 hours.

Protection Reaction of Hydroxyl Group

The hydroxyl group of compound (VI) can be protected with a protective group generally used in this field.

Examples of the protective group include methoxymethyl ether, methylthiomethyl ether, benzyloxymethyl ether or the like substituted methyl ether based protective group, 1-methoxyethyl ether, 2,2,2-trichloroethyl ether or the like substituted ethyl ether based protective group, benzyl ether, p-methoxybenzyl ether or the like substituted benzyl ether based protective group, triethylsilyl, t-butyldimethylsilyl or the like silyl ether based protective group, acetyl or the like ester based protective group and methoxycarbonyl, 2,2,2-trichloroethoxycarbonyl or the like carbonate based protective group.

Oxidation Reaction

In order to obtain the compound (VIII) from the compound (VII), a method generally used in this field may be employed, but the compound (VIII) can be obtained, for example, by subjecting the starting compound to a stoichiometric oxidation using osmium tetroxide or the like oxidizing agent or a catalytic oxidation reaction using a co-oxidizing agent, thereby once passing through diol, and then subjecting it to a general oxidation reaction such as periodic acid decomposition. Alternatively, the compound (VIII) can also be obtained by subjecting the compound (VII) to a general ozone decomposition accompanied by a reductive treatment in a solvent.

Examples of the oxidizing agent which can be used in the diol formation reaction include potassium permanganate, osmium tetroxide and the like, and examples of the co-oxidizing agent include hydrogen peroxide, hydrogen peroxide aqueous solution, perchloric acid, sodium perchloride and the like perchlorates, N-methylmorpholine-N-oxide, potassium hexacyanoferrate(III) and the like.

Examples of the solvent which can be used in the diol formation reaction include methanol, ethanol, t-butanol or the like alcohol solvent, acetone, methyl ethyl ketone or the like ketone solvent, dichloromethane, dichloroethane or the like chlorine based solvent, diethyl ether, tetrahydrofuran, dioxane or the like ether solvent, hexane, pentane, benzene or the like hydrocarbon solvent or water, and a mixed solvent thereof. The reaction temperature for diol formation may be generally within the range of from −78 to 100° C., preferably within the range of from −78° C. to room temperature. The reaction period may be generally within the range of from 5 minutes to 120 hours, preferably within the range of from 30 minutes to 48 hours.

The periodic acid decomposition of diol can be carried out using periodic acid, a periodate or the like as the oxidizing agent in a solvent such as methanol, ethanol, t-butanol or the like alcohol solvent, acetone, methyl ethyl ketone or the like ketone solvent, dichloromethane, dichloroethane or the like chlorine based solvent, diethyl ether, tetrahydrofuran, dioxane or the like ether solvent, hexane, pentane, benzene or the like hydrocarbon solvent or water, or a mixed solvent thereof.

The reaction temperature for periodic acid decomposition may be generally within the range of from −20 to 100° C., preferably within the range of from 0° C. to room temperature.

The reaction period may be generally within the range of from 5 minutes to 120 hours, preferably within the range of from 30 minutes to 48 hours.

Examples of the solvent which can be used in the ozone decomposition include methanol, ethanol, propanol or the like alcohol solvent, acetone, methyl ethyl ketone or the like ketone solvent, dichloromethane, dichloroethane or the like chlorine based solvent, diethyl ether, tetrahydrofuran, dioxane or the like ether solvent, hexane, pentane or the like hydrocarbon solvent or a mixed solvent thereof.

The ozone decomposition may be carried out at a temperature generally within the range of from −78 to 100° C., preferably within the range of from −78° C. to room temperature. The reaction period may be generally within the range of from 5 minutes to 120 hours, preferably within the range of from 30 minutes to 48 hours.

Reductive Amination Reaction

In order to obtain the compound (X) from the compound (VIII), a method generally used in this field may be employed. For example, the compound (X) can be obtained by allowing the compound (VIII) to react with a basic compound H-G and then treating it with a reducing agent.

Examples of the reducing agent which can be used include lithium aluminum hydride, sodium borohydride, sodium cyanoborohydride or the like complex hydrogen compound and diborane, or hydrogenation in the presence of Raney nickel, palladium-carbon or the like catalyst may be employed. Examples of the solvent which can be used include methanol, ethanol, propanol or the like alcohol solvent, diethyl ether, tetrahydrofuran, dioxane or the like ether solvent, hexane, pentane, benzene, toluene, xylene or the like hydrocarbon solvent or a mixed solvent thereof.

The reductive amination reaction may be carried out at a temperature generally within the range of from −78 to 100° C., preferably within the range of from −10° C. to room temperature.

The reaction period may be generally within the range of from 5 minutes to 120 hours, preferably within the range of from 30 minutes to 48 hours.

Reduction Reaction

A compound (IX) in which $R^5$ is hydrogen atom can be obtained by reducing carbonyl group of the compound (VIII).

The reduction can be carried out by a method generally used in this field. For example, a method in which the compound is treated in the presence of a reducing agent or a method in which hydrogenation is carried out in the presence of a catalyst can be used.

Examples of the reducing agent include borohydride compound and aluminum hydride compound. For example, sodium borohydride, lithium aluminum hydride and the like can be exemplified. Also, palladium, Raney nickel, platinum oxide and the like can be exemplified as the catalyst.

A solvent may be used in this reaction by optionally selecting it corresponding to the reducing agent, and its examples include methanol, ethanol, propanol or the like alcohol solvent, N,N-dimethylformamide, acetamide, dimethylacetamide or the like amide solvent, chloroform, dichloromethane, carbon tetrachloride or the like chlorine based solvent, diethyl ether, tetrahydrofuran, dioxane or the like ether solvent, hexane, pentane, benzene, toluene, xylene or the like hydrocarbon solvent or a mixed solvent thereof.

The reaction temperature may be generally within the range of from −78° C. to 100° C., preferably within the range of from −78° C. to room temperature.

The reaction period may be generally within the range of from 5 minutes to 120 hours, preferably within the range of from 30 minutes to 48 hours.

Addition Reaction of Alkyl Group

A compound (IX) in which $R^5$ is other than hydrogen atom can be obtained by allowing the compound (VIII) to react with an alkyl metal compound.

The alkyl group addition reaction may be carried out by a method generally used in this field. For example, a method in which the compound is treated with an alkyl lithium, an alkylmagnesium halide or the like can be cited.

Examples of the alkyl metal compound include methyl lithium, ethyl lithium or the like alkyl lithium and methylmagnesium iodide, ethylmagnesium bromide or the like alkylmagnesium halide.

A solvent may be used in this reaction, and its examples include diethyl ether, tetrahydrofuran, dioxane or the like ether solvent, hexane, pentane, benzene, toluene, xylene or the like hydrocarbon solvent or a mixed solvent thereof.

The reaction temperature may be generally within the range of from –78° C. to 100° C., preferably within the range of from –78° C. to room temperature.

The reaction period may be generally within the range of from 5 minutes to 120 hours, preferably within the range of from 30 minutes to 48 hours.

Substitution Reaction of Amino Group

Corresponding compound (X) can be obtained by converting the hydroxyl group of compound (IX) into a halogen, sulfonic acid ester or the like leaving group and then subjecting it to substitution reaction with a basic compound H-G.

In order to convert the hydroxyl group into a halogen, sulfonic acid ester or the like leaving group, it may be carried out by a method generally used in this field. Examples of the halogenation method include a method in which the compound is treated with a phosphorus trihalide, a phosphorus pentahalide or the like in dichloromethane, chloroform or the like solvent and a method in which the compound is treated with a Vilsmeyer reagent such as N,N-dimethylchloroholminium chloride or bromide in N,N-dimethylformamide, dioxane or the like solvent. As the sulfonylation method, a method in which the compound is treated with methanesulfonyl chloride, p-toluenesulfonyl chloride or the like in a solvent in the presence of an appropriate base can be exemplified.

The substitution reaction of a derivative of the compound (IX) with the basic compound H-G can be carried out by a method generally used in this field. For example, a substituted compound (X) can be obtained by heating a mixture of the derivative of compound (IX) with basic compound H-G in acetonitrile or the like solvent in the presence of potassium carbonate or the like base.

Deprotection Reaction

The protective group of the hydroxyl group of compound (X) can be deprotected under a deprotection reaction condition generally used for the used protective group.

Dehydration Reaction

The compound (I) of interest can be obtained by dehydrating the compound (XI). The dehydration can be carried out by a method generally used in this field. For example, a method in which the compound is heated in the presence of an acid can be cited.

The acid which can be used may be either an organic acid or an inorganic acid. Hydrochloric acid, sulfuric acid, hydrobromic acid, potassium hydrogensulfate and the like can be exemplified as the inorganic acid, and p-toluenesulfonic acid, methanesulfonic acid, oxalic acid and the like can be exemplified as the organic acid. An inorganic acid is desirable as the acid. In addition to these, alumina can also be used.

A solvent may be used in this reaction, and its examples include N,N-dimethylformamide, acetamide, dimethylacetamide or the like amide solvent, chloroform, dichloromethane, carbon tetrachloride or the like halogenated hydrocarbon solvent, diethyl ether, tetrahydrofuran, dioxane or the like ether solvent and benzene, toluene, xylene or the like aromatic hydrocarbon solvent. A mixed solvent thereof may also be used.

The reaction temperature may be generally within the range of from –20° C. to 150° C., preferably within the range of from 0° C. to 100° C.

The reaction period may be generally within the range of from 5 minutes to 72 hours, preferably within the range of from 10 minutes to 24 hours.

In addition, a compound in which its alkenyl group moiety is in trans form can also be obtained by a method shown in the following.

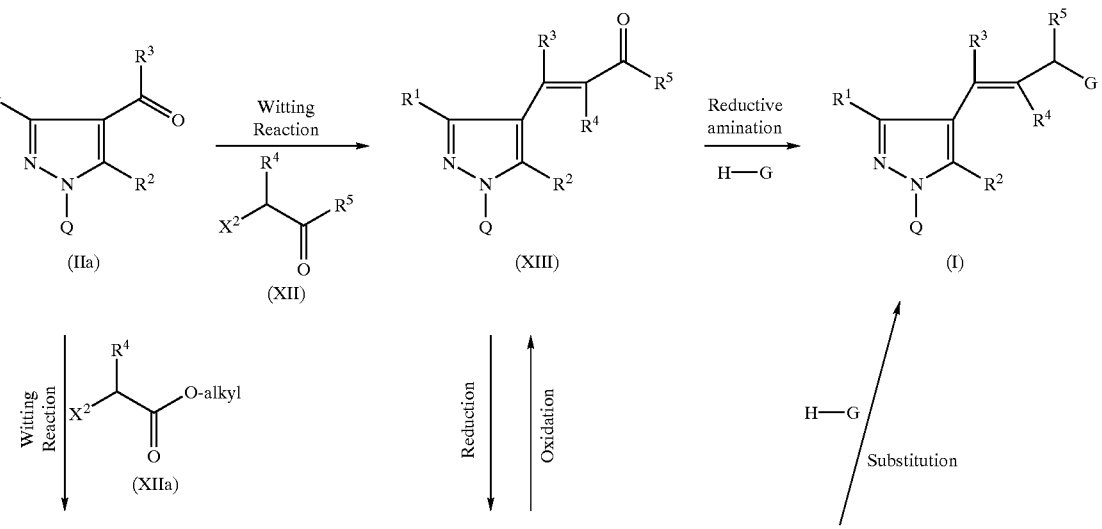

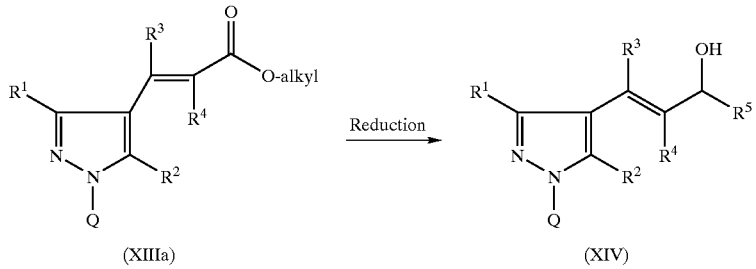

(XIIIa) → (XIV)

($X^2$ represents a trialkylphosphonium group, a dialkylphosphoryl group, a dialkylphosphono group or a trialkyl phosphoranylidene group, and $R^1$, $R^2$, $R^3$, $R^4$, $R^5$, Q and G are as defined in the foregoing.)

That is, the compound (I) can be obtained by allowing the compound (IIa) to undergo Witting reaction with a compound (XII) and subjecting the thus obtained α,β unsaturated carbonyl compound (XIII) to reductive amination reaction with a basic compound H-G. When the compound (XIII) is an α,β unsaturated aldehyde ($R^5$=H in the formula), it can also be obtained by allowing the compound (IIa) to undergo Witting reaction with a compound (XIIa), subjecting the thus obtained α,β unsaturated carbonyl compound (XIIIa) to reduction reaction and then oxidizing the thus obtained compound (XIV). Also, it is possible to obtain the compound (I) by subjecting the compound (XIII) to reduction reaction, converting the hydroxyl group of the thus obtained compound (XIV) into a leaving group and then carrying out its substitution reaction with a basic compound H-G.

Each reaction step is described.

Witting Reaction

In order to obtain the compound (XIII) from the compound (IIa), it can be effected by carrying out a method generally used in this field. For example, the compound (XIII) can be obtained by treating the compound (IIa) with the compound (XII) in a solvent under a basic reaction condition or a neutral reaction condition.

Examples of the base include n-butyl lithium, phenyl lithium, sodium hydride, potassium t-butoxide, sodium ethoxide and 1,8-diazabicyclo[5.4.0]undec-7-ene (DBU).

Examples of the solvent which can be used include diethyl ether, tetrahydrofuran, dioxane or the like ether solvent, benzene, toluene, xylene or the like aromatic hydrocarbon solvent, methanol, ethanol, propanol or the like alcohol solvent, N,N-dimethylformamide, acetamide, dimethylacetamide or the like amide solvent and chloroform, dichloromethane, carbon tetrachloride or the like halogenated hydrocarbon solvent. A mixed solvent thereof may also be used.

The reaction temperature may be generally within the range of from 30° C. to 150° C., preferably within the range of from 50° C. to 100° C.

The reaction period may be generally within the range of from 5 minutes to 72 hours, preferably within the range of from 10 minutes to 24 hours.

Reductive Amination Reaction

In order to obtain the compound (I) from the compound (XIII), a method generally used in this field may be employed. For example, the compound (I) can be obtained by allowing the compound (XIII) to react with a basic compound H-G and then treating it with a reducing agent.

Examples of the reducing agent which can be used include lithium aluminum hydride, sodium borohydride, sodium cyanoborohydride or the like complex hydrogen compound. Examples of the solvent which can be used include methanol, ethanol, propanol or the like alcohol solvent, diethyl ether, tetrahydrofuran, dioxane or the like ether solvent, hexane, pentane, benzene, toluene, xylene or the like hydrocarbon solvent or a mixed solvent thereof.

The reductive amination reaction may be carried out at a temperature generally within the range of from −78 to 100° C., preferably within the range of from −10° C. to room temperature.

The reaction period may be generally within the range of from 5 minutes to 120 hours, preferably within the range of from 30 minutes to 48 hours.

Reduction Reaction

By reducing the carbonyl group of compound (XIII) or the ester group of compound (XIIIa), the corresponding alcohol (XIV) can be obtained. The reduction can be carried out by a method generally used in this field. For example, a method in which the compound is treated in the presence of a reducing agent can be employed.

Examples of the reducing agent include boron hydride compounds and aluminum hydride compounds. Preferably, diisobutylaluminum hydride can be used.

A solvent may be used in this reaction by optionally selecting it corresponding to the reducing agent, and its examples include methanol, ethanol, propanol or the like alcohol solvent, N,N-dimethylformamide, acetamide, dimethylacetamide or the like amide solvent, chloroform, dichloromethane, carbon tetrachloride or the like chlorine based solvent, diethyl ether, tetrahydrofuran, dioxane or the like ether solvent, hexane, pentane, benzene, toluene, xylene or the like hydrocarbon solvent or a mixed solvent thereof.

The reaction temperature may be generally within the range of from −78° C. to 100° C., preferably within the range of from −78° C. to room temperature.

The reaction period may be generally within the range of from 5 minutes to 120 hours, preferably within the range of from 30 minutes to 48 hours.

Oxidation Reaction

In older to obtain the compound (XIII) from the compound (XIV), it may be effected by carrying out a method generally used in this field. For example, a method in which the compound is treated in the presence of an oxidizing agent can be employed. As the oxidizing agent, silver oxide, lead tetracetate, a chrome based oxidizing agent, a manganese based oxidizing agent and the like can be used, and manganese dioxide can be preferably used.

A solvent may be used in this reaction by optionally selecting it corresponding to the reducing agent, and its examples include acetone, ethyl methyl ketone or the like ketone solvent, N,N-dimethylformamide, acetamide, dimethylacetamide or the like amide solvent, chloroform, dichloromethane, carbon tetrachloride or the like chlorine based solvent, diethyl ether, tetrahydrofuran, dioxane or the like ether solvent, hexane, pentane, benzene, toluene, xylene or the like hydrocarbon solvent, pyridine or the like basic solvent, acetic acid, phosphoric acid or the like acidic solvent or a mixed solvent thereof.

The reaction temperature may be generally within the range of from −78° C. to 100° C.

The reaction period may be generally within the range of from 5 minutes to 120 hours, preferably within the range of from 30 minutes to 48 hours.

Substitution Reaction of Amino Group

Corresponding complex (I) can be obtained by converting the hydroxyl group of compound (XIV) into a halogen, sulfonic acid ester or the like leaving group and then subjecting it to substitution reaction with a basic compound H-G.

In order to convert the hydroxyl group into a halogen, sulfonic acid ester or the like leaving group, it may be carried out by a method generally used in this field.

Examples of the halogenation method include a method in which the compound is treated with a phosphorus trihalide, a phosphorus pentahalide or the like in dichloromethane, chloroform or the like solvent, a method in which the compound is treated with hexachloroacetone or with carbon tetrachloride and triphenylphosphine in dichloromethane, chloroform or the like solvent and a method in which the compound is treated with a Vilsmeyer reagent such as N,N-dimethylchloroholminium chloride or bromide in N,N-dimethylformamide, dioxane or the like solvent.

As the sulfonylation method, a method in which the compound is treated with methanesulfonyl chloride, p-toluenesulfonyl chloride or the like in a solvent in the presence of an appropriate base can be exemplified.

The substitution reaction of a derivative of the compound (XIV) with the basic compound H-G can be carried out by a method generally used in this field. For example, the compound (I) can be obtained by heating a mixture of the derivative of compound (XIV) with basic compound H-G in acetonitrile or the like solvent in the presence of potassium carbonate or the like base.

As occasion demands, the compound of this invention can be made into a physiologically acceptable salt by converting it using hydrochloric acid, sulfuric acid, phosphoric acid or the like inorganic acid or formic acid, acetic acid, methanesulfonic acid or the like organic acid.

In addition, the free form or salt of the compound of this invention may exist as a hydrate.

The antitumor agent of this invention can be administered as various injections such as for intravenous injection, intramuscular injection and subcutaneous injection, or by oral administration and the like various methods. Among these administration methods, intravenous injection by an aqueous preparation and oral administration are desirable.

The aqueous preparation can be prepared by making the compound into an acid addition product with a pharmacologically acceptable acid. In the case of oral administration, the compound may be either its free form or salt form.

Regarding the preparation method of pharmaceutical preparations, they can be prepared by generally used various preparation methods of pharmaceutical preparations, by selecting an appropriate pharmaceutical preparation in response to each administration method.

Among dosage forms of the antitumor agent of this invention, tablets, powders, granules, capsules, solutions, syrups, elixirs, oily or aqueous suspensions and the like can be exemplified as the oral preparations.

Regarding the injections, the preparation may contain stabilizers, antiseptics and solubilizing agents, and a solution which may contain these auxiliary agents may be made into a solid preparation by freeze-drying or the like means after putting it into a container, which is dissolved when used. Also, one dose may be contained in a container or multiple doses may be contained in the same container.

Solutions, suspensions, emulsions and the like can be exemplified as the liquid preparations, and a suspending agent, an emulsifying agent or the like can be used as an additive agent when these pharmaceutical preparations are prepared.

It is desirable that the antitumor agent containing the compound of this invention is administered as the compound once a day per adult, by repeating it at an appropriate interval. In addition, the dose is within the range of from 1 mg to 3 g, preferably within the range of from 5 mg to 2 g.

Next, antitumor effects of the compound of this invention obtained in the aforementioned manner are shown with reference to test examples.

Test Example 1

A human pulmonary carcinoma strain PC-12 which had been subcultured using RPMI 1640 containing 10% fetal calf serum, 2 mM of L-glutamine and 100 μg/ml of kanamycin sulfate was inoculated into a 96 well microplate at an inoculum size of $1.0 \times 1.0^3$ cells/150 μl/well, and 50 μl/well of a sample was added 24 hours thereafter. The cells were then cultured for 3 days, and a 5 mg/ml solution of MTT (3-(4,5-dimethylthiazol-2-yl)-2,5-diphenyl-2H-tetrazolium bromide) was dispensed in 20 μl/well portions. Four hours thereafter, the culture medium was discarded, dimethyl sulfoxide was dispensed in 150 μl/well portions and the absorbance was measured at 540 nm. The antitumor effect was shown by $GI_{50}$ value (ng/ml) as a drug concentration which reduced cell growth of the drug-added group to 50% of the control group.

TABLE 1

|  | $GI_{50}$ Value (ng/ml) PC-12 |
| --- | --- |
| Compound of Example 1 | 36.5 |
| Compound of Example 2 | 12.1 |
| Compound of Example 3 | 20.9 |
| Compound of Example 4 | 12.1 |
| Compound of Example 11 | 2.49 |
| Compound of Example 12 | 1.60 |
| Compound of Example 13 | 0.601 |
| Compound of Example 15 | 26.6 |
| Compound of Example 19 | 2.35 |
| Compound of Example 21 | 3.39 |
| Compound of Example 26 | 6.29 |
| Compound of Example 27 | 9.30 |
| Compound of Example 28 | 0.725 |
| Compound of Example 29 | 1.54 |
| Compound of Example 54 | 11.3 |
| 5-FU | 35.5 |

As is evident from Table 1, the compounds synthesized in this invention showed antitumor activity, so that they can be used as antitumor agents for the treatment of various tumors.

Test Example 2

<Coordination Inhibition Test>

Rotation speed of the rotary rod (3 cm in diameter) of RotaRod apparatus (mfd. by Natsume Seisaku-sho) was set to 10 rpm, and mice (Balb/c) which stood on the rod for 60 seconds or more were selected. After 1, 4 or 24 hours of the oral administration of each test sample, these mice were put on the rod, and the mice which dropped within 60 seconds were regarded as coordination inhibition action positive. The results are shown in Table 2.

TABLE 2

Coordination inhibition test

| | | T/C** | | |
|---|---|---|---|---|
| Compound | Dose | After 1 hour | After 4 hours | After 24 hours |
| Example 28 of Japanese Patent Application No. 7-247096 | 10 mg | 3/10 | 8/10 | 0/10 |
| 10 mg × 5 times (IR 94%)* | 3 mg | 6/10 | 3/10 | 0/10 |
| Example 13 | 12 mg | 1/6 | 2/6 | —*** |
| 5 mg × 4 times (IR 92%)* | 10 mg | 0/6 | 0/6 | — |
| | 5 mg | 0/6 | 0/6 | — |
| Example 54 | 30 mg | 0/6 | 0/6 | — |
| 10 mg × 4 times (IR 89%)* | 10 mg | 0/6 | 0/6 | — |
| Control | 0 mg | 0/6 | 0/6 | 0/6 |

*Mouse fibrosarcoma Meth A was subcutaneously transplanted into mice (d0), each test sample was orally administered continuously for 4 days (d7–10) or 5 days (d7–11), and the mice were dissected on the 17th day to judge the antitumor effect (IR).
**The number of coordination inhibition positive mice/the number of tested mice.
***Not carried out.

Among these compounds, a compound typified by Example 22 of a previously applied patent (Japanese Patent Application No. 7-247096) showed strong coordination inhibition action by a single dose (10 mg of dose in the case of Example 22 of Japanese Patent Application No. 7-247096) at around the maximum tolerated dose expressing the antitumor action when orally administered to mice. On the other hand, a series of compounds disclosed by this invention showed completely no coordination inhibition action or extremely weak action at a dose showing the drug efficacy IR of 58% or more or by single administration at more larger dose.

BEST MODE FOR CARRYING OUT THE INVENTION

Next, this invention is described further in detail with reference to examples (in structural formulae in the examples, Me means methyl group and Boc means t-butoxycarbonyl group).

EXAMPLE 1

3-[3-[1-(4-Amino-2-pyrimidinyl)-5-methyl-4-pyrazolyl]-2-trans-propen-1-yl]-9-fluoro-2,3,4,4a,5,6-hexahydro-1H-pyrazino[1,2-a]quinoline hydrochloride (isomer A)

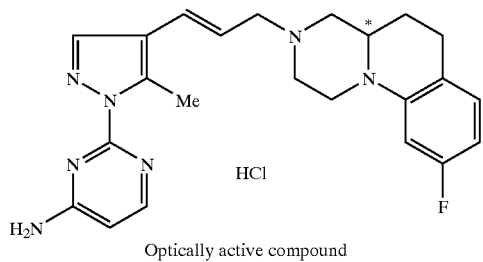

Optically active compound (1) 2-Hydrazino-4-(4-methoxybenzylamino)pyrimidine

A 21 ml portion of 4-methoxybenzylamine was added to a mixture consisting of 15.7 g of 2,4-dichloropyrimidine, 14.4 g of potassium carbonate and 60 ml of dimethylformamide, which was cooled to 0° C., and then the resulting mixture was stirred at room temperature for 48 hours. The reaction solution was poured into ice water and stirred for 1 hour, and then the resulting precipitate was collected by filtration. The thus obtained solid was dissolved in 280 ml of tetrahydrofuran, mixed with 44 ml of 80% hydrazine aqueous solution and 23.5 g of potassium carbonate and then heated under reflux for 24 hours. After cooling to room temperature, the reaction solution was concentrated under a reduced pressure, and the resulting residue was mixed with water and stirred at room temperature for 1 hour. The insoluble matter was collected by filtration, washed with water and then dried to obtain 17.1 g of the title compound.

$^1$H-NMR (CDCl$_3$) δ: 3.80 (s, 3H), 4.45 (br, 2H), 5.00–5.20 (br, 1H), 5.78 (d, 1H, J=6 Hz), 6.16 (br, 1H), 6.88 (d, 2H, J=9 Hz), 7.24 (d, 2H, J=9 Hz), 7.87 (d, 1H, J=6 Hz).

(2) Ethyl 1-[4-(4-methoxybenzylamino)-2-pyrimidinyl]-5-methyl-4-pyrazolecarboxylate A 7.35 g portion of the compound obtained in Example 1-(1) was added to 60 ml of an ethanol solution containing 6.70 g of ethyl ethoxymethyleneacetoacetate, and the mixture was stirred at room temperature for 30 minutes and then heated under reflux for 2 hours. After cooling to room temperature, the solvent was evaporated under a reduced pressure, the residue was applied to a silica gel column chromatography and developed with a mixed solvent of hexane-ethyl acetate (1:2), and then the fractions containing the compound of interest were concentrated to obtain 8.64 g of the title compound.

$^1$H-NMR (CDCl$_3$) δ: 1.37 (t, 3H, J=7 Hz), 2.92 (s, 3H), 3.81 (s, 3H), 4.31 (q, 2H, J=7 Hz), 4.51 (br, 2H), 6.30 (d, 1H, J=6 Hz), 6.89 (d, 2H, J=9 Hz), 7.25 (d, 2H, J=9 Hz), 8.05 (s, 1H), 8.25 (d, 1H, J=6 Hz).

(3) 1-[4-(4-Methoxybenzylamino)-2-pyrimidinyl]-5-methyl-4-pyrazolecarbaldehyde

In an atmosphere of nitrogen, 120 ml of a dichloromethane solution containing 7.0 g of the compound obtained in Example 1-(2) was cooled to −78° C., 76 ml of diisobutylaluminum hydride (1 M hexane solution) was added thereto over 30 minutes and then the mixture was stirred at the same temperature for 5 hours. The reaction solution was mixed with 100 ml of 10% potassium tartarate aqueous solution and stirred at room temperature for 15 hours. The reaction solution was extracted with a methanol-chloroform (1:9) mixed solvent, and then the organic layer was dried and the solvent was evaporated under a reduced pressure. A 120 ml portion of dioxane and 14.9 g of activated manganese dioxide were added to the resulting residue and stirred at room temperature for 24 hours. The insoluble matter was removed by celite filtration and the resulting filtrate was concentrated. The residue was mixed with ether and stirred at room temperature for 3 hours, and then the resulting precipitate was collected by filtration to obtain 5.38 g of the title compound.

$^1$H-NMR (CDCl$_3$) δ: 2.92 (s, 3H), 3.81 (s, 3H), 4.40–4.60 (br, 2H), 6.33 (d, 1H, J=6 Hz), 6.90 (d, 2H, J=9 Hz), 7.25 (d, 2H, J=9 Hz), 8.10 (s, 1H), 8.26 (d, 1H, J=6 Hz), 10.00 (s, 1H).

(4) Ethyl 3-[1-[4-(4-methoxybenzylamino)-2-pyrimidinyl]-5-methyl-4-pyrazolyl]-2-trans-propenoate A mixture consisting of 5.38 g of the compound obtained in Example 1-(3), a mixture of 6.95 g of (carboethoxymethylene)triphenylphosphorane and 80 ml of toluene was stirred at 80° C. for 16 hours. The reaction solution was stirred at room temperature for 24 hours and then the resulting precipitate was collected by filtration to obtain 4.45 g of the title compound.

¹H-NMR (CDCl₃) δ: 1.33 (t, 3H, J=7 Hz), 2.71 (s, 3H), 3.81 (s, 3H), 4.25 (q, 2H, J=7 Hz), 4.45–4.60 (br, 2H), 6.26 (d, 1H, J=16 Hz), 6.28 (d, 1H, J=6 Hz), 6.89 (d, 2H, J=8 Hz), 7.25 (d, 2H, J=8 Hz), 7.61 (d, 1H, J=16 Hz), 7.92 (s, 1H), 8.24 (d, 1H, J=6 Hz).

(5) Ethyl 3-[1-(4-amino-2-pyrimidinyl)-5-methyl-4-pyrazolyl]-2-trans-propenoate

A 5.83 g portion of the compound obtained in Example 1-(4) was dissolved in 150 ml of trifluoroacetic acid and heated under reflux for 19 hours. The reaction solution was concentrated under a reduced pressure, mixed with saturated sodium bicarbonate aqueous solution, extracted with 10% methanol-chloroform and dried with anhydrous sodium sulfate, and then the solvent was evaporated under a reduced pressure. By washing the resulting residue with ether, 2.07 g of the title compound was obtained as a white powder.

¹H-NMR (CDCl₃) δ: 1.34 (t, 3H, J=7 Hz), 2.75 (s, 3H), 3.15 (br s, 2H), 4.25–4.27 (m, 2H), 6.27 (d, 1H, J=16 Hz), 6.47 (d, 1H, J=6 Hz), 7.60 (d, 1H, J=16 Hz), 7.94 (s, 1H), 8.14 (d, 1H, J=6 Hz).

(6) 3-[1-(4-Amino-2-pyrimidinyl)-5-methyl-4-pyrazolyl]-2-trans-propenal

A 100 ml portion of dichloromethane was added to 2.07 g of the compound obtained in Example 1-(5), 25 ml of diisobutylaluminum hydride (1 M hexane solution) was added dropwise thereto at −78° C. in an atmosphere of nitrogen, and the mixture was stirred at the same temperature for 15 minutes and then at ice temperature for 30 minutes. The reaction solution was mixed with saturated potassium tartarate aqueous solution, stirred at room temperature, extracted with 10% methanol-chloroform and dried with anhydrous sodium sulfate, and then the solvent was evaporated under a reduced pressure. The water layer was applied to an HP-20 column chromatography, eluted with methanol and then combined with the aforementioned extract and concentrated. The residue was mixed with 100 ml of 1,4-dioxane and 5.27 g of activated manganese dioxide, and stirred at 50° C. for 16 hours. The insoluble matter was filtered through celite, further washed with an organic layer of chloroform-methanol-water (7:3:1) and then the solvent was evaporated. By recrystallizing the resulting residue from ethanol-ether, 1.00 g of the title compound was obtained as a slightly brown powder.

¹H-NMR (CD₃OD-CDCl₃) δ: 2.78 (s, 3H), 6.39 (d, 1H, J=5 Hz), 6.56 (dd, 1H, J=16 Hz, 8 Hz), 7.44 (d, 1H, J=16 Hz), 7.96 (s, 1H), 8.14 (d, 1H, J=5 Hz), 9.62 (d, 1H, J=8 Hz).

(7) 7-Fluoro-2-quinolinecarboxylic acid

A mixture consisting of 9.1 ml of bromine and 8 ml of acetic acid was added to a mixture consisting of 9.64 g of 7-fluoroquinaldine, 30 g of sodium acetate and 60 ml of acetic acid at 70° C. over 20 minutes. The reaction solution was stirred at 90° C. for 1 hour, cooled to room temperature and then concentrated under a reduced pressure. After adding water to the residue, the insoluble matter was collected by filtration and washed with water to obtain 20.0 g of 7-fluoro-2-tribromoquinoline. The thus obtained compound was mixed with 200 ml of concentrated sulfuric acid and stirred at 125° C. for 20 hours, and then the reaction solution was poured into about 600 ml of ice water. The thus obtained acidic aqueous solution was alkalified by adding 28% ammonia aqueous solution, adjusted to around pH 4 by adding 1 N phosphoric acid aqueous solution and then extracted with chloroform. The organic layer was dried and then concentrated, the thus obtained residue was applied to a silica gel column chromatography and developed with a chloroform-methanol (9:1) mixed solvent, and then the fractions containing the compound of interest were concentrated to obtain 9.04 g of the title compound.

¹H-NMR (CDCl₃) δ: 7.52 (t, 1H, J=9 Hz), 7.80 (d, 1H, J=9 Hz), 7.97 (dd, 1H, J=6 Hz, 9 Hz), 8.27 (d, 1H, J=8 Hz), 8.43 (d, 1H, J=8 Hz).

(8) 7-Fluoro-2-[N-(1-phenylethyl)carbamoyl]-1,2,3,4-tetrahydroquinoline (diastereomer A and diastereomer B)

A 9.0 g portion of the compound obtained in Example 1-(7) was dissolved in 300 ml of acetic acid, mixed with 1.0 g of platinum oxide and then subjected to 6 hours of catalytic hydrogenation. The insoluble matter was removed by filtration, the resulting filtrate was concentrated to dryness, and then the residue was dissolved in ethyl acetate and washed with water and saturated brine. The organic layer was dried with anhydrous sodium sulfate and then the solvent was evaporated under a reduced pressure. The thus obtained residue was dissolved in 300 ml of dichloromethane, mixed with 8.5 g of (s)-(−)-1-phenylethylamine, 8.6 g of dimethylaminopyridine and 17 g of 1-ethyl-3-(3-dimethylaminopropyl)carbodiimide hydrochloride and then stirred at room temperature for 20 hours. The reaction solution was washed with water, 1 N phosphoric acid aqueous solution and saturated brine in that order and dried with anhydrous sodium sulfate, and then the solvent was evaporated under a reduced pressure. The residue was applied to a silica gel column chromatography and developed with an ethyl acetate-hexane (2:5) mixed solvent to obtain 5.78 g of a low polar isomer (diastereomer A) and 5.17 g of a high polar isomer (diastereomer B) of the title compound.

Diastyereomer A;

¹H-NMR (CDCl₃) δ: 1.45 (d, 3H, J=7 Hz), 1.85–1.94 (m, 1H), 2.30–2.38 (m, 1H), 2.50–2.59 (m, 1H), 2.65–2.75 (m, 1H), 3.96 (q, 1H, J=5 Hz), 4.19 (d, 1H, J=5 Hz), 5.12–5.20 (m, 1H), 6.32 (dd, 1H, J=2 Hz, 10 Hz), 6.41 (dt, 1H, J=2 Hz, 8 Hz), 6.88 (d, 1H, J=8 Hz), 6.93 (t, 1H, J=8 Hz), 7.25–7.40 (m, 5H).

Diastereomer B;

¹H-NMR (CDCl₃) δ: 1.49 (d, 3H, J=7 Hz), 1.83–1.91 (m, 1H), 2.24–2.32 (m, 1H), 2.37–2.45 (m, 1H), 2.60–2.67 (m, 1H), 4.01 (q, 1H, J=5 Hz), 4.24 (d, 1H, J=5 Hz), 5.10–5.17 (m, 1H), 6.36 (dd, 1H, J=2 Hz, 10 Hz), 6.42 (dt, 1H, J=2 Hz, 8 Hz), 6.90 (t, 1H, J=8 Hz), 6.85–6.95 (br, 1H), 7.15–7.30 (m, 5H).

(9) 7-Fluoro-2-[N-(1-phenylethyl)-N-tert-butoxycarbonylaminomethyl]-1,2,3,4-tetrahydroquinoline (diastereomner A)

A 5.78 g portion of the diastereomer A obtained in Example 1-(8) was dissolved in 80 ml of tetrahydrofuran and mixed with 16 ml of borane-dimethyl sulfide complex while stirring at 0° C., and then the mixture was stirred at room temperature for 3 days. This was mixed with 6 N hydrochloric acid aqueous solution, stirred for 1 hour and then neutralized using saturated sodium bicarbonate aqueous solution. After extraction with chloroform the organic layer was washed with saturated brine and dried with anhydrous sodium sulfate, and then the solvent was evaporated under a reduced pressure. The residue was dissolved in 56 ml of dioxane, mixed with 5.5 g of di-tert-butyl dicarboxylate and then stirred at room temperature for 40 hours. After evaporation of the solvent under a reduced pressure, the residue was applied to a silica gel column chromatography and developed with an ethyl acetate-hexane (1:9) mixed solvent, and then the fractions containing the compound of interest were concentrated to obtain 7.61 g of the title compound.

¹H-NMR (CDCl₃) δ: 1.20–1.30 (m, 1H), 1.53 (s, 9H), 1.54 (d, 3H, J=9 Hz), 1.79–1.82 (m, 1H), 2.50–2.70 (m, 2H), 2.95–3.10 (br, 1H), 3.18 (dd, 1H, J=14 Hz, 3 Hz), 3.25–3.45

(br, 1H), 5.70–5.85 (br, 1H), 6.19 (td, 1H, J=8 Hz, 2 Hz), 6.77 (dd, 1H, J=8 Hz, 7 Hz), 7.30–7.45 (m, 6H).

(10) 9-Fluoro-3-(1-phenylethyl)-2,3,4,4a,5,6-hexahydro-1-oxopyrazino[1,2-a]quinoline (diastereomer A)

A 7.61 g portion of the compound obtained in Example 1-(9) was dissolved in 50 ml of tetrahydrofuran and mixed with 2.45 ml of pyridine and 1.75 ml of chloroacetyl chloride while stirring at 0° C., and then the mixture was stirred at room temperature for 30 minutes. The reaction solution was mixed with ice water and extracted with ethyl acetate, and then the organic layer was washed with saturated brine and dried with anhydrous sodium sulfate. After evaporation of the solvent under a reduced pressure, the thus obtained residue was dissolved in 20 ml of tetrahydrofuran, mixed with 25 ml of trifluoroacetic acid and then stirred at room temperature for 2 hours and further at 50° C. for 1 hour. The reaction solution was concentrated to dryness under a reduced pressure, and then the residue was dissolved in 50 ml of dimethylformamide, mixed with 4.6 g of potassium carbonate and stirred at 50° C. for 1 hour. The reaction solution was cooled to room temperature, diluted with water and then extracted with ethyl acetate. The organic layer was washed with saturated brine and dried with anhydrous sodium sulfate and then the solvent was evaporated under a reduced pressure. The residue was applied to a silica gel column chromatography and developed with an ethyl acetate-hexane (1:9) mixed solvent, and then the fractions containing the compound of interest were concentrated to obtain 5.09 g of the title compound.

$^1$H-NMR (CDCl$_3$) δ: 1.40 (d, 3H, J=7 Hz), 1.75–1.95 (m, 2H), 2.25 (dd, 1H, J=12 Hz, 9 Hz), 2.80 (dd, 1H, J=8 Hz, 5 Hz), 2.96 (ddd, 1H, J=12 Hz, 5 Hz, 2 Hz), 3.07 (d, 1H, J=17 Hz), 3.37 (q, 1H, J=7 Hz), 3.58–3.65 (m, 1H), 3.78 (dd, 1H, J=17 Hz, 2 Hz), 6.77 (td, 1H, J=8 Hz, 2 Hz), 7.03 (dd, 1H, J=8 Hz, 6 Hz), 7.25–7.40 (m, 5H), 7.93 (dd, 1H, J=12 Hz, 2 Hz).

(11) 9-Fluoro-3-(1-phenylethyl)-2,3,4,4a,5,6-hexahydro-1H-pyrazino[1,2-a]quinoline (diastereomer A)

A tetrahydrofuran solution (30 ml) containing 5.09 g of the compound obtained in Example 1-(10) was added to a diborane solution prepared by suspending 5.9 g of sodium borohydride in 20 ml of tetrahydrofuran and mixing it with 25.6 ml of boron trifluoride diethyl ether complex, and the mixture was heated under reflux for 2 hours. The reaction solution was cooled to 0° C., mixed with 6 N hydrochloric acid aqueous solution and then stirred at 80° C. for 1 hour and further at room temperature for 48 hours. This was neutralized using saturated sodium bicarbonate aqueous solution and extracted with chloroform, and then the organic layer was dried with anhydrous sodium sulfate. After evaporation of the solvent under a reduced pressure, the thus obtained residue was applied to a silica gel column chromatography and developed with an ethyl acetate-hexane (1:9) mixed solvent, and then the fractions containing the compound of interest were concentrated to obtain 2.52 g of the title compound.

$^1$H-NMR (CDCl$_3$) δ: 1.39 (d, 3H, J=6 Hz), 1.56–1.81 (m, 3H), 2.18–2.25 (m, 1H), 2.57–2.63 (m, 1H), 2.70–2.78 (m, 2H), 2.78–2.98 (m, 2H), 3.18 (dd, 1H, J=11 Hz, 3 Hz), 3.35 (q, 1H, J=7 Hz), 3.66 (d, 1H, J=11 Hz), 6.34 (td, 1H, J=8 Hz, 2 Hz), 6.46 (dd, 1H, J=13 Hz, 2 Hz), 6.85 (t, 1H, J=8 Hz), 7.23–7.33 (m, 5H).

(12) 9-Fluoro-2,3,4,4a,5,6-hexahydro-1H-pyrazino[1,2-a]quinoline (enantiomer A)

A 2.52 g portion of the compound obtained in Example 1-(11) was dissolved in 40 ml of methanol, mixed with 2.54 g of ammonium formate and 2.5 g of 10% palladium-carbon and then heated under reflux for 1.5 hours. The insoluble matter was removed by filtration, and then the filtrate was concentrated under a reduced pressure. The residue was mixed with saturated brine and extracted with chloroform, the organic layer was dried with anhydrous sodium sulfate and then the solvent was evaporated under a reduced pressure. The thus obtained residue was applied to a silica gel column chromatography and developed with a methanol-chloroform (7:10) mixed solvent, and then the fractions containing the compound of interest were concentrated to obtain 1.56 g of the title compound.

$^1$H-NMR (CDCl$_3$) δ: 1.67–1.78 (m, 1H), 1.89–1.96 (m, 1H), 2.63–2.72 (m, 2H), 2.76–2.84 (m, 1H), 2.95–3.04 (m, 2H), 3.13–3.32 (m, 2H), 3.67–3.76 (m, 1H), 6.40 (td, 1H, J=8 Hz, 2 Hz), 6.47 (dd, 1H, J=12 Hz, 2 Hz), 6.90 (t, 1H, J=8 Hz).

(13) 3-[3-[1-(4-Amino-2-pyrimidinyl)-5-methyl-4-pyrazolyl]-2-trans-propen-1-yl]-9-fluoro-2,3,4,4a,5,6-hexahydro-1H-pyrazino[1,2-a]quinoline hydrochloride (isomer A)

A mixture consisting of 120 mg of the compound obtained in Example 1-(12), 133 mg of the aldehyde obtained in Example 1-(6) and 20 ml of ethanol was stirred at 80° C. for 1 hour, cooled to room temperature and mixed with 0.33 ml of acetic acid, and then 110 mg of sodium cyanoborohydride was added thereto in three portions at 1 hour intervals. After 13 hours of stirring at room temperature, the reaction solution was mixed with water and saturated sodium carbonate aqueous solution and extracted with chloroform. The organic layer was dried with anhydrous sodium sulfate, the solvent was evaporated under a reduced pressure, the thus obtained residue was applied to a silica gel column chromatography and developed with a methanol-chloroform (2:98) mixed solvent, and then the fractions containing the compound of interest were concentrated. A 166 mg portion of the thus obtained residue was dissolved in 10 ml of isopropyl alcohol with heating, 0.45 ml of 1 N hydrochloric acid-ethanol was added during the heating, and then this was allowed to stand at room temperature for 10 hours and the resulting precipitate was collected by filtration to obtain 105 mg of the title compound.

Melting point: 188–194° C. (decomposition)

$^1$H-NMR (DMSO-d$_6$) δ: 1.55 (m, 1H), 1.98–2.10 (m, 1H), 2.57 (s, 3H), 2.60–3.00 (m, 2H), 3.00–3.20 (m, 2H), 3.25–3.45 (m, 4H), 3.50–3.60 (m, 1H), 3.85–3.95 (m, 1H), 4.05–4.15 (m, 1H), 6.17 (dt, 1H, J=16 Hz, 7 Hz), 6.41 (d, 1H, J=6 Hz), 6.47 (td, 1H, J=8 Hz, 2 Hz), 6.78 (d, 1H, J=16 Hz), 6.78–6.80 (m, 1H), 6.98 (t, 1H, J=8 Hz), 7.34 (brs, 2H), 7.96 (s, 1H), 8.11 (d, 1H, J=6 Hz), 10.6–10.7 (br, 1H).

EXAMPLE 2

3-[3-[1-(4-amino-2-pyrimidinyl)-5-methyl-4-pyrazolyl]-2-trans-propen-1-yl]-9-fluoro-2,3,4,4a,5,6-hexahydro-1H-pyrazino[1,2-a]quinoline hydrochloride (isomer B)

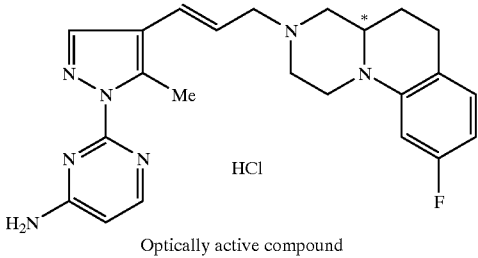

Optically active compound (1) 7-Fluoro-2-[N-(1-phenylethyl)-N-tert-butoxycarbonylaminomethyl]-1,2,3,4,-tetrahydroquinoline (diastereomer B)

A 5.17 g portion of the diastereomer B obtained in Example 1-(8) was allowed to undergo the same reaction of Example 1-(9) and then subjected to its after-treatment, thereby obtaining 6.93 g of the title compound.

$^1$H-NMR (CDCl$_3$) δ: 1.30–1.60 (m, 1H), 1.47 (s, 9H), 1.54 (d, 3H, J=9 Hz), 2.50–2.55 (m, 2H), 3.00–3.20 (m, 3H), 5.25–5.45 (br, 1H), 6.10 (dd, 1H, J=11 Hz, 2 Hz), 6.23 (td, 1H, J=8 Hz, 2 Hz), 6.78 (dd, 1H, J=8 Hz, 7 Hz), 7.20–7.40 (m, 5H).

(2) 9-Fluoro-3-(1-phenylethyl)-2,3,4,4a,5,6-hexahydro-1-oxopyrazino[1,2-a]quinoline (diastereomer B)

A 6.93 g portion of the compound obtained in Example 2-(1) was allowed to undergo the same reaction of Example 1-(10) and then subjected to its after-treatment, thereby obtaining 5.28 g of the title compound.

$^1$H-NMR (CDCl$_3$) δ: 1.41 (d, 3H, J=7 Hz), 1.83–1.90 (m, 2H), 2.02 –2.15 (m, 1H), 2.50 (dd, 1H, J=12 Hz, 6 Hz), 2.79–2.94 (m, 2H), 3.33 (s, 2H), 3.42 (q, 1H, J=6 Hz), 3.50–3.62 (m, 1H), 6.78 (td, 1H, J=8 Hz, 2 Hz), 7.04 (dd, 1H, J=8 Hz, 7 Hz), 7.26–7.40 (m, 5H), 7.81 (dd, 1H, J=12 Hz, 2 Hz).

(3) 9-Fluoro-3-(1-phenylethyl)-2,3,4,4a,5,6-hexahydro-1H-pyrazino[1,2-a]quinoline (diastereomer B)

A 5.28 g portion of the compound obtained in Example 2-(2) was allowed to undergo the same reaction of Example 1-(11) and then subjected to its after-treatment, thereby obtaining 2.45 g of the title compound.

$^1$H-NMR (CDCl$_3$) δ: 1.39 (d, 3H, J=6 Hz), 1.68–1.80 (m, 1H), 1.86–2.13 (m, 3H), 2.63–2.70 (m, 1H), 2.74–2.85 (m, 2H), 3.04–3.12 (m, 2H), 3.35–3.40 (m, 1H), 3.48–3.53 (m, 1H), 6.34 (td, 1H, J=8 Hz, 2 Hz), 6.40 (dd, 1H, J=13 Hz, 2 Hz), 6.87 (t, 1H, J=8 Hz), 7.24–7.33 (m, 5H).

(4) 9-Fluoro-2,3,4,4a,5,6-hexahydro-1H-pyrazino[1,2-a]quinoline (enantiomer B)

A 2.45 g portion of the compound obtained in Example 2-(3) was allowed to undergo the same reaction of Example 1-(12) and then subjected to its after-treatment, thereby obtaining 1.57 g of the title compound.

Its $^1$H-NMR spectrum completely coincided with the spectrum of the compound obtained in Example 1-(12).

(5) 3-[3-[1-(4-Amino-2-pyrimidinyl)-5-methyl-4-pyrazolyl]-2-trans-propen-1-yl]-9-fluoro-2,3,4,4a,5,6-hexahydro-1H-pyrazino[1,2-a]quinoline hydrochloride (isomer B)

A 128 mg portion of the compound obtained in Example 2-(4) and 142 mg of the aldehyde obtained in Example 1-(6) were allowed to undergo the same reaction of Example 1-(13) and then subjected to the after-treatment, thereby obtaining 104 mg of the title compound.

Melting point: 192–194° C. (decomposition)

Its $^1$H-NMR spectrum completely coincided with the spectrum of the compound obtained in Example 1-(13).

EXAMPLE 3

(+/−)-3-[3-[1-(4-Amino-2-pyrimidinyl)-5-methyl-4-pyrazolyl]-2-trans-propen-1-yl]-9-fluoro-2,3,4,4a,5,6-hexahydro-1H-pyrazino[2,1-c]-1,4-benzoxazine hydrochloride

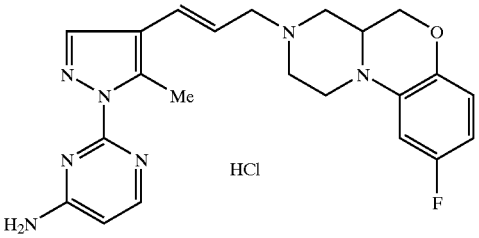

(1) 1-(4-Fluoro-2-nitrophenoxy)-2,3-epoxypropane

A mixture consisting of 31.4 g of 4-fluoro-2-nitrophenol, 100 ml of epichlorohydrin, 9.1 g of sodium hydroxide, 40 ml of water and 900 ml of ethanol was stirred at 80° C. for 10 hours. After cooling the reaction solution to room temperature, the insoluble matter was removed by filtration and the filtrate was concentrated to dryness under a reduced pressure. The resulting residue was dissolved in an ether-hexane (1:1) mixed solvent, washed with water and saturated brine and dried with anhydrous sodium sulfate, and then the solvent was evaporated under a reduced pressure. The residue was applied to a silica gel column chromatography and developed with a chloroform-hexane (3:1) mixed solvent, and then the fractions containing the compound of interest were concentrated to obtain 27.9 g of the title compound.

$^1$H-NMR (CDCl$_3$) δ: 2.84 (dd, 1H, J=5 Hz, 2 Hz), 2.93 (t, 1H, J=5 Hz), 3.36–3.40 (m, 1H), 4.10 (dd, 1H, J=11 Hz, 5 Hz), 4.41 (dd, 1H, J=11 Hz, 3 Hz), 7.14 (dd, 1H, J=9 Hz, 4 Hz), 7.24–7.30 (m, 1H), 7.60 (dd, 1H, J=8 Hz, 3 Hz).

(2) 1-(4-Fluoro-2-nitrophenoxy)-2-hydroxy-3-phthalimidopropane

A fixture consisting of 4.49 g of the compound obtained in Example 3-(1), 3.10 g of phthalimide, 0.21 ml of pyridine and 20 ml of butanol was heated under reflux for 16 hours, and then the solvent was evaporated under a reduced pressure. The resulting residue was applied to a silica gel column chromatography and developed with a methanol-chloroform (2:98) mixed solvent, and then the fractions containing the compound of interest were concentrated to obtain 3.90 g of the title compound.

$^1$H-NMR (CDCl$_3$) δ: 3.07 (d, 1H, J=6 Hz), 3.99 (dd, 1H, J=14 Hz, 5 Hz), 4.03 (dd, 1H, J=14 Hz, 6 Hz), 4.14 (dd, 1H, J=9 Hz, 5 Hz), 4.22 (dd, 1H, J=9 Hz, 4 Hz), 4.30–4.40 (m, 1H), 7.10 (dd, 1H, J=9 Hz, 4 Hz), 7.25–7.31 (m, 1H), 7.65 (dd, 1H, J=8 Hz, 3 Hz), 7.74 (2H, dd, J=5 Hz, 3 Hz), 7.87 (dd, 2H, J=5 Hz, 3 Hz).

(3) 6-Fluoro-3-phthalimidomethyl-1,4-benzoxazine

A 3.85 g portion of the compound obtained in Example 3-(2) was dissolved in 12 ml of acetone and, while keeping the liquid temperature at 15° C. to 20° C., 10 ml of John's reagent (prepared from 4 g of chromic acid, 2 ml of concentrated sulfuric acid and 8 ml of water) was added thereto, and then the mixture was stirred at room temperature for 3 hours. The reaction solution was diluted by adding water and then the insoluble matter was collected by filtration. The thus obtained compound was dissolved in 200 ml of ethanol and subjected to 24 hours of catalytic hydrogenation in the presence of Raney nickel. After removing the insoluble matter by filtration, the resulting filtrate was concentrated to dryness and the thus obtained crystalline residue was dissolved in 50 ml of ethanol with heating. After cooling to room temperature, this was mixed with 6.1 ml of acetic acid and 1.3 g of sodium cyanoborohydride and stirred for 1 hour. The reaction solution was mixed with water and saturated sodium bicarbonate aqueous solution and extracted with chloroform. The organic layer was washed with saturated brine and dried with anhydrous sodium sulfate, and then the solvent was evaporated under a reduced pressure. The thus obtained residue was applied to a silica gel column chromatography and developed with chloroform, and then the fractions containing the compound of interest were concentrated to obtain 1.79 g of the title compound.

$^1$H-NMR (CDCl$_3$) δ: 3.75–3.97 (m, 4H), 4.19–4.24 (m, 2H), 6.27–6.32 (m, 1H), 6.66–6.70 (m, 1H), 7.75 (dd, 2H, J=5 Hz, 3 Hz), 7.87 (dd, 2H, J=5 Hz, 3 Hz).

(4) 3-Aminomethyl-6-fluoro-1,4-benzoxazine

A 1.79 g portion of the compound obtained in Example 3-(3) was dissolved in 40 ml of ethanol, mixed with 0.9 ml of hydrazine monohydrate and then heated under reflux for 3 hours. The solvent was evaporated, and the thus obtained residue was dissolved in water, mixed with 6 ml of acetic acid and stirred at room temperature for 30 minutes and then at 0° C. for 30 minutes. The insoluble matter was removed by filtration, and the resulting filtrate was alkalified using 10% sodium hydroxide aqueous solution and then extracted with chloroform. The organic flyer was dried with anhydrous sodium sulfate and then the solvent was evaporated under a reduced pressure to obtain 972 mg of the title compound.

$^1$H-NMR (CDCl$_3$) δ: 2.70 (dd, 1H, J=12 Hz, 8 Hz), 2.92 (dd, 1H, J=12 Hz, 5 Hz), 3.30 (m, 1H), 3.93 (dd, 1H, J=11 Hz, 7 Hz), 4.17 (dd, 1H, J=11 Hz, 4 Hz), 4.35 (brs, 1H), 6.28–6.35 (m, 2H), 6.68 (dd, 1H, J=8 Hz, 5 Hz).

(5) 3-Benzylaminomethyl-6-fluoro-1,4-benzoxazine

A 972 mg portion of the compound obtained in Example 3-(4) and 553 mg of benzaldehyde were dissolved in 30 ml of ethanol and stirred at 50° C. for 1 hour, and then the reaction solution was concentrated to dryness. The residue was dissolved in 30 ml of freshly added ethanol and mixed with 1.53 ml of acetic acid, and then the mixture was mixed with 1.0 g of sodium cyanoborohydride and stirred at room temperature for 2 hours. After concentration of the reaction solution, the residue was mixed with 1 N sodium hydroxide aqueous solution and extracted with chloroform. The organic layer was dried with anhydrous sodium sulfate, the solvent was evaporated under a reduced pressure and then the thus obtained residue was applied to a silica gel column chromatography and developed with a methanol-chloroform mixed solvent (2:98), and then the fractions containing the compound of interest were concentrated to obtain 1.03 g of the title compound.

$^1$H-NMR (CDCl$_3$) δ: 2.61 (dd, 1H, J=12 Hz, 9 Hz), 2.80 (dd, 1H, J=12 Hz, 4 Hz), 3.40–3.48 (m, 1H), 3.80, 3.81 (ABq, 2H, J=13 Hz), 3.87 (dd, 1H, J=10 Hz, 7 Hz), 4.16 (ddd, J=10 Hz, 3 Hz, 1 Hz), 4.41 (brs, 1H), 6.25–6.32 (m, 2H), 6.64–6.70 (m, 1H), 6.64–6.70 (m, 1H), 7.20–7.36 (m, 5H).

(6) 3-Benzyl-1,2-dioxo-9-fluoro-2,3,4,4a,5,6-hexahydro-1H-pyrazino[2,1-c]-1,4-benzoxazine A 1.02 g portion of the compound obtained in Example 3-(5) was mixed with 2 ml of diethyl oxalate and heated at 110° C. for 11 hours and then at 150° C. for 3 hours. The reaction solution was concentrated under a reduced pressure, and the resulting residue was recrystallized from ether to obtain 777 mg of the title compound as a slightly pink powder.

(7) 3-Benzyl-9-fluoro-2,3,4,4a,5,6-hexahydro-1H-pyrazino[2,1-c]-1,4-benzoxazine

A 94.2 mg portion of sodium borohydride was suspended in 15 ml of tetrahydrofuran, boron trifluoride diethyl ether complex was added dropwise thereto at room temperature, and the mixture was stirred for 1 hour. Next, 677 mg of the compound obtained in Example 3-(6) was added in several portions to the reaction solution and heated under reflux for 2 hours. The reaction solution was poured in small portions into 60 ml of ice-cooled concentrated hydrochloric acid and stirred overnight. This was alkalified by adding saturated sodium bicarbonate aqueous solution and then extracted with chloroform, and the organic layer was washed with saturated brine. This was dried with anhydrous sodium sulfate, the solvent was evaporated, the resulting residue was applied to a silica gel column chromatography and eluted with an ethyl acetate-hexane (1:6–1:5) mixed solvent, and then the fractions containing the compound of interest were concentrated to obtain 575 mg of the title compound as a colorless oil.

$^1$H-NMR (CDCl$_3$) δ: 1.82 (t, 1H, J=11 Hz), 2.28 (dt, 1H, J=4 Hz, 12 Hz), 2.79–2.89 (m, 2H), 2.95–2.98 (m, 2H), 3.18–3.20 (m, 2H), 3.52–3.54 (m, 1H), 3.51, 3.59 (ABq, 2H, J=13 Hz), 3.92 (dd, 1H, J=9 Hz, 11 Hz), 4.10 (dd, 1H, J=3 Hz, 11 Hz), 6.36 (dt, 1H, J=3 Hz, 9 Hz), 6.47 (dd, 1H, J=3 Hz, 11 Hz), 6.66 (dd, 1H, J=5 Hz, 9 Hz), 7.33–7.34 (m, 5H).

(8) 9-Fluoro-2,3,4,4a,5,6-hexahydro-1H-pyrazino[2,1-c]-1,4-benzoxazine

A 575 mg portion of the compound obtained in Example 3-(7) was dissolved in 20 ml of methanol, mixed with 608 mg of ammonium formate and 580 mg of 10% palladium-carbon and then heated under reflux for 1 hour. The insoluble matter was removed by filtration, the solvent was evaporated, the thus obtained residue was mixed with saturated brine, extracted with chloroform and dried with anhydrous sodium sulfate, and then the solvent was evaporated to obtain 369 mg of the title compound as a colorless oil.

$^1$H-NMR (CDCl$_3$) δ: 2.48 (dd, 1H, J=11 Hz, 12 Hz), 2.70 (dd, 1H, J=3 Hz, 12 Hz), 2.88–3.00 (m, 2H), 3.05–3.15 (m, 2H), 3.51 (ddd, 1H, J=2 Hz, 3 Hz, 12 Hz), 3.92 (dd, 1H, J=9 Hz, 11 Hz), 4.13 (dd, 1H, J=3 Hz, 11 Hz), 6.37 (ddd, 1H, J=3 Hz, 8 Hz, 9 Hz), 6.47 (dd, 1H, J=3 Hz, 11 Hz), 6.66 (dd, 1H, J=5 Hz, 9 Hz).

(9) (+/−)-3-[3-[1-(4-Amino-2-pyrimidinyl)-5-methyl-4-pyrazolyl]-2-trans-propen-1-yl]-9-fluoro-2,3,4,4a,5,6-hexahydro-1H-pyrazino[2,1-c]-1,4-benzoxazine hydrochloride A 190 mg portion of the compound obtained in Example 3-(8) was allowed to react with 209 mg of the aldehyde obtained in Example 1-(6) in the same manner as described in Example 1-(13) and then subjected to the after-treatment, thereby obtaining 307 mg of the title compound as a while powder.

Melting point: 192–199° C.

$^1$H-NMR (DMSO-d$_6$) δ: 2.69 (s, 3H), 2.82–2.88 (m, 1H), 3.05–3.12 (M, 1H), 3.26 (t, 1H, J=12 Hz), 3.56 (d, 2H, J=18 Hz), 3.69–3.72 (m, 1H), 3.88–4.00 (m, 3H), 4.09 (d, 1H, J=13 Hz), 4.31 (dd, 1H, J=3 Hz, 12 Hz), 6.30 (dt, 1H, J=16

Hz, 7 Hz), 6.50 (dt, 1H, J=3 Hz, 8 Hz), 6.58 (d, 1H, J=7 Hz), 6.75 (dd, J=6 Hz, 8 Hz), 6.82 (d, 1H, J=16 Hz), 6.89 (dd, 1H, J=3 Hz, 12 Hz), 8.07 (d, 1H, J=7 Hz), 8.25 (s, 1H), 11.79 (br s, 1H).

EXAMPLE 4

(+/−)-2-[3-[1-(4-Amino-2-pyrimidinyl)-5-methyl-4-pyrazolyl]-2-trans-propen-1-yl]-1,2,3,4,10,10a-hexahydropyrazino[1,2-a]indole hydrochloride

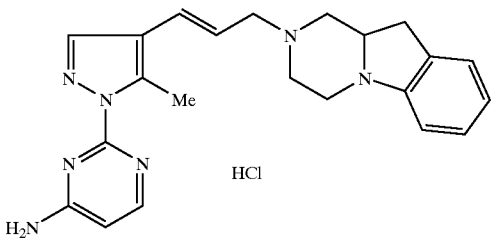

A 76 mg portion of (+/−)-1,2,3,4,10,10a-hexahydropyrazino[1,2-a]indole was allowed to react with 77 mg of the aldehyde obtained in Example 1-(6) in the same manner as described in Example 1-(13) and then subjected to the after-treatment, thereby obtaining 100 mg of the title compound as a while powder.

Melting point: 173–176° C. (decomposition)

$^1$H-NMR (DMSO-d$_6$) δ: 2.65 (s, 3H), 2.6–2.7 (m, 1H), 2.9–3.1 (m, 1H), 3.3–3.6 (m, 5H), 3.8–4.0 (m, 4H), 6.16 (dt, 1H, J=16, 7 Hz), 6.29 (s, 1H), 6.65 (d, 1H, J=7 Hz), 6.42 (d, 1H, J=5 Hz), 6.67 (t, 1H, J=7 Hz), 6.75 (d, 1H, J=16 Hz), 7.07 (t, 1H, J=7 Hz), 7.12 (d, 1H, J=7 Hz), 7.3–7.4 (bs, 2H), 7.94 (s, 1H), 8.11 (d, 1H, J=5 Hz), 11.0–10.9 (m, 1H).

EXAMPLE 5

2-[3-[1-(2-Amino-6-dimethylamino-4-pyrimidinyl)-5-methyl-4-pyrazolyl]-2-trans-propen-1-yl]-1,2,3,4-tetrahydropyrazino[1,2-a]indole

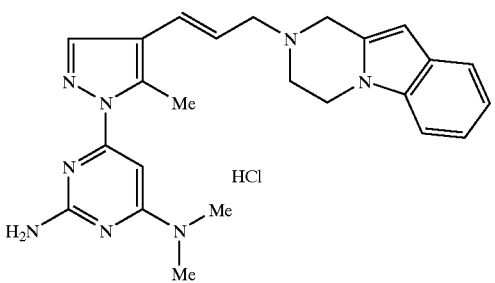

(1) 3-[1-(2-Amino-6-dimethylamino-4-pyrimidinyl)-5-methyl-4-pyrazolyl]-2-trans-propenol In an atmosphere of nitrogen, 30 ml of a dichloromethane solution containing 0.78 g of the ester obtained in Example 5-(5) was cooled to −78° C., 8.0 ml of diisobutylaluminum hydride (1 M hexane solution) was added thereto over 20 minutes and then the mixture was stirred at the same temperature for 1 hour. The react ion solution was mixed with saturated potassium tartarate aqueous solution and stirred at room temperature for 2 hours. The organic layer was separated, washed with saturated brine and dried with anhydrous sodium sulfate, and then the solvent was evaporated under a reduced pressure to obtain 0.44 g of the title compound.

$^1$H-NMR (DMSO-d$_6$) δ: 2.62 (s, 3H), 3.02 (s, 6H), 4.08 (bs, 2H), 6.13 (dt, 1H, J=16 Hz, 6 Hz), 6.22 (s, 1H), 6.40 (d, 1H, J=16 Hz), 7.86 (s, 1H).

(2) 2-Amino-4-dimethylamino-6-[4-(3-chloro-1-trans-propen-1-yl)-5-methyl-1-pyrazolyl]pyrimidine A 100 mg portion of the compound obtained in Example 5-(1) was suspended in 1 ml of dichloromethane which, under ice-cooling, was subsequently mixed with 1 ml of hexachloroacetone and 100 mg of triphenylphosphine and stirred for 2 hours. The thus obtained residue was purified by a silica gel column chromatography {developed with a methanol-chloroform (2:98) mixed solvent} to obtain 30 mg of the title compound.

$^1$H-NMR (CDCl$_3$) δ: 2.64 (s, 3H), 3.10 (s, 6H), 4.06 (d, 2H, J=6 Hz), 4.73 (bd, 2H), 6.06 (dt, 1H, J=16 Hz, 6 Hz), 6.37 (s, 1H), 6.45 (d, 1H, J=16 Hz), 7.74 (s, 1H).

(3) 2-[3-[1-(2-Amino-6-dimethylamino-4-pyrimidinyl)-5-methyl-4-pyrazolyl]-2-trans-propen-1-yl]-1,2,3,4-tetrahydropyrazino[1,2-a]indole A 30 mg portion of the compound obtained in Example 5-(2) was dissolved in 30 ml of tetrahydrofuran, mixed with 400 mg of 1,2,3,4-tetrahydropyrazino[1,2-a]indole and 10 ml of triethylamine and heated under reflux for 3 days. The reaction solution was diluted with chloroform, washed with saturated brine and dried with anhydrous sodium sulfate, and then the solvent was evaporated under a reduced pressure. The thus obtained residue was purified by a silica gel column chromatography {developed with a methanol-chloroform (2:98) mixed solvent} to obtain 7 mg of the title compound.

$^1$H-NMR (CDCl$_3$) δ: 2.64 (s, 3H), 3.01 (s, 6H), 3.36 (d, 2H, J=6 Hz), 3.59 (d, 2H, J=6 Hz), 3.69 (d, 2H, J=6 Hz), 4.09 (s, 2H), 4.71 (bs, 2H), 6.05 (dt, 1H, J=16, 6 Hz), 6.19 (s, 1H), 6.45 (d, 1H, J=16 Hz), 7.09 (t, 1H, J=7 Hz), 7.14 (t, 1H, J=7 Hz), 7.32 (d, 1H, J=7 Hz), 7.67 (d, 1H, J=7 Hz), 7.73 (s, 1H).

EXAMPLE 6

3-[3-[1-(4-Amino-2-pyrimidinyl)-5-methyl-4-pyrazolyl]-2-trans-propen-1-yl]-7,9-difluoro-2,3,4,4a,5,6-hexahydro-1H-pyrazino[1,2-a]quinoline hydrochloride (isomer A)

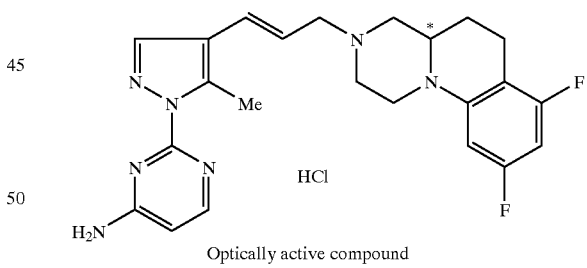

Optically active compound

A mixture consisting of 101 mg of 7,9-difluoro-2,3,4,4a,5,6-hexahydro-1H-pyrazino[1,2-a]quinoline (enantiomer A), 103 mg of 3-[1-(4-amino-2-pyrimidinyl)-5-methyl-4-pyrazolyl]-2-trans-propenal and 20 ml of ethanol was stirred at 80° C. for 1 hour, cooled to room temperature and mixed with 0.26 ml of acetic acid, and then 135 mg of sodium cyanoborohydride was added thereto in three portions at 1 hour intervals. After 16 hours of stirring at room temperature, the reaction solution was mixed with water and saturated sodium carbonate aqueous solution and extracted with chloroform. The organic layer was dried with anhydrous sodium sulfate, the solvent was evaporated under a reduced pressure, the thus obtained residue was applied to a silica gel column chromatography (270 to 400 mesh, 25 g) and developed with a methanol-chloroform (2.5:97.5) mixed solvent, and then the fractions containing the compound of interest were concentrated. A 212 mg portion of the thus obtained residue was dissolved in 5 ml of isopropyl alcohol with heating, 0.5 ml of 1 N hydrochloric acid-ethanol was added during the heating, and then this was allowed to stand at room temperature for 3 hours and the resulting precipitate was collected by filtration to obtain 157 mg of the title compound.

$^1$H-NMR (DMSO-d$_6$) δ: 1.55–1.75 (m, 1H) , 2.00–2.15 (m, 1H), 2.60 (s, 3H), 2.6–2.8 (m, 1H) , 2.8–3.0 (m, 1H) , 3.0–3.15 (m, 1H), 3.15–3.3 (m, 1H), 3.4–3.6 (m, 4H), 3.8–4.0 (m, 2H), 4.13 (d, 1H, J=13 Hz), 6.21 (dt, 1H, J=16 Hz, 7 Hz), 6.46 (d, 1H, J=6 Hz), 6.49 (dt, 1H, J=9 Hz, 2 Hz), 6.69 (d, 1H, J=12 Hz), 6.79 (d, 1H, J=16 Hz) 7.60 (brs, 2H), 7.99 (s, 1H), 8.10 (d, 1H, J=6 Hz), 11.42 (brs, 1H)

EXAMPLE 7

3-[3-[1-(4-Amino-2-pyrimidinyl)-5-methyl-4-pyrazolyl]-2-trans-propen-1-yl]-7,9-difluoro-2,3,4,4a,5,6-hexahydro-1H-pyrazino[1,2-a]quinoline hydrochloride (isomer B)

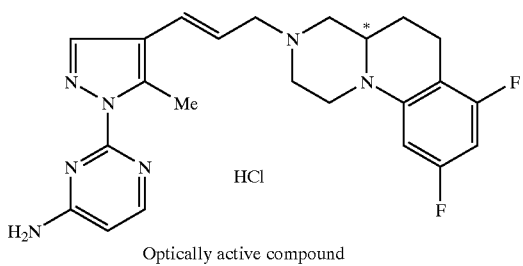

Optically active compound

Using 106 mg of 7,9-difluoro-2,3,4,4a,5,6-hexahydro-1H-pyrazino[1,2-a]quinoline (enantiomer B) and 108 mg of 3-[1-(4-amino-2-pyrimidinyl)-5-methyl-4-pyrazolyl]-2-trans-propenal, the reaction and after-treatment was carried out in the same manner as described in Example 6 to obtain 140 mg of the title compound.

$^1$H-NMR (DMSO-d$_6$) 67: Coincided with the data of Example 6.

EXAMPLE 8

(+/−)-2-[3-[1-(4-Amino-2-pyrimidinyl)-5-methyl-4-pyrazolyl]-2-trans-propen-1-yl]-7-fluoro-1,2,3,4,10,10a-hexahydropyrazino-[1,2-a]indole hydrochloride

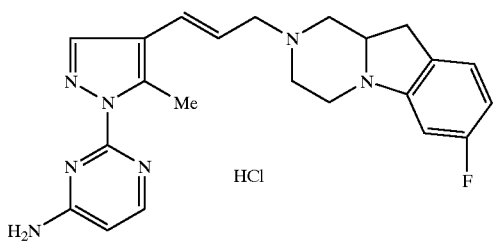

(1) (3-Fluorophenyl)hydrazine

A 10 g portion of 3-fluoroaniline was suspended in 100 ml of concentrated hydrochloric acid, 50 ml of 13% sodium nitrite aqueous solution was gradually added thereto under ice-cooling, and the mixture was stirred at the same temperature for 10 minutes. Next, a suspension consisting of 75 g of tin chloride dihydrate and 50 ml of concentrated hydrochloric acid was added thereto, and the mixture was stirred for 1 hour while gradually returning to room temperature. Under ice-cooling, the reaction solution was adjusted to a pH value of about 9 by adding sodium hydroxide and extracted with chloroform, and then the thus obtained organic layer was dried with anhydrous sodium sulfate and the solvent was evaporate d under a reduced pressure. The residue was made into hydrochloride with 1 N hydrochloric acid/ethanol and then recrystallized from an ether-ethanol mixed solvent to obtain 11 g of the title compound as a white powder.

$^1$H-NMR (DMSO-d$_6$) δ: 6.7–6.9 (m, 3H), 7.29 (q, 1H, J=8 Hz) 8.46 (brs, 1H), 10.11 (brs, 3H).

(2) Ethyl 3-(3-fluoro-1-hydrazinimine)propanoate

A mixture consisting of 10 g of the compound obtained in Example 8-(1) 7.2 g of ethyl pyruvate and 30 ml of pyridine was heated under reflux for 10 hours. The reaction solution was cooled to room temperature and diluted with water and then the resulting precipitate was collected by filtration to obtain 13 g of the title compound as a yellow solid.

$^1$H-NMR (CDCl$_3$) δ: 1.38 (t, 3H, J=7 Hz) , 2.11 (s, 3H) , 4.32 (q, 2H, J=7 Hz) , 6.65 (dt, 1H, J=8 Hz, 2 Hz) , 6.89 (dd, 1H, J=8 Hz, 2 Hz), 7.02 (dt, 1H, J=11 Hz, 2 Hz) , 7.22 (m, 1H) , 7.72 (s, 1H)

(3) Ethyl 4-fluoro-2-indolecarboxylate and ethyl 6-fluoro-2-indolecarboxylate

A 50 g portion of polyphosphoric acid was added to 14.2 g of the compound obtained in Example 8-(2) and stirred at 120° C. for 10 minutes. The reaction solution was cooled to room temperature, diluted with water and then extracted with ethyl acetate. The organic layer was washed with saturated brine and dried with anhydrous sodium sulfate, and then the solvent was evaporated. The thus obtained residue was applied to a silica gel column chromatography and developed with a hexane-ethyl acetate (20:1) mixed solvent, thereby obtaining 3.0 g of ethyl 4-fluoro-2-indolecarboxylate and 1.0 g of ethyl 6-fluoro-2-indolecarboxylate, respectively.

Ethyl 4-fluoro-2-indolecarboxylate: $^1$H-NMR (CDCl$_3$) 67: 1.43 (t, 3H, J=7 Hz), 4.43 (q, 2H, J=7 Hz), 6.91 (dd, 1H, J=10 Hz, 8 Hz), 7.22 (d, 1H, J=8 Hz), 7.38 (s, 1H), 7.39 (dt, 1H, J=8 Hz, 5 Hz).

Ethyl 6-fluoro-2-indolecarboxylate: $^1$H-NMR (CDCl$_3$) 67: 1.42 (t, 3H, J=7 Hz), 4.41 (q, 2H, J=7 Hz), 6.93 (dt, 1H, J=9 Hz, 2 Hz), 7.09 (dd, 1H, J=9 Hz, 2 Hz), 7.21 (s, 1H), 7.61 (dd, 1H, J=9 Hz, 5 Hz), 9.08 (brs, 1H).

(4) Ethyl 6-fluoro-1-(2-phthalimidoethyl)-2-indolecarboxylate

A 1.0 g portion of ethyl 6-fluoro-2-indolecarboxylate was dissolved in 50 ml of dimethylformamide, mixed under ice-cooling with a suspension consisting of 0.3 g of 60% sodium hydride and 10 ml of dimethylformamide, stirred at the same temperature for 30 minutes, further mixed with 5.0 g of N-(2-bromoethyl)phthalimide and then stirred for 24 hours while gradually returning to room temperature. After terminating the reaction by adding water, this was extracted with ethyl acetate. The organic layer was washed with saturated brine and dried with anhydrous sodium sulfate, and then the solvent was evaporated. The thus obtained residue was applied to a silica gel column chromatography and developed with a hexane-ethyl acetate (9:1) mixed solvent, thereby obtaining 0.74 g of the title compound.

$^1$H-NMR (CDCl$_3$) 67 : 1.35 (t, 3H, J=7 Hz), 4.12 (t, 2H, J=6 Hz), 4.31 (q, 2H, J=7 Hz), 4.79 (t, 2H, J=6 Hz), 6.76 (dt, 1H, J=9 Hz, 2 Hz) , 6.98 (dd, 1H, J=9 Hz, 2 Hz), 7.30 (s, 1H), 7.51 (dd, 1H, J=9 Hz, 5 Hz), 7.64 (dt, 2H, J=7 Hz, 2 Hz), 7.73 (dd, 2H, J=7 Hz, 2 Hz).

(5) 7-Fluoro-1,2,3,4-tetrahydropyrazino-[1,2-a]indol-1-one

A 1.0 g portion of the compound obtained in Example 8-(4) was dissolved in 50 ml of ethanol, mixed with 0.5 ml of hydrazine monohydrate and then stirred at 50°20 C. for 18 hours. The reaction solution was cooled to room temperature, diluted with chloroform and then washed with 1 N sodium hydroxide aqueous solution and saturated brine in that order. The organic layer was dried with anhydrous sodium sulfate and then the solvent was evaporated to obtain 0.48 g of the title compound.

$^1$H-NMR (DMSO-d$_6$) δ: 3.6–3.7 (m, 2H), 4.24 (t, 2H, J=6 Hz), 6.98 (dt, 1H, J=9 Hz, 2 Hz), 7.05 (s, 1H), 7.43 (dd, 1H, J=9 Hz, 2 Hz), 7.69 (dd, 1H, J=9 Hz, 5 Hz), 8.14 (brs, 1H).

(6) 7-Fluoro-1,2,3,4-tetrahydropyrazino-[1,2-a]indole

A 0.47 g portion of the compound obtained in Example 8-(5) was suspended in 50 ml of tetrahydrofuran, mixed with 0.2 g of lithium aluminum hydride and then stirred at 60° C. for 8 hours. The reaction solution was cooled to 0° C., mixed carefully with saturated potassium tartarate aqueous solution to terminate the reaction and then extracted with chloroform. The organic layer was washed with saturated brine and dried with anhydrous sodium sulfate, and then the solvent was evaporated to obtain 0.46 g of the title compound.

$^1$H-NMR (CDCl$_3$) δ: 3.36 (t, 2H, J=6 Hz), 3.95 (t, 2H, J=6 Hz), 4.19 (s, 2H), 6.16 (s, 1H), 6.86 (ddd, 1H, J=9 Hz, 8 Hz, 2 Hz), 6.94 (dd, 1H, J 9 Hz, 2 Hz), 7.43 (dd, 1H, J=8 Hz, 5 Hz).

(7) 2-tert-Butoxycarbonyl-7-fluoro-1,2,3,4-tetrahydropyrazino-[1,2-a]indole

A 0.46 g portion of the compound obtained in Example 8-(6) was dissolved in 50 ml of methylene chloride and mixed with 0.63 g of di-tert-butyl dicarbonate under ice-cooling, and then 0.4 ml of triethylamine was added dropwise thereto. The reaction solution was stirred for 8 hours while gradually returning to room temperature, and then the solvent was evaporated under a reduced pressure. The thus obtained residue was applied to a silica gel column chromatography and developed with an ethyl acetate-hexane (6:1) mixed solvent, and then the fractions containing the compound of interest were concentrated to obtain 0.62 g of the title compound as a yellow oily substance.

$^1$H-NMR (CDCl$_3$) δ: 1.50 (s, 9 H), 3.92 (t, 2H, J=6 Hz), 4.02 (t, 2H, J=6 Hz), 4.78 (s, 2H), 6.23 (s, 1H), 6.87 (ddd, 1H, J=9 Hz, 8 Hz, 2 Hz), 6.94 (dd, 1H, J=9 Hz, 2 Hz), 7.45 (dd, 1H, J=8 Hz, 5 Hz)

(8) (+/−)-2-tert-Butoxycarbonyl-7-fluoro-1,2,3,4,10,10a-hexahydropyrazino-[1,2-a]indole A 0.62 g portion of the compound obtained in Example 8-(7) was dissolved in 20 ml of methanol and mixed with 1.4 ml of acetic acid, and then this was mixed with 1.3 g of sodium cyanoborohydride and stirred at room temperature for 4 days. After adding saturated sodium bicarbonate aqueous solution to the reaction solution, ethanol was evaporated under a reduced pressure, and the residue was extracted with ethyl acetate. The organic layer was dried with anhydrous sodium sulfate and the solvent was evaporated to obtain 0.66 g of the title compound.

$^1$H-NMR (CDCl$_3$) δ: 1.48 (s, 9 H), 2.54 (dd, 1H, J=15 Hz, 8 Hz), 2.9–3.0 (m, 4H), 3.4–3.5 (m, 2H), 4.0–4.2 (m, 2H), 6.14 (dd, 1H, J=10 Hz, 2 Hz), 6.32 (ddd, 1H, J=10 Hz, 8 Hz, 2 Hz), 6.96 (dd, 1H, J=8 Hz, 6 Hz).

(9) (+/−)12-[3-[1-(4-Amino-2-pyrimidinyl)-5-methyl-4-pyrazolyl]-2-trans-propen-1-yl]-7-fluoro-1,2,3,4,10,10a-hexahydropyrazino-[1,2-a]indole hydrochloride A 200 mg portion of the compound obtained in Example 8-(8) was mixed with 10 ml of concentrated hydrochloric acid and stirred for 10 minutes. The reaction solution was diluted with water, adjusted to a pH value of about 9 by adding sodium bicarbonate and extracted with chloroform. The organic layer was dried with anhydrous sodium sulfate and then the solvent was evaporated under a reduced pressure. A 115 mg portion of the thus obtained residue was dissolved in 20 ml of ethanol, mixed with 80 mg of 3-[1-(4-amino-2-pyrimidinyl)-5-methyl-4-pyrazolyl]-2-trans-propenal and stirred at room temperature for 2 hours. Next, this was mixed with 100 μl of acetic acid and then with 50 mg of sodium cyanoborohydride and stirred at room temperature for 3 days. The reaction solution was mixed with saturated sodium bicarbonate aqueous solution, ethanol was evaporated under a reduced pressure, and then the residue was extracted with chloroform. The organic layer was dried with anhydrous sodium sulfate, the solvent was evaporated, the thus obtained residue was applied to a silica gel column chromatography and developed with a chloroform-methanol (49:1) mixed solvent, and then the fractions containing the compound of interest were concentrated. The residue was made into hydrochloride with 1 N hydrochloric acid/ethanol and then recrystallized from ethanol to obtain 50 mg of the title compound as a white powder.

$^1$H-NMR (DMSO-d$_6$) δ: 2.53 (S, 3H), 2.57 (dd, 1H, J=15 Hz, 8 Hz), 2.9–3.0 (m, 4H), 3.4–3.5 (m, 2H), 4.0–4.2 (m, 4H), 6.11 (dt, 1H, J=16 Hz, 7 Hz), 6.39 (ddd, 1H, J=10 Hz, 8 Hz, 2 Hz), 6.40 (d, 1H, J=6 Hz), 6.51 (dd, 1H, J=10 Hz, 2 Hz , 6.71 (d, 1H, J=16 Hz), 6.07 (dd, 1H, J=8 Hz, 6 Hz), 7.29 (brs, 2H), 7.90 (s, 1H), 8.10 (d, 1H, J=6 Hz), 10.93 (brs, 1H)

EXAMPLE 9

(+/−)-2-[3- [1-(4-Amino-2-pyrimidinyl)-5-methyl-4-pyrazolyl]-2-trans-propen-1-yl]-9-fluoro-1,2,3,4,10,10a -hexahydropyrazino-[1,2-a]indole hydrochloride

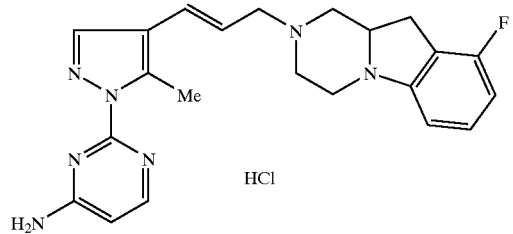

(1) 9-Fluoro-1,2,3,4-tetrahydropyrazino-[1,2-a]indol-1-one

A 1.0 g portion of ethyl 4-fluoro-2-indolecarboxylate was subjected to the same reactions and after-treatments of Example 8-(4) and (5) to obtain 0.3 g of the title compound.

$^1$H-NMR (CDCl$_3$) δ: 3.79 (t, 2H, J=6 Hz), 4.31 (t, 2H, J=6 Hz), 6.81 (dd, 1H, J=10 Hz, 7 Hz), 7.2–7.3 (m, 3H).

(2) 9-Fluoro-1,2,3,4-tetrahydropyrazino-[1,2-a]indole

A 0.3 g portion of the compound obtained in Example 9-(1) was subjected to the same reaction and after-treatment of Example 8-(6) to obtain 0.3 g of the title compound.

$^1$H-NMR (CDCl$_3$) 67 : 3.37 (t, 2H, J=6 Hz), 4.02 (t, 2H, J=6 Hz), 4.22 (s, 2H), 6.27 (s, 1H), 6.77 (ddd, 1H, J=10 Hz, 7 Hz, 2 Hz), 7.0–7.1 (m, 2H).

(3) 2-tert-Butoxycarbonyl-9-fluoro-1,2,3,4-tetrahydropyrazino-[1,2-a]indole

A 0.3 g portion of the compound obtained in Example 9-(2) was subjected to the same reaction and after-treatment of Example 8-(7) to obtain 0.5 g of the title compound as a yellow oily substance.

¹H-NMR (CDCl₃) δ: 1.53 (s, 9 H), 3.93 (t, 2H, J=6 Hz), 4.09 (t, 2H, J=6 Hz), 4.81 (s, 2H), 6.36 (s, 1H), 6.78 (ddd, 1H, J=11 Hz, 7 Hz, 2 Hz), 7.0–7.1 (m, 2H). (4) (+/−)-2-tert-Butoxycarbonyl-9-fluoro-1,2,3,4,10,10a-hexahydropyrazino-[1,2-a]indole A 0.5 g portion of the compound obtained in Example 9-(3) was subjected to the same reaction and after-treatment of Example 8-(8) to obtain 0.35 g of the title compound.

¹H-NMR (CDCl₃) δ: 1.63 (s, 9H), 2.54 (dd, 1H, J=15 Hz, 9 Hz), 2.7–3.1 (m, 6H), 3.4–3.6 (m, 2H), 6.19 (d, 1H, J=8 Hz), 6.35 (t, 1H, J=8 Hz), 6.9–7.0 (m, 1H). (5) (+/−)-2-[3-[1-(4-Amino-2-pyrimidinyl)-5-methyl-4-pyrazolyl]-2-trans-propen-1-yl]-9-fluoro-1,2,3,4,10, 10a-hexahydropyrazino-[1,2-a]indole hydrochloride Using 350 mg of the compound obtained in Example 9-(4) and 160 mg of 3-[1-(4-amino-2-pyrimidinyl)-5-methyl-4-pyrazolyl]-2-trans-propenal, the same reaction and after-treatment of Example 8-(9) were carried out to obtain 50 mg of the title compound as a white powder.

¹H-NMR (DMSO-d₆) δ: 2.57 (s, 3H), 2.7–4.2 (m, 10H), 4.35–4.45 (m, 1H), 6.15 (dt, 1H, J=16 Hz, 7 Hz), 6.42 (d, 1H, J=6 Hz), 6.64 (t, 1H, J=9 Hz), 6.7–6.8 (m, 2H), 7.39 (brs, 2H), 7.94 (s, 1H), 8.11 (d, 1H, J=6 Hz)

EXAMPLE 10

(+/−)-3-[3-[1-(4-Amino-2-pyrimidinyl)-5-methyl-4-pyrazolyl]-2-trans-propen-1-yl]-7,9-difluoro-2,3,4,4a,5,6-hexahydro-1H-pyrazino[2,1-c]-1,4-benzoxazine hydrochloride

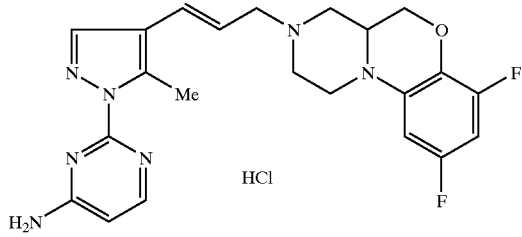

(1) 1-(2,4-Difluoro-6-nitrophenoxy)-2,3-epoxypropane

A mixture consisting of 12.62 g of 2,4-difluoro-6-nitrophenol, 36 ml of epichlorohydrin, 3.3 g of sodium hydroxide, 15 ml of water and 320 ml of ethanol was stirred at 80° C. for 24 hours. After cooling the reaction solution to room temperature, the insoluble matter was removed by filtration and the filtrate was concentrated to dryness under a reduced pressure. The resulting residue was dissolved in an ether-hexane (1:2) mixed solvent, washed with water and saturated brine and dried with anhydrous sodium sulfate, and then the solvent was evaporated under a reduced pressure. The residue was applied to a silica gel column chromatography and developed with an ethyl acetate-hexane (1:9) mixed solvent, and then the fractions containing the compound of interest were concentrated to obtain 11.28 g of the title compound.

¹H-NMR (CDCl₃) δ: 2.69 (dd, 1H, J=5 Hz, 3 Hz), 2.88 (t, 1H, J=5 Hz), 3.3–3.45 (m, 1H), 4.15 (ddd, 1H, J=12 Hz, 6 Hz, 1 Hz), 4.40 (dd, 1H, J=12 Hz, 3 Hz), 7.15 (ddd, 1H, J=11 Hz, 7 Hz, 3 Hz), 7.40 (ddd, 1H, J=7 Hz, 3 Hz, 2 Hz)

(2) 1-(2,4-Difluoro-6-nitrophenoxy)-2-hydroxy-3-phthalimidopropane

A mixture consisting of 11.28 g of the compound obtained in Example 10-(1), 14.4 g of phthalimide, 0.5 ml of pyridine and 50 ml of butanol was heated under reflux for 20 hours, and then the solvent was evaporated under a reduced pressure. The resulting residue was applied to a silica gel column chromatography (270 to 400 mesh, 300 g) and developed with an ethyl acetate-hexane (1:4) mixed solvent, and then the fractions containing the compound of interest were concentrated to obtain 6.2 g of the title compound.

¹H-NMR (CDCl₃) δ: 3.05 (d, 1H, J=6 Hz), 3.96 (dd, 1H, J=14 Hz, 4 Hz), 4.00 (dd, 1H, J=14 Hz, 7 Hz), 4.2–4.4 (m, 3H), 7.16 (ddd, 1H, J=10 Hz, 7 Hz, 3 Hz), 7.43 (dt, 1H, J=8 Hz, 3 Hz), 7.74 (dd, 2H, J=5 Hz, 3 Hz), 7.88 (dd, 2H, J=5 Hz, 3 Hz).

(3) 6,8-Difluoro-3-phthalimidomethyl-3,4-dihydro-2H-1,4-benzoxazine

A 16.2 g portion of the compound obtained in Example 10-(2) was dissolved in 30 ml of acetone and, while keeping the liquid temperature at 15° C. to 20° C., 20 ml of John's reagent (prepared from 8.2 g of chromic acid, 4 ml of concentrated sulfuric acid and 16 ml of water) was added thereto, and then the mixture was stirred at room temperature for 2 hours. The reaction solution was diluted by adding water and then the insoluble matter was collected by filtration. The thus obtained compound was dissolved in 200 ml of ethanol and subjected to 8 hours of catalytic hydrogenation in the presence of Raney nickel. After removing the insoluble matter by filtration, the resulting filtrate was concentrated to dryness and the thus obtained crystalline residue was dissolved in 70 ml of ethanol with heating. After cooling to room temperature, this was mixed with 10 ml of acetic acid and 3.0 g of sodium cyanoborohydride and stirred for 4 hours. The reaction solution was mixed with water and saturated sodium bicarbonate aqueous solution, and extracted with chloroform. The organic layer was washed with saturated brine and dried with anhydrous sodium sulfate, and then the solvent was evaporated under a reduced pressure. The thus obtained residue was applied to a silica gel column chromatography (200 g) and developed with chloroform, and then the fractions containing the compound of interest were concentrated to obtain 2.79 g of the title compound.

¹H-NMR (CDCl₃) δ: 3.75–4.00 (m, 4H), 4.29 (dd, 1H, J=11 Hz, 3 Hz), 4.43 (brs, 1H), 6.12 (dt, 1H, J=10 Hz, 2 Hz) 6.20 (ddd, 1H, J=11 Hz, 9 Hz, 2 Hz), 7.76 (dd, 2H, J=5 Hz, 3 Hz), 7.88 (dd, 2H, J=5 Hz, 3 Hz).

(4) 3-Aminomethyl-6,8-difluoro-3,4-dihydro-2H-1,4-benzoxazine

A 12.78 g portion of the compound obtained in Example 10-(3) was dissolved in 60 ml of ethanol, mixed with 1.32 ml of hydrazine monohydrate and then heated under reflux for 5 hours. The solvent was evaporated, and the thus obtained residue was dissolved in water, mixed with 10 ml of acetic acid, and stirred at room temperature for 3 hours and then at 0° C. for 2 hours. The insoluble matter was removed by filtration, and the resulting filtrate was alkalified using 5% sodium hydroxide aqueous solution and then extracted with a methanol-chloroform (1:99) mixed solvent. The organic layer was dried with anhydrous sodium sulfate and then the solvent was evaporated under a reduced pressure to obtain 1.61 g of the title compound.

¹H-NMR (CDCl₃) δ: 2.71 (dd, 1H, J=13 Hz, 8 Hz), 2.95 (dd, 1H, J=13 Hz, 5 Hz), 3.37–3.44 (m, 1H), 3.97 (dd, 1H, J=11 Hz, 6 Hz), 4.23 (dd, 1H, J=11 Hz, 3 Hz), 4.45–4.70 (m, 1H), 6.14 (dt, 1H, J=10 Hz, 3 Hz), 6.21 (ddd, 1H, J=11 Hz, 8 Hz, 3 Hz).

(5) 3-Benzylaminomethyl-6,8-difluoro-3,4-dihydro-2H-1,4-benzoxazine

A 11.61 g portion of the compound obtained in Example 10-(4) and 833 mg of benzaldehyde were dissolved in 50 ml of ethanol and stirred at 50° C. for 0.5 hour, and then the reaction solution was concentrated to dryness. The residue was dissolved in 50 ml of freshly added ethanol and mixed with 2.3 ml of acetic acid, and then the mixture was mixed with 1.7 g of sodium cyanoborohydride and stirred at room temperature for 2 hours. After concentration of the reaction solution, the residue was mixed with 1 N sodium hydroxide aqueous solution and extracted with chloroform. The organic layer was dried with anhydrous sodium sulfate, the solvent was evaporated under a reduced pressure, the thus obtained residue was applied to a silica gel column chromatography and developed with a methanol-chloroform mixed solvent (2:98), and then the fractions containing the compound of interest were concentrated to obtain 1.85 g of the title compound.

$^1$H-NMR (CDCl$_3$) δ: 2.61 (dd, 1H, J=12 Hz, 10 Hz), 2.83 (dd, 1H, J=12 Hz, 4 Hz), 3.45–3.50 (m, 1H), 3.81 and 3.82 (ABq, 2H, J=14 Hz) 3.90 (dd, 1H, J=11 Hz, 7 Hz), 4.23 (dd, J=11 Hz, 3 Hz), 4.60 (brs, 1H), 6.11 (dt, 2H, J=10 Hz, 2 Hz), 6.20 (ddd, 1H, J=11 Hz, 9 Hz, 2 Hz) , 7.25–7.40 (m, 5H).

(6) 3-Benzyl-1,2-dioxo-7,9-difluoro-2,3,4,4a,5,6-hexahydro-1H-pyrazino[2,1-c]-1,4-benzoxazine A 11.85 g portion of the compound obtained in Example 10-(5) was mixed with 3.5 ml of diethyl oxalate and heated at 110° C. for 22 hours and then at 150° C. for 5 hours. The reaction solution was concentrated under a reduced pressure, and the resulting residue was recrystallized from ether to obtain 1.49 g of the title compound as a white powder.

$^1$H-NMR (CDCl$_3$) 67 : 3.31 (dd, 1H, J=12 Hz, 4 Hz), 3.45 (t, 1H, J=12 Hz), 3.85 (dd, 1H, J=12 Hz, 10 Hz), 4.32–4.45 (m, 3 H), 4.67 and 4.71 (ABq, 2H, J=15 Hz), 6.71 (m, 1H), 7.25–7.45 (m, 5H), 8.470 (m, 1H)

(7) 3-Benzyl-7,9-difluoro-2,3,4,4a,5,6-hexahydro-1H-pyrazino [2,1-c]-1,4-benzoxazine A 1.97 g portion of sodium borohydride was suspended in 30 ml of tetrahydrofuran, 8.3 ml of boron trifluoride diethyl ether complex was added dropwise thereto at room temperature, and the mixture was stirred for 1 hour. Next, 11.45 g of the compound obtained in Example 10-(6) was added in several portions to the reaction solution and heated under reflux for 4 hours. The reaction solution was poured in small portions into 30 ml of ice-cooled concentrated hydrochloric acid and stirred overnight. This was alkalified by adding saturated sodium bicarbonate aqueous solution and then extracted with chloroform, and the organic layer was washed with saturated brine. This was dried with anhydrous sodium sulfate, the solvent was evaporated, the resulting residue was applied to a silica gel column chromatography (100 g) and eluted with an ethyl acetate-hexane (1:4) mixed solvent, and then the fractions containing the compound of interest were concentrated to obtain 1.54 g of the title compound as a light yellow solid.

$^1$H-NMR (CDCl$_3$) δ: 1.84 (t, 1H, J=11 Hz), 2.26 (dt, 1H, J=12 Hz, 3 Hz), 2.80–2.84 (m, 1H), 2.89 (dt, 1H, J=12 Hz, 3 Hz), 2.94–3.00 (m, 1H), 3.23–3.30 (m, 1H), 3.51, 3.58 (ABq, 2H, J=13 Hz), 3.65–3.72 (m, 1H), 3.92 (dd, 1H, J=10 Hz, 9 Hz), 4.20 (dd, 1H, J=10 Hz, 3 Hz), 6.25–6.32 (m, 2H), 7.25–7.36 (m, 5H).

(8) 7,9-Difluoro-2,3,4,4a,5,6-hexahydro-1H-pyrazino[2,1-c]-1,4-benzoxazine

A 11.54 g portion of the compound obtained in Example 10-(7) was dissolved in 50 ml of methanol, mixed with 1.53 g of ammonium formate and 1.5 g of 10% palladium-carbon (containing 50% water) and then heated under reflux for 3 hours. The insoluble matter was removed by filtration, the solvent was evaporated, and the thus obtained residue was mixed with saturated brine and extracted with chloroform. After drying with anhydrous sodium sulfate, the solvent was evaporated, the thus obtained residue was applied to a silica gel column chromatography (270 to 400 mesh, 70 g) and eluted with a methanol-chloroform (7:93) mixed solvent, and then the fractions containing the compound of interest were concentrated to obtain 607 mg of the title compound as a white solid.

$^1$H-NMR (CDCl$_3$) δ: 2.51 (t, 1H, J=11 Hz), 2.75 (dt, 1H, J=12 Hz, 3 Hz), 2.93 (dt, 1H, J=12 Hz, 3 Hz), 3.02 (dt, 1H, J=11 Hz, 2 Hz), 3.10–3.25 (m, 2H), 3.51 (dt, 1H, J=11 Hz, 2 Hz), 3.96 (dd, 1H, J=11 Hz, 9 Hz), 4.24 (dd, 1H, J=11 Hz, 3 Hz), 6.26–6.35(m, 2H)

(9) (+/−)-3-[3-[1-(4-Amino-2-pyrimidinyl)-5-methyl-4-pyrazolyl]-2-trans-propen-1-yl]-7,9-difluoro-2,3,4,4a,5,6-hexahydro-1H -pyrazino[2,1-c]-1,4-benzoxazine hydrochloride Using 118 mg of the compound obtained in Example 10-(8) and 119 mg of 3-[1-(4-amino-2-pyrimidinyl)-5-methyl-4-pyrazolyl]-2-trans-propenal, the same reaction and after-treatment of Example 6 were carried out to obtain 176 mg of the title compound.

$^1$H-NMR (DMSO -d$_6$) 67 : 2.57 (s, 3H), 2.7–4.2 (m, 10 H), 4.35–4.45 (m, 1H), 6.15 (dt, 1H, J=16 Hz, 7 Hz), 6.42 (d, 1H, J=6 Hz), 6.64 (t, 1H, J=9 Hz) , 6.7–6.8 (m, 2H) , 7.39 (brs, 2H), 7.94 (s, 1H), 8.11 (d, 1H, J=6 Hz).

EXAMPLE 11

1-[1-[2-Amino-6-(2-hydroxyethyl)amino-4-pyrimidinyl]-5-methyl-4-pyrazolyl]-3-[4-(3,5-difluorophenyl)-1-piperazinyl]-1-trans-propene

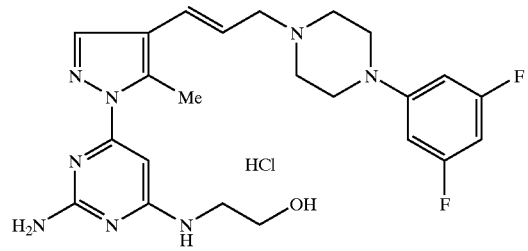

(1) 1-[1-(2-Amino-6-chloro-4-pyrimidinyl)-5-methyl-4-pyrazolyl]-3-[4-(3,5-difluorophenyl)-1-piperazinyl]-1-trans-propene A 2.2 g portion of 1-[1-(2-amino-6-benzyloxy-4-pyrimidinyl)-5-methyl-4-pyrazolyl]-3-[4-(3,5-difluorophenyl)-1-piperazinyl]-1-trans-propene was mixed with 12 ml of trifluoroacetic acid and 0.6 ml of thioanisole, and then stirred at room temperature for 1 hour. The reaction solution was concentrated, the residue was mixed with diethyl ether and stirred at room temperature, and then the precipitate was collected by filtration. The thus obtained compound was mixed with 12 ml of phosphorus oxychloride and stirred at 60 to 80° C. for 3 hours. After concentration of the reaction solution, ice pieces were gradually added to the residue under ice-cooling, and then the reaction solution was neutralized using sodium bicarbonate to which chloroform had been added. After five times of extraction with chloroform-methanol (9:1) from the water layer, the organic layers were combined, washed with saturated brine and dried with anhydrous sodium sulfate, and then the solvent was evaporated. The resulting residue was applied to a silica gel column chromatography and developed with a chloroform-methanol (49:1) mixed solvent, and then the fractions containing the compound of interest were concentrated The residue was mixed with an ether-hexane mixed solvent and the resulting precipitate was collected by filtration to obtain 970 mg of the title compound as a white powder.

¹H-NMR (CDCl₃) δ: 2.60–2.65 (m, 4H), 2.70 (s, 3H), 3.15–3.25 (m, 6H), 5.15 (brs, 2H), 6.09 (dt, 1H, J=16 Hz, 7 Hz) , 6.26 (tt, 1H, J=9 Hz, 2 Hz) , 6.37 (dd, 2H, J=11 Hz, 2 Hz) , 6.39 (d 1H, J=16 Hz), 7.32 (s, 1H), 7.81 (s, 1H).

(2) 1-[1-[2-Amino-6-(2-hydroxyethyl)amino-4-pyrimidinyl]-5-methyl-4-pyrazolyl]-3-[4-(3,5-difluorophenyl)-1-piperazinyl]-1-trans-propene A 455 mg portion of the compound obtained in Example 11-(1) was suspended in 30 ml of ethanol, mixed with 5 ml of ethanolamine and then heated under reflux for 30 hours. The reaction solution was cooled to room temperature and concentrated under a reduced pressure, and then the residue was mixed with water and saturated sodium bicarbonate aqueous solution and extracted 10 times with a chloroform-methanol (9:1) mixed solvent. The organic layers were dried with anhydrous sodium sulfate, the solvent was evaporated, and then the thus obtained solid was washed with a chloroform-ether mixed solvent to obtain 458 mg of the title compound as a white powder.

Melting point: 176–181° C.

¹H-NMR (DMSO-d₆) δ: 2.62 (s, 3H), 3.12 (d, 2H, J=6 Hz), 3.15–3.25 (m, 4H), 3.25–3.40 (m, 6H), 3.45–3.55 (m, 2H), 4.70 (t, 1H, J=5 Hz), 6.06 (dt, 1H, J=16 Hz, 7 Hz), 6.14 (s, 2H), 6.15 (s, 1H), 6.41 (d, 1H, J=16 Hz), 6.44 (tt, 1H, J=9 Hz, 2 Hz), 6.59 (dd, 2H, J=11 Hz, 2 Hz), 7.04 (brs, 1H) , 7.88 (s, 1H).

EXAMPLE 12

1-[1-[2-Amino-6-di(2-hydroxyethyl)amino-4-pyrimidinyl]-5-methyl-4-pyrazolyl]-3-(4-(3,5-difluorophenyl)-1-piperazinyl]-1-trans-propene hydrochloride

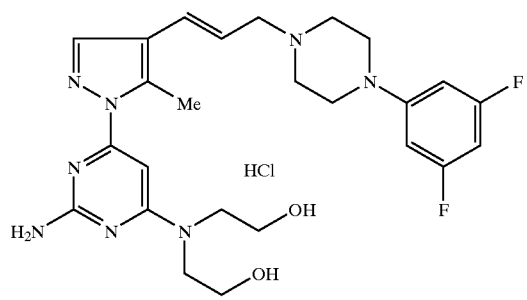

A 446 mg portion of the compound obtained in Example 11-(1) was suspended in 20 ml of ethanol, mixed with 265 mg of 2,2'-iminodiethanol and heated under reflux for 16 hours. This was further mixed with 265 mg of 2,2'-iminodiethanol and heated under reflux for 6 hours and then mixed with 140 mg of potassium carbonate and heated under reflux for 17 hours. The reaction solution was cooled to room temperature and concentrated under a reduced pressure, and then the residue was mixed with saturated brine and extracted with chloroform. The organic layer was dried with anhydrous sodium sulfate, the solvent was evaporated, the thus obtained residue was applied to a silica gel column chromatography and developed with a chloroform-methanol (19:1–9:1) mixed solvent, and then the fractions containing the compound of interest were concentrated. The residue was made into hydrochloride with 1 N hydrochloric acid/ethanol and then recrystallized from ethanol to obtain 218 mg of the title compound as a white powder.

Melting point: 184–187° C.

¹H-NMR (DMSO-d₆) δ: 2.64 (s, 3H), 3.09–3.18 (m, 4H), 3.44–3.98 (m, 14H), 6.21 (dt, 1H, J=16 Hz, 8 Hz), 6.43 (s, 1H), 6.58 (t, 1H, J=9 Hz) , 6.73 (d, 2H, J=9 Hz) , 6.80 (d, 2H, J=16 Hz), 8.11 (s, 1H), 10.70 (brs, 1H).

EXAMPLE 13

1-[1-[2-Amino-6-(3-hydroxy-1-azetidinyl)-4-pyrimidinyl]-5-methyl-4-pyrazolyl]-3-[4-(3,5-difluorophenyl)-1-piperazinyl]-1-trans-propene hydrochloride

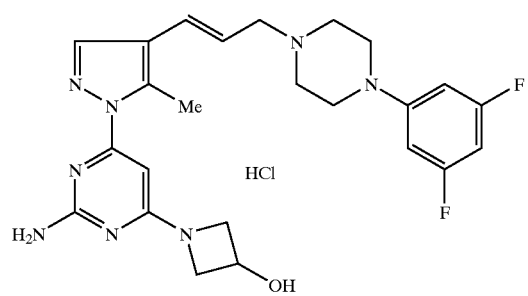

A 552 mg portion of N-benzhydryl-3-hydroxyazetidine hydrochloride was dissolved in ethanol containing 80% water, mixed with 500 mg of 10% palladium-carbon (water content 50.1%) and then subjected to 6 hours of catalytic hydrogenation under 5 atmospheres. The catalyst was removed by filtration, and the filtrate was concentrated under a reduced pressure. The residue was dissolved in 20 ml of ethanol, mixed with 446 mg of the compound obtained in Example 11-(1) and then heated under reflux for 2 days. The reaction solution was concentrated under a reduced pressure, the thus obtained residue was applied to a silica gel chromatography and developed with a chloroform-methanol (19:1) mixed solvent, and then the fractions containing the compound of interest were concentrated. The residue was made into hydrochloride with 1 N hydrochloric acid/ethanol and then recrystallized from ethanol to obtain 367 mg of the title compound as a white powder.

Melting point: 195–199° C.

¹H-NMR (DMSO-d₆) δ: 2.67 (s , 3H), 3.05–3.13 (m, 2H), 3.22–3.25 (m, 2H), 3.49 (d, 2H, J=10 Hz), 3.92–3.97 (m, 6H), 4.35–4.45 (m, 2H), 4.60–4.66 (m, 1H), 6.15 (s, 1H), 6.25 (dt, 1H, J=16 Hz, 8 Hz), 6.57 (t, 1H, J=9 Hz) , 6.73 (d, 2H, J=9 Hz), 6.80 (d, 2H, J=16 Hz), 7.73 (brs, 2H), 8.14 (s, 1H), 11.34 (brs, 2H).

EXAMPLE 14

1-[1-[2-Amino-6-(2-tert-butoxycarbonylaminoethyl)
amino-4-pyrimidinyl]]5-methyl-pyrazolyl]-3-[4-(3,5-
difluorophenyl)-1-piperazinyl]-1-trans-propene

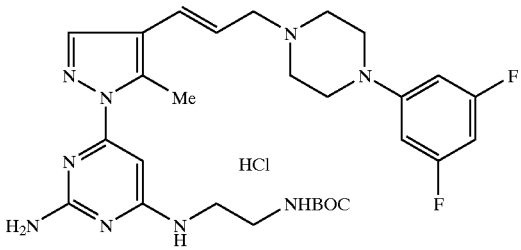

(1) Ethyl 1-(2-amino-6-chloro-4-pyrimidinyl)-5-methyl-4-pyrazolecarboxylate

A 16.4 g portion of 2-amino-4,6-dichloropyrimidine was mixed 300 ml of ethanol and then with 25 ml of hydrazine monohydrate and 13.8 g of potassium carbonate, and the mixture was heated under reflux for 2 hours. The reaction solution was concentrated under a reduced pressure, water was added to the thus obtained residue and then the resulting precipitate was collected by filtration. A 300 ml portion of ethanol and 16.3 g of ethoxymethyleneacetoacetic acid ethyl ester were added to 14.0 g of white powder of the thus obtained 2-amino-6-chloro-4-hydrazinopyrimidine, and the mixture was stirred at room temperature for 40 minutes and then heated under reflux for 2 hours. After cooling the reaction solution to room temperature, the resulting precipitate was collected by filtration to obtain 21.9 g of the title compound as a white powder.

$^1$H-NMR (CDCl$_3$) δ: 1.38 (t, 3H, J=7 Hz), 3.00 (s, 3H), 4.33 (q, 2H, J=7 Hz), 5.26 (brs, 2H), 7.33 (s, 1H), 8.02 (s, 1H).

(2) 1-(2-Amino-6-chloro-4-pyrimidinyl)-5-methyl-4-pyrazolecarbaldehyde

A 14.1 g portion of the compound obtained in Example 14-(1) was dissolved in 600 ml of methylene chloride and, in an atmosphere of nitrogen, the solution was cooled to −78°C., mixed with 200 ml of diisobutylaluminum hydride (1 M hexane solution) and then stirred at the same temperature for 5 hours. The reaction solution was mixed with 1 liter of 10% potassium tartarate aqueous solution, stirred at room temperature for 4 hours and then mixed with 500 ml of methanol and further stirred for 1 hour. After separation of the organic layer, the water layer was extracted three times with chloroform and then ten times with a chloroform-methanol (9:1) mixed solvent. The organic layers were combined and dried with anhydrous sodium sulfate, and then the solvent was evaporated under a reduced pressure. The thus obtained residue was dissolved in 600 ml of 1,4-dioxane, mixed with 42 g of activated manganese dioxide and then stirred at room temperature for 12 hours. The insoluble matter was removed by filtration and then the filtrate was concentrated to obtain 9.8 g of the title compound as a white solid.

$^1$H-NMR (CDCl$_3$) δ: 3.01 (s, 3H), 5.61 (brs, 1H), 7.32 (s, 1H), 8.08 (s, 1H), 10.00 (s, 1H).

(3) Ethyl 3-[1-(2-amino-6-chloro-4-pyrimidinyl)-5-methyl-4-pyrazolyl]-2-trans-propenoate A mixture consisting of 3.90 g of the compound obtained in Example 14-(2), 6.86 g of (carboethoxymethylene) triphenylphosphorane and 150 ml of toluene was stirred at 80° C. for 19 hours. The reaction solution was allowed to stand at room temperature for 8 hours and then the thus formed precipitate was collected by filtration to obtain 4.11 g of the title compound as a white solid.

$^1$H-NMR (CDCl$_3$) δ: 1.34 (t, 3H, J=7 Hz), 2.79 (s, 3H), 4.26 (q, 2H, J=7 Hz), 5.58 (brs, 1H), 5.38 (s, 2H), 6.27 (d, 1H, J=16 Hz), 7.31 (s, 1H), 7.59 (d, 1H, J=16 Hz), 7.91 (s, 1H).

(4) Ethyl 3-[1-[2-amino-6-(2-tert-butoxycarbonylaminoethyl)amino-4-pyrimidinyl]-5-methyl-4-pyrazolyl]-2-trans-propenoate A 300 mg portion of the compound obtained in Example 14-(3) was suspended in 100 ml of ethanol, mixed with 1.3 ml of ethylenediamine and heated under reflux for 4 days. After evaporation of the solvent under a reduced pressure, the residue was dissolved in 20 ml of methylene chloride and mixed with 1.06 g of di-tert-butyl dicarbonate, and then 163 μl of triethylamine was added dropwise thereto. After stirring of the reaction solution at room temperature for 3 days, the solvent was evaporated under a reduced pressure, the thus obtained residue was applied to a silica gel chromatography and developed with an ethyl acetate-hexane (4:1) mixed solvent, and then the fractions containing the compound of interest were concentrated to obtain 386 mg of the title compound as a white solid.

$^1$H-NMR (CDCl$_3$) δ: 1.33 (t, 3H, J=7 Hz), 1.43 (s, 9H), 2.73 (s, 3H), 3.31–3.38 (m, 2H), 3.45–3.49 (m, 2H), 4.25 (q, 2H, J=7 Hz), 4.77 (brs, 2H), 4.96 (brs, 1H), 5.27 (brs, 1H), 6.22 (d, 1H, J=16 Hz), 6.29 (s, 1H), 7.59 (d, 1H, J=16 Hz), 7.83 (s, 1H).

(5) 3-[1-[2- Amino-6-(2-tert-butoxycarbonylaminoethyl) amino-4-pyrimidinyl]-5-methyl-4-pyrazolyl]-2-trans-propenal A 386 mg portion of the compound obtained in Example 14-(4) was dissolved in 20 ml of methylene chloride and, in an atmosphere of nitrogen, the solution was cooled to −78° C., mixed with 5 ml of diisobutylaluminum hydride (1 M hexane solution) and then stirred at the same temperature for 3 hours. The reaction solution was mixed with 10% potassium tartarate aqueous solution, stirred at room temperature for 4 hours and then extracted with chloroform. The organic layer was dried with anhydrous sodium sulfate, and then the solvent was evaporated under a reduced pressure. The thus obtained residue was dissolved in 20 ml of 1,4-dioxane, mixed with 619 mg of activated manganese dioxide and then stirred at room temperature for 15 hours. The insoluble matter was removed by celite filtration and then the filtrate was concentrated to obtain 341 mg of the title compound as a white solid.

$^1$H-NMR (CDCl$_3$) 67 : 1.44 (s, 9H), 2.77 (s, 3H), 3.33–3.37 (m, 2H), 3.43–3.49 (m, 2H), 4.78 (brs, 2H), 4.95 (brs, 1H), 5.32 (brs, 1H), 6.31 (s, 1H), 6.52 (dd, 1H, J=16 Hz, 8 Hz), 7.38 (d, 1H, J=16 Hz), 7.86 (s, 1H), 9.63 (d, 1H, J=8 Hz).

(6) 1-[1-[2-Amino-6-(2-tert-butoxycarbonylaminoethyl) amino-4-pyrimidinyl]-5-methyl-pyrazolyl]-3-[4-(3,5-difluorophenyl)-1-piperazinyl]-1-trans-propene A 341 mg portion of the compound obtained in Example 14-(5) was dissolved in 25 ml of ethanol, mixed with 248 mg of 1-(3,5-difluorophenyl)piperazine hydrochloride and 147 μl of triethylamine and stirred at room temperature for 4 hours. Next, this was mixed with 364 μl of acetic acid and then with 138 mg of sodium cyanoborohydride and stirred at room temperature for 14.5 hours. The reaction solution was mixed with saturated sodium bicarbonate aqueous solution, ethanol was evaporated under a reduced pressure and then the residue was extracted with chloroform. The organic layer was dried with anhydrous sodium sulfate, the solvent was evaporated, the thus obtained residue was applied to a silica gel chromatography and developed with a chloroform-methanol (49:1) mixed solvent, and then the fractions containing the compound of interest were concentrated to obtain 217 mg of the title compound as a white powder.

$^1$H-NMR (CDCl$_3$) δ: 1.42 (s, 9H), 2.49–2.64 (m, 4H), 2.63 (s, 3H), 3.17 (d, 2H, J=7 Hz), 3.20–3.23 (m, 4H), 3.29–3.33 (m, 2H), 3.38–3.45 (m, 2H), 4.97 (brs, 2H), 5.23 (brs, 1H), 5.53 (brs, 1H), 6.03 (dt, 1H, J=16 Hz, 7 Hz), 6.24 (t, 1H, J=9 Hz), 6.26 (s, 1H), 6.35–6.39 (m, 3H), 7.73 (s, 1H).

EXAMPLE 15

1-[1-[2-Amino-6-(2-aminoethyl)amino-4-pyrimidinyl]-5-methyl-4-pyrazolyl]-3-[4-(3,5-difluorophenyl)-1-piperazinyl]-1-trans-propene hydrochloride

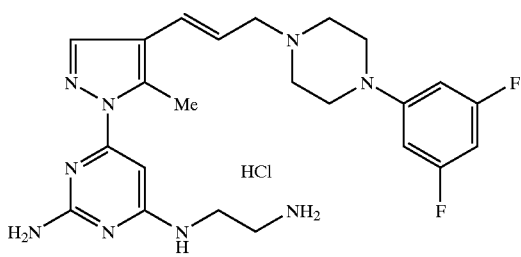

A 212 mg portion of the compound obtained in Example 14-(6) was dissolved in 20 ml of methylene chloride, mixed with 10 ml of trifluoroacetic acid and stirred at room temperature for 15 hours. After concentration of the reaction solution, the residue was mixed with saturated sodium bicarbonate aqueous solution and extracted with a chloroform-methanol (9:1) mixed solvent. After drying of the organic layer with anhydrous sodium sulfate, the solvent was evaporated, and the thus obtained residue was made into hydrochloride by adding 1 N hydrochloric acid/ethanol and then recrystallized from ethanol to obtain 159 mg of the title compound as a white powder.

Melting point: 237–251° C. (decomposition)

$^1$H-NMR (DMSO-d$_6$) δ: 2.65 (s, 3, H), 3.05–3.16 (m, 4H), 3.25 (t, 2H, J=12 Hz), 3.50 (t, 2H, J=11 Hz), 3.62 (brs, 2H), 3.91–3.97 (m, 4H), 6.24 (dt, 1H, J=16 Hz, 7 Hz), 6.43 (s, 1H), 6.56 (t, 1H, J=9 Hz), 6.72 (d, 2H, J=9 Hz), 6.80 (d, 1H, J=16 Hz), 8.12 (s, 1H), 8.17 (brs, 3H), 11.27 (brs, 1H).

EXAMPLE 16

1-[1-[2-Amino-6-(6-tert-butoxycarbonylaminohexyl)amino-4-pyrimidinyl]-5-methyl-4-pyrazolyl]-3-[4-(3,5-difluoropheyl)-1-piperazinyl]-1-trans-propene

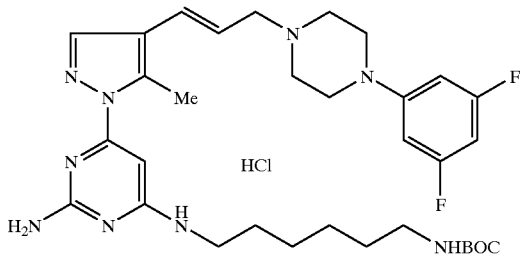

(1) Ethyl 3-[1-[2-amino-6-(6-tert-butoxycarbonylaminohexyl)amino-4-pyrimidinyl]-5-methyl-4-pyrazolyl]-2-trans-propenoate By changing ethylenediamine of Example 14-(4) to hexamethylenediamine, the same reaction and after-treatment of Example 14-(4) were carried out to obtain 299 mg of the title compound as a white solid from 300 mg of the compound obtained in Example 14-(3).

$^1$H-NMR (CDCl$_3$) δ: 1.33 (t, 3H, J=7 Hz), 1.36–1.49 (m, 4H), 1.44 (s, 9H), 1.56–1.63 (m, 4H), 2.73 (s, 3H), 3.09–3.13 (m, 2H), 3.28–3.31 (m, 2H), 4.25 (q, 2H, J=7 Hz), 4.53 (brs, 1H), 4.74 (brs, 2H), 4.87 (brs, 1H), 6.22 (d, 1H, J=16 Hz), 6.27 (s, 1H), 7.59 (d, 1H, J=16 Hz), 7.84 (s, 1H).

(2) 3-[1-[2-Amino-6-(6-tert-butoxycarbonylaminohexyl)amino-4-pyrimidinyl]-5-methyl-4-pyrazolyl]- trans-propenal Using 299 mg of the compound obtained in Example 16-(1), the same reaction and after-treatment of Example 14-(5) were carried out to obtain 278 mg of the title compound as a white solid.

$^1$H-NMR (CDCl$_3$) δ: 1.37–1.61 (m, 8H), 1.44 (s, 9H), 2.78 (s, 3H), 3.08–3.16 (m, 2H), 3.26–3.33 (m, 2H), 4.53 (brs, 1H), 4.75 (brs, 2H), 4.88 (brs, 1H), 6.29 (s, 1H), 6.53 (dd, 1H, J=16 Hz, 8 Hz), 7.39 (d, 1H, J=16 Hz), 7.87 (s, 1H), 9.63 (d, 1H, J=8 Hz).

(3) 1-[1-[2-Amino-6-(6-tert-butoxycarbonylaminohexyl)amino-4-pyrimidinyl]-5-methyl-4-pyrazolyl]-3-[4-(3,5-difluorophenyl)-1-piperazinyl]-1-trans-propene Using 278 mg of the compound obtained in Example 16-(2), the same reaction and after-treatment of Example 14-(6) were carried out to obtain 305 mg of the title compound as a white solid.

$^1$H-NMR (CDCl$_3$) δ: 1.34 (brs, 4H), 1.44 (s, 9H), 1.55–1.59 (m, 2H), 2.55–2.68 (m, 4H), 2.64 (s, 3H), 3.08–3.11 (m, 2H), 3.18 (d, 2H, J=7 Hz), 3.21–3.22 (m, 4H), 3.23–3.28 (m, 2H), 4.64 (brs, 1H), 4.85 (brs, 2H), 5.00 (brs, 1H), 6.03 (dt, 1H, J=16 Hz, 7 Hz), 6.24 (t, 1H, J=9 Hz), 6.26 (s, 1H), 6.35–6.40 (m, 3H), 7.74 (s, 1H).

EXAMPLE 17

1-[1-[2-Amino-6-(6-aminohexyl)amino-4-pyrimidinyl]-5-methyl-4-pyrazolyl]-3-[4-(3,5-difluorophenyl)-1-piperazinyl]-1-trans-propene hydrochloride

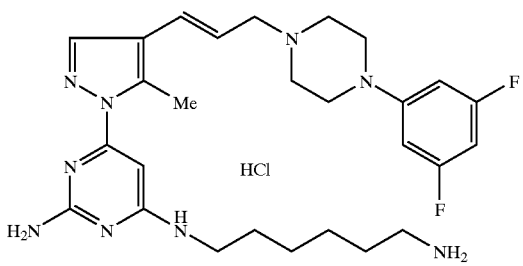

Using 300 mg of the compound obtained in Example 16-(3), the same reaction and after-treatment of Example 15 were carried out and recrystallized from ether-isopropanol to obtain 195 mg of the title compound as a pink white solid.

Melting point: 212–217° C. (decomposition)

$^1$H-NMR (DMSO-d$_6$) δ: 1.26–1.38 (m, 4H), 1.51–1.60 (m, 4H), 2.65 (s, 3H), 2.74–2.79 (m, 2H), 3.05–3.17 (m, 2H), 3.25 (t, 2H, J=12 Hz), 3.51–3.72 (m, 4H), 3.92–3.97 (m, 4H), 6.25 (dt, 1H, J=16 Hz, 7 Hz), 6.55–6.59 (m, 2H), 6.72 (d, 2H, J=1Hz), 6.80 (d, 1H, J=16 Hz), 7.92 (brs, 3H), 8.14 (s, 1H), 11.32 (brs, 1H).

EXAMPLE 18

1-[1-[2-Amino-6-(3-tert-butoxycarbonylamino-1-azetidinyl)-4-pyrimidinyl]-5-methyl-4-pyrazolyl]-3-[4-(3,5-difluorophenyl)-1-piperazinyl]-1-trans-propene

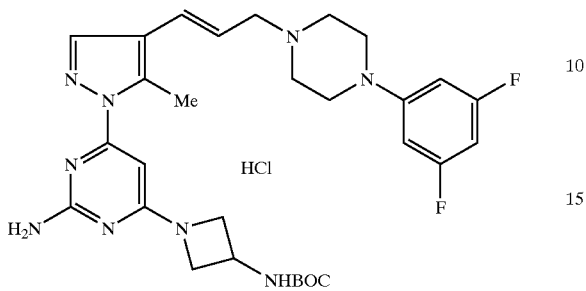

(1) Ethyl 3-[1-[2-amino-6-(3-tert-butoxycarbonylamino-1-azetidinyl)-4-pyrimidinyl]-5-methyl-4-pyrazolyl]-2-trans-propenoate A 628 mg portion of N-benzhydryl-3-tert-butoxycarbonylaminoazetidine was dissolved in 50 ml of ethanol, mixed with 600 mg of 10% palladium-carbon (water content 50.1%) and then subjected to 19 hours of catalytic hydrogenation under 5 atmospheres. The catalyst was removed by filtration, and the filtrate was concentrated under a reduced pressure. The residue was dissolved in 50 ml of ethanol, mixed with 286 mg of the compound obtained in Example 14-(3) and 259 µl of triethylamine, and then heated under reflux for 2 days. The reaction solution was concentrated under a reduced pressure, and the thus obtained residue was mixed with water and extracted with chloroform. After drying the organic layer with anhydrous sodium sulfate, the solvent was evaporated under a reduced pressure, the thus obtained residue was applied to a silica gel chromatography and developed with a chloroform-methanol (49:1) mixed solvent, and then the fractions containing the compound of interest were concentrated to obtain 593 mg of the title compound as a white solid.

$^1$H-NMR (CDCl$_3$) δ: 1.33 (t, 3H, J=7 Hz), 1.45 (s, 9H), 2.73 (s, 3H), 3.86 (dd, 2H, J=5 Hz, 9 Hz), 4.25 (q, 2H, J=7 Hz), 4.37 (t, 2H, J=8 Hz), 4.61 (brs, 1H), 4.78 (brs, 2H), 4.97 (brs, 1H), 6.13 (s, 1H), 6.22 (d, 1H, J=16 Hz), 7.59 (d, 1H, J=16 Hz), 7.38 (s, 1H).

(2) 3-[1-[2-Amino-6-(3-tert-butoxycarbonylamino-1-azetidinyl)-4-pyrimidinyl]-5-methyl-4-pyrazolyl]-2-trans-propenal Using 593 mg of the compound obtained in Example 18-(1), the same reaction and after-treatment of Example 14-(5) were carried out to obtain 575 mg of the title compound as a colorless oil.

$^1$H-NMR (CDCl$_3$) δ: 1.45 (s, 9H), 2.78 (s, 3H), 3.87 (dd, 2H, J=5 Hz, 9 Hz), 4.38 (t, 2H, J=5 Hz), 4.58–4.68 (m, 1H), 4.81 (brs, 2H), 5.97 (brs, 1H), 6.15 (s, 1H), 6.52 (d, 1H, J=16 Hz, 8 Hz), 7.38 (d, 1H, J=16 Hz), 7.87 (s, 1H), 9.63 (d, 1H, J=8 Hz).

(3) 1-[1-[2-Amino-6-(3-tert-butoxycarbonylamino-1-azetidinyl)-4-pyrimidinyl]-5-methyl-4-pyrazolyl]-3-[4-(3,5-difluorophenyl)-1-piperazinyl]-1-trans-propene Using 534 mg of the compound obtained in Example 18-(2), the same reaction and after-treatment of Example 14-(6) were carried out to obtain 378 mg of the title compound as a white powder.

$^1$H-NMR (CDCl$_3$) δ: 1.44 (s, 9H), 1.55–1.59 (m, 2H), 2.55–2.68 (m, 4H), 2.64 (s, 3H), 3.08–3.11 (m, 2H), 3.18 (d, 2H, J=7 Hz), 3.21–3.22 (m, 4H), 3.23–3.28 (m, 2H), 4.64 (brs, 1H), 4.85 (brs, 2H), 5.00 (brs, 1H), 6.03 (dt, 1H, J=16 Hz, 7 Hz), 6.24 (t, 1H, J=9 Hz), 6.26 (s, 1H), 6.35–6.40 (m, 3H), 7.74 (s, 1H).

EXAMPLE 19

1-[1-[2-Amino-6-(3-amino-1-azetidinyl)-4-pyrimidinyl]-5-methyl-4-pyrazolyl]-3-[4-(3,5-difluorophenyl)-1-piperazinyl]-1-trans-propene hydrochloride

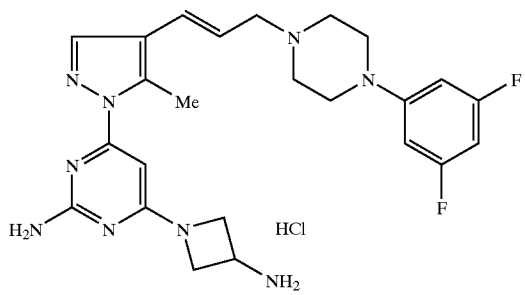

Using 378 mg of the compound obtained in Example 18-(3), the same reaction and after-treatment of Example 15 were carried out to obtain 282 mg of the title compound as a pink white solid.

Melting point: 218–224° C. (decomposition)

$^1$H-NMR (DMSO-d$_6$) δ: 2.68 (s, 3H), 3.09 (dd, 2H, J=10 Hz, 21 Hz), 3.26 (t, 2H, J=12 Hz), 3.49 (d, 2H, J=11 Hz), 3.90–3.98 (m, 4H), 4.18–4.25 (m, 3H), 4.42–4.46 (m, 2H), 6.20 (s, 1H), 6.23 (dt, 1H, J=16 Hz, 8 Hz), 6.57 (dt, 1H, J=2 Hz, 9 Hz), 6.72 (d, 2H, J=9 Hz), 6.76 (d, 1H, J=18 Hz), 8.32 (s, 1H), 8.76 (brs, 3H), 11.43 (brs, 1H).

EXAMPLE 20

1-[1-[4-Amino-6-(2-hydroxyethyl)amino-4-pyrimidinyl]-5-methyl-4-pyrazolyl]-3-[4-(3,5-difluorophenyl)-1-piperazinyl]-1-trans-propene hydrochloride

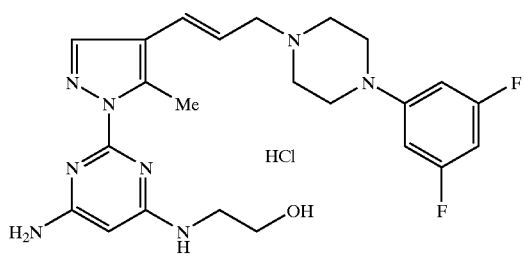

(1) 2,6-Dichloro-4-(4-methoxybenzyl)aminopyrimidine and 4,6-dichloro-2-(4-methoxybenzyl)aminopyrimidine A 27.5 g portion of 2,4,6-trichloropyrimidine was suspended in a mixed solvent of 200 ml ethanol and 200 ml methylene chloride, to which, under ice-cooling, was subsequently added dropwise 30 ml of 4-methoxybenzylamine. After 19 hours of stirring at the same temperature, 10 ml of 4-methoxybenzylamine was further added dropwise and the mixture was stirred for 18 hours. The reaction solution was mixed with 200 ml of 0.5 N phosphoric acid aqueous solution and extracted with chloroform, and then the organic layer was washed with saturated brine. After drying with anhydrous sodium sulfate, the solvent was evaporated under a reduced pressure, and the thus obtained residue was applied to a silica gel chromatography and developed with a chloroform-hexane (3:1) mixed solvent to obtain 13.3 g of 4,6-dichloro-2-(4-methoxybenzyl)aminopyrimidine and further developed with a chloroform-ethyl acetate (1:3) mixed solvent to obtain 24.2 g of 2,6-dichloro-4-(4-methoxybenzyl)aminopyrimidine. 2,6-Dichloro-4-(4-methoxybenzyl)aminopyrimidine $^1$H-NMR (CDCl$_3$) δ: 3.81 (s, 1H), 4.40 (brs, 2H), 6.26 (s, 1H), 6.89 (d, 2H, J=9 Hz), 7.22 (d, 2H, J=8 Hz). 4,6-Dichloro -2-(4-methoxybenzyl)aminopyrimidine $^1$H-NMR (CDCl$_3$) δ: 3.80 (s, 1H), 4.54 (d, 2H, J=6 Hz), 5.68 (brs, 1H), 6.62 (s, 1H), 6.87 (d, 2H, J=8 Hz), 7.25 (d, 2H, J=9 Hz).

(2) Ethyl 1-[4-chloro-6-(4-methoxybenzyl)amino-2-pyrimidinyl]-5-methyl-4-pyrazolecarboxylate A 5.57 g portion of 2,6-dichloro-4-(4-methoxybenzyl) aminopyrimidine was suspended in 20 ml of tetrahydrofuran, mixed with 3.0 ml of hydrazine monohydrate and heated under reflux for 24 hours. After evaporation of the solvent under a reduced pressure, water was added to the residue and the resulting precipitate was collected by filtration to obtain 5.06 g of 4-chloro-2-hydrazino-6-(4-methoxybenzyl)aminopyrimidine as a white solid. This was suspended in 150 ml of ethanol and mixed with 3.37 g of ethoxymethyleneacetoacetic acid ethyl ester at room temperature, and the mixture was stirred for 1 hour and then heated under reflux for 15 hours. By concentrating the reaction solution to dryness under a reduced pressure, 7.22 g of the title compound was obtained as a white solid.

$^1$H-NMR (CDCl$_3$) δ: 1.37 (t, 3H, J=7 Hz), 2.92 (s, 3H), 3.80 (s, 3H), 4.31 (q, 2H, J=7 Hz), 4.45 (brs, 2H), 6.32 (s, 1H), 6.89 (d, 2H, J=7 Hz), 7.22 (d, 2H, J=7 Hz), 8.03 (s, 1H).

(3) 1-[4-Chloro-6-(4-methoxybenzyl)amino-2-pyrimidinyl]-5-methyl-4-pyrazolecarbaldehyde Using 5.77 g of the compound obtained in Example 20-(2), the same reaction and after-treatment of Example 14-(2) were carried out to obtain 5.31 g of the title compound as a white solid.

$^1$H-NMR (CDCl$_3$) δ: 2.93 (s, 3H), 3.81 (s, 3H), 4.45 (brs, 2H), 6.35 (s, 1H), 6.90 (d, 2H, J=8 Hz), 7.23 (d, 2H, J=8 Hz), 8.09 (s, 1H), 10.00 (s, 1H).

(4) Ethyl 3-[[4-chloro-6-(4-methoxybenzyl)amino-2-pyrimidinyl]-5-methyl-4-pyrazolyl]-2-trans-propenoate A 5.11 g portion of the compound obtained in Example 20-(3) was dissolved in 130 ml of toluene, mixed with 5.22 g of (carboethoxymethylene)triphenylphosphorane and then heated under reflux for 16 hours in an atmosphere of nitrogen. The reaction solution was concentrated under a reduced pressure, the resulting residue was applied to a silica gel chromatography and developed with an ethyl acetate-hexane (1:2) mixed solvent, and then the fractions containing the compound of interest were concentrated to obtain 5.34 g of the title compound as a white solid.

$^1$H-NMR (CDCl$_3$) δ: 1.32 (t, 3H, J=7 Hz), 2.71 (s, 3H), 3.81 (s, 3H), 4.25 (q, 2H, J=7 Hz), 4.46 (brs, 2H), 5.90 (brs, 1H), 6.26 (d, 1H, J=16 Hz), 6.29 (s, 1H), 6.89 (d, 2H, J=8 Hz), 7.23 (d, 2H, J=8 Hz), 7.58 (d, 1H, J=16 Hz), 7.92 (s, 1H).

(5) 3-[[4-Chloro-6-(4-methoxybenzyl)amino-2-pyrimidinyl]-5-methyl-4-pyrazolyl]-2-trans-propenal Using 5.34 g of the compound obtained in Example 20-(4), the same reaction and after-treatment of Example 14-(5) were carried out to obtain 3.38 g of the title compound as a white solid.

$^1$H-NMR (CDCl$_3$) δ: 2.76 (s, 3H), 3.81 (s, 3H), 4.26 (brs, 2H), 6.32 (s, 1H), 6.55 (dd, 1H, J=8 Hz, 16 Hz), 6.90 (d, 2H, J=8 Hz), 7.24 (d, 2H, J=9 Hz), 7.39 (d, 1H, J=16 Hz), 7.96 (s, 1H), 9.65 (d, 1H, J=9 Hz).

(6) 1-[1-[4-Chloro-6-(4-methoxybenzyl)amino-2-pyrimidinyl]-5-methyl-4-pyrazolyl]-3-[4-(3,5-difluorophenyl)-1-piperazinyl]-1-trans-propene Using 398 mg of the compound obtained in Example 20-(5), the same reaction and after-treatment of Example 14-(6) were carried out to obtain 378 mg of the title compound as a white solid.

$^1$H-NMR (CDCl$_3$) δ: 2.55–2.65 (m, 7H), 3.17–3.21 (m, 6H), 3.79 (s, 3H), 4.40 (brs, 2H), 6.06 (dt, 1H, J=16 Hz, 7 Hz), 6.21 (t, 1H, J=9 Hz), 6.25 (s, 1H), 6.35–6.39 (m, 3H), 6.87 (d, 2H, J=8 Hz), 7.20 (d, 2H, J=8 Hz), 7.80 (s, 1H).

(7) 1-[1-(4-Amino-6-chloro-2-pyrimidinyl)-5-methyl-4-pyrazolyl]-3-[4-(3,5-difluorophenyl)-1-piperazinyl]-1-trans-propene A 780 mg portion of the compound obtained in Example 20-(6) was dissolved in 30 ml of trifluoroacetic acid, mixed with 500 μl of anisole and heated under reflux for 15 hours. The solvent was evaporated under a reduced pressure, and the residue was mixed with 100 ml of saturated sodium bicarbonate aqueous solution and then extracted with a chloroform-methanol (9:1) mixed solvent. The organic layer was dried with anhydrous sodium sulfate, the solvent was evaporated under a reduced pressure, the thus obtained residue was applied to a silica gel chromatography and developed with a chloroform-methanol (49:1-19:1) mixed solvent, and then the fractions containing the compound of interest were concentrated to obtain 502 mg of the title compound as a white powder.

$^1$H-NMR (CDCl$_3$) δ: 2.61–2.65 (m, 7H), 3.17–3.23 (m, 6H), 5.79 (brs, 2H), 6.07 (dt, 1H, J=16 Hz, 7 Hz), 6.24 (t, 1H, J=8 Hz), 6.32 (s, 1H), 6.34–6.40 (m, 3H), 7.82 (s, 1H).

(8) 1-[1-[4-Amino-6-(2-hydroxyethyl)amino-2-pyrimidinyl]-5-methyl-4-pyrazolyl]-3-[4-(3,5-difluorophenyl)-1-piperazinyl]-1-trans-propene hydrochloride A 584 mg portion of the compound obtained in Example 20-(7) was suspended in 50 ml of ethanol, mixed with 790 μl of ethanolamine and heated under reflux for 4 days. The solvent was evaporated under a reduced pressure, and the residue was mixed with water and extracted with a chloroform-methanol (9:1) mixed solvent. The organic layer was dried with anhydrous sodium sulfate, the solvent was evaporated under a reduced pressure, the thus obtained residue was applied to a silica gel chromatography and developed with a chloroform-methanol (9:1) mixed solvent, and then the fractions containing the compound of interest were concentrated. The residue was made into hydrochloride with 1 N hydrochloric acid/ethanol and then recrystallized from an ethanol-isopropanol mixed solvent to obtain 107 mg of the title compound as a white powder.

Melting point: 198–208° C.

$^1$H-NMR (DMSO-d$_6$) δ: 2.67 (s, 3H), 3.09–3.78 (m, 10H), 3.95–3.98 (m, 4H), 5.58 (s, 1H), 6.31 (dt, 1H, J=16 Hz, 8 Hz), 6.57 (t, 1H, J=9 Hz), 6.73 (d, 2H, J=9 Hz), 6.83 (d, 2H, J=16 Hz), 8.31 (s, 1H), 11.08 (brs, 1H).

EXAMPLE 21

1-[1-[4-Amino-6-(3-hydroxy-1-azetidinyl)-2-pyrimidinyl]-5-methyl-4-pyrazolyl]-3-[4-(3,5-difluorophenyl)-1-piperazinyl]-1-trans-propene hydrochloride

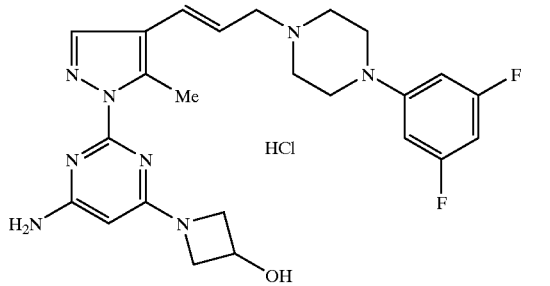

Using 500 mg of the compound obtained in Example 20-(7), the same reaction and after-treatment of Example 13 were carried out to obtain 150 mg of the title compound as a white solid.

Melting point: 213–220° C. (decomposition)

$^1$H-NMR (DMSO-$d_6$) δ: 2.64 (s, 3H), 3.09–3.11 (m, 2H), 3.25 (t, 2H, J=12 Hz, 3.51 (t, 2H, J=12 Hz), 3.85–3.98 (m, 6H), 4.30–4.34 (m, 2H), 4.61–4.66 (m, 1H), 5.28 (s, 1H), 6.31 (dt, 1H, J=15 Hz, 7 Hz), 6.56 (t, 1H, J=9 Hz), 6.72 (d, 2H, J=9 Hz), 6.83 (d, 2H, J=15 Hz), 7.50 (brs, 2H), 8.27 (s, 1H), 11.33 (brs, 2H).

EXAMPLE 22

1-[1-[4-Amino-6-(1-pyrrolidinyl)-2-pyrimidinyl]-5-methyl-4-pyrazolyl]-3-[4-(3,5-difluorophenyl)-1-piperazinyl]-1-trans-propene hydrochloride

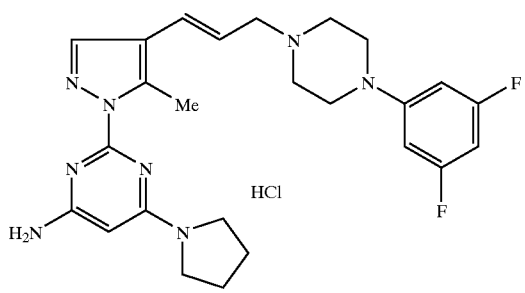

A 24 mg portion of the compound obtained in Example 20-(7) was suspended in 10 ml of ethanol, mixed with 21 μl of pyrrolidine and heated under reflux for 24 hours. The solvent was evaporated under a reduced pressure, and the thus obtained residue was separated and purified by applying it to a preparative TLC and developing with a lower layer of chloroform-methanol-water=20:3:1. The thus obtained compound was made into hydrochloride with 1 N hydrochloric acid/ethanol and then recrystallized from ethanol-ether to obtain 25 mg of the title compound as a white solid.

Melting point: 195–201° C. (decomposition)

$^1$H-NMR (DMSO-$d_6$) δ: 1.99 (brs, 4H), 2.70 (s, 3H), 3.07–3.98 (m, 12H), 5.45 (s, 1H), 6.36 (dt, 1H, J=16 Hz, 7 Hz), 6.56 (t, 1H, J=8 Hz), 6.72 (d, 2H, J=10 Hz), 6.85 (d, 2H, J=16 Hz), 8.33 (s, 1H), 11.4 (brs, 1H).

EXAMPLE 23

1-[1-[4-Amino-6-(4-methyl-1-piperazinyl)-2-pyrimidinyl]-5-methyl-pyrazolyl]-3-[4-(3,5-difluorophenyl)-1-piperazinyl]-1-trans-propene hydrochloride

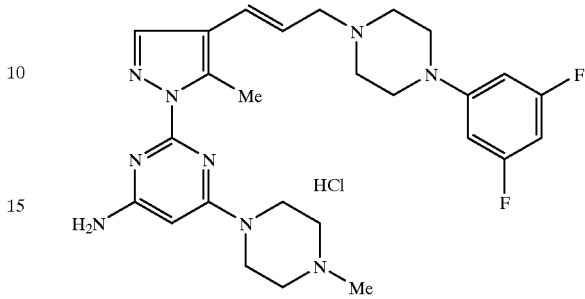

By changing pyrrolidine of Example 22 to N-methylpiperazine and using 24 mg of the compound obtained in Example 20-(7), the same reaction and after-treatment of Example 22 were carried out to obtain 26mg of the title compound as a white solid.

Melting point: 235–243° C. (decomposition)

$^1$H-NMR (DMSO$_6$) δ: 2.61 (s, 3H), 2.79 (s, 3H), 3.09–3.18 (m, 4H), 3.25 (t, 2H, J=3 Hz), 3.44–3.98 (m, 10H), 4.31 (d, 2H), 5.78 (s, 1H), 6.25 (dt, 1H, J=16 Hz, 7 Hz), 6.57 (t, 1H, J=10 Hz), 6.72 (d, 2H, J=10 Hz), 6.82 (d, 2H, J=16 Hz), 7.35 (brs, 2H), 8.12 (s, 1H), 11.32 (brs, 2H).

EXAMPLE 24

1-[1-(4-Amino-6-morpholino-2-pyrimidinyl)-5-methyl-4-pyrazolyl]-3-[4-(3,5-difluorophenyl)-1-piperazinyl]-1-trans-propene hydrochloride

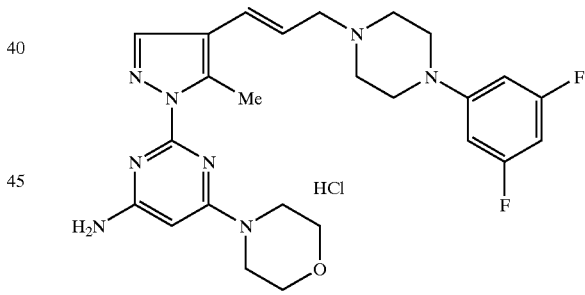

A 293 mg portion of the compound obtained in Example 20-(7) was suspended in 100 ml of ethanol, mixed with 287 μl of morpholine and heated under reflux for 5 days. The solvent was evaporated under a reduced pressure, the residue was applied to a silica gel chromatography and developed with a chloroform-methanol (97:3) mixed solvent, and then the fractions containing the compound of interest were concentrated. The resulting residue was made into hydrochloride with 1 N hydrochloric acid/ethanol and then recrystallized from an ethanol-isopropanol mixed solvent to obtain 225 mg of the title compound as a white powder.

Melting point: 234–238° C. (decomposition)

$^1$H-NMR (DMSO-$d_6$) δ: 2.61 (s, 3H), 3.09–3.98 (m, 18H), 5.68 (s, 1H), 6.27 (dt, 1H, J=16 Hz, 8 Hz), 6.58 (t, 1H, J=10 Hz), 6.73 (d, 2H, J=10 Hz), 6.81 (d, 2H, J=16 Hz), 8.17 (s, 1H), 10.90 (brs, 2H).

EXAMPLE 25

1-[[4-(1-Azetidinyl)-6-(4-methoxybenzyl)amino-2-pyrimidinyl]-5-methyl-4-pyrazolyl]-3-(4-(3,5-difluorophenyl)-1-piperazinyl]-1-trans-propene

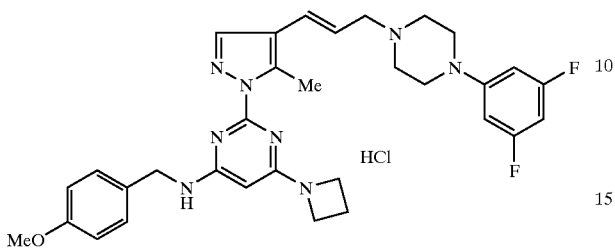

(1) Ethyl 3-[[4-(1-azetidinyl)-6-(4-methoxybenzyl)amino-2-pyrimidinyl]-5-methyl-4-pyrazolyl]-2-trans-propenoate A 428 mg portion of the compound obtained in Example 20-(4) was suspended in 100 ml of ethanol, mixed with 468 mg of azetidine hydrochloride and then heated at 100° C. for 3 days in a sealed tube. After evaporation of the solvent under a reduced pressure, the residue was mixed with water and extracted with chloroform. After drying of the organic layer with anhydrous sodium sulfate, the solvent was evaporated under a reduced pressure to obtain 403 mg of the title compound as a slightly brown powder.

$^1$H-NMR (CDCl$_3$) δ: 1.32 (t, 3H, J=7 Hz), 2.35–2.43 (m, 2H), 2.69 (s, 3H), 3.80 (s, 3H), 4.03–4.06 (m, 4H), 4.23 (q, 2H, J=7 Hz), 4.35 (d, 2H, J=5 Hz), 4.97 (s, 1H), 5.38 (brs, 1H), 6.22 (d, 1H, J=16 Hz), 6.87 (d, 2H, J=7 Hz), 7.24 (d, 2H, J=7 Hz), 7.60 (d, 1H, J=16 Hz), 7.87 (s, 1H).

(2) 3-[[4-(1-Azetidinyl)-6-(4-methoxybenzyl)amino-2-pyrimidinyl]-5-methyl-4-pyrazolyl]-2-trans-propenal Using 403 mg of the compound obtained in Example 25-(1), the same reaction and after-treatment of Example 14-(5) were carried out to obtain 375 mg of the title compound as a white solid.

$^1$H-NMR (CDCl$_3$) δ: 2.35–2.46 (m, 2H), 2.74 (s, 3H), 3.80 (s, 3H), 4.03–4.06 (m, 4H), 4.36 (brs, 2H), 4.99 (s, 1H), 5.35 (brs, 1H), 6.47–6.58 (m, 1H), 6.84–6.89 (m, 2H), 7.23–7.27 (m, 2H), 7.35–7.43 (m, 1H), 7.90 (s, 1H), 9.63 (brs, 1H).

(3) 1-[[4-(1-Azetidinyl)-6-(4-methoxybenzyl)amino-2-pyrimidinyl]-5-methyl-4-pyrazolyl]-3-[4-(3,5-difluorophenyl)-1-piperazinyl]-1-trans-propene Using 363 mg of the compound obtained in Example 25-(2), the same reaction and after-treatment of Example 14-(6) were carried out to obtain 255 mg of the title compound as a slightly brown oil.

$^1$H-NMR (CDCl$_3$) δ: 2.35–2.39 (m, 2H), 2.53–2.66 (m, 4H), 2.61 (s, 3H), 3.18–3.24 (m, 6H), 3.79 (s, 3H), 4.03 (t, 4H, J=9 Hz), 4.34 (d, 2H, J=5 Hz), 4.95 (s, 1H), 5.49 (brs, 1H), 6.01 (dt, 1H, J=16 Hz, 7 Hz), 6.24 (dt, 1H, J=2, 9 Hz), 6.36 (d, 2H, J=9 Hz), 6.38 (d, 1H, J=16 Hz), 6.86 (d, 2H, J=8 Hz), 7.23 (d, 2H, J=9 Hz), 7.76 (s, 1H).

EXAMPLE 26

1-[[4-Amino-6-(1-azetidinyl)-2-pyrimidinyl]-5-methyl-4-pyrazolyl]-3-[4-(3,5-difluorophenyl)-1-piperazinyl]-1-trans-propene hydrochloride

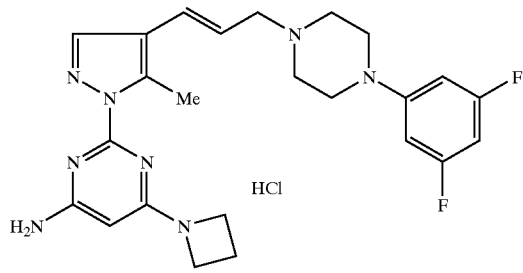

A 255 mg portion of the compound obtained in Example 25-(3) was dissolved in 30 ml of trifluoroacetic acid, mixed with 2 ml of anisole and then heated under reflux for 23 hours. The solvent was evaporated under a reduced pressure, and the residue was mixed with saturated sodium bicarbonate aqueous solution and then extracted with a chloroform-methanol (9:1) mixed solvent. The organic layer was dried with anhydrous sodium sulfate, the solvent was evaporated under a reduced pressure, the thus obtained residue was applied to a silica gel chromatography and developed with a chloroform-methanol (98:2) mixed solvent, and then the fractions containing the compound of interest were concentrated. The resulting residue was made into hydrochloride with 1 N hydrochloric acid/ethanol and then recrystallized from ethanol to obtain 54 mg of the title compound as a white powder.

Melting point: 190–196° C. (decomposition)

$^1$H-NMR (DMSO-d$_6$) δ: 2.37–2.41 (m, 2H), 2.63 (s, 3H), 3.08–3.49 (m, 6H), 3.95–3.98 (m, 4H), 4.09–4.12 (m, 4H), 5.23 (s, 1H), 6.29 (dt, 1H, J=16 Hz, 8 Hz), 6.57 (t, 1H, J=9 Hz), 6.73 (d, 1H, J=9 Hz), 6.82 (d, 1H, J=16 Hz) 8.23 (s, 1H), 11.17 (brs, 1H).

EXAMPLE 27

3-[3-[1-[2-Amino-6-(2-hydroxyethyl)amino-4-pyrimidinyl]-5-methyl-4-pyrazolyl]-2-trans-propen-1-yl]-7,9-difluoro-2,3,4,4a,5,6-hexahydro-1H-pyrazino[1,2-a]quinoline hydrochloride

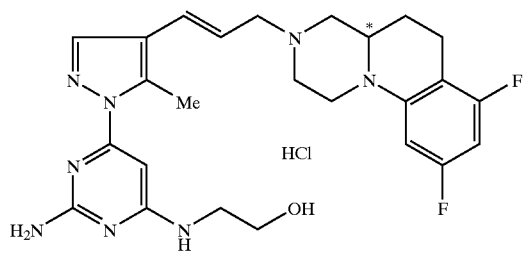

Optically active compound (1) 2-Tribromomethyl-5,7-difluoroquinoline

A mixture of 28.4 ml of bromine and 25 ml of acetic acid was added to a mixture consisting of 33 g of 5,7-difluoroquinaldine, 94 g of sodium acetate and 190 ml of acetic acid over 30 minutes at 70° C. The reaction solution was stirred at 90° C. for 1 hour, cooled to room temperature, mixed with water and then extracted twice with ethyl acetate. The organic layer was washed with 10% sodium thiosulfate aqueous solution, saturated sodium bicarbonate aqueous solution, water and saturated brine in that order and then dried with anhydrous sodium sulfate. By evaporating the solvent under a reduced pressure, 71.9 g of the title compound was obtained as a light brown solid.

$^1$H-NMR (CDCl$_3$) δ: 7.15 (td, 1H, J=9 Hz, 2 Hz), 7.69 (d, 1H, J=9 Hz), 8.25 (d, 1H, J=9 Hz), 8.49 (d, 1H, J=9 Hz).

(2) 5,7-Difluoro-2-quinolinecarboxylic acid

A 17.4 g portion of the compound obtained in Example 27-(1) was mixed with 180 ml of concentrated sulfuric acid and stirred at 130° C. for 20 hours and then at 150° C. for 20 hours, and the reaction solution was poured into about 800 ml of ice water. The thus obtained acidic aqueous solution was alkalified by adding 28% ammonia aqueous solution, adjusted to around pH 4 by adding 1 N phosphoric acid aqueous solution and then extracted with chloroform. The organic layer was washed with saturated brine and dried with anhydrous sodium sulfate, and then the solvent was evaporated under a reduced pressure. The residue was applied to a silica gel column chromatography and developed with a chloroform-methanol (9:1) mixed solvent, and then the fractions containing the compound of interest were concentrated to obtain 2.58 g of the title compound.

$^1$H-NMR (CDCl$_3$) δ: 7.96 (t, 1H, J=10 Hz), 7.84 (d, 1H, J=8 Hz), 8.16 (d, 1H, J=8 Hz), 8.63 (d, 1H, J=8 Hz).

(3) 5,7-Difluoro-2-[N-(1-phenylethyl)carbamoyl]-1,2,3,4-tetrahydroquinoline (diastereomer A and diastereomer B)

A 2.58 g portion of the compound obtained in Example 27-(2) was dissolved in 100 ml of acetic acid, mixed with 300 mg of platinum oxide and then subjected to 6 hours of catalytic hydrogenation. The insoluble matter was removed by filtration, the resulting filtrate was concentrated to dryness, the residue was dissolved in chloroform, washed with semi-saturated brine and dried with anhydrous sodium sulfate, and then the solvent was evaporated under a reduced pressure. The thus obtained residue was dissolved in 80 ml of dichloromethane, mixed with 2.20 g of (s)-(-)-1-phenylethylamine, 2.24 g of dimethylaminopyridine and 4.44 g of 1-ethyl-3-(3-dimethylaminopropyl)carbodiimide hydrochloride and then stirred at room temperature for 15 hours. The reaction solution was washed with water, 1 N phosphoric acid aqueous solution and saturated brine in that order and dried with anhydrous sodium sulfate, and then the solvent was evaporated under a reduced pressure. The residue was applied to a silica gel column chromatography and developed with an ethyl acetate-hexane (1:4) mixed solvent to obtain 1.05 g of a low polar isomer (diastereomer A) and then with an ethyl acetate-hexane (1:2) mixed solvent to obtain 1.22 g of a high polar isomer (diastereomer B), as the title compound.

Diastereomer A;

$^1$H-NMR (CDCl$_3$) δ: 1.46 (d, 3H, J=7 Hz), 1.85–1.93 (m, 1H), 2.25–2.33 (m, 1H), 2.41–2.50 (m, 1H), 2.71–2.81 (m, 1H), 3.95 (q, 1H, J=5 Hz), 4.36 (d, 1H, J=4 Hz), 5.16 (m, 1H), 6.13 (dt, 1H, J=10 Hz, 2 Hz), 6.21 (td, 1H, J=9 Hz, 2 Hz), 6.67 (d, 1H, J=8 Hz), 7.25–7.40 (m, 5H).

Diastereomer B;

$^1$H-NMR (CDCl$_3$) δ: 1.49 (d, 3H, J=7 Hz), 1.83–1.92 (m, 1H), 2.20–2.37 (m, 2H), 2.66–2.73 (m, 1H), 3.98 (q, 1H, J=5 Hz), 4.42 (d, 1H, J=4 Hz), 5.13 (m, 1H), 6.13–6.26 (m, 2H), 6.70 (d, 1H, J=6 Hz), 7.15–7.31 (m, 5H).

(4) 5,7-Difluoro-2-[N-(1-phenylethyl)-N-tert-butoxycarbonylaminomethyl]-1,2,3,4-tetrahydroquinoline (diastereomer B)

A 1.22 g portion of the diastereomer B obtained in Example 27-(3) was dissolved in 15 ml of tetrahydrofuran and mixed with 3.9 ml of borane-dimethyl sulfide complex while stirring at 0° C., and then the mixture was stirred at room temperature for 3 days. This was mixed with 6 N hydrochloric acid aqueous solution, stirred for 2 hours and then neutralized using saturated sodium bicarbonate aqueous solution. After extraction with chloroform, the organic layer was washed with saturated brine and dried with anhydrous sodium sulfate, and then the solvent was evaporated under a reduced pressure. The residue was dissolved in 10 ml of 1,4-dioxane, mixed with 1.06 ml of di-tert-butyl dicarboxylate and then stirred at room temperature for 39 hours. After evaporation of the solvent under a reduced pressure, the residue was applied to a silica gel column chromatography and developed with an ethyl acetate-hexane (1:9) mixed solvent, and then the fractions containing the compound of interest were concentrated to obtain 1.39 g of the title compound.

$^1$H-NMR (CDCl$_3$) δ: 1.25–1.40 (m, 1H), 1.48 (s, 9H), 1.53 (d, 3H, J=7 Hz), 2.25–2.40 (m, 1H), 2.50–2.65 (m, 1H), 3.00–3.20 (m, 3H), 5.25–5.50 (m, 1H), 5.92 (d, 1H, J=10 Hz), 6.02 (td, 1H, J=9 Hz, 2 Hz), 7.25–7.40 (m, 5H).

(5) 7,9-Difluoro-3-(1-phenylethyl)-2,3,4,4a,5,6-hexahydro-1-oxopyrazino[1,2-a]quinoline (diastereomer B)

A 1.39 g portion of the compound obtained in Example 27-(4) was dissolved in 10 ml of tetrahydrofuran and mixed with 0.43 ml of pyridine and 0.31 ml of chloroacetyl chloride while stirring at 0° C., and the mixture was stirred at the same temperature for 30 minutes and then at room temperature for 30 minutes. The reaction solution was mixed with ice water and extracted with ethyl acetate, and then the organic layer was washed with saturated brine and dried with anhydrous sodium sulfate. After evaporation of the solvent under a reduced pressure, the thus obtained residue was dissolved in 4 ml of tetrahydro furan, mixed with 5 ml of trifluoroacetic acid and then stirred at room temperature for 30 minutes and further at 50° C. for 2 hours. The reaction solution was concentrated to dryness under a reduced pressure, and then the residue was dissolved in 10 ml of dimethylformamide, mixed with 0.9 g of potassium carbonate and stirred at 50° C. for 1 hour. The reaction solution was cooled to room temperature, diluted with water and then extracted with ethyl acetate. The organic layer was washed with saturated brine and dried with anhydrous sodium sulfate and then the solvent was evaporated under a reduced pressure. The residue was applied to a silica gel column chromatography and developed with an ethyl acetate-hexane (1:4) mixed solvent, and then the fractions containing the compound of interest were concentrated to obtain 935 mg of the title compound.

$^1$H-NMR (CDCl$_3$) δ: 1.41 (d, 3H, J=7 Hz), 1.88–2.10 (m, 2H), 2.52 (dd, 1H, J=12 Hz, 6 Hz), 2.65–3.00 (m, 3H), 3.33 and 3.34 (ABq, 2H, J=17 Hz), 3.42 (q, 1H, J=7 Hz), 3.50–3.60 (m,1 1H), 6.59 (td, 1H, J=10 Hz, 2 Hz), 7.25–7.40 (m, 5H), 7.69 (dt, 1H, J=11 Hz, 2 Hz).

(6) 7,9-Difluoro-3-(1-phenylethyl)-2,3,4,4a,5,6-hexahydro-1H-pyrazino[1,2-a]quinoline (diastereomer B)

A 930 mg portion of the compound obtained in Example 27-(5) was dissolved in 14 ml of tetrahydrofuran, mixed with 3 ml of borane-dimethyl sulfide complex and stirred for 5 days. The reaction solution was poured into 20 ml of 6 N hydrochloric acid aqueous solution, stirred at room temperature for 1 hour, adjusted to a pH value of about 9 by adding sodium bicarbonate and then extracted with chloroform. The organic layer was dried with anhydrous sodium sulfate, the solvent was evaporated under a reduced pressure, the thus obtained residue was applied to a silica gel column chromatography and developed with an ethyl acetate-hexane (1:9) mixed solvent, and then the fractions containing the compound of interest were concentrated to obtain 722 mg of the title compound.

$^1$H-NMR (CDCl$_3$) δ: 1.39 (d, 3H, J=6 Hz), 1.55–1.75 (m, 1H), 1.89–1.95 (m, 2H), 2.04–2.11 (m, 1H), 2.54–2.64 (m, 1H), 2.73–2.83 (m, 3H), 3.05–3.11 (m, 2H), 3.38 (q, 1H, J=6 Hz), 3.46–3.52 (m, 1H), 6.13–6.23 (m, 2H), 7.23–7.40 (m, 5H).

(7) 7,9-Difluoro-2,3,4,4a,5,6-hexahydro-1H-pyrazino[1,2-a]quinoline (enantiomer B)

A 722 mg portion of the compound obtained in Example 27-(6) was dissolved in 10 ml of methanol, mixed with 0.69 g of ammonium formate and 0.68 g of 10% palladium-carbon and then heated under reflux for 1.5 hours. The insoluble matter was removed by filtration, and then the filtrate was concentrated under a reduced pressure. The residue was mixed with saturated brine and extracted with chloroform, the organic layer was dried with anhydrous sodium sulfate and then the solvent was evaporated under a reduced pressure. The thus obtained residue was applied to a silica gel column chromatography and developed with a methanol-chloroform (1:9) mixed solvent, and then the fractions containing the compound of interest were concentrated to obtain 412 mg of the title compound.

$^1$H-NMR (CDCl$_3$) δ: 1.60–1.72 (m, 1H), 1.87–1.95 (m, 1H), 2.54–2.63 (m, 2H), 2.70–2.81 (m, 2H), 2.85–2.97 (m, 2H), 3.01–3.06 (m, 1H), 3.10–3.15 (m, 1H), 3.60 (brd, 1H, J=12 Hz), 6.18 (td, 1H, J=9 Hz, 2 Hz), 6.28 (d, 1H, J=13 Hz).

(8) 3-[3-[1-[2-Amino-6-(4-methoxybenzyloxy)-4-pyrimidinyl]-5-methyl-4-pyrazolyl]-2-trans-propen-1-yl]-7,9-difluoro-2,3,4,4a,5,6-hexahydro-1H-pyrazino[1,2-a]quinoline (isomer B)

A mixture consisting of 220 mg of the compound obtained in Example 27-(7), 357 mg of 3-[[2-amino-6-(4-methoxybenzyloxy)-4-pyrimidinyl]-5-methyl-4-pyrazolyl]-2-trans-propenal and 20 ml of ethanol was stirred at 60° C. for 20 minutes, cooled to room temperature and mixed with 0.56 ml of acetic acid, and then 286 mg of sodium cyanoborohydride was added thereto in two portions at 3 hour intervals. After 15 hours of stirring at room temperature, the reaction solution was mixed with water and saturated sodium carbonate aqueous solution and extracted with chloroform. The organic layer was dried with anhydrous sodium sulfate, the solvent was evaporated under a reduced pressure, the thus obtained residue was applied to a silica gel column chromatography and developed with a methanol-chloroform (1:99) mixed solvent, and then the fractions containing the compound of interest were concentrated to obtain 428 mg of the title compound.

$^1$H-NMR (CDCl$_3$) δ: 1.55–1.75 (m, 1H), 1.85–2.00 (m, 2H), 2.66 (s, 3H), 2.50–3.20 (m, 8H), 3.63 (brd, 1H, J=12 Hz), 4.93 (brs, 2H), 5.34 (s, 2H), 6.04 (dt, 1H, J=16 Hz, 7 Hz), 6.19 (td, 1H, J=9 Hz, 2 Hz), 6.25–6.32 (m, 1H), 6.38 (d, 1H, J=16 Hz), 6.67 (s, 1H), 7.25–7.50 (m, 5H), 7.77 (s, 1H).

(9) 3-[3-[1-(2-Amino-6-chloro-4-pyrimidinyl)-5-methyl-4-pyrazolyl]-2-trans-propen-1-yl]-7,9-difluoro-2,3,4,4a,5,6-hexahydro-1H-pyrazino[1,2-a]quinoline (isomer B)

A 428 mg portion of the compound obtained in Example 27-(8) was mixed with 10 ml of trifluoroacetic acid and 0.11 ml of thioanisole and then stirred at room temperature for 2 hours. The reaction solution was concentrated, the residue was mixed with diethyl ether and stirred at room temperature, and then the precipitate was collected by filtration. A 439 mg portion of the thus obtained compound was mixed with 10 ml of phosphorus oxychloride and stirred at 90° C. for 6 hours. After concentration of the reaction solution, the residue was mixed with water and saturated sodium bicarbonate aqueous solution and extracted four times with chloroform-methanol (9:1). The organic layers were dried with anhydrous sodium sulfate and then the solvent was evaporated under a reduced pressure. The resulting residue was applied to a silica gel column chromatography and developed with a chloroform-methanol (99:1) mixed solvent, and then the fractions containing the compound of interest were concentrated to obtain 177 mg of the title compound as a white powder.

$^1$H-NMR (CDCl$_3$) δ; 1.65–1.80 (m, 1H), 1.90–2.00 (m, 2H), 2.20–2.30 (m, 1H), 2.50–3.30 (m, 8H), 2.70 (s, 3H), 3.64 (brd, 1H, J=12 Hz), 5.15 (s, 2H), 6.08 (dt, 1H, J=16 Hz, 7 Hz), 6.19 (td, 1H, J=9 Hz, 2 Hz), 6.29 (d, 1H, J=13 Hz), 6.39 (d, 1H, J=16 Hz), 7.31 (s, 1H), 7.81 (s, 1H).

(10) 3-[3-[1-[2-Amino-6-(2-hydroxyethyl)amino-4-pyrimidinyl]-5-methyl-4-pyrazolyl]-2-trans-propen-1-yl]-7,9-difluoro-2,3,4,4a,5,6-hexahydro-1H-pyrazino[1,2-a]quinoline hydrochloride (isomer B)

An 18 mg portion of the compound obtained in Example 27-(9) was dissolved in 5 ml of ethanol, mixed with 1 ml of ethanolamine and then heated under reflux for 26 hours. The reaction solution was cooled to room temperature, diluted with water and then extracted with chloroform. The organic layer was dried with anhydrous sodium sulfate, the solvent was evaporated, the thus obtained residue was applied to a preparative TLC and developed with a chloroform-methanol (95:5) mixed solvent, and then 15 mg of free form of the title compound was obtained from the fractions containing the compound of interest. The thus obtained compound was dissolved in 2 ml of hot ethanol and mixed with 1 N hydrochloric acid/ethanol, and the thus precipitated powder was collected by filtration to obtain 6 mg of the title compound.

Melting point: 200° C. or more (decomposition)

$^1$H-NMR (DMSO-d$_6$) δ: 1.55–1.70 (m, 1H), 2.00–2.10 (m, 1H), 2.50–2.75 (m, 2H), 2.65 (s, 3H), 2.80–2.95 (m, 1H), 3.00–3.30 (m, 2H), 3.30–3.65 (m, 7H), 3.80–4.00 (m, 2H), 4.13 (brd, 1H, J=13 Hz), 6.24 (dt, 1H, J=16 Hz, 7 Hz), 6.45 (s, 1H), 6.50 (td, 1H, J=9 Hz, 2 Hz), 6.69 (d, 1H, J=13 Hz), 6.80 (d, 1H, J=16 Hz), 8.12 (s, 1H), 11.25 (brs, 1H).

EXAMPLE 28

3-[3-[1-[2-Amino-6-[N-methyl-N-(2-hydroxyethyl) amino-4-pyrimidinyl]-5-methyl-4-pyrazolyl]-2-trans-propen-1-yl]-7,9-difluoro-2,3,4,4a,5,6-hexahydro-1H-pyrazino[1,2-a]quinoline hydrochloride (isomer B)

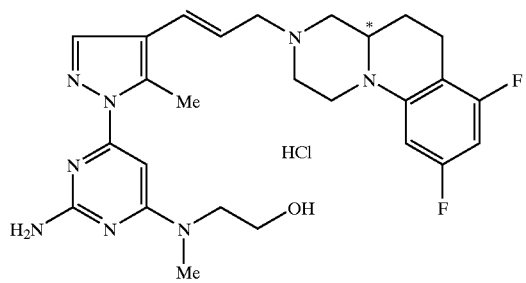

Optically active compound

Using 18 mg of the compound obtained in Example 27-(9) and changing ethanolamine of Example 27-(10) to N-methyl-N-(2-hydroxyethyl)amine, the same reaction and after-treatment of Example 27-(10) were carried out to obtain 5 mg of the title compound.

Melting point: 206–211° C. (decomposition)

$^1$H-NMR (DMSO-d$_6$) δ: 1.55–1.70 (m, 1H), 2.00–2.10 (m, 1H), 2.45–2.75 (m, 2H), 2.67 (s, 3H), 2.80–2.95 (m, 1H), 3.07 (s, 3H), 3.00–3.65 (m, 9H), 3.80–4.00 (m, 2H), 4.13 (brd, 1H, J=12 Hz), 6.17 (dt, 1H, J=16 Hz, 7 Hz), 6.27 (s, 1H), 6.48 (td, 1H, J=9 Hz, 2 Hz), 6.67 (d, 1H, J=13 Hz), 6.77 (d, 1H, J=16 Hz), 7.95 (s, 1H), 11.08 (brs, 1H).

EXAMPLE 29

3-[3-[1-[2-Amino-6-di(2-hydroxyethyl)amino-4-pyrimidinyl]-5-methyl-4-pyrazolyl]-2-trans-propen-1-yl]-7,9-difluoro -2,3,4,4a,5,6-hexahydro-1H-pyrazino[1,2-a]quinoline hydrochloride (isomer B)

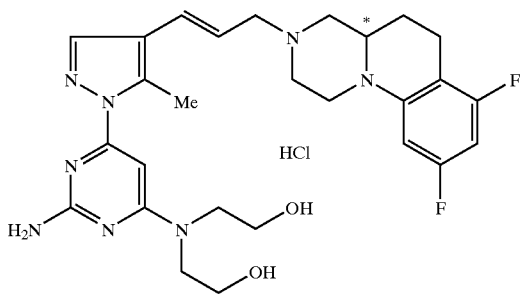

Optically active compound

Using 18 mg of the compound obtained in Example 27-(9) and changing ethanolamine of Example 27-(10) to 2,2'-iminodiethanol, the same reaction and after-treatment of Example 27-(10) were carried out to obtain 6 mg of the title compound.

Melting point: 161–166° C. (decomposition)

$^1$H-NMR (DMSO-d$_6$) δ: 1.55–1.70 (m, 1H), 2.00–2.10 (m, 1H), 2.50–2.75 (m, 2H), 2.66 (s, 3H), 2.80–3.70 (m, 12H), 3.67 (t, 2H, J=5 Hz), 3.80–4.00 (m, 2H), 4.13 (brd, 1H, J=13 Hz), 6.16 (dt, 1H, J=16 Hz, 7 Hz), 6.30 (s, 1H), 6.51 (td, 1H, J=9 Hz, 2 Hz), 6.69 (d, 1H, J=13 Hz), 6.78 (d, 1H, J=16 Hz), 7.97 (s, 1H), 8.55 (brs, 1H)

EXAMPLE 30

(+/−)-3-[3-[1-[2-Amino-6-(3-hydroxy-1-azetidinyl)-4-pyrimidinl]-2-trans-propen-1-yl]-7,9-difluoro -2,3,4,4a,5,6-hexahydro-1H-pyrazino[2,1-c]-1,4-benzoxazine hydrochloride

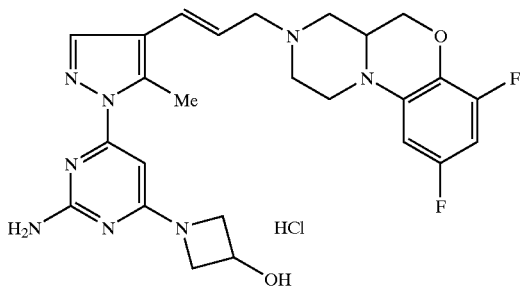

An 83 mg portion of 3-[1-[2-amino-6-(3-hydroxy-1-azetidinyl)-4-pyrimidinyl]-5-methyl-4-pyrazolyl]-2-trans-propenal was suspended in 11 ml of ethanol, mixed with 63 mg of (+/−)-7,9-difluoro-2,3,4,4a,5,6-hexahydro-1H-pyrazino[2,1-c]-1,4-benzoxazine and stirred at 80° C. for 1 hour. The reaction solution was cooled to room temperature and mixed with 158 μl of acetic acid and then with 52 mg of sodium cyanoborohydride, and the mixture was stirred at room temperature for 14 hours. The reaction solution was mixed with water and saturated sodium bicarbonate aqueous solution and extracted four times with chloroform, the organic layer was dried with anhydrous sodium sulfate, and then the solvent was evaporated. The thus obtained residue was applied to a silica gel column chromatography (270 to 400 mesh, 80 g) and developed with a chloroform-methanol (95:5) mixed solvent, and then the fractions containing the compound of interest were concentrated. The residue (102 mg) was treated with 1 N hydrochloric acid/ethanol and then recrystallized from isopropyl alcohol to obtain 77 mg of the title compound.

$^1$H-NMR (DMSO-d$_6$) δ: 2.67 (s, 3H), 2.80–4.45 (m, 15H), 4.55–4.65 (m, 1H), 6.03 (s, 1H), 6.17 (dt, 1H, J=16 Hz, 7 Hz), 6.65 (t, 1H, J=9 Hz), 6.75–6.80 (m, 3H), 8.01 (s, 1H), 11.19 (brs, 1H).

EXAMPLE 31

1-[1-[4-Amino-6-(2-hydroxyethylamino)-1,3,5-triazin-2-yl]-5-methyl-4-pyrazolyl]-3-[4-(3,5-difluorophenyl)-1-piperazinyl]-1-trans-propene hydrochloride

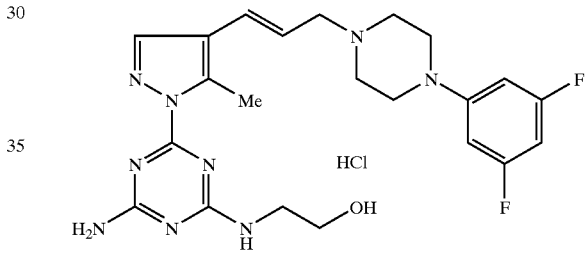

(1) 2-Chloro-4-(2-hydroxyethylamino)-6-(4-methoxybenzylamino)-1,3,5-triazine

A 1.43 g (5.01 mmol) portion of 2,4-dichloro-6-(4-methoxybenzylamino)-1,3,5-triazine was suspended in 100 ml of ethanol, mixed with 303 μl (5.01 mmol) of 2-aminoethanol and 693 mg of potassium carbonate and stirred at 45° C. for 1 day. After evaporation of the solvent under a reduced pressure, water was added to the residue and the resulting precipitate was collected by filtration to obtain 1.56 g (quantitative) of the title compound as a white powder.

$^1$H-NMR (CDCl$_3$) δ: 3.57–3.61 (m, 2H), 3.76–3.79 (m, 2H), 3.80 (s, 3H), 4.47–4.54 (m, 2H), 6.86 (d, 2H, J=9 Hz), 7.21 (d, 2H, J=8 Hz).

(2) Ethyl 1-[4-(2-hydroxyethylamino)-6-(4-methoxybenzylamino)-1,3,5-triazin-2-yl]-5-methyl-4-pyrazolecarboxylate A 1.55 g (5.00 mmol) portion of the compound obtained in Example 31-(1) was suspended in 30 ml of ethanol, mixed with 1.56 ml (50.1 mmol) of hydrazine monohydrate and 692 mg (5.00 mmol) of potassium carbonate and heated under reflux for 21 hours. After evaporation of the solvent under a reduced pressure, the residue was mixed with water and extracted with a chloroform-methanol (9:1) mixed solvent. The organic layers were combined and dried with anhydrous sodium sulfate, and then the solvent was evaporated under a reduced pressure. The thus obtained residue was dissolved in 30 ml of ethanol and mixed with 582 mg (3.13 mmol) of ethyl 2-(ethoxymethylene)acetoacetate, and the mixture was stirred at room temperature for 2 hours and then heated under reflux for 16 hours. The solvent was evaporated under a reduced pressure, the thus obtained residue was applied to a silica gel chromatography and developed with a chloroform-methanol (97:3) mixed solvent, and then the fractions containing the compound of interest were concentrated to obtain 1.10 g (51%) of the title compound as a light white powder.

$^1$H-NMR (CDCl$_3$) δ: 1.36 (t, 3H, J=7 Hz), 1.65 (brs, 1H), 2.93, 2.98 (each s, 3H), 3.56–3.64 (m, 2H), 3.79 (s, 3H), 3.75–3.86 (m, 2H), 4.30 (q, 4H, J=7 Hz), 4.51–4.59 (m, 2H), 5.63–6.03 (m, 2H), 6.87 (d, 2H, J=8 Hz), 7.23 (d, 2H, J=8 Hz), 8.00, 8.02 (each s, 1H).

(3) 1-[4-(2-Hydroxyethylamino)-6-(4-methoxybenzylamino)-1,3,5-triazin-2-yl]-5-methyl-4-pyrazolecarbaldehyde A 1.10 g (2.57 mmol) portion of the compound obtained in Example 31-(2) was dissolved in 100 ml of methylene chloride and, in an atmosphere of nitrogen, the solution was cooled to −78° C., mixed with 11 ml of diisobutylaluminum hydride (1 M hexane solution), stirred at the same temperature for 1 hour, further mixed with 5 ml of diisobutylaluminum hydride (1 M hexane solution) and stirred for 1 hour. The reaction solution was mixed with 500 ml of 10% potassium tartarate aqueous solution and stirred at room temperature for 16 hours. After separation of the organic layer, the water layer was extracted twice with chloroform and then five times with a chloroform-methanol (9:1) mixed solvent. The organic layers were combined and dried with anhydrous sodium sulfate, and then the solvent was evaporated under a reduced pressure. The thus obtained residue was dissolved in 100 ml of 1,4-dioxane, mixed with 1.79 g of activated manganese dioxide and then stirred at room temperature for 2 days. The insoluble matter was removed by celite filtration and then the filtrate was concentrated to obtain 686 mg (70%) of the title compound as a white solid.

$^1$H-NMR (CDCl$_3$) δ: 2.83–2.94 (m, 3H), 3.53–3.88 (m, 7H), 4.47–4.63 (m, 2H), 6.81–6.87 (m, 2H), 7.18–7.23 (m, 2H), 7.99–8.07 (m, 1H), 10.02 (s, 1H).

(4) Ethyl 3-[[4-(2-hydroxyethylamino)-6-(4-methoxybenzylamino)-1,3,5-triazin-2-yl]-5-methyl-4-pyrazolyl]-2-trans-propenoate A mixture composed of 686 mg of the compound obtained in Example 31-(3), 653 mg of (carboxyethoxymethylene)triphenylphosphorane and 100 ml of toluene was heated under reflux for 19 hours. After evaporation of the solvent under a reduced pressure, the residue was cooled to room temperature and the resulting precipitate was collected by filtration to obtain 440 mg (54%) of the title compound as a white solid.

$^1$H-NMR (CDCl$_3$) δ: 1.32 (t, 3H, J=7 Hz), 2.69–2.75 (m, 3H), 3.55–3.64 (m, 2H), 3.78–3.82 (m, 5H), 4.24 (q, 2H, J=7 Hz), 4.52–4.59 (m, 2H), 5.55–5.91 (m, 2H), 6.25 (d, 1H, J=16 Hz), 6.87 (d, 2H, J=8 Hz), 7.25 (d, 2H, J=8 Hz), 7.57 (d, 1H, J=16 Hz), 7.89–7.91 (m, 1H).

(5) 3-[[4-(2-Hydroxyethylamino)-6-(4-methoxybenzylamino)-1,3,5-triazin-2-yl]-5-methyl-4-pyrazolyl]-2-trans-propenal A 440 mg portion of the compound obtained in Example 31-(4) was dissolved in 40 ml of methylene chloride and, in an atmosphere of nitrogen, the solution was cooled to −78° C., mixed with 5.0 ml of diisobutylaluminum hydride (1 M hexane solution), stirred at the same temperature for 30 minutes, and then stirred at 0° C. for 1 hour. The reaction solution was cooled to −78° C., mixed with 10% potassium tartarate aqueous solution and stirred at room temperature for 4 hours, and then the organic layer was separated and the water layer was extracted three times with chloroform and ten times with a chloroform-methanol (9:1) mixed solvent. The organic layers were combined and dried with anhydrous sodium sulfate, and then the solvent was evaporated under a reduced pressure. The thus obtained residue was dissolved in 50 ml of 1,4-dioxane, mixed with 844 mg of activated manganese dioxide and then stirred at room temperature for 18 hours. The insoluble matter was removed by celite filtration and then the filtrate was concentrated to obtain 784 mg (97%) of the title compound as a white solid.

$^1$H-NMR (CDCl$_3$) δ: 2.68–2.76 (m, 3H), 3.53–3.78 (m, 7H), 4.50–5.56 (m, 2H), 5.86–6.39 (m, 2H), 6.48–6.54 (m, 1H), 6.83–6.87 (m, 2H), 7.21–7.25 (m, 2H), 7.33 (d, 1H, J=16 Hz), 7.85–7.91 (m, 1H), 9.61 (d, 1H, J=8 Hz)

(6) 1-[1-[4-(2-Hydroxyethylamino)-6-(4-methoxybenzylamino)-1,3,5-triazin-2-yl]-5-methyl-4-pyrazolyl]-3-[4-(3,5-difluorophenyl)-1-piperazinyl]-1-trans-propene A 384 mg portion of the compound obtained in Example 31-(5) was dissolved in 50 ml of ethanol, mixed with 291 mg of 1-(3,5-difluorophenyl)piperazine and stirred at room temperature for 16 hours. Next, after adding 537 μl of acetic acid, 147 mg of sodium cyanoborohydride was added thereto by dividing it into 3 portions over 4 hours, and then the mixture was stirred at room temperature for 2 days. Saturated sodium bicarbonate aqueous solution was added to the reaction solution, ethanol was evaporated under a reduced pressure, and then the residue was extracted with chloroform. The organic layer was dried with anhydrous sodium sulfate, the solvent was evaporated, the thus obtained residue was applied to a silica gel chromatography and developed with a chloroform-methanol (49:1) mixed solvent, and then the fractions containing the compound of interest were concentrated to obtain 365 mg (66%) of the title compound as a white powder.

$^1$H-NMR (CDCl$_3$) δ: 2.61–2.63 (m, 3H), 3.16–3.23 (m, 6H), 3.53–3.79 (m, 7H), 4.54–4.58 (m, 2H), 6.03–6.12 (m, 1H), 6.24 (dt, 1H, J=9 Hz, 2 Hz), 6.34–6.37 (m, 2H), 6.86 (d, 2H, J=8 Hz), 7.23 (d, 2H, J=8 Hz), 7.81 (s, 1H).

(7) 1-[1-[4-Amino-6-(2-hydroxyethylamino)-1,3,5-triazin-2-yl]-5-methyl-4-pyrazolyl]-3-[4-(3,5-difluorophenyl)-1-piperazinyl]-1-trans-propene hydrochloride A 365 mg portion of the compound obtained in Example 31-(6) was mixed with 50 ml of trifluoroacetic acid and 1 ml of thioanisole and then heated under reflux for 2 days. After evaporation of the solvent under a reduced pressure, the residue was mixed with 100 ml of saturated sodium bicarbonate aqueous solution and then extracted with a chloroform-methanol (9:1) mixed solvent. The organic layer was dried with anhydrous sodium sulfate, the solvent was evaporated under a reduced pressure, the thus obtained residue was applied to a silica gel chromatography and developed with a chloroform-methanol (19:1) mixed solvent, and then the fractions containing the compound of interest were concentrated. The resulting residue was made into hydrochloride with 1 N hydrochloric acid/ethanol and then recrystallized from ethanol to obtain 188 mg (54%) of the title compound as a white powder.

$^1$H-NMR (DMSO-d$_6$) δ: 2.68 (s, 3H), 3.10 (dd, 2H, J=21 Hz, 9 Hz), 3.24 (t, 2H, J=8 Hz), 3.38–3.43 (m, 2H), 3.49–3.57 (m, 4H), 3.94–3.98 (m, 4H), 6.21–6.30 (m, 1H), 6.57 (t, 1H, J=9 Hz), 6.72 (d, 2H, J=9 Hz), 6.81 (d, 1H, J=16 Hz), 8.20 (s, 1H), 11.25 (brs, 1H).

EXAMPLE 32

1-[1-[4-Amino-6-(3-hydroxy-1-azetidinyl)-1,3,5-triazin-2-yl]-5-methyl-4-pyrazolyl]-3-[4-(3,5-difluorophenyl)-1-piperazinyl]-1-1-trans-propene hydrochloride

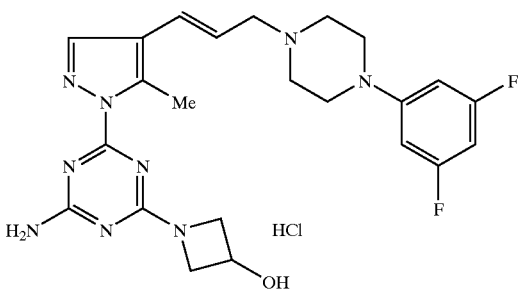

(1) 2-Chloro-4-(3-hydroxy-1-azetidinyl)-6-(4-methoxybenzylamino)-1,3,5-triazine

A 1.47 g (5.16 mmol) portion of 2,4-dichloro-6-(4-methoxybenzylamino)-1,3,5-triazine was suspended in 100 ml of ethanol, mixed with 568 mg (5.18 mmol) of 3-hydroxyazetidine hydrochloride and 1.43 g of potassium carbonate and stirred at room temperature for 7 hours. After evaporation of the solvent under a reduced pressure, water was added to the residue and the resulting precipitate was collected by filtration to obtain 1.54 g (93%) of the title compound as a white powder.

$^1$H-NMR (CDCl$_3$/CD$_3$OD) δ: 3.80 (s, 3H), 3.83–4.01 (m, 2H), 4.28–4.50 (m, 2H), 4.64 (brs, 1H), 6.83–6.85 (m, 2H), 7.22 (m, 1H, J=9 Hz).

(2) Ethyl 1-[4-(3-hydroxy-1-azetidinyl)-6-(4-methoxybenzylamino)-1,3,5-triazin-2-yl]-5-methyl-4-pyrazolecarboxylate Using 1.54 g (4.79 mmol) of the compound obtained in Example 32-(1), the same reaction and after-treatment of Example 31-(2) were carried out to obtain 1.80 g (85%) of the title compound as a light yellow powder.

$^1$H-NMR (CDCl$_3$) δ: 1.36 (t, 3H, J=7 Hz), 2.95 (s, 3H), 3.79 (s, 3H), 4.03 (dd, 2H, J=10 Hz, 4 Hz), 4.30 (q, 2H, J=7 Hz), 4.41 (t, 2H, J=7 Hz), 4.55 (d, 2H, J=6 Hz), 4.77 (brs, 1H), 5.76 (brs, 1H), 6.85 (d, 2H, J=9 Hz), 7.24 (d, 2H, J=9 Hz), 8.00 (s, 1H).

(3) 1-[4-(3Hydroxy-1-azetidinyl)-6-(4-methoxybenzylamino)-1,3,5-triazin-2-yl]-5-methyl-4-pyrazolecarbaldehyde Using 1.80 g (4.10 mmol) of the compound obtained in Example 32-(2), the same reaction and after-treatment of Example 31-(3) were carried out to obtain 1.24 g (77%) of the title compound as a white solid.

(4) Ethyl 3-[[4-(3-hydroxy-1-azetidinyl)-6-(4-methoxybenzylamino)-1,3,5-triazin-2-yl]-5-methyl-4-pyrazolyl]-2-trans-propenoate Using 1.24 g of the compound obtained in Example 32-(3) and 1.15 g of (carboethoxymethylene) triphenylphosphorane, the same reaction and after-treatment of Example 31-(4) were carried out to obtain 1.08 g (74%) of the title compound as a white solid.

$^1$H-NMR (CDCl$_3$) δ: 1.32 (t, 3H, J=7 Hz), 2.72 (s, 3H), 3.80 (s, 3H), 4.03 (d, 2H, J=7 Hz), 4.24 (q, 2H, J=7 Hz), 4.41 (t, 2H, J=7 Hz), 4.55 (d, 2H, J=6 Hz), 4.78 (brs, 1H), 5.71 (brs, 1H), 6.24 (d, 1H, J=16 Hz), 6.85 (d, 2H, J=9 Hz), 7.24 (d, 2H, J=9 Hz), 7.58 (d, 1H, J=16 Hz), 7.94 (s, 1H).

(5) 3-[[4-(3-Hydroxy-1-azetidinyl)-6-(4-methoxybenzylamino)-1,3,5-triazin-2-yl]-5-methyl-4-pyrazolyl]-2-trans-propenal Using 1.08 g of the compound obtained in Example 32-(4), the same reaction and after-treatment of Example 31-(5) were carried out to obtain 784 mg (80%) of the title compound as a white solid.

$^1$H-NMR (CDCl$_3$) δ: 2.77 (s, 3H), 3.80 (s, 3H), 4.04 (dd, 2H, J=10 Hz, 4 Hz), 4.42 (t, 2H, J=7 Hz), 4.55 (d, 2H, J=6 Hz), 4.80 (brs, 1H), 5.75 (brs, 1H), 6.55 (dd, 1H, J=16 Hz, 8 Hz), 6.86 (d, 2H, J=9 Hz), 7.24 (d, 2H, J=9 Hz), 7.37 (d, 1H, J=16 Hz), 7.96 (s, 1H), 9.63 (d, 1H, J=8 Hz).

(6) 1-[1-[4-(3-Hydroxy-1-azetidinyl)-6-(4-methoxybenzylamino)-1,3,5-triazin-2-yl]-5-methyl-4-pyrazolyl]-3-[4-(3,5-difluorophenyl)-1-piperazinyl]-1-trans-propene Using 577 mg of the compound obtained in Example 32-(5), the same reaction and after-treatment of Example 31-(6) were carried out to obtain 627 mg (56%) of the title compound as a white powder.

$^1$H-NMR (CDCl$_3$) δ: 2.61–2.63 (m, 3H), 3.20–3.23 (m, 6H), 3.78 (s, 3H), 3.96–4.01 (m, 2H), 4.38 (t, 2H, J=7 Hz), 4.54 (d, 2H, J=6 Hz), 4.75 (brs, 1H), 5.77 (brs, 1H), 6.05 (dt, 1H, J=16 Hz, 8 Hz), 6.24 (dt, 1H, J=9 Hz, 2 Hz), 6.36 (d, 2H, J=9 Hz), 6.38 (d, 2H, J=9 Hz), 6.84 (d, 2H, J=8 Hz), 7.24 (d, 2H, J=8 Hz), 7.83 (s, 1H).

(7) 1-[1-[4-Amino-6-(3-hydroxy-1-azetidinyl)-1,3,5-triazin-2-yl]-5-methyl-4-pyrazolyl]-3-[4-(3,5-difluorophenyl)-1-piperazinyl]-1-trans-propene hydrochloride Using 627 mg of the compound obtained in Example 32-(6), the same reaction and after-treatment of Example 31-(7) were carried out to obtain 360 mg (59%) of the title compound as a white powder.

$^1$H-NMR (DMSO-d$_6$) δ: 2.62 (s, 3H), 3.08–3.23 (m, 4H), 3.51 (d, 2H, J=11 Hz), 3.88–3.98 (m, 6H), 4.22–4.30 (m, 2H), 4.54–4.60 (m, 1H), 6.22 (dt, 1H, J=16 Hz, 8 Hz), 6.57 (t, 1H, J=9 Hz), 6.73 (d, 2H, J=9 Hz), 6.79 (d, 1H, J=16 Hz), 8.07 (s, 1H), 10.88 (brs, 1H).

EXAMPLE 33

1-[1-[2-Amino-6-(3-hydroxy-1-pyrrolidinyl)-4-pyrimidinyl]-5-methyl-4-pyrazolyl]-3-[4-(3,5-difluorophenyl)-1-piperazinyl]-1-trans-propene hydrochloride

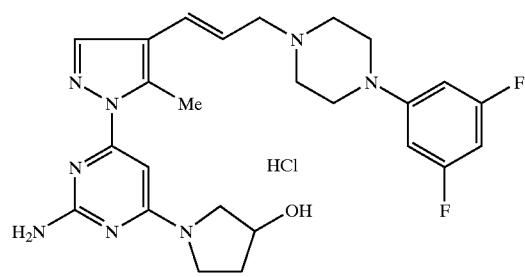

A 23 mg (0.05 mmol) portion of the compound obtained in Example 11-(1) was suspended in 2 ml of ethanol and then mixed with 13.5 mg of 3-hydroxypyrrolidine and heated under reflux for 6 days. After evaporation of the solvent under a reduced pressure, the residue was applied to a silica gel column chromatography and developed with a chloroform-methanol (19:1) mixed solvent, and the fractions containing the compound of interest were concentrated. The residue was made into hydrochloride with 1 N hydrochloric acid/ethanol and then recrystallized from an ethanol-ether mixed solvent to obtain 10 mg of the title compound as a slightly brown powder.

$^1$H-NMR (DMSO-$d_6$) δ: 1.94–2.03 (m, 2H), 2.67 (s, 3H), 3.07–3.71 (m, 10H), 3.94–3.98 (m, 4H), 4.42 (s, 1H), 6.25–6.40 (m, 2H), 6.58 (t, 1H, J=9 Hz), 6.73 (d, 2H, J=9 Hz), 6.80 (d, 2H, J=16 Hz), 8.14 (s, 1H), 11.08 (brs, 1H)

EXAMPLE 34

1-[1-[2-Amino-6-[(2S)-2-hydroxymethyl-1-pyrrolidinyl]-4-pyrimidinyl]-5-methyl-4-pyrazolyl]-3-[4-(3,5-difluorophenyl)-1-piperazinyl]-1-trans-propene hydrochloride

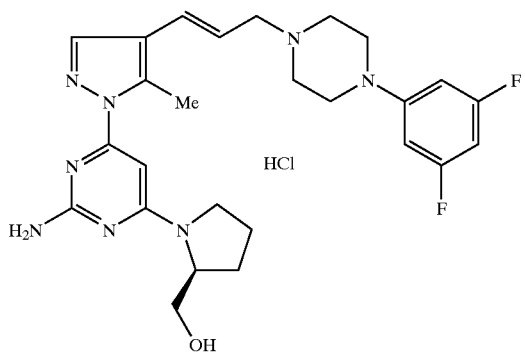

Using 23 mg (0.05 mmol) of the compound obtained in Example 11-(1) and 15.7 mg of (S)-2-hydroxymethylpyrrolidine, the same reaction and after-treatment of Example 33 were carried out to obtain 6 mg of the title compound as a slightly brown powder.

$^1$H-NMR (DMSO-$d_6$) δ: 1.99–2.08 (m, 3H), 2.66 (s, 3H), 3.08–3.52 (m, 10H), 3.94–3.98 (m, 4H), 6.21 (dt, 1H, J=16 Hz, 8 Hz), 6.59 (t, 1H, J=9 Hz), 6.73 (d, 2H, J=9 Hz), 6.80 (d, 2H, J=16 Hz), 8.12 (s, 1H), 10.83 (brs, 1H)

EXAMPLE 35

1-[1-[2-Amino-6-[N-methyl-(2-hydroxyethyl)amino]-4-pyrimidinyl]-5-methyl-4-pyrazolyl]-3-[4-(3,5-difluorophenyl)-1-piperazinyl]-1-trans-propene hydrochloride

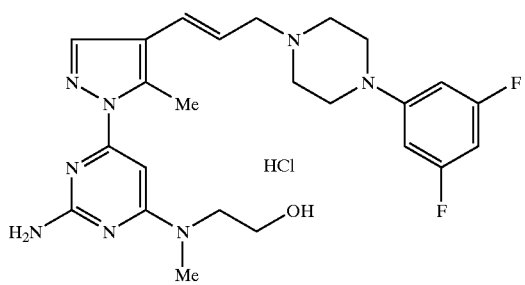

Using 446 mg (1.0 mmol) of the compound obtained in Example 11-(1) and 803 μl of N-methyl-2-aminoethanol, the same reaction and after-treatment of Example 33 were carried out to obtain 230 mg of the title compound as a slightly pink powder.

$^1$H-NMR (DMSO-$d_6$) δ: 2.65 (s, 3H), 3.08–3.26 (m, 7H), 3.50 (d, 2H, J=12 Hz), 3.63–3.79 (m, 4H), 3.94–3.98 (m, 4H) 6.24 (dt, 1H, J=16 Hz, 8 Hz), 6.47 (brs, 1H), 6.58 (t, 1H, J=9 Hz), 6.73 (d, 2H, J=9 Hz), 6.81 (d, 2H, J=16 Hz), 8.15 (s, 1H), 11.19 (brs, 1H)

EXAMPLE 36

1-[1-[2-Amino-6-(3-hydroxypropyl)amino-4-pyrimidinyl]-5-methyl-4-pyrazolyl]-3-[4-(3,5-difluorophenyl)-1-piperazinyl ]-1-trans-propene hydrochloride

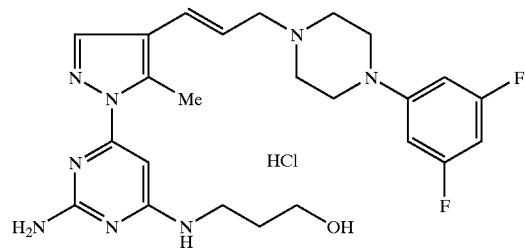

Using 23 mg (0.05 mmol) of the compound obtained in Example 11-(1) and 201 μl of 3-aminopropanol, the same reaction and after-treatment of Example 33 were carried out to obtain 27 mg of the title compound as a slightly brown powder.

$^1$H-NMR (DMSO-$d_6$) δ: 1.70–1.73 (m, 2H), 2.64 (s, 3H), 3.08–3.66 (m, 10H), 3.94–3.98 (m, 4H), 6.24 (dt, 1H, J=16 Hz, 8 Hz), 6.43 (brs, 1H), 6.57 (t, 1H, J=9 Hz), 6.73 (d, 2H, J=9 Hz), 6.80 (d, 2H, J=16 Hz), 8.15 (s, 1H), 11.03 (brs, 1H)

EXAMPLE 37

1-[1-[2-Amino-6-(4-hydroxybutyl)amino-4-pyrimidinyl]-5-methyl-4-pyrazolyl]-3-[4-(3,5-difluorophenyl)-1-piperazinyl]-1-trans-propene hydrochloride

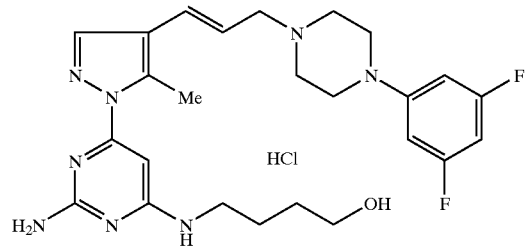

Using 23 mg (0.05 mmol) of the compound obtained in Example 11-(1) and 238 μl of 4-aminobutanol, the same reaction and after-treatment of Example 33 were carried out to obtain 22 mg of the title compound as a slightly brown powder.

$^1$H-(DMSO-$d_6$) δ: 1.48–1.61 (m, 4H), 2.64 (s, 3H), 3.08–3.52 (m, 10H), 3.94–3.98 (m, 4H), 6.23 (dt, 1H, J=16 Hz, 8 Hz), 6.42 (brs, 1H), 6.57 (t, 1H, J=9 Hz), 6.73 (d, 2H, J=9 Hz), 6.80 (d, 2H, J=16 Hz), 8.16 (s, 1H), 10.95 (brs, 1H)

EXAMPLE 38

1-[1-[2-Amino-6-[(3S,4S)-3,4-dihydroxy-1-pyrrolidinyl]-4-pyrimidinyl]-5-methyl-4-pyrazolyl]-3-[4-(3,5-difluorophenyl)-1-piperazinyl]-1-trans-propene hydrochloride

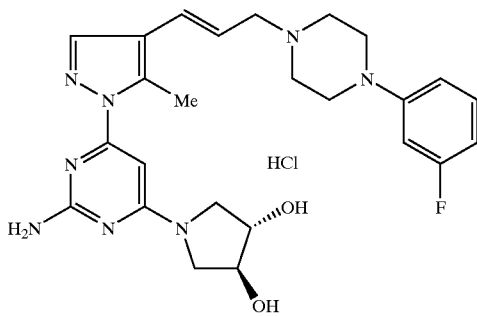

A 650 mg (3.36 mmol) portion of (3S,4S)-1-benzyl -3,4-dihydrxypyrrolidine was dissolved in 100 ml of ethanol and then mixed with 500 mg of palladium hydroxide-carbon and subjected to 16 hours of catalytic hydrogenation at 50° C. After removing the insoluble matter by filtration, the solvent was evaporated under a reduced pressure, and then the residue was dissolved in 50 ml of ethanol, mixed with 500 mg (1.12 mmol) of the compound obtained in Example 11-(1) and heated under reflux for day. The solvent was evaporated under a reduced pressure, the residue was applied to a silica gel chromatography and developed with an organic layer of chloroform-methanol-water (20:3:1), and then the fractions containing the compound of interest were concentrated. The residue was made into hydrochloride with 1 N hydrochloric acid/ethanol and then recrystallized from ethanol to obtain 485 mg of the title compound as a white powder.

$^1$H-NMR (DMSO-$d_6$) δ: 2.51 (s, 3H), 3.09–3.68 (m, 10H), 3.95–3.98 (m, 4H), 4.09 (s, 2H), 6.23 (dt, 1H, J=16 Hz, 8 Hz), 6.27 (brs, 1H), 6.58 (t, 1H, J=9 Hz), 6.73 (d, 2H, J=9 Hz), 6.81 (d, 2H, J=16 Hz), 8.16 (s, 1H), 10.79 (brs, 1H)

EXAMPLE 39

1-[1-[2-Amino-6-(3-hydroxypiperidino)-4-pyrimidinyl]-5-methyl-4-pyrazolyl]-3-[4-(3,5-difluorophenyl)-1-piperazinyl]-1-trans-propene hydrochloride

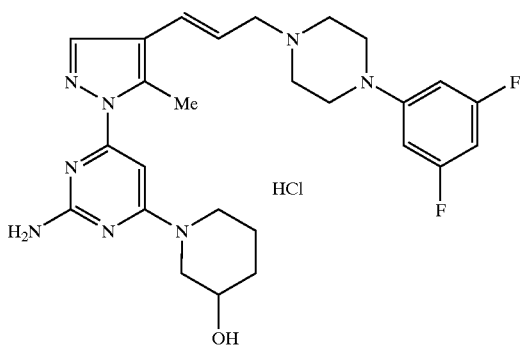

Using 23 mg (0.05 mmol) of the compound obtained in Example 11-(1) and 26 mg of 3-hydroxypiperidine, the same reaction and after-treatment of Example 33 were carried out to obtain 24 mg of the title compound as a white powder.

$^1$H-NMR (DMSO-$d_6$) δ: 1.35–1.49 (m, 2H), 1.68–1.75 (m, 1H), 1.83–1.92 (m, 1H), 2.63 (s, 3H), 3.07–3.55 (m, 10H), 3.90–3.97 (m, 5H), 6.25 (dt, 1H, J=16 Hz, 8 Hz), 6.43 (s, 1H), 6.59 (t, 1H, J=9 Hz), 6.74 (d, 2H, J=9 Hz), 6.79 (d, 2H, J=16 Hz), 8.09 (s, 1H), 10.59 (brs, 1H)

EXAMPLE 40

1-[1-[2-Amino-6-(4-hydroxypiperidino)-4-pyrimidinyl]-5-methyl-4-pyrazolyl]-3-[4-(3,5-difluorophenyl)-1-piperazinyl]-1-trans-propene hydrochloride

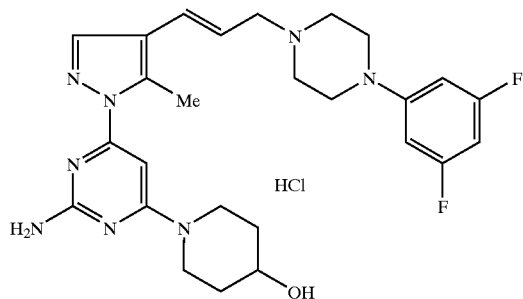

Using 23 mg (0.05 mmol) of the compound obtained in Example 11-(1) and 26 mg of 4-hydroxypiperidine, the same reaction and after-treatment of Example 33 were carried out to obtain 24 mg of the title compound as a white powder.

$^1$H-NMR (DMSO-$d_6$) δ: 1.36–1.48 (m, 2H), 1.78–1.87 (m, 2H), 2.63 (s 3H), 3.07–3.97 (m, 15H), 6.25 (dt, 1H, J=16 Hz, 8 Hz), 6.55 (s, 1H), 6.58 (t, 1H, J=Hz), 6.73 (d, 2H, J=9 Hz), 6.80 (d, 2H, J=16 Hz), 8.14 (s, 1H), 11.42 (brs, 1H)

EXAMPLE 41

1-[1-[2-Amino-6-[(2R)-2-hydroxymethyl-1-pyrrolidinyl]-4-pyrimidinyl]-5-methyl-4-pyrazolyl]-3-[4-(3,5-difluorophenyl)-1-piperazinyl]-1-trans-propene hydrochloride

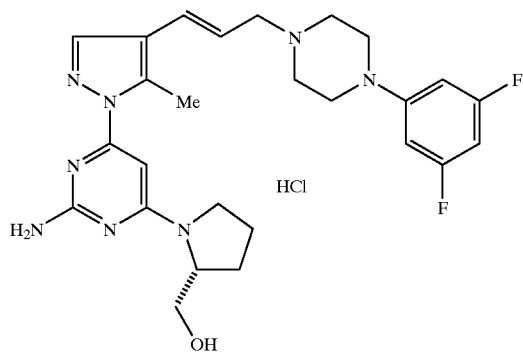

Using 23 mg (0.05 mmol) of the compound obtained in Example 11-(1) and 15.7 mg of (R)-2-hydroxymethylpyrrolidine, the same reaction and after-treatment of Example 33 were carried out to obtain 20 mg of the title compound as a slightly brown powder.

$^1$H-NMR (DMSO-$d_6$) δ: 1.96–2.07 (m, 4H), 2.65 (s, 3H), 3.06–3.50 (m, 10H), 3.93–3.97 (m, 4H), 6.21–6.23 (m, 2H), 6.58 (t, 1H, J=9 Hz), 6.72 (d, 2H, J=9 Hz), 6.79 (d, 2H, J=16 Hz), 8.12 (s, 1H), 11.00 (brs, 1H)

EXAMPLE 42

1-[1-(2-Amino-6-carboxymethylamino-4-pyrimidinyl)-5-methyl-4-pyrazolyl]-3-[4-(3,5-difluorophenyl)-1-piperazinyl]-1-trans-propene hydrochloride

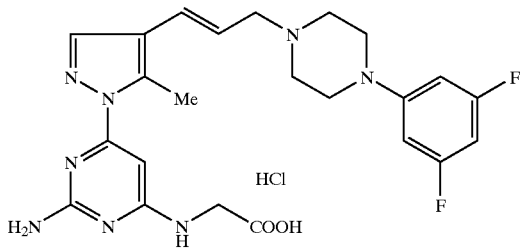

A 23 mg (0.05 mmol) portion of the compound obtained in Example 11-(1) was suspended in 2 ml of 80% ethanol aqueous solution and then mixed with 19.4 mg of glycine and 40 μl of triethylamine, and heated under reflux for 7 days. After evaporation of the solvent under a reduced pressure, the residue was purified by applying it to a silica gel chromatography and developing with an organic layer of chloroform-methanol-water (7:3:1). The resulting residue was made into hydrochloride with 1 N hydrochloric acid/ethanol and then recrystallized from an ethanol-ether mixed solvent to obtain 14 mg of the title compound as a slightly brown powder.

$^1$H-NMR (DMSO-$d_6$) δ: 2.67 (s, 3H), 3.07–3.58 (m, 6H), 3.95–3.98 (m, 4H), 4.10 (s, 2H), 6.12–6.23 (m, 1H), 6.29 (brs, 1H), 6.59 (t, 1H, J=9 Hz), 6.73 (d, 2H, J=9 Hz), 6.79 (d, 2H, J=16 Hz), 8.10 (s, 1H), 10.78 (brs, 1H)

EXAMPLE 43

1-[1-[2-Amino-6-[(3R)-3-hydroxy-1-pyrrolidinyl]-4-pyrimidinyl)-5-methyl-4-pyrazolyl]-3-[4-(3,5-difluorophenyl)-1-piperazinyl]-1-trans-propene hydrochloride

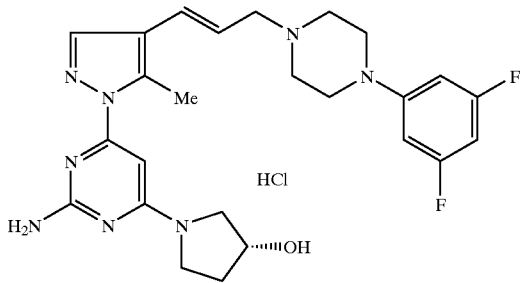

A 500 mg portion of the compound obtained in Example 11-(1) was suspended in 50 ml of ethanol and then mixed with 416 mg of (R)-(−)-3-hydroxypyrrolidine hydrochloride and 1.56 mg of triethylamine and heated under reflux for 20 hours. After evaporation of the solvent under a reduced pressure, the residue was applied to a silica gel chromatography and developed with a chloroform-methanol (19:1) mixed solvent, and then the fractions containing the compound of interest were concentrated. The resulting residue was made into hydrochloride with 1 N hydrochloric acid/ethanol and then recrystallized from ethanol to obtain 440 mg of the title compound as a white powder.

$^1$H-NMR (DMSO-$d_6$) δ: 1.94–2.02 (m, 2H), 2.67 (s, 3H), 3.07–3.19 (m, 4H), 3.46–3.58 (m, 4H), 3.92–3.98 (m, 4H), 4.41 (s, 1H), 6.13–6.28 (m, 2H), 6.59 (t, 1H, J=9 Hz), 6.73 (d, 2H, J=9 Hz), 6.80 (d, 2H, J=16 Hz), 8.13 (s, 1H), 10.92 (brs, 1H)

EXAMPLE 44

1-[1-[2-Amino-5-methoxy-6-(3-hydroxy-1-azetidinyl)-4-pyrimidinyl]-5-methyl-4-pyrazolyl]-3-[4-(3,5-difluorophenyl)-1-piperazinyl]-1-trans-propene hydrochloride

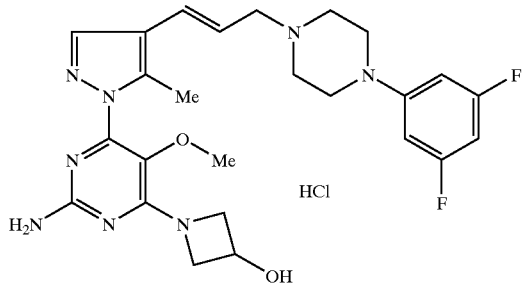

(1) 2-Amino-4,6-dihydroxy-5-methoxypyrimidine

A mixture composed of 12 g of guanidine hydrochloride, 9 g of sodium ethoxide and 100 ml of ethanol was heated under reflux for 1 hour, and then the reaction solution was cooled to room temperature, further mixed with 10 g of dimethyl methoxymalonate and heated under reflux for 48 hours. The reaction solution was cooled to room temperature, adjusted to a pH value of about 4 by adding 1 N hydrochloric acid solution and stirred, and then the thus precipitated powder was collected by filtration to obtain 2.0 g of the title compound.

$^1$H-NMR (DMSO-$d_6$) δ: 3.32 (s, 3H), 6.31 (brs, 2H), 10.41 (brs, 2H).

(2) 2-Amino-4-chloro-6-hydrazino-5-methoxypyrimidine

A 2.0 g portion of the compound obtained in Example 44-(1) was mixed with 10 ml of phosphorus oxychloride and stirred at 60 to 80° C. for 5 hours. The reaction solution was gradually added to ice water and stirred and then the resulting precipitate was collected by filtration. A 0.45 g portion of the thus obtained 2-amino-4,6-dichloro-5-methoxypyrimidine was mixed with 20 ml of ethanol and then mixed with 0.14 g of hydrazine monohydrate and 0.5 g of potassium carbonate and heated under reflux for 72 hours. After evaporation of the solvent under a reduced pressure, the residue was mixed with water and extracted with a chloroform-methanol (9:1) mixed solvent. The organic layer was dried with anhydrous sodium sulfate and then the solvent was evaporated under a reduced pressure to obtain 0.39 g of the title compound.

$^1$H-NMR (DMSO-$d_6$) δ: 3.31 (s, 2H), 3.55 (s, 3H), 4.24 (brs, 1H), 6.24 (brs, 2H).

(3) ethyl 1-(2-amino-6-chloro-5-methoxy-4-pyrimidinyl)-5-methyl-4-pyrazolecarboxylate A 0.39 g portion of the compound obtained in Example 44-(2) was mixed with 50 ml of ethanol and 0.42 g of ethyl 2-(ethoxymethylene)acetoacetate, stirred at room temperature for 20 minutes and then heated under reflux for 24 hours. The reaction solution was concentrated, the thus obtained residue was applied to a silica gel chromatography and developed with a hexane-ethyl acetate (6:1) mixed solvent, and then the fractions containing the compound of interest were concentrated to obtain 0.36 g of the title compound.

¹H-NMR (CDCl₃) δ: 1.38 (t, 3H, J=7 Hz), 2.58 (s, 3H), 3.59 (s, 3H), 4.33 (q, 2H, J=7 Hz), 5.20 (brs, 2H), 8.09 (s, 1H)

(4) 1-(2-Amino-6-chloro-5-methoxy-4-pyrimidinyl)-5-methyl-4-pyrazolecarbaldehyde Using 0.36 g of the compound obtained in Example 44-(3), the same reaction and after-treatment of Example 31-(3) were carried out to obtain 0.17 g of the title compound as a white solid.

¹H-NMR (CDCl₃) δ: 2.62 (s, 3H), 3.64 (s, 3H), 5.21 (brs, 2H), 8.12 (s, 1H), 10.00 (s, 1H).

(5) Ethyl 3-[1-(2-amino-6-chloro-5-methoxy-4-pyrimidinyl)-5-methyl-4-pyrazolyl]-2-trans-propenoate Using 170 mg of the compound obtained in Example 44-(4) and 270 mg of (carboethoxymethylene)triphenylphosphorane, the same reaction and after-treatment of Example 31-(4) were carried out to obtain 30 mg of the title compound.

¹H-NMR (CDCl₃) δ: 1.30 (t, 3H, J=7 Hz), 2.40 (s, 3H), 3.59 (s, 3H), 4.26 (q, 2H, J=7 Hz), 5.23 (brs, 2H), 6.29 (d, 1H, J=16 Hz), 7.58 (d, 1H, J=16 Hz), 7.95 (s, 1H).

(6) Ethyl 3-[1-[2-amino-6-(3-hydroxy-1-azetidinyl)-5-methoxy-4-pyrimidinyl]-5-methyl-4-pyrazolyl]-2-trans-propenoate The compound obtained in Example 44-(5) was suspended in 20 ml of a solvent, mixed with 20 mg of 3-hydroxyazetidine hydrochloride and 30 mg of potassium carbonate and heated under reflux for 18 hours. The reaction solution was cooled to room temperature and concentrated under a reduced pressure, and then the residue was mixed with saturated brine and extracted with chloroform The organic layer was dried with anhydrous sodium sulfate, the solvent was evaporated, the thus obtained residue was applied to a silica gel column chromatography and developed with a chloroform-methanol (49:1) mixed solvent, and then the fractions containing the compound of interest were concentrated to obtain 30 mg of the title compound.

¹H-NMR (CDCl₃) δ: 1.33 (t, 3H, J=7 Hz), 2.37 (s, 3H), 3.25 (s, 3H), 4.09 (dd, 2H, J=10 Hz, 4 Hz), 4.25 (q, 2H, J=7 Hz), 4.47 (t, 2H, J=10 Hz), 4.7–4.8 (m, 3H), 6.21 (d, 1H, J=16 Hz), 7.58 (d, 1H, J=16 Hz), 7.90 (s, 1H).

(7) 3-[1-[2-Amino-6-(3-hydroxy-1-azetidinyl)-5-methoxy-4-pyrimidinyl]-5-methyl-4-pyrazolyl]-2-trans-propenal Using 30 mg of the compound obtained in Example 44-(6), the same reaction and after-treatment of Example 31-(5) were carried out to obtain 20 mg of the title compound as a white solid.

¹H-MR (CDCl₃) δ: 2.42 (s, 3H), 3.29 (s, 3H), 4.10 (dd, 2H, J=10 Hz, 4 Hz), 4.48 (t, 2H, J=10 Hz), 4.7–4.8 (m, 3H), 6.52 (dd, 1H, J=16 Hz, 8 Hz), 7.37 (d, 1H, J=16 Hz), 7.94 (s, 1H), 9.62 (d, 1H, J=8 Hz).

(8) 1-[1-[2-Amino-5-methoxy-6-(3-hydroxy-1-azetidinyl)-4pyrimidinyl]-5-methyl-4-pyrazolyl]-3-[4-(3,5-difluorophenyl)-1-piperazinyl]-1-trans-propene hydrochloride (D84-6058)

Using 20 mg of the compound obtained in Example 44-(7) 16 mg of 1-(3,5-difluorophenyl)piperazine hydrochloride and 10 μl of acetic acid, the same reaction and after-treatment of Example 31-(6) were carried out to obtain 11 mg of the title compound as a white powder.

¹H-NMR (DMSCO-d₆) δ: 2.28 (s, 3H) , 3.0–3.1 (m, 2H), 3.1–3.2 (m, 2H), 3.21 (s, 3H), 3.50 (d, 2H, J 7 Hz), 3.8–4.0 (m, 6H), 3.3–3.5 (m, 2H), 3.5–3.6 (m, 1H), 6.15 (dt, 1H, J=16 Hz, 7 Hz), 6.57 (tt, 1H, J=9 Hz, 2 Hz), 6.72 (dd, 2H, J=9 Hz, 2 Hz), 6.74 (d, 1H, J=16 Hz) 8.03 (s, 1H), 10.97 (brs, 1H)

EXAMPLE 45

1-[1-[2-Amino-6-(N-hydroxy-N-methylamino)-4-pyrimidinyl]-5-methyl-4-pyrazolyl]-3-[4-(3,5-difluorophenyl)-1-piperazinyl]-1-trans-propene hydrochloride

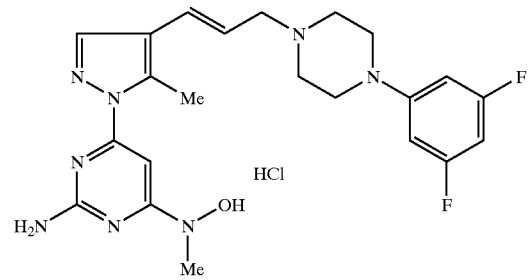

A 23 mg (0.05 mmol) portion of the compound obtained in Example 11-(1) was suspended in 50 ml of ethanol and then mixed with 22 mg of N-methylhydroxylammonium chloride and 36 mg of potassium carbonate and heated under reflux for 7 days. After evaporation of the solvent under a reduced pressure, the residue was purified by applying it to a silica gel chromatography and developing with an organic layer of chloroform-methanol-water (7:3:1). The resulting residue was made into hydrochloride with 1 N hydrochloric acid/ethanol and then recrystallized from an ether-ethanol mixed solvent to obtain 14 mg of the title compound as a dark gray powder.

¹H-NMR (DMSO-d₆) δ: 2.67 (s, 3H), 3.07–3.12 (m, 2H), 3.24 (t, 2H, J=12 Hz), 3.41 (s, 3H), 3.49 (d, 2H, J=10 Hz), 3.85–3.97 (m, 4H), 6.24 (dt, 1H, J=16 Hz, 8 Hz), 6.55 (s, 1H), 6.58 (t, 1H, J=9 Hz), 6.73 (d, 2H, J=9 Hz), 6.80 (d, 2H, J=16 Hz), 8.13 (s, 1H), 11.36 (brs, 1H)

EXAMPLE 46

1-[1-[2-Amino-6-[(2S)-1-hydroxy-2-propylamino]-4-pyrimidinyl]-5-methyl-4-pyrazolyl]-3-[4-(3,5-difluorophenyl)-1-piperazinyl]-1-trans-propene hydrochloride

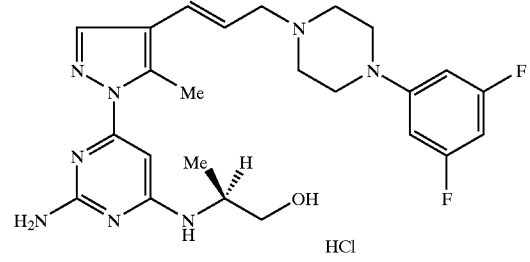

Using 446 mg (1.0 mmol) of the compound obtained in Example 11-(1) and 751 mg of L-alaninol, the same reaction and after-treatment of Example 33 were carried out to obtain 454 mg of the title compound as a white powder.

¹H-NMR (DMSO-d₆) δ: 1.15 (d, 3H, J=6 Hz), 2.63 (s, 3H), 3.08 (d, 2H, J=11 Hz), 3.25 (t, 2H, J=12 Hz), 3.39–3.50 (m, 4H), 3.93–3.97 (m, 4H), 4.16 (brs, 1H), 6.25 (dt, 1H, J=16 Hz, 8 Hz), 6.51 (s, 1H), 6.58 (t, 1H, J=9 Hz), 6.73 (d, 2H, J=10 Hz), 6.81 (d, 2H, J=16 Hz), 8.16 (s, 1H), 11.45 (brs, 1H)

EXAMPLE 47

1-[1-[2-Amino-6-(2-hydroxyethoxy)-4-pyrimidinyl]-5-methyl-4-pyrazolyl]-3-[4-(3,5-difluorophenyl)-1-piperazinyl]-1-trans-propene hydrochloride

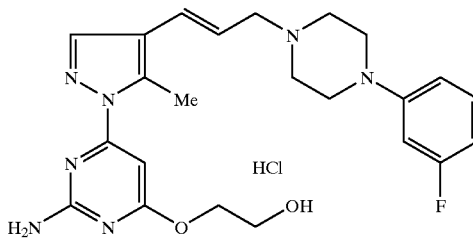

A 446 mg (1.0 mmol) portion of the compound obtained in Example 11-(1) and 558 μl of ethylene glycol were suspended in 40 ml of tert-butanol and then mixed with 691 mg of potassium carbonate and heated under reflux for 7 days. After evaporation of the solvent under a reduced pressure, the residue was applied to a silica gel chromatography and developed with an organic layer of chloroform-methanol (19:1), and then the fractions containing the compound of interest were concentrated. The resulting residue was made into hydrochloride with 1 N hydrochloric acid/ethanol and then recrystallized from ethanol to obtain 290 mg of the title compound as a white powder.

$^1$H-NMR (DMSO-$d_6$) δ: 2.69 (s, 3H), 3.08 (d, 2H, J=11 Hz), 3.20 (t, 2H, J=12 Hz), 3.50 (d, 2H, J=12 Hz), 3.68 (t, 2H, J=5 Hz), 3.91–3.98 (m, 4H), 4.27 (t, 2H, J=5 Hz), 6.17 (dt, 1H, J=16 Hz, 8 Hz), 6.33 (s, 1H), 6.59 (t, 1H, J=9 Hz), 6.73 (d, 2H, J=9 Hz), 6.79 (d, 2H, J=16 Hz), 8.03 (s, 1H), 10.99 (brs, 1H)

EXAMPLE 48

1-[1-[2-Amino-6-[(2S)-1-hydroxy-3-methyl-2-butylamino]-4-pyrimidinyl]-5-methyl-4-pyrazolyl]-3-[4-(3,5-difluorophenyl)-1-piperazinyl]-1-trans-propene hydrochloride

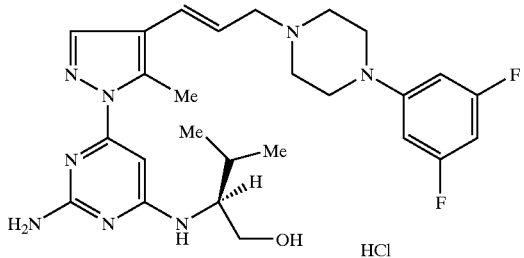

Using 23 mg (0.05 mmol) of the compound obtained in Example 11-(1) and 27 mg of D-valinol, the same reaction and after-treatment of Example 33 were carried out to obtain 13 mg of the title compound as a slightly pink powder.

$^1$H-NMR (DMSO-$d_6$) δ: 0.92 (t, 6H, J=7 Hz), 1.87–2.00 (m, 1H), 2.64 (s, 3H), 3.10–3.97 (m, 13H), 6.23–6.29 (m, 1H), 6.52–6.61 (m, 2H), 6.73 (d, 2H, J=9 Hz), 6.80 (d, 2H, J=16 Hz), 8.15 (s, 1H), 11.22 (brs, 1H)

EXAMPLE 49

1-[1-[2-Amino-6-[(1S)-2-hydroxy-1-phenyl-1-ethylamino]-4-pyrimidinyl]-5-methyl-4-pyrazolyl]-3-[4-(3,5-difluorophenyl)-1-piperazinyl]-1-trans-propene hydrochloride

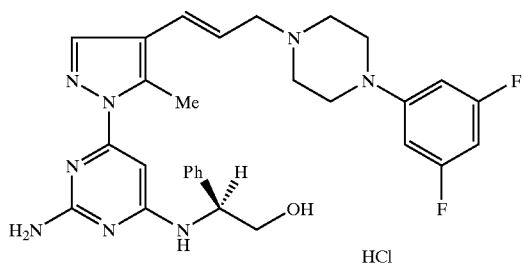

Using 23 mg (0.05 mmol) of the compound obtained in Example 11-(1) and 35 mg of (S)-(+)-phenylglycinol, the same reaction and after-treatment of Example 33 were carried out to obtain 13 mg of the title compound as a slightly pink powder.

$^1$H-NMR (DMSO-$d_6$) δ: 2.61 (s, 3H), 3.07–3.97 (m, 13H), 5.23–5.31 (m, 1H), 6.18–6.27 (m, 1H), 6.59 (t, 2H, J=9 Hz), 6.73 (d, 2H, J=9 Hz), 6.79 (d, 2H, J=16 Hz), 7.27 (d, 1H, J=7 Hz), 7.35 (t, 2H, J=8 Hz), 7.41 (d, 2H, J=6 Hz), 8.14 (s, 1H), 11.07 (brs, 1H)

EXAMPLE 50

1-[1-[2-Amino-6-(1,3-dihydroxy-2-propylamino)-4-pyrimidinyl]-5-methyl-4-pyrazolyl]-3-[4-(3,5-difluorophenyl)-1-piperazinyl]-1-trans-propene hydrochloride

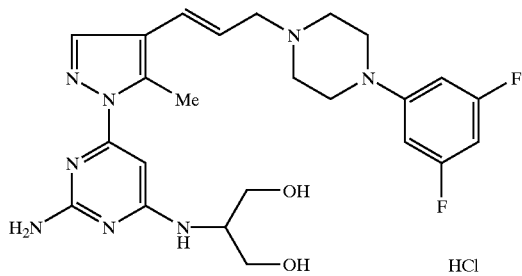

Using 23 mg (0.05 mmol) of the compound obtained in Example 11-(1) and 24 mg of serinol, the same reaction and after-treatment of Example 33 were carried out to obtain 13 mg of the title compound as a white powder.

$^1$H-NMR (DMSO-$d_6$) δ: 2.63 (s, 3H), 3.01–3.11 (m, 2H), 3.25 (t, 2H, J=12 Hz), 3.47–3.55 (m, 6H), 3.93–3.97 (m, 4H), 4.08 (brs, 1H), 6.25 (dt, 1H, J=16 Hz, 8 Hz), 6.51 (s, 1H), 6.58 (t, 2H, J=9 Hz), 6.73 (d, 2H, J=10 Hz), 6.81 (d, 2H, J=16 Hz), 8.16 (s, 1H), 11.43 (brs, 1H)

EXAMPLE 51

1-[1-[2-Amino-6-[(3R)-3-(1-hydroxy-1-methyl)
ethyl-1-pyrrolidinyl]-4-pyrimidinyl]-5-methyl-4-
pyrazolyl]-3-[4-(3,5-difluorophenyl)-1-piperazinyl]-
1-trans-propene hydrochloride

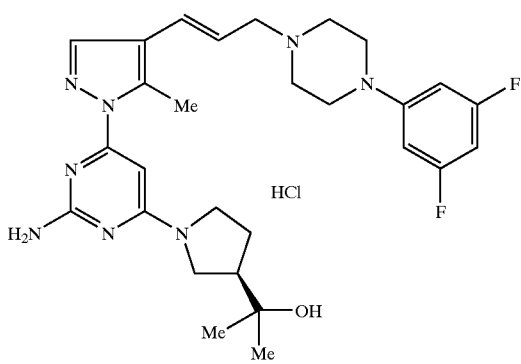

A 1.6 g portion of (3R)-3-(1-hydroxy-1-methyl)ethyl-1-[(1S)-1-phenyl-1-ethyl]pyrrolidine was dissolved in 20 ml of 80% water-containing ethanol and mixed with 2.0 g of 10% palladium-carbon (water content 50.1%) to carry out 4 hours of catalytic hydrogenation under 4 atmospheres and under infrared lamp irradiation. The catalyst was removed by filtration, and the resulting filtrate was concentrated under a reduced pressure. The residue was dissolved in 20 ml of ethanol, mixed with 0.45 g of the compound obtained in Example 11-(1) and 0.5 g of potassium carbonate and then heated under reflux for 2 days. The reaction solution was cooled to room temperature and concentrated under a reduced pressure, and then the residue was mixed with saturated brine and extracted with chloroform. The organic layer was dried with anhydrous sodium sulfate, the solvent was evaporated, the thus obtained residue was applied to a silica gel column chromatography and developed with a chloroform-methanol (19:1) mixed solvent, and then the fractions containing the compound of interest were concentrated. The resulting residue was made into hydrochloride with 1 N hydrochloric acid/ethanol and then recrystallized from ethanol to obtain 0.4 g of the title compound as a white powder.

$^1$H-NMR (DMSO-$d_6$) δ: 1.12 (s, 3H), 1.13 (s, 3H), 1.9–2.0 (m, 2H), 2.2–2.3 (m, 1H), 2.66 (s, 3H), 3.1–3.2 (m, 2H), 3.2–3.3 (m, 2H), 3.3–3.5 (m, 6H), 3.9–4.0 (m, 4H), 6.0–6.2 (m, 2H), 6.58 (t, 1H, J=10 Hz), 6.73 (d, 2H, J=10 Hz), 6.77 (d, 1H, J=16 Hz), 8.02 (s, 1H), 10.85 (bs, 1H)

EXAMPLE 52
1-[1-[2-Amino-6-[(3R,4R)-3,4-dihydroxy-1-
pyrrolidinyl]-4-pyrimidinyl]-5-methyl-4-pyrazolyl]-
3-[4-(3,5-difluorophenyl)-1-piperazinyl]-1-trans-
propene hydrochloride

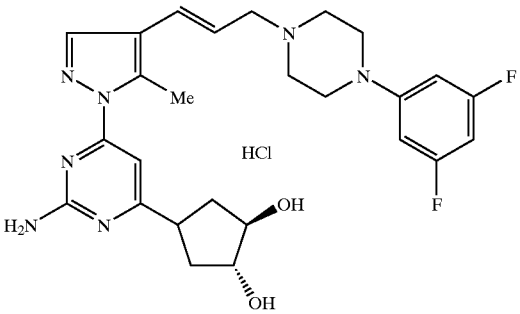

A 387 mg (2.00 mmol) portion of (3R,4R)-1-benzyl-3,4-dihydroxypyrrolidine was dissolved in 50 ml of ethanol, mixed with 3 ml of 1 N hydrochloric acid and 300 mg of palladium hydroxide on carbon and subjected to 3 days of catalytic hydrogenation at 50° C. After removal of the insoluble matter by filtration and subsequent evaporation of the solvent under a reduced pressure, the residue was dissolved in 40 ml of ethanol, mixed with 400 mg (0.90 mmol) of the compound obtained in Example 11-(1) and 625 μl of triethylamine, and then heated under reflux for 1 day. After evaporation of the solvent under a reduced pressure, the residue was applied to a silica gel chromatography and developed with an organic layer of chloroform-methanol-water (20:3:1), and then the fractions containing the compound of interest were concentrated. The resulting residue was made into hydrochloride with 1 N hydrochloric acid/ethanol and then recrystallized from ethanol to obtain 375 mg of the title compound as a white powder.

$^1$H-NMR (DMSO-$d_6$) δ: 2.67 (s, 3H), 3.07–3.72 (m, 10H), 3.92–3.98 (m, 4H), 4.10 (s, 2H), 6.25 (dt, 1H, J=16 Hz, 8 Hz), 6.32 (brs, 1H), 6.59 (t, 1H, J=9 Hz), 6.73 (d, 2H, J=9 Hz), 6.81 (d, 2H, J=16 Hz), 8.17 (s, 1H), 11.38 (brs, 1H)

EXAMPLE 53
1-[1-[2-Amino-6-[cis-3,4-dihydroxy-1-pyrrolidinyl)-
4-pyrimidinyl]-5-methyl-4-pyrazolyl]-3-[4-(3,5-
difluorophenyl)-1-piperazinyl]-1-trans-propene
hydrochloride

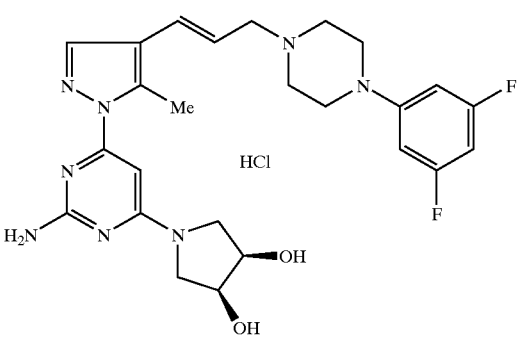

Using 580 mg (3.00 mmol) of cis-1-benzyl-3,4-dihydroxypyrrolidine and 400 mg (0.90 mmol) of the compound obtained in Example 11-(1), the same reaction and after-treatment of Example 33 were carried out to obtain 121 mg of the title compound as a slightly pink powder.

$^1$H-NMR (DMSO-d$_6$) δ: 2.66 (s, 3H), 3.07–3.70 (m, 10H), 3.92–3.98 (m, 4H), 4.16 (s, 2H), 6.21–6.28 (m, 1H), 6.59 (t, 1H, J=9 Hz), 6.73 (d, 2H, J=9 Hz), 6.81 (d, 2H, J=16 Hz), 8.15 (s, 1H), 11.22 (brs, 1H)

EXAMPLE 54

1-[1-[2-Amino-6-(3-hydroxy-3-methyl-1-azetidinyl)-4-pyrimidinyl]-5-methyl-4-pyrazolyl]-3-[4-(3,5-difluorophenyl)-1-piperazinyl]-1-trans-propene hydrochloride

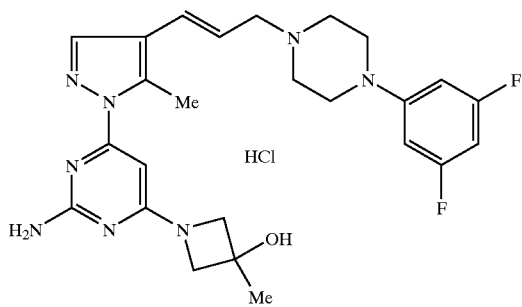

A 329 mg (1.30 mmol) portion of 1-benzhydryl-3-hydroxy-3-methylazetidine was dissolved in 50 ml of ethanol, mixed with 300 mg of 10% palladium-carbon (water content 50.1%) and subjected to 18 hours of catalytic hydrogenation under 6 atmospheres. After removal of the insoluble matter by filtration and subsequent evaporation of the solvent under a reduced pressure, the residue was dissolved in 50 ml of ethanol, mixed with 400 mg (0.90 mmol) of the compound obtained in Example 11-(1) and 625 μl of triethylamine and then heated under reflux for 1 day. After evaporation of the solvent under a reduced pressure, the residue was applied to a silica gel chromatography and developed with a chloroform-methanol (97:3) mixed solvent, and then the fractions containing the compound of interest were concentrated. The resulting residue was made into hydrochloride with 1 N hydrochloric acid/ethanol and then recrystallized from ethanol to obtain 246 mg of the title compound as a white powder.

$^1$H-NMR (DMSO-d$_6$) δ: 2.66 (s, 3H), 3.06–3.11 (m, 2H), 3.19–3.22 (m, 2H), 3.48 (d, 2H, J=12 Hz), 3.90–4.06 (m, 6H), 6.13 (s, 1H), 6.23 (dt, 1H, J=16 Hz, 8 Hz), 6.57 (t, 1H, J=9 Hz), 6.72 (d, 2H, J=9 Hz), 6.79 (d, 2H, J=16 Hz), 8.12 (s, 1H)

EXAMPLE 55

1-[1-[2-Amino-6-[(3S)-3-hydroxy-1-pyrrolidinyl]-4-pyrimidinyl]-5-methyl-4-pyrazolyl]-3-[4-(3,5-difluorophenyl)-1-piperazinyl]-1-trans-propene hydrochloride

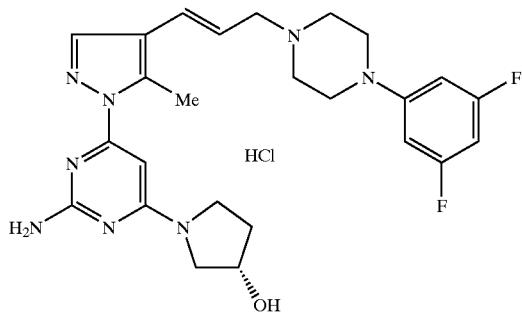

A 936 mg (5.00 mmol) portion of (3S)-1-tert-butoxycarbonyl-3-hydroxypyrrolidine was dissolved in 10 ml of methylene chloride and then mixed with 5 ml of trifluoroacetic acid and stirred at room temperature for 15 hours. After evaporation of the solvent under a reduced pressure, the residue was dissolved in 50 ml of ethanol and then, using 400 mg (0.90 mmol) of the compound obtained in Example 11-(1) and 691 mg of potassium carbonate, the same reaction and after-treatment of Example 45 were carried out to obtain 451 mg of the title compound as a white powder.

$^1$H-NMR (DMSO-d$_6$) δ: 1.96–2.03 (m, 2H), 2.67 (s, 3H), 3.07–3.12 (m, 2H), 3.24 (t, 2H, J=12 Hz), 3.50 (d, 2H, J=12 Hz), 3.62 (s, 2H), 3.92–3.98 (m, 4H), 4.43 (s, 1H), 6.25 (dt, 1H, J=16 Hz, 8 Hz), 6.33 (s, 1H), 6.58 (t, 1H, J=9 Hz), 6.73 (d, 2H, J=9 Hz), 6.81 (d, 2H, J=16 Hz), 8.16 (s, 1H), 11.30 (brs, 1H)

EXAMPLE 56

1-[1-[2-Amino-6-[3-[(1-hydroxy-1-methyl)-1-ethyl]-1-azetidinyl]-4-pyrimidinyl]-5-methyl-4-pyrazolyl]-3-[4-(3,5-difluorophenyl)-1-piperazinyl]-1-trans-propene hydrochloride

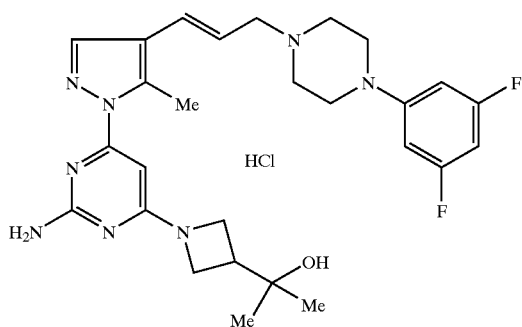

A 421 mg (1.50 mmol) portion of 1-benzhydryl-3-[(1-hydroxy-1-methyl)-1-ethyl]azetidine was dissolved in 50 ml of ethanol, mixed with 400 mg of 10% palladium-carbon (water content 50.1%) and subjected to 13 hours of catalytic hydrogenation at 50° C. After removal of the insoluble matter by filtration and subsequent evaporation of the solvent under a reduced pressure, the residue was dissolved in 50 ml of ethanol, mixed with 300 mg (0.67 mmol) of the compound obtained in Example 11-(1) and 93 mg of potassium carbonate and then heated under reflux for 1 day. After evaporation of the solvent under a reduced pressure, the residue was applied to a silica gel chromatography and developed with a chloroform-methanol (19:1) mixed solvent, and then the fractions containing the compound of interest were concentrated. The resulting residue was made into hydrochloride with 1 N hydrochloric acid/ethanol and then recrystallized from ethanol to obtain 361 mg of the title compound as a light flesh color powder.

$^1$H-NMR (DMSO-$d_6$) δ: 1.06 (s, 6H), 2.67 (s, 3H), 2.75–2.79 (m, 1H), 3.07–3.12 (m, 2H), 3.23 (t, 2H, J=12 Hz), 3.50 (d, 2 H, J=11 Hz), 3.91–3.97 (m, 4H), 4.13 (s, 4H), 6.13 (s, 1H), 6.25 (dt, 1H, J=16 Hz, 8 Hz), 6.58 (t, 1H, J=9 Hz), 6.73 (d, 2H, J=9 Hz), 6.80 (d, 2H, J=16 Hz), 8.15 (s, 1H), 11.27 (brs, 1H)

EXAMPLE 57

1-[1-[2-Amino-6-(3-hydroxymethyl-1-azetidinyl)-4-pyrimidinyl]-5-methyl-4-pyrazolyl]-3-[4-(3,5-difluorophenyl)-1-piperazinyl]-1-trans-propene hydrochloride

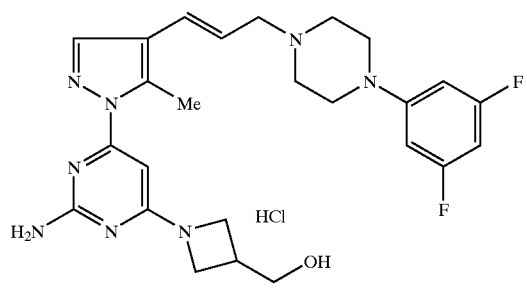

A 477 mg (1.88 mmol) portion of 1-benzhydryl-3-hydroxymethylazetidine was dissolved in 100 ml of ethanol, mixed with 500 mg of 10% palladium-carbon (water content 50.1%) and subjected to 19 hours of catalytic hydrogenation under 7 atmospheres. After removal of the insoluble matter by filtration and subsequent evaporation of the solvent under a reduced pressure, the residue was dissolved in 30 ml of ethanol, mixed with 300 mg (0.67 mmol) of the compound obtained in Example 11-(1) and 93 mg of potassium carbonate and then heated under reflux for 1 day. After evaporation of the solvent under a reduced pressure, the residue was applied to a silica gel chromatography and developed with an organic layer of chloroform-methanol (19:1), and then the fractions containing the compound of interest were concentrated. The resulting residue was made into hydrochloride with 1 N hydrochloric acid/ethanol and then recrystallized from ethanol to obtain 336 mg of the title compound as a white powder.

$^1$H-NMR (DMSO-$d_6$) δ: 2.67 (s, 3H), 2.75–2.82 (m, 1H), 3.07–3.12 (m, 2H), 3.24 (t, 2H, J=12 Hz), 3.49 (d, 2H, J=11 Hz), 3.56 (d, J=6 Hz), 3.91–3.97 (m, 6H), 4.23 (s, 2H), 6.13 (s, 1H), 6.25 (dt, 1H, J=16 Hz, 8 Hz), 6.58 (t, 1H, J=9 Hz), 6.73 (d, 2H, J=9 Hz), 6.80 (d, 2H, J=16 Hz), 8.15 (s, 1H), 11.33 (brs, 1H)

EXAMPLE 58

1-[1-[2-Amino-6-[(2S,4S)-4-hydroxy-2-hydroxymethyl-1-pyrrolidinyl]-4-pyrimidinyl]-5-methyl-4-pyrazolyl]-3-[4-(3,5-difluorophenyl)-1-piperazinyl]-1-trans-propene hydrochloride

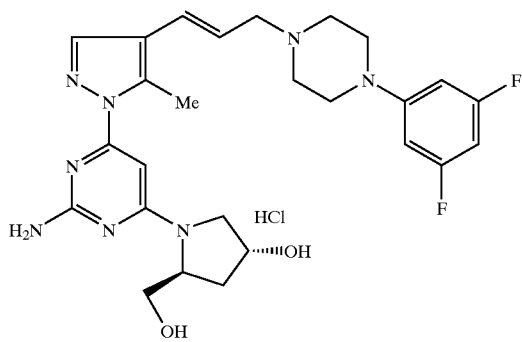

Using 446 mg of the compound obtained in Example 11-(1) and 1.43 g of (2S,4S)-4-hydroxy-2-hydroxymethylpyrrolidine, the same reaction and after-treatment of Example 33 were carried out to obtain 348 mg of the title compound as a white powder.

$^1$H-NMR (DMSO-$d_6$) δ: 1.85–2.00 (m, 1H), 2.10–2.20 (m, 1H), 2.67 (s, 3H), 3.00–4.05 (m, 15H), 4.40–4.50 (m, 1H), 6.21 (dt, 1H, J=16 Hz, 7 Hz), 6.20–6.50 (br, 1H), 6.50–6.65 (m, 1H), 6.73 (d, 2H, J=11 Hz), 6.80 (d, 1H, J=16 Hz), 8.07 (s, 1H), 11.24 (brs, 1H)

EXAMPLE 59

1-[1-[2-Amino-6-[(3R)-3-hydroxymethyl-1-pyrrolidinyl]-4-pyrimidinyl]-5-methyl-4-pyrazolyl]-3-[4-(3,5-difluorophenyl)-1-piperazinyl]-1-trans-propene hydrochloride

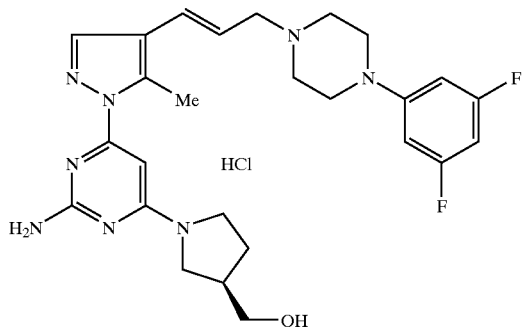

Using 446 mg of the compound obtained in Example 11-(1) and 503 mg of (3R)-3-hydroxymethylpyrrolidine, the same reaction and after-treatment of Example 33 were carried out to obtain 452 mg of the title compound as a white powder.

$^1$H-NMR (DMSO-$d_6$) δ: 1.75–1.90 (m, 1H), 2.00–2.15 (m, 1H) 2.68 (s, 3H), 3.00–4.05 (m, 17H), 6.26 (dt, 1H, J=16 Hz, 7 Hz), 6.32 (s, 1H), 6.57 (t, 1H, J=9 Hz), 6.73 (d, 2H, J=9 Hz), 6.81 (d, 1H, J=16 Hz), 8.15 (s, 1H), 11.34 (brs, 1H)

EXAMPLE 60

1-[1-[2-Amino-6-[(3S)-3-hydroxymethyl-1-pyrrolidinyl]-4-pyrimidinyl]-5-methyl-4-pyrazolyl]-3-[4-(3,5-difluorophenyl)-1-piperazinyl]-1-trans-propene hydrochloride

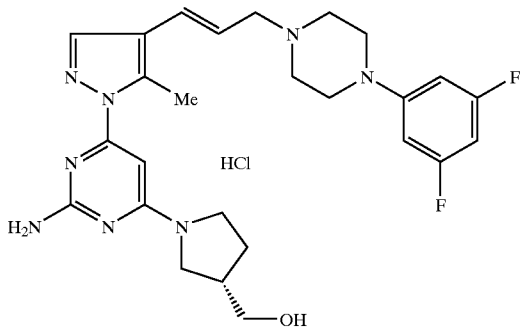

Using 446 mg of the compound obtained in Example 11-(1) and 567 mg of (3S)-3-hydroxymethylpyrrolidine, the same reaction and after-treatment of Example 33 were carried out to obtain 458 mg of the title compound as a white powder.

$^1$H-NMR (DMSO-$d_6$) δ: 1.75–1.90 (m, 1H), 2.00–2.15 (m, 1H), 2.69 (s, 3H), 3.00–4.05 (m, 17H), 6.26 (dt, 1H, J=16 Hz, 7 Hz), 6.31 (s, 1H), 6.57 (t, 1H, J=9 Hz), 6.73 (d, 2 H, J=9 Hz), 6.81 (d, 1H, J=16 Hz), 8.15 (s, 1H), 11.18 (brs, 1H)

EXAMPLE 61

1-[1-[2-Amino-6-[(3R,4R)-3-hydroxy-4-hydroxymethyl-1-pyrrolidinyl]-4-pyrimidinyl]-5-methyl-4-pyrazolyl]-3-[4-(3,5-difluorophenyl)-1-piperazinyl]-1-trans-propene hydrochloride

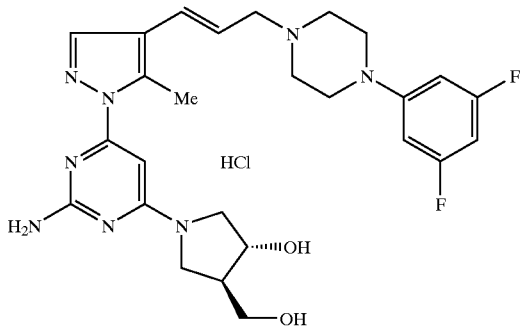

A 18 ml portion of borane-tetrahydrofuran complex (1 M tetrahydrofuran solution) was added at 0° C. to a dry tetrahydro furan (50 ml) solution containing 1.59 g of (3R,4R)-1-[(1S)-phenethyl]-3-hydroxy-4-(tert-butyldimethylsiloxymethyl)pyrrolidin-2-one, and the mixture was stirred at room temperature for 30 hours. The reaction solution was mixed with 30 ml of water-containing ethanol (water:ethanol=1:4) and 5 ml of triethylamine, and then heated under reflux for 1 hour. The reaction solution was concentrated, mixed with water and extracted three times with chloroform, the organic layers were dried with anhydrous sodium sulfate, and then the solvent was evaporated under a reduced pressure. The residue (1.05 g) was mixed with 40 ml of ethanol and 1.0 g of 10% palladium-carbon (water content 50.1%), and subjected to 28 hours of catalytic hydrogenation under 4.5 atmospheres. After removal of the insoluble matter by filtration and subsequent concentration under a reduced pressure, the thus obtained residue was subjected to the same reaction and after-treatment of Example 33 using 446 mg of the compound obtained in Example 11-(1), and then the fractions containing the compound of interest were concentrated. The thus obtained residue was mixed with 6 ml of acetic acid, 3 ml of water and 3 ml of tetrahydrofuran, and stirred at 80° C. for 6 hours. After concentration of the reaction solution, the residue was mixed with saturated sodium bicarbonate aqueous solution and extracted five times with chloroform. The organic layer was dried with anhydrous sodium sulfate, the solvent was evaporated under a reduced pressure, the thus obtained residue was applied to a silica gel chromatography and developed with a chloroform-methanol (92:8) mixed solvent, and then the fractions containing the compound of interest were concentrated. The resulting residue was made into hydrochloride with 1 N hydrochloric acid/ethanol and then recrystallized from ethanol to obtain 326 mg of the title compound as a white powder.

$^1$H-NMR (DMSO-$d_6$) δ: 2.25–2.40 (m, 1H), 2.68 (s, 3H), 3.00–4.05 (m, 16H), 4.25–4.30 (m, 1H), 6.26 (dt, 1H, J=16 Hz, 7 Hz), 6.33 (brs, 1H), 6.58 (t, 1H, J=9 Hz), 6.73 (d, 2H, J=11 Hz), 6.82 (d, 1H, J=16 Hz), 8.16 (s, 1H), 11.25 (brs, 1H)

EXAMPLE 62

1-[1-[2-Amino-6-[(3R)-3-[(1R or S)-1-hydroxyethyl]-1-pyrrolidinyl)-4-pyrimidinyl]-5-methyl-4-pyrazolyl]-3-[4-(3,5-difluorophenyl)-1-piperazinyl]-1-trans-propene hydrochloride (isomer A)

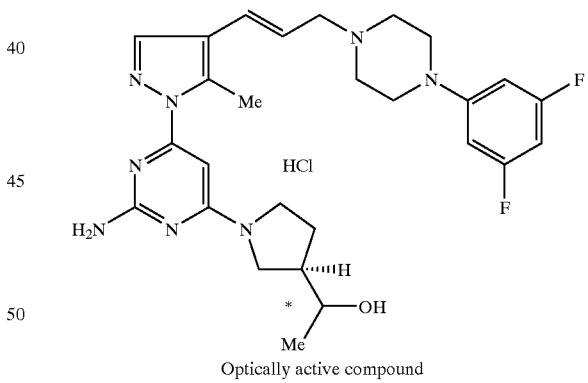

Optically active compound

Using 0.95 g of (3R)-3-[(1R or S)-1-hydroxyethyl]-1-(S)-1-phenethyl]pyrrolidine, 0.4 g of the compound obtained in Example 11-(1) and 0.2 g of potassium carbonate, the same reaction and after-treatment of Example 51 were carried out to obtain 0.35 g of the title compound (isomer of Example 63) as a white powder.

$^1$H-NMR (DMSO-$d_6$) δ: 1.08 (d, 3H, J=7 Hz), 1.7–1.8 (m, 1H), 2.0–2.1 (m, 1H), 2.1–2.2 (m, 1H), 2.65 (s, 3H), 3.0–3.1 (m, 4H), 3.2–3.4 (m, 3H), 3.5–3.6 (m, 3H), 3.9–4.0 (m, 4H), 4.5–4.7 (m, 1H), 6.07 (s, 1H), 6.13 (dt, 1H, J=16 Hz, 7 Hz), 6.28 (brs, 2H), 6.58 (t, 1H, J=10 Hz), 6.72 (d, 2H, J=10 Hz), 6.76 (d, 1H, J=16 Hz), 7.97 (s, 1H), 10.56 (brs, 1H)

EXAMPLE 63

1-[1-[2-Amino-6-[(3R)-3-[(1S or R)-1-hydroxyethyl]-1-pyrrolidinyl]-4-pyrimidinyl]-5-methyl-4-pyrazolyl]-3-[4-(3,5-difluorophenyl)-1-piperazinyl]-1-trans-propene hydrochloride (isomer B)

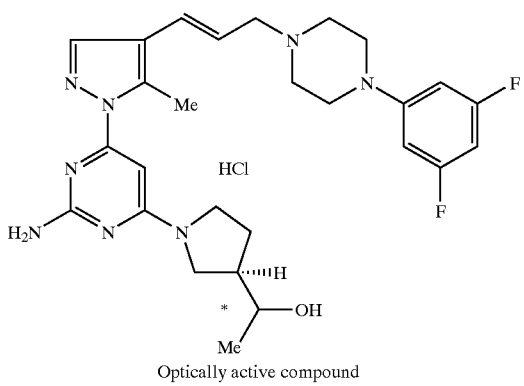

Optically active compound

Using 0.62 g of (3R)-3-[(1S or R)-1-hydroxyethyl]-1-(S)-1-phenethyl]pyrrolidine, 0.4 g of the compound obtained in Example 11-(1) and 0.2 g of potassium carbonate, the same reaction and after-treatment of Example 51 were carried out to obtain 0.3 g of the title compound (isomer of Example 62) as a white powder.

$^1$H-NMR (DMSO-d$_6$) δ: 1.10 (d, 3H, J=7 Hz), 1.5–1.7 (m, 1H), 1.8–1.9 (m, 1H), 2.0–2.1 (m, 1H), 2.66 (6, 3H), 3.0–3.2 (m, 4H), 3.2–3.4 (m, 3H), 3.4–3.5 (m, 3H), 3.9–4.0 (m, 4H), 4.6–4.7 (m, 1H), 6.06 (s, 1H), 6.13 (dt, 1H, J=16 Hz, 7 Hz), 6.24 (brs, 2H), 6.57 (t, 1H, J=10 Hz), 6.71 (d, 2H, J=10 Hz), 6.75 (d, 1H, J=16 Hz), 7.96 (s, 1H), 10.69 (brs, 1H)

EXAMPLE 64

1-[1-[2-Amino-6-[(3S,4S)-3-hydroxy-4-hydroxymethyl-1-pyrrolidinyl]-4-pyrimidinyl]-5-methyl-4-pyrazolyl]-3-[4-(3,5-difluorophenyl)-1-piperazinyl]-1-trans-propene hydrochloride

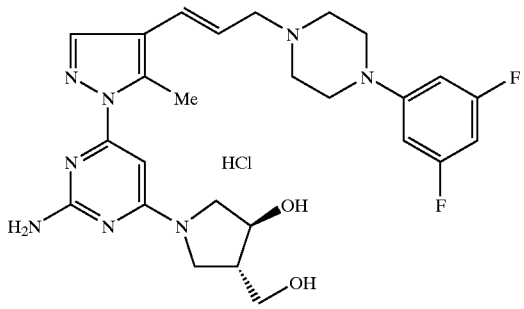

Using 1.87 mg of (3S,4S)-1-[(1S)-1-phenethyl]-3-hydroxy-4-(tert-butyldimethylsiloxymethyl)-2-pyrrolidone and 300 mg of the compound obtained in Example 11-(1), the same reaction and after-treatment of Example 61 were carried out to obtain 30 mg of the title compound as a white powder.

$^1$H-NMR (DMSO-d$_6$) δ: 2.25–2.40 (m, 1H), 2.67 (s, 3H), 3.00–4.05 (m, 16H), 4.15–4.25 (m, 1H), 6.22 (dt, 1H, J=16 Hz, 7 Hz), 6.20–6.35 (br, 1H), 6.58 (t, 1H, J=9 Hz), 6.73 (d, 2H, J=11 Hz), 6.81 (d, 1H, J=16 Hz), 8.15 (s, 1H), 10.95 (brs, 1H)

EXAMPLE 65

1-[1-[2-Amino-6-[(2S,4S)-2-carbamoyl-4-hydroxy-1-pyrrolidinyl]-4-pyrimidinyl]-5-methyl-4-pyrazolyl]-3-[4-(3,5-difluorophenyl)-1-piperazinyl]-1-trans-propene hydrochloride

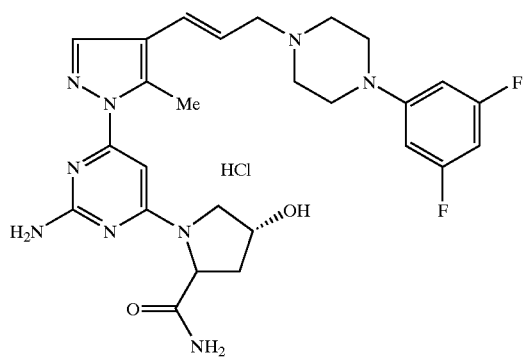

Using 116 mg (0.44 mmol) of (2S,4S)-1-benzyloxycarbonyl-4-hydroxypyrrolidine-2-carboxamide, 89 mg (0.2 mmol) of the compound obtained in Example 11-(1) and 28 mg of potassium carbonate, the same reaction and after-treatment of Example 56 were carried out to obtain 4 mg of the title compound as a white powder.

$^1$H-NMR (DMSO-d$_6$) δ: 1.99–4.36 (m, 19H), 6.03 (s, 1H), 6.15 (dt, 1H, J=16 Hz, 8 Hz), 6.58 (t, 1H, J=9 Hz), 6.72 (d, 2H, J=9 Hz), 6.78 (d, 2H, J=16 Hz), 8.03 (s, 1H), 10.63 (brs, 1H)

EXAMPLE 66

1-[1-[2-Amino-6-[(3R,4S)-3-hydroxy-4-[(1-hydroxy-1-methyl)-1-ethyl]-1-pyrrolidinyl]-4-pyrimidinyl]-5-methyl-4-pyrazolyl]-3-[4-(3,5-difluorophenyl)-1-piperazinyl]-1-trans-propene hydrochloride

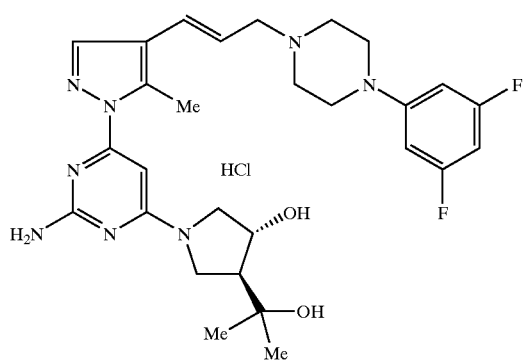

Using 0.42 g of (3R,4S)-3-hydroxy-4-[(1-hydroxy-1-methyl)-1-ethyl]-1-[(S)-1-phenethyl]pyrrolidine, 0.25 g of the compound obtained in Example 11-(1) and 0.4 g of potassium carbonate, the same reaction and after-treatment of Example 51 were carried out to obtain 0.11 g of the title compound as a white powder.

$^1$H-NMR (DMSO-d$_6$) δ: 1.13 (s, 3H), 1.14 (s, 3H), 2.0–2.1 (m, 1H), 2.66 (s, 3H), 3.0–3.2 (m, 4H), 3.2–3.4 (m, 4H), 3.51 (d, 2H, J=7 Hz), 3.9–4.0 (m, 4H), 4.2–4.3 (m, 1H), 6.0–6.2 (m, 2H), 6.58 (t, 1H, J=10 Hz), 6.72 (d, 2H, J=10 Hz), 6.74 (d, 1H, J=16 Hz), 8.01 (s, 1H)

EXAMPLE 67

1-[1-[2-Amino-6-[(2S,4S)-2-(N-methylcarbamoyl)-4-hydroxy-1-pyrrolidinyl]-4-pyrimidinyl]-5-methyl-4-pyrazolyl]-3-[4-(3,5-difluorophenyl)-1-piperazinyl]-1-trans-propene hydrochloride

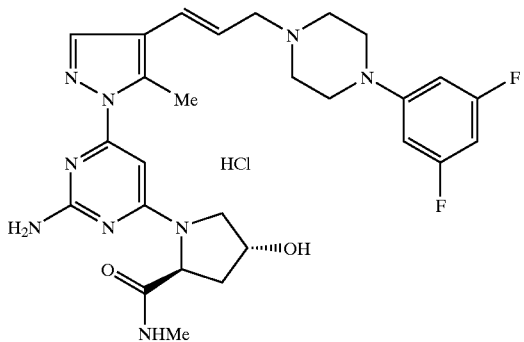

Using 231 mg (0.83 mmol) of N-methyl-(2S,4S)-1-benzyloxycarbonyl-4-hydroxypyrrolidine-2-carboxamide, 178 mg (0.4 mmol) of the compound obtained in Example 11-(1) and 55 mg of potassium carbonate, the same reaction and after-treatment of Example 56 were carried out to obtain 33 mg of the title compound as an orange powder.

$^1$H-NMR (DMSO-$d_6$) δ: 2.02–2.31 (m, 2H), 2.59 (d, 3H, J=4 Hz), 2.62 (s, 3H), 3.08 (d, 2H, J=4 Hz), 3.25 (t, 2H, J=12 Hz), 3.48 (d, 2H, J=12 Hz), 3.74–3.77 (m, 2H), 3.92–3.96 (m, 4H), 4.41–4.64 (m, 4H), 6.14 (s, 1H), 6.24 (dt, 1H, J=16 Hz, 8 Hz), 6.56 (t, 1H, J=9 Hz), 6.72 (d, 2H, J=9 Hz), 6.80 (d, 2H, J=16 Hz), 8.15 (s, 1H), 11.51 (brs, 1H)

EXAMPLE 68

1-[1-[2-Amino-6-[(2S,4S)-2-(N,N-dimethylcarbamoyl)-4-hydroxy-1-pyrrolidinyl]-4-pyrimidinyl]-5-methyl-4-pyrazolyl]-3-[4-(3,5-difluorophenyl)-1-piperazinyl]-1-trans-propene hydrochloride

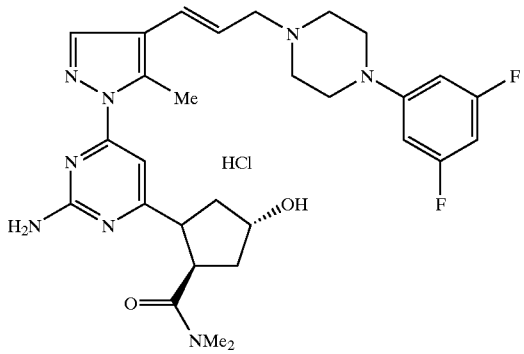

Using 374 mg (1.28 mmol) of N,N-dimethyl-(2S,4S)-1-benzyloxycarbonyl-4-hydroxypyrrolidine-2-carboxamide, 223 mg (0.5 mmol) of the compound obtained in Example 11-(1) and 69 mg of potassium carbonate, the same reaction and after-treatment of Example 56 were carried out to obtain 162 mg of the title compound as a white powder.

$^1$H-NMR (DMSO-$d_6$) δ: 1.99–2.39 (m, 2H), 2.64 (s, 3H), 2.82 (s, 3H), 3.06–3.12 (m, 5H), 3.22–3.28 (m, 2H), 3.47–4.41 (m, 10H), 6.21–6.25 (m, 2H), 6.57 (t, 1H, J=9 Hz) 6.72 (d, 2H, J=9 Hz), 6.80 (d, 2H, J=16 Hz), 8.14 (s, 1H), 11.21 (brs, 1H)

EXAMPLE 69

1-[1-[2-Amino-6-[(3R,4S)-3-hydroxy-4-hydroxymethyl-1-pyrrolidinyl]-4-pyrimidinyl]-5-methyl-4-pyrazolyl]-3-[4-(3,5-difluorophenyl)-1-piperazinyl]-1-trans-propene hydrochloride

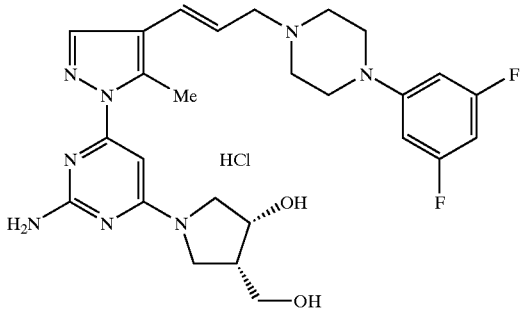

Using 0.19 g of (3R,4S)-3-hydroxy-4-(hydroxymethyl)-1-((S)-1-phenethyl)pyrrolidine, 0.2 g of the compound obtained in Example 11-(1) and 0.2 g of potassium carbonate, the same reaction and after-treatment of Example 51 were carried out to obtain 0.11 g of the title compound as a white powder.

$^1$H-NMR (DMSO-$d_6$) δ: 2.2–2.3 (m, 1H), 2.66 (s, 3H), 3.0–3.2 (m, 4H), 3.3–3.4 (m, 2H), 3.4–3.6 (m, 2H), 3.67 (d, 2H, J=7 Hz), 3.9–4.0 (m, 6H), 4.2–4.3 (m, 1H), 6.0–6.2 (m, 2H), 6.58 (t, 1H, J=10 Hz), 6.74 (d, 2H, J=10 Hz), 6.78 (d, 1H, J=16 Hz), 8.04 (s, 1H), 10.75 (brs, 1H)

EXAMPLE 70

1-[1-[2-Amino-6-[(3R,4S)-3-hydroxy-4-(1-hydroxy-1-methyl-1-ethyl)-1-pyrrolidinyl]-4-pyrimidinyl]-5-methyl-4-pyrazolyl]-3-[4-(3,5-difluorophenyl)-1-piperazinyl]-1-trans-propene hydrochloride

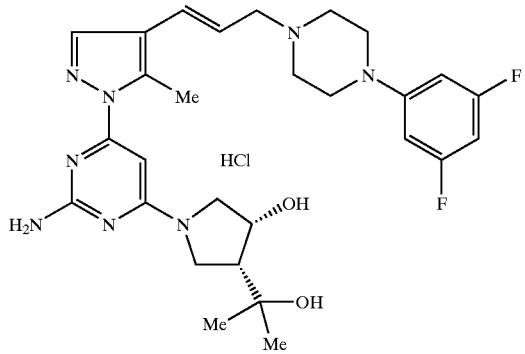

Using 0.5 g of (3R,4R)-3-hydroxy-4-(1-hydroxy-1-methyl-1-ethyl)-1-[(S)-1-phenethyl]pyrrolidine, 0.25 g of the compound obtained in Example 11-(1) and 0.3 g of potassium carbonate, the same reaction and after-treatment of Example 51 were carried out to obtain 0.26 g of the title compound as a white powder.

$^1$H-NMR (DMSO-$d_6$) δ: 1.15 (s, 3H), 1.31 (s, 3H), 2.0–2.2 (m, 1H), 2.66 (s, 3H), 3.0–3.1 (m, 2H), 3.1–3.2 (m, 2H), 3.2–3.4 (m, 4H), 3.50 (d, 2H, J=7 Hz), 3.9–4.0 (m, 4H), 4.4–4.5 (m, 1H), 6.0–6.2 (m, 2H), 6.58 (dt, 1H, J=10 Hz, 2 Hz), 6.72 (dd, 2H, J=10 Hz), 6.77 (d, 1H, J=16 Hz), 8.02 (s, 1H), 10.84 (brs, 1H)

EXAMPLE 71

1-[2-Amino-6-[(3S,4S)-dihydroxypyrrolidino]-4-pyrimidinyl]-5-methyl-4-pyrazolyl)-3-[(2S)-4-(3,5-difluorophenyl)-2-methylpiperazin-1-yl]-1-trans-propene hydrochloride

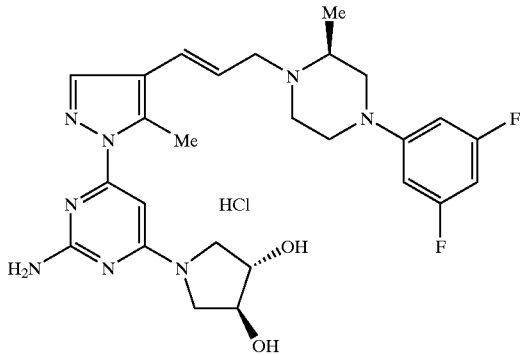

(1) (3S)-1-(3,5-Difluorophenyl)-3-methylpiperazine

A mixture composed of 2.48 g of (S)-2-methylpiperazine, 3.97 g of 3,5-difluorobromobenzene, 2.76 g of sodium tert-butoxide, 326 mg of dichlorobis[(tri-ortho-tolyl)phosphine]palladium (II) ($PdCl_2[P(o-tolyl)_3]_2$) and 100 ml of toluene was stirred at 100° C. for 24 hours in an atmosphere of nitrogen. After removal of the insoluble matter by filtration, the filtrate was washed with water and then with saturated brine. The organic layer was dried with anhydrous sodium sulfate and then concentrated under a reduced pressure, the residue was applied to a silica gel column chromatography (270 to 400 mesh, 100 g) and developed with a methanol-chloroform (6:94) mixed solvent, and then the fractions containing the compound of interest were concentrated to obtain 1.89 g of the title compound.

$^1$H-NMR (CDCl$_3$) δ: 1.13 (d, 3H, J=6 Hz), 2.38 (dd, 1H, J=12 Hz, 10 Hz), 2.74 (td, 1H, J 12 Hz, 3 Hz), 2.90–3.01 (m, 1H), 2.98 (td, 1H, J=12 Hz, 3 Hz), 3.11 (ddd, 1H, J=12 Hz, 3 Hz, 2 Hz), 3.48 (dm, 2H, J=10 Hz), 6.24 (tt, 1H, J=9 Hz, 2 Hz), 6.36 (dd, 2H, J=11 Hz, 2 Hz).

(2) 3-[1-[2-Amino-6-chloro-4-pyrimidinyl]-5-methyl-4-pyrazolyl]-2-trans-propenal Using 11.3 g of ethyl 3-[1-[2-amino-6-chloro-4-pyrimidinyl]-5-methyl-4-pyrazolyl]-2-trans-propenoate, the same reaction and after-treatment of Example 31-(5) were carried out to obtain 4.04 g of the title compound.

$^1$H-NMR (CDCl$_3$) δ: 2.83 (s, 3H), 5.24 (bs, 2H), 6.56 (dd, 1H, J=16 Hz, 9 Hz), 7.35 (s, 1H), 7.39 (d, 1H, J=16 Hz), 7.93 (s, 1H), 9.66 (d, 1H, J=9 Hz).

(3) 1-[(2-Amino-6-chloro-4-pyrimidinyl)-5-methyl-4-pyrazolyl)-3-[(2S)-4-(3,5-difluorophenyl)-2-methylpiperazin-1-yl]-1-trans-propene Using 418 mg of the compound obtained in Example 71-(2), 420 mg of the compound obtained in Example 71-(1) and 1.13 ml of acetic acid, the same reaction and after-treatment of Example 31-(6) were carried out to obtain 71 mg of the title compound from the fractions containing the compound of interest.

$^1$H-NMR (CDCl$_3$) δ: 1.20 (d, 3H, J=6 Hz), 2.35–2.45 (m, 1H), 2.50–2.80 (m, 2H), 2.69 (s, 3H), 2.95–3.10 (m, 3H), 3.35–3.50 (m, 2H), 3.60–3.70 (m, 1H), 5.18 (s, 2H), 6.09 (ddd, 1H, J=16 Hz, 8 Hz, 6 Hz), 6.24 (tt, 1H, J=9 Hz, 2 Hz), 6.33–6.38 (m, 2H), 6.38 (d, 1H, J=16 Hz), 7.31 (s, 1H), 7.80 (s, 1H).

(4) 1-[2-Amino-6-[(3S,4S)-dihydroxypyrrolidino]-4-pyrimidinyl]-5-methyl-4-pyrazolyl)-3-[(2S)-4-(3,5-difluorophenyl)-2-methylpiperazin-1-yl]-1-trans-propene hydrochloride Using 71 mg of the compound obtained in Example 71-(2) and 49 mg of (3S,4S)-dihydroxypyrrolidine, the same reaction and after-treatment of Example 33 were carried out to obtain 62 mg of the title compound as a white powder.

$^1$H-NMR (DMSO-d$_6$) δ: 1.46 (d, 3H, J=3 Hz), 2.69 (s, 3H), 3.00–4.20 (m, 15H), 6.20–6.40 (m, 2H), 6.55 (t, 1H, J=9 Hz), 6.74 (d, 2H, J=10 Hz), 6.89 (d, 1H, J=16 Hz), 8.21 (s, 1H), 11.43 (brs, 1H)

EXAMPLE 72

1-[2-Amino-6-[(3S,4S)-dihydroxypyrrolidino]-4-pyrimidinyl]-5-methyl-4-pyrazolyl]-3-[(2R)-4-(3,5-difluorophenyl)-2-methylpiperazin-1-yl]-1-trans-propene hydrochloride

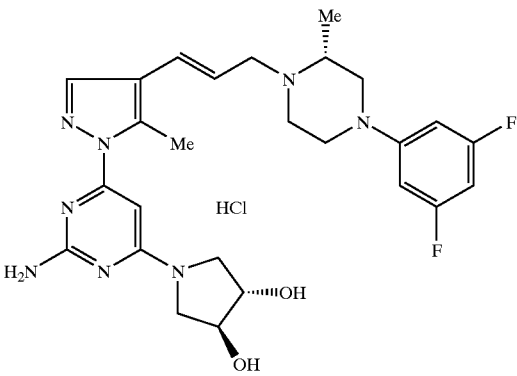

(1) (3R)-1-(3,5-Difluorophenyl)-3-methylpiperazine

Using 1.97 g of (R)-2-methylpiperazine instead of (S)-2-methylpiperazine, the same reaction and after-treatment of Example 71-(1) were carried out to obtain 1.55 g of the title compound $^1$H-NMR (CDCl$_3$) δ: 1.13 (d, 3H, J=6 Hz), 2.38 (dd, 1H, J=12 Hz, 10 Hz), 2.74 (td, 1H, J=12 Hz, 3 Hz), 2.90–3.01 (m, 1H), 2.98 (td, 1H, J=12 Hz, 3 Hz), 3.11 (ddd, 1H, J=12 Hz, 3 Hz, 2 Hz), 3.48 (dm, 2H, J=10 Hz), 6.24 (tt, 1H, J=9 Hz, 2 Hz), 6.36 (dd, 2H, J=11 Hz, 2 Hz).

(2) 1-[(2-Amino-6-chloro-4-pyrimidinyl)-5-methyl-4-pyrazolyl]-3-[(2R)-4-(3,5-difluorophenyl)-2-methylpiperazin-1-yl]-1-trans-propene Using 145 mg of the compound obtained in Example 11-(1), 145 mg of the compound obtained in Example 31-(6) and 394 μl of acetic acid, the same reaction and after-treatment of Example 33 were carried out to obtain 33 mg of the title compound.

Its NMR spectrum coincided with that of the compound obtained in Example 71-(2).

(3) 1-[2-Amino-6-[(3S,4S)-dihydroxypyrrolidino]-4-pyrimidinyl]-5-methyl-4-pyrazolyl]-3-[(2R)-4-(3,5-difluorophenyl)-2-methylpiperazin-1-yl]-1-trans-propene hydrochloride Using 33 mg of the compound obtained in Example 72-(2) and 23 mg of (3S,4S)-dihydroxypyrrolidine, the same reaction and after treatment of Example 33 were carried out to obtain 22 mg of the title compound as a white powder.

¹H-NMR (DMSO-d₆) δ: Coincided with that of the compound obtained in Example 71-(3).

EXAMPLE 73

1-[1-[2-Amino-6-(3-hydroxy-1-azetidinyl)-4-pyrimidinyl]-5-methyl-4-pyrazolyl]-3-[(2S)-4-(3,5-difluorophenyl)-2-methyl-1-piperazinyl]-1-trans-propene hydrochloride

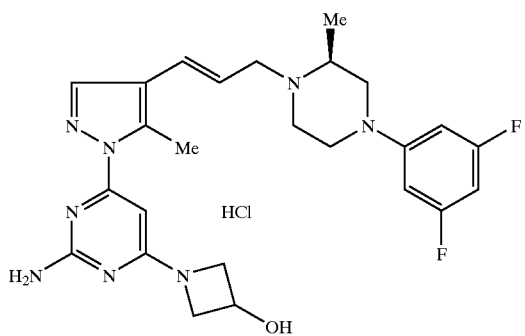

(1) Ethyl 3-[1-[2-amino-6-(3-hydroxy-1-azetidinyl)-4-pyrimidinyl]-5-ethyl-4-pyrazolyl]-2-trans-propenoate A 4.14 g portion of ethyl 3-[1-[2-amino-6-chloro-4-pyrimidinyl]-5-ethyl-4-pyrazolyl]-2-trans-propenoate was suspended in 150 ml of ethanol, mixed with 3.07 g of 3-hydroxyazetidine hydrochloride and 7.8 ml of triethylamine and then heated under reflux for 2 days. The reaction solution was allowed to stand at room temperature, and then the resulting precipitate was collected by filtration to obtain 4.10 g of the title compound as colorless crystals.

¹H-NMR (DMSO-d₆) δ: 1.25 (t, 3H, J=7 Hz), 2.72 (s, 3H), 3.72 (dd, 2H, J=9 Hz, 4 Hz), 4.10–4.25 (m, 4H), 4.50–4.60 (m, 1H), 5.73 (d, 1H, J=6 Hz), 5.96 (s, 1H), 6.41 (s, 2H), 6.42 (d, 1H, J=16 Hz), 7.52 (d, 1H, J=16 Hz), 8.19 (s, 1H).

(2) 3-[1-[2-Amino-6-(3-hydroxy-1-azetidinyl)-4-pyrimidinyl]-5-methyl-4-pyrazolyl]-2-trans-propenal Using 4.0 g of the compound obtained in Example 73-(1), the same reaction and after-treatment of Example 31-(5) were carried out to obtain 1.76 g of the title compound.

¹H-NMR (DMSO-d₆) δ: 2.81 (s, 3H), 3.73 (dd, 2H, J=9 Hz, 4 Hz), 4.19 (dd, 2H, J=6 Hz, 7 Hz), 4.50–4.60 (m, 1H), 5.74 (d, 1H, J=7 Hz), 5.90 (s, 1H), 6.43 (s, 2H), 6.66 (dd, 1H, J=16 Hz, 8 Hz), 7.72 (d, 1H, J=16 Hz), 8.22 (s, 1H), 9.61 (d, 1H, J=6 Hz).

(3) 1-[1-[2-Amino-6-(3-hydroxy-1-azetidinyl)-4-pyrimidinyl]-5-methyl-4-pyrazolyl]-3-[(2S)-4-(3,5-difluorophenyl)-2-methyl-1-piperazinyl]-1-trans-propene hydrochloride Using 450 mg of the compound obtained in Example 73-(2), 414 mg of the compound obtained in Example 71-(1) and 686 μl of acetic acid, the same reaction and after-treatment of Example 30 were carried out to obtain 113 mg of the title compound.

¹H-NMR (DMSO-d₆) δ: 1.45 (d, 3H, J=6 Hz), 2.68 (s, 3H), 3.00–4.20 (m, 11H), 4.30–4.40 (m, 2H), 4.55–4.70 (m, 1H), 6.09 (s, 1H), 6.24 (dt, 1H, J=16 Hz, 7 Hz), 6.55 (t, 1H, J=9 Hz) 6.74 (d, 2H, J=10 Hz), 6.87 (d, 1H, J=16 Hz) 8.12 (s, 1H), 11.16 (brs, 1H)

EXAMPLE 74

1-[1-[2-Amino-6-(3-hydroxy-1-azetidinyl)-4-pyrimidinyl]-5-methyl-4-pyrazolyl]-3-[(2R)-4-(3,5-difluorophenyl)-2-methyl-1-piperazinyl]-1-trans-propene hydrochloride

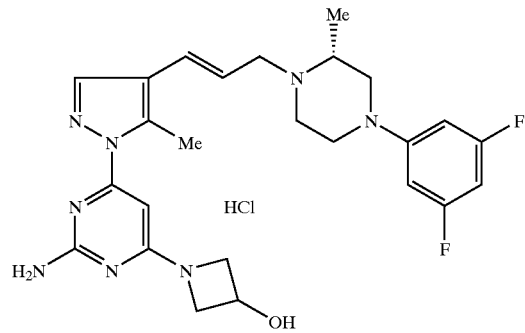

Using 450 mg of 3-[1-[2-amino-6-(3-hydroxy-1-azetidinyl)-4-pyrimidinyl]-5-methyl-4-pyrazolyl]-2-trans-propenal, 414 mg of the compound obtained in Example 72-(1) and 688 μl of acetic acid, the same reaction and after-treatment of Example 30 were carried out to obtain 213 mg of the title compound as a white powder.

¹H-NMR (DMSO-d₆) δ: 1.44 (d, 3H, J=6 Hz), 2.68 (s, 3H), 3.00–4.20 (m, 11H), 4.25–4.35 (m, 2H), 4.55–4.70 (m, 1H), 6.02 (s, 1H), 6.20 (dt, 1H, J=16 Hz, 7 Hz), 6.56 (t, 1H, J=9 Hz), 6.74 (d, 2H, J=10 Hz), 6.86 (d, 1H, J=16 Hz), 8.06 (s, 1H), 10.92 (brs, 1H)

EXAMPLE 75

1-[1-[4-Amino-6-(3-hydroxy-1-azetidinyl)-4-pyrimidinyl]-5-methyl-4-pyrazolyl]-3-[(2S)-4-(3,5-difluorophenyl)-2-methyl-1-piperazinyl]-1-trans-propene hydrochloride

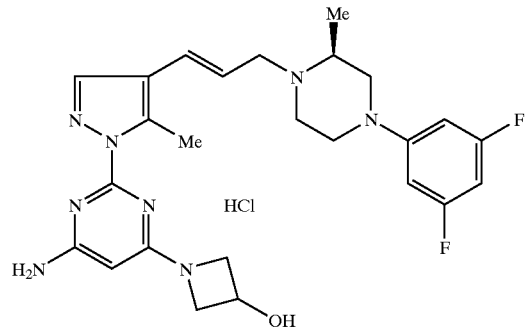

(1) 1-[1-[4-Chloro-6-(4-methoxybenzyl)amino-2-pyrimidinyl]-5-methyl-4-pyrazolyl]-3-[(2S)-4-(3,5-difluorophenyl)-2-methyl-1-piperazinyl]-1-trans-propene Using 590 mg of 3-[[4-chloro-6-(4-methoxybenzyl)amino-2-pyrimidinyl]-5-methyl-4-pyrazolyl]-2-trans-propenal, 180 mg of the compound obtained in Example 71-(1) and 688 μl of acetic acid, the same reaction and after-treatment of Example 31-(6) were carried out to obtain 288 mg of the title compound.

¹H-NMR (CDCl₃) δ: 1.20 (d, 3H, J=6 Hz), 2.40–2.50 (m, 1H), 1.50–2.80 (m, 2H), 2.64 (s, 3H), 2.90–3.15 (m, 3H) 3.35–3.50 (m, 2H), 3.60–3.70 (m, 1H), 3.81 (s, 3H), 4.30–4.60 (brs, 2H), 6.08 (dt, 1H, J=16 Hz, 7 Hz), 6.20–6.30

(m, 1H), 6.25 (s, 1H), 6.30–6.45 (m, 2H), 6.38 (d, 1H, J=16 Hz), 6.89 (d, 2H, J=8 Hz), 7.23 (d, 2H, J=8 Hz), 7.83 (s, 1H).

(2) 1-[1-(4-Amino-6-chloro-2-pyrimidinyl)-5-propyl-4-pyrazolyl]-3-[(2S)-4-(3,5-difluorophenyl)-2-methyl-1-piperazinyl]-1-trans-propene Using 288 mg of the compound obtained in Example 75-(1), the same reaction and after-treatment of Example 31-(7) were carried out to obtain 230 mg of the title compound.

$^1$H-NMR (CDCl$_3$) δ: 1.20 (d, 3H, J=6 Hz), 2.30–2.50 (m, 1H), 2.55–2.80 (m, 2H), 2.69 (s, 3H), 2.90–3.10 (m, 3H), 3.35–3.50 (m, 2H), 3.65 (dd, 1H, J=13 Hz, 5 Hz), 5.18 (s, 2H), 6.09 (ddd, 1H, J=16 Hz, 8 Hz, 6 Hz), 6.24 (tt, 1H, J=9 Hz, 2 Hz), 6.33–6.38 (m, 2H), 6.38 (d, 1H, J=16 Hz) 7.31 (s, 1H), 7.80 (s, 1H).

(3) 1-[1-[4-Amino-6-(3-hydroxy-1-azetidinyl)-2-pyrimidinyl]-5-methyl-4-pyrazolyl]-3-[(2S)-4-(3,5-difluorophenyl)-2-methyl-1-piperazinyl]-1-trans-propene hydrochloride Using 230 mg of the compound obtained in Example 75-(2), 164 mg of 3-hydroxy-1-azetidine hydrochloride and 138 mg of potassium carbonate, the same reaction and after-treatment of Example 45 were carried out to obtain 213 mg of the title compound as a white powder.

$^1$H-NMR (DMSO-d$_6$) δ: 1.46 (d, 3H, J=6 Hz), 2.64 (s, 3H), 3.00–4.20 (m, 11H), 4.25–4.40 (m, 2H), 4.60–4.70 (m, 1H), 5.29 (s, 1H), 6.35 (dt, 1H, J=16 Hz, 7 Hz), 6.56 (t, 1H, J=9 Hz), 6.74 (d, 2H, J=11 Hz), 6.91 (d, 1H, J=16 Hz), 8.30 (s, 1H), 11.59 (brs, 1H)

EXAMPLE 76

1-[1-[4-Amino-6-(3-hydroxy-1-azetidinyl)-4-pyrimidinyl]-5-methyl-4-pyrazolyl]-3-[(2R)-4-(3,5-difluorophenyl)-2-methyl-1-piperazinyl]-1-trans-propene hydrochloride

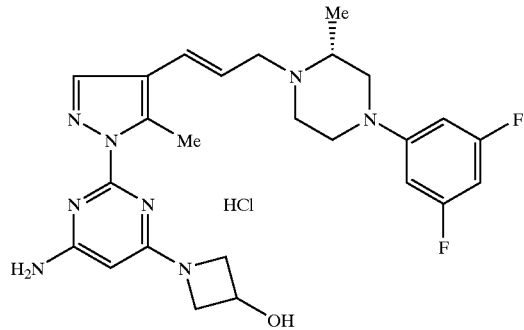

(1) 1-[1-[4-Chloro-6-(4-methoxybenzyl)amino-2-pyrimidinyl]-5-methyl-4-pyrazolyl]-3-[(2R)-4-(3,5-difluorophenyl)-2-methyl-1-piperazinyl]-1-trans-propene Using 590 mg of 3-[[4-chloro-6-(4-methoxybenzyl)amino-2-pyrimidinyl]-5-methyl-4-pyrazolyl]-2-trans-propenal and 180 mg of the compound obtained in Example 72-(1), the same reaction, after-treatment and purification of Example 31-(6) were carried out to obtain 286 mg of the title compound. Its NMR spectrum coincided with that of the compound obtained in Example 75-(1).

(2) 1-[1-(4-Amino-6-chloro-2-pyrimidinyl)-5-propyl-4-pyrazolyl]-3-[(2R)-4-(3,5-difluorophenyl)-2-methyl-1-piperazinyl]-1-trans-propene Using 286 mg of the compound obtained in Example 76-(1), the same reaction, after-treatment and purification of Example 31-(7) were carried out to obtain 220 mg of the title compound. Its NMR spectrum coincided with that of the compound obtained in Example 75-(2).

(3) 1-[1-[4-Amino-6-(3-hydroxy-1-azetidinyl)-4-pyrimidinyl]-5-methyl-4-pyrazolyl]-3-[(2R)-4-(3,5-difluorophenyl)-2-methyl-1-piperazinyl]-1-trans-propene hydrochloride Using 230 mg of the compound obtained in Example 76-(1), the same reaction, after-treatment and purification of Example 45 were carried out to obtain 154 mg of the title compound as a white powder.

$^1$H-NMR (DMSO-d$_6$) δ: 1.47 (d, 3H, J=6 Hz), 2.65 (s, 3H), 3.00–4.20 (m, 11H), 4.30–4.40 (m, 2H), 4.60–4.70 (m, 1H), 5.30 (s, 1H), 6.37 (dt, 1H, J=16 Hz, 7 Hz), 6.55 (t, 1H, J=9 Hz), 6.74 (d, 2H, J=11 Hz), 6.92 (d, 1H, J=16 Hz) 8.34 (s, 1H), 11.77 (brs, 1H)

EXAMPLE 77

3-[3-[1-[2-Amino-6-[(3S,4S)-dihydroxypyrrolidino]-4-pyrimidinyl]-5-methyl-4-pyrazolyl]-2-trans-propen-1-yl]-9-fluoro-2,3,4,4a,5,6-hexahydro-1H-pyrazino[2,1-c]-1,4-benzoxazine hydrochloride (isomer A)

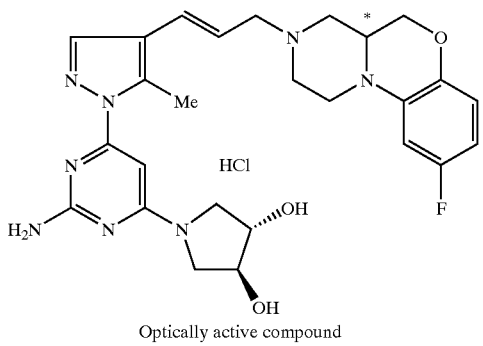

Optically active compound (1) 2-(4-Fluoro-2-nitrophenoxy)-1,1-dimethoxyethane

A DMF solution (50 ml) of 16.7 g of 2,2-dimethoxyethanol was added to dry DMF (60 ml) suspension of 4.32 g of sodium hydride at room temperature over 20 minutes. After 1 hour of stirring at room temperature, the reaction solution was cooled to 0° C., mixed with a DMF (20 ml) solution of 23.9 g of 2,5-difluoronitrobenzene and then stirred at 0° C. for 1 hour. The reaction solution was poured into 700 ml of ice water and extracted twice with a hexane-ethyl acetate (9:1) mixed solvent. The organic layer was washed with water and saturated brine in that order and dried with anhydrous sodium sulfate, and then the solvent was evaporated under a reduced pressure to obtain 35.88 g of the title compound as a light red oil.

$^1$H-NMR (CDCl$_3$) δ: 3.49 (s, 6H), 4.10 (d, 2H, J=5 Hz), 4.70 (t, 1H, 5 Hz), 7.09 (dd, 1H, J=9 Hz), 7.28 (dt, 1H, J=3 Hz, 8 Hz), 7.60 (dd, 1H, J=8 Hz, 3 Hz).

(2) 2-(2-Acetylamino-4-fluorophenoxy)-1,1-dimethoxyethane

A 35.88 g portion of the compound obtained in Example 77-(1) was dissolved in 500 ml of methanol, mixed with 7.0 g of 10% palladium-carbon (water content 50%) and subjected to 5 hours off catalytic hydrogenation under pressure (4 atmospheres), and then the insoluble matter was removed by filtration and the solvent was evaporated under a reduced pressure. The residue was dissolved in chloroform and dried with anhydrous sodium sulfate, and then the solvent was evaporated. The residue was mixed with 400 ml of ether and 32 ml of diisopropylethylamine, and an ether (30 ml) solution of 12.8 ml of acetyl chloride was added to the mixture over 10 minutes while stirring at room temperature.

After 2 hours of stirring at room temperature, the insoluble matter was removed by filtration, and the filtrate was washed with water, 1 N hydrochloric acid aqueous solution, saturated sodium bicarbonate aqueous solution, water and saturated brine in that order and then dried with anhydrous sodium sulfate. By concentrating the thus obtained solution to dryness under a reduced pressure, 36.01 g of the title compound was obtained as a light yellow solid.

$^1$H-NMR (CDCl$_3$) δ: 2.20 (s, 3H), 3.46 (s, 6H), 4.00 (d, 2H, J=5 Hz), 4.68 (t, 1H, J=5 Hz), 6.69 (dt, 1H, J=9 Hz, 4 Hz), 6.88 (dd, 1H, J=9 Hz, 5 Hz), 8.22 (dd, 1H, J=11 Hz, 3 Hz), 8.20–8.30 (brs, 1H).

(3) 4-Acetyl-6-fluoro-3-methoxy[1,4]benzoxazine

A 80 mg portion of p-toluenesulfonic acid was added to 130 ml of toluene and dehydrated by azeotropy using Dean-Stark apparatus. The solution cooled to room temperature was mixed with a toluene (10 ml) solution of 2.3 g of the compound obtained in Example 77-(2) and then stirred at 75° C. for 15 hours. After cooling, the reaction solution was diluted by adding 100 ml of ethyl acetate and washed with saturated sodium bicarbonate, water and saturated brine in that order. The organic layer was dried with anhydrous sodium sulfate, the solvent was evaporated under a reduced pressure, the thus obtained residue was applied to a silica gel column chromatography and developed with an ethyl acetate-hexane (1:4) mixed solvent, and then the fractions containing the compound of interest were concentrated to obtain 1.07 g of the title compound.

$^1$H-NMR (CDCl$_3$) δ: 2.38 (s, 3H), 3.35 (s, 3H), 4.13 (dd, 1H, J=11 Hz, 2 Hz), 4.46 (dd, 1H, J=11 Hz, 2 Hz), 5.4–6.0 (m, 1H), 6.80–7.20 (m, 3H).

(4) 4-Acetyl-3-cyano-6-fluoro[1,4]benzoxazine

A mixture composed of 1.058 g of the compound obtained in Example 77-(3), 38 ml of ether and 0.094 ml of BF$_3$-ether complex was mixed with 0.63 ml of cyanotrimethylsilane and stirred at room temperature for 8 hours. The reaction solution was further mixed with 0.094 ml of BF$_3$-ether complex and 0.63 ml of cyanotrimethylsilane, stirred at room temperature for 24 hours, diluted by adding 100 ml of ethyl acetate and then washed with saturated sodium bicarbonate, water and saturated brine in that order. After drying the organic layer with anhydrous sodium sulfate, the solvent was evaporated under a reduced pressure to obtain 1.034 g of the title compound.

$^1$H-NMR (CDCl$_3$) δ: 2.41 (s, 3H), 4.18 (dd, 1H, J=11 Hz, 3 Hz), 4.62 (dd, 1H, J=11 Hz, 2 Hz), 5.96–6.15 (m, 1H), 6.90–7.10 (m, 3H).

(5) N-[(S)-1-Phenylethyl]-6-fluoro[1,4]benzoxazine-3-carboxamide (isomer A and isomer B)

A 1.034 g portion of the compound obtained in Example 77-(4) was added to 30 ml of 6 N hydrochloric acid and stirred at 100° C. for 13 hours and then the reaction solution was concentrated to dryness under a reduced pressure. The residue was mixed with water and extracted with a methanol-chloroform (5:95) mixed solvent and then the organic layer was dried with anhydrous sodium sulfate. The residue was mixed with 40 ml of dichloromethane, 0.94 ml of (S)-(–)-phenethylamine, 1.19 g of dimethylaminopyridine and 1.4 g of 1-ethyl-3-(3-dimethylaminopropyl)carbodiimide hydrochloride and stirred at room temperature for 5 days. The reaction solution was diluted with chloroform and then washed with water, 1 N phosphoric acid aqueous solution, water and saturated brine in that order and dried with anhydrous sodium sulfate. After evaporation of the solvent, the residue was applied to a silica gel column chromatography and developed with an ethyl acetate-hexane (2:3) mixed solvent to obtain 347 mg of isomer A of the title compound as colorless crystals from the low polarity fractions. Also, 367 mg of isomer B of the title compound was obtained as a colorless syrup from the high polarity fractions.

Isomer A $^1$H-NMR (CDCl$_3$) δ: 1.43 (d, 3H, J=6.8 Hz), 3.96 (dd, 1H, J=10 7 Hz, 3.4 Hz), 4.04 (dt, 1H, J=5.9 Hz, 3.4 Hz), 4.18 (d, 1H, J=5.9 Hz), 4.53 (dd, 1H, J=10.7 Hz, 3.4 Hz), 5.09–5.17 (m, 1H), 6.42–6.47 (m, 2H), 6.80 (dd, 1H, J=9.8 Hz, 5.4 Hz), 6.88 (d, 1H, J=7.8 Hz), 7.27–7.37 (m, 5H).

Isomer B $^1$H-NMR (CDCl$_3$) δ: 1.49 (d, 3H, J=6.8 Hz), 3.95 (dd, 1H, J=10 7 Hz, 3.4 Hz), 4.09 (dt, 1H, J=5.9 Hz, 3.4 Hz), 4.26 (d, 1H, J=5.9 Hz), 4.49 (dd, 1H, J=10.7 Hz, 3.4 Hz), 5.09–5.17 (m, 1H), 6.42–6.49 (m, 2H), 6.79 (dd, 1H, J=8.8 Hz, 5.4 Hz), 6.88 (d, 1H, J=7.8 Hz), 7.12–7.28 (m, 5H).

(6) N-tert-Butoxycarbonyl-N-[(S)-1-phenylethyl]aminomethyl-6-fluoro[1,4]benzoxazine (isomer A)

A 2.08 g portion of the isomer A obtained in Example 77-(5) was dissolved in 30 ml of tetrahydrofuran, mixed with 6.93 ml of 10 N borane-dimethyl sulfide complex while stirring at 0° C. and then stirred at room temperature for 1 day. This was mixed with 6 N hydrochloric acid aqueous solution, stirred for 1 hour and then neutralized using saturated sodium bicarbonate aqueous solution. After extraction with chloroform, the organic layer was washed with saturated brine and dried with anhydrous sodium sulfate and then the solvent was evaporated under a reduced pressure. The residue was dissolved in 50 ml of dioxane, mixed with 3.18 ml of di-tert-butyl dicarbonate and then stirred at room temperature for 6 hours. After evaporation of the solvent under a reduced pressure, the residue was applied to a silica gel column chromatography and developed with an ethyl acetate-hexane (1:4) mixed solvent, and then the fractions containing the compound of interest were concentrated to obtain 2.05 g of the title compound.

$^1$H-NMR (CDCl$_3$) δ: 1.49 (s, 9H), 1.52 (d, 3H, J=7 Hz), 2.96 (brs, 1H), 3.18 (dd, 1H, J=15 Hz, 4 Hz), 3.40 (brs, 1H), 3.79 (dd, 1H, J=11 Hz, 6 Hz), 4.03 (dd, 1H, J=11 Hz, 2 Hz), 5.69 (brs, 1H), 6.22 (dt, 1H, J=8 Hz, 3 Hz), 6.59 (dd, 1H, J=9 Hz, 5 Hz), 7.33–7.39 (m, 5H).

(7) 9-Fluoro-3-[(S)-1-phenylethyl]-2,3,4,4a,5,6-hexahydro-2-oxopyrazino[2,1-c]benzoxazine (isomer A)

A 2.05 g portion of the compound obtained in Example 77-(6) was dissolved in 15 ml of tetrahydrofuran and mixed with 644 μl of pyridine, and 1.5 ml of tetrahydrofuran solution containing 465 μl of chloroacetyl chloride was added dropwise to the mixture which was stirred at 0° C. After 2.5 hours of stirring at room temperature, the reaction solution was mixed with ice water and extracted with ethyl acetate, and the organic layer was washed with saturated brine and dried with anhydrous sodium sulfate. After evaporation of the solvent under a reduced pressure, the thus obtained residue was dissolved in 15 ml of tetrahydrofuran, mixed with 20 ml of trifluoroacetic acid, and stirred at room temperature for 1 hour and then at 50° C. for 3 hours. After concentration of the reaction solution to dryness under a reduced pressure, the residue was dissolved in 15 ml of dimethylformamide, mixed with 1.32 g of potassium carbonate and stirred at 50° C. for 1 hour. The reaction solution was cooled to room temperature, diluted with water and then extracted with ethyl acetate. The organic layer was washed with saturated brine and dried with anhydrous sodium sulfate, and then the solvent was evaporated under a reduced pressure. The residue was applied to a silica gel column chromatography and developed with an ethyl acetate-hexane (1:9) mixed solvent, and the fractions containing the compound of interest were concentrated to obtain 1.88 g of the title compound as a slightly brown oil.

¹H-NMR (CDCl₃) δ: 1.41 (d, 3H, J=7 Hz), 2.09 (dd, 1H, J=12 Hz, 9 Hz), 2.97 (ddd, 1H, J=12 Hz, 5 Hz, 2 Hz), 3.08 (d, 1H, J=17 Hz), 3.39 (q, 1H, J=7 Hz), 3.84–3.87 (m, 2H), 4.14 (d, 1H, J=8 Hz), 6.74–6.81 (m, 2H), 7.27–7.37 (m, 5H), 8.19 (dd, 1H, J=12 Hz, 2 Hz).

(8) 9-Fluoro-3-[1-(S)-1-phenylethyl]-2,3,4,4a,5,6-hexahydro-1H-pyrazino[2,1-c]benzoxazine (isomer A)

A 1.88 g portion of the compound obtained in Example 77-(7) was dissolved in 30 ml of tetrahydrofuran, mixed with 6 ml of 10 N borane-dimethyl sulfide complex while stirring at 0° C. and then stirred at room temperature for 3 days. This was mixed with ethanol and then with 6 N hydrochloric acid aqueous solution. After 1 hour of stirring, this was neutralized using saturated sodium bicarbonate aqueous solution. After extraction with chloroform, the organic layer was washed with saturated brine and dried with anhydrous sodium sulfate, and then the solvent was evaporated under a reduced pressure. The thus obtained residue was applied to a silica gel column chromatography and developed with a chloroform-methanol (98:2) mixed solvent, and then the fractions containing the compound of interest were concentrated to obtain 1.33 g of the title compound as a white powder.

¹H-NMR (CDCl₃) δ: 1.39 (d, 3H, J=6 Hz), 1.68 (t, 1H, J=11 Hz), 2.24 (dt, 1H, J=12 Hz, 3 Hz), 2.66–2.70 (m, 1H), 2.87 (dt, 1H, J=12 Hz, 3 Hz), 3.06–3.13 (m, 1H), 3.18–3.22 (m, 1H), 3.38 (q, 1H, J=7 Hz), 3.57 (d, 1H, J=13 Hz), 3.83 (dd, J=11 Hz, 9 Hz), 4.01 (dd, 1H, J=11 Hz, 3 Hz), 6.35 (dt, 1H, J=11 Hz, 3 Hz), 6.47 (dd, 1H, J=11 Hz, 3 Hz), 6.64 (dd, 1H, J=8 Hz, 5 Hz), 7.23–7.35 (m, 5H).

(9) 9-Fluoro-2,3,4,4a,5,6-hexahydro-(1H)-pyrazino[2,1-c]benzoxazine (isomer A)

A 1.33 g portion of the compound obtained in Example 77-(8) was dissolved in 50 ml of methanol, mixed with 1.34 g of ammonium formate and 1.35 g of 10% palladium-carbon and then heated under reflux for 2 hours. After removal of the insoluble matter by filtration, the filtrate was concentrated under a reduced pressure. The residue was mixed with saturated sodium bicarbonate aqueous solution and extracted with chloroform, and then the organic layer was dried with anhydrous sodium sulfate and the solvent was evaporated under a reduced pressure to obtain 1.56 g of the title compound as a brown oil.

¹H-NMR (CDCl₃) δ: 2.49 (t, 1H, J=11 Hz), 2.71 (dt, 1H, J=12 Hz, 3 Hz), 2.93 (dt, 1H, J=16 Hz, 3 Hz), 3.00 (d, 1H, J=12 Hz), 3.07–3.16 (m, 2H), 3.52 (d, 1H, J=12 Hz), 3.93 (dd, 1H, J=11 Hz, 9 Hz), 4.14 (dd, 1H, J=11 Hz, 3 Hz), 6.38 (dt, 1H, J=9 Hz, 3 Hz), 6.48 (dd, 1H, J=11 Hz, 3 Hz), 6.67 (dd, 1H, J=9 Hz, 6 Hz).

(10) 3-[3-[1-(2-Amino-4-chloro-6-pyrimidinyl)-5-methyl-4-pyrazolyl]-2-trans-propen-1-yl]-9-fluoro-2,3,4,4a,5,6-hexahydro-1H-pyrazino[2,1-c]-1,4-benzoxazine (isomer A)

A 229 mg portion of the compound obtained in Example 77-(9) was dissolved in 20 ml of ethanol, mixed with 264 mg of 3-[1-(2-amino-4-chloro-6-pyrimidinyl)-5-methyl-4-pyrazolyl]-2-trans-propenal and 286 µl of acetic acid and then stirred at room temperature for 4 hours. Next, this was mixed with 157 mg of sodium cyanoborohydride and stirred at room temperature for 2 days. Ethanol was evaporated under a reduced pressure, and the residue was mixed with saturated sodium bicarbonate aqueous solution and extracted with chloroform. The organic layer was dried with anhydrous sodium sulfate, the solvent was evaporated, the thus obtained residue was applied to a silica gel chromatography and developed with a chloroform-methanol (97:3) mixed solvent, and then the fractions containing the compound of interest were concentrated to obtain 248 mg of the title compound as a white powder.

¹H-NMR (CDCl₃) δ: 1.85 (t, 1H, J=11 Hz), 2.27 (dt, 1H, J=12 Hz, 3 Hz), 2.68 (s, 3H), 2.81–2.95 (m, 2H), 3.07 (d, 1H, J=12 Hz), 3.14–3.27 (m, 3H), 3.57 (d, 1H, J=12 Hz), 3.95 (dd, 1H, J=10 Hz, 9 Hz), 4.17 (dd, 1H, J=11 Hz, 3 Hz), 5.43 (brs, 2H), 6.07 (dt, 1H, J=16 Hz, 7 Hz), 6.36–6.40 (m, 2H), 6.49 (dd, 1H, J=11 Hz, 3 Hz), 6.68 (dd, 1H, J=9 Hz, 6 Hz), 7.29 (s, 1H), 7.80 (s, 1H).

(11) 3-[3-[1-[2-Amino-6-[(3S,4S)-dihydroxypyrrolidino]-4-pyrimidinyl]-5-methyl-4-pyrazolyl]-2-trans-propen-1-yl]-9-fluoro-2,3,4,4a,5,6-hexahydro-1H-pyrazino[2,1-c]-1,4-benzoxazine hydrochloride (isomer A)

Using 37 mg (0.08 mmol) of the compound obtained in Example 77-(10) and 25 mg of (3S,4S)-dihydroxypyrrolidine, the same reaction and after-treatment of Example 33 were carried out to obtain 27 mg of the title compound as a white powder.

¹H-NMR (DMSO-d₆) δ: 2.66 (s, 3H), 2.83 (q, 1H, J=10 Hz), 3.05–3.08 (m, 1H), 3.24 (t, 1H, J=12 Hz), 3.54 (d, 1H, J=12 Hz), 3.62–3.70 (m, 4H), 3.87–3.98 (m, 3H), 4.06–4.09 (m, 3H), 4.29 (dd, 1H, J=11 Hz, 3 Hz), 6.24 (dt, 2H, J=16 Hz, 7 Hz), 6.31 (s, 1H), 6.49 (dt, 1H, J=9 Hz, 3 Hz), 6.73 (dd, 1H, J=9 Hz, 6 Hz), 6.80 (d, 1H, J=16 Hz), 6.87 (dd, 1H, J=12 Hz, 3 Hz), 8.14 (s, 1H), 11.80 (brs, 1H)

EXAMPLE 78

3-[3-[1-[2-Amino-6-[(3S,4S)-dihydroxypyrrolidino]-4-pyrimidinyl]-5-methyl-4-pyrazolyl]-2-trans-propen-1-yl]-9-fluoro-2,3,4,4a,5,6-hexahydro-1H-pyrazino[2,1-c]-1,4-benzoxazine hydrochloride (isomer B)

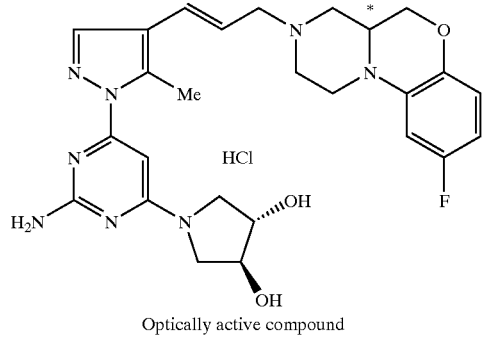

Optically active compound (1) N-tert-Butoxycarbonyl-N-[(S)-1-phenylethyl] aminomethyl-6-fluoro[1,4]benzoxazine (isomer B)

Using 2.43 g of the isomer B obtained in Example 77-(5), the same reaction, after-treatment and purification of Example 77-(6) were carried out to obtain 2.69 g of the title compound.

¹H-NMR (CDCl₃) δ: 1.47 (s, 9H), 1.48 (s, 3H), 3.02–3.11 (m, 2H), 3.32 (s, 1H), 3.54 (dd, 1H, J=11 Hz, 4 Hz), 3.69 (d, 1H, J=10 Hz), 4.03 (dd, 1H, J=11 Hz, 2 Hz), 5.41 (brs, 1H), 6.21–6.28 (m, 2H), 6.61 (dd, 1H, J=9 Hz), 7.27–7.36 (m, 5H).

(2) 9-Fluoro-3-[1-(S)phenylethyl]-2,3,4,4a,5,6-hexahydro-2-oxopyrazino[2,1-c]benzoxazine (isomer B)

Using 2.69 g of the compound obtained in Example 78-(1), the same reaction, after-treatment and purification of Example 77-(7) were carried out to obtain 1.45 g of the title compound as a slightly brown oil.

¹H-NMR (CDCl₃) δ: 1.42 (d, 3H, J=6 Hz), 2.09 (dd, 1H, J=12 Hz, 7 Hz), 3.04 (dd, 1H, J=12 Hz, 3 Hz), 3.24 (d, 1H,

J=17 Hz), 3.41 (d, 1H, J=17 Hz), 3.47 (q, 1H, J=7 Hz), 3.85 (dt, 1H, J=6 Hz, 3 Hz), 4.05 (t, 1H, J=10 Hz), 4.19 (dd, 1H, J=10 Hz, 3 Hz), 6.73–6.82 (m, 2H), 7.28–7.37 (m, 5H), 8.06 (dd, 1H, J=11 Hz, 3 Hz).

(3) 9-Fluoro-3-[1-(S)phenylethyl]-2,3,4,4a,5,6-hexahydro-(1H)-pyrazino[2,1-c]benzoxazine (isomer B)

Using 1.45 g of the compound-obtained in Example 78-(2), the same reaction, after-treatment and purification of Example 77-(8) were carried out to obtain 1.52 g of the title compound as a white powder.

$^1$H-NMR (CDCl$_3$) δ: 1.39 (d, 3H, J=7 Hz), 1.83 (t, 1H, J=11 Hz), 2.14 (dt, 1H, J=11 Hz, 3 Hz), 2.74 (dt, 1H, J=11 Hz, 3 Hz), 2.82–2.86 (m, 1H), 2.99–3.03 (m, 1H), 3.18–3.25 (m, 1H), 3.39–3.44 (m, 2H), 3.94 (d, 1H, J=11 Hz, 9 Hz), 4.16 (dd, 1H, J=11 Hz, 3 Hz), 6.35 (dt, 1H, J=11 Hz, 3 Hz), 6.42 (dd, 1H, J=11 Hz, 3 Hz), 6.66 (dd, 1H, J=9 Hz, 5 Hz), 7.23–7.33 (m, 5H).

(4) 9-Fluoro-2,3,4,4a,5,6-hexahydro-(1H)-pyrazino[2,1-c]benzoxazine (isomer B)

Using 1.52 g of the compound obtained in Example 78-(3), the same reaction, after-treatment and purification of Example 77-(9) were carried out to obtain 762 mg of the title compound as a dark brown oil.

$^1$H-NMR (CDCl$_3$) δ: 2.54 (t, 1H, J=11 Hz), 2.71 (t, 1H, J=12 Hz), 2.96 (dt, 1H, J=16 Hz, 3 Hz), 3.04 (d, 1H, J=13 Hz), 3.19 (d, 2H, J=11 Hz), 3.56 (d, 1H, J=12 Hz), 3.94 (t, 1H, J=11 Hz), 4.15 (dd, 1H, J=11 Hz, 3 Hz), 6.39 (dt, 1H, J=9 Hz, 3 Hz), 6.49 (dd, 1H, J=11 Hz, 3 Hz), 6.68 (dd, 1H, J=9 Hz, 6 Hz).

(5) 3-[3-[1-(2-Amino-4-chloro-6-pyrimidinyl)-5-methyl-4-pyrazolyl]-2-trans-propen-1-yl]-9-fluoro-2,3,4,4a,5,6-hexahydro-1H-pyrazino[2,1-c]-1,4-benzoxazine (isomer B)

Using 229 mg of the compound obtained in Example 78-(4) and 264 mg of 3-[1-(2-Amino-4-chloro-6-pyrimidinyl)-5-methyl-4-pyrazolyl]-2-trans-2-propenal, the same reaction, after-treatment and purification of Example 77-(10) were carried out to obtain 248 mg of the title compound as a white powder.

$^1$H-NMR (CDCl$_3$) δ: 1.88 (t, 1H, J=11 Hz), 2.29 (dt, 1H, J=12 Hz, 3 Hz), 2.68 (s, 3H), 2.91 (dt, 1H, J=12 Hz, 3 Hz), 2.97 (d, 1H, J=11 Hz), 3.11 (d, 1H, J=11 Hz), 3.20–3.27 (m, 3H), 3.58 (d, 1H, J=12 Hz), 3.95 (dd, 1H, J=11 Hz, 9 Hz), 4.17 (dd, 1H, J=11 Hz, 3 Hz), 5.52 (brs, 2H), 6.07 (dt, 1H, J=16 Hz, 7 Hz), 6.36–6.40 (m, 2H), 6.49 (dd, 1H, J=11 Hz, 3 Hz), 6.68 (dd, 1H, J=9 Hz, 6 Hz), 7.29 (s, 1H) 7.81 (s, 1H).

(6) 3-[3-[1-[2-Amino-6-[(3S,4S)-dihydroxypyrrolidino]-4-pyrimidinyl]-5-methyl-4-pyrazolyl]-2-trans-propen-1-yl]-9-fluoro-2,3,4,4a,5,6-hexahydro-1H-pyrazino[2,1-c]-1,4-benzoxazine hydrochloride (isomer B)

Using 32 mg of the compound obtained in Example 78-(5) and 22 mg of (3S,4S)-dihydroxypyrrolidine, the same reaction, after-treatment and purification of Example 33 were carried out to obtain 27 mg of the title compound as a white powder.

$^1$H-NMR (DMSO-d$_6$) δ: 2.66 (s, 3H), 2.83 (q, 1H, J=10 Hz), 3.05–3.08 (m, 1H), 3.25 (t, 1H, J=12 Hz), 3.54 (d, 1H, J=12 Hz), 3.63–3.71 (m, 4H), 3.87–3.98 (m, 3H), 4.06–4.10 (m, 3H), 4.29 (dd, 1H, J=11 Hz, 3 Hz), 6.24 (dt, 2H, J=16 Hz, 7 Hz), 6.32 (s, 1H), 6.49 (dt, 1H, J=9 Hz, 3 Hz), 6.74 (dd, 1H, J=9 Hz, 6 Hz), 6.80 (d, 1H, J=16 Hz), 6.87 (dd, 1H, J=12 Hz, 3 Hz), 8.14 (s, 1H), 11.87 (brs, 1H)

EXAMPLE 79

3-[3-[1-[2-Amino-6-(3-hydroxy-1-azetidinyl)-4-pyrimidinyl]-5-methyl-4-pyrazolyl]-2-trans-propen-1-yl]-9-fluoro-2,3,4,4a,5,6-hexahydro-1H-pyrazino[2,1-c]-1,4-benzoxazine hydrochloride (isomer A)

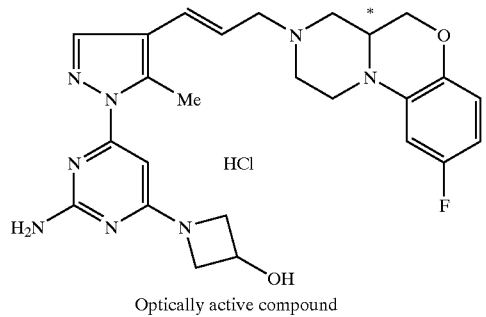

Optically active compound

Using 248 mg of the compound obtained in Example 77-(10), 179 mg of 3-hydroxyazetidine hydrochloride and 150 mg of potassium carbonate, the same reaction and after-treatment of Example 45 were carried out to obtain 241 mg of the title compound as a white powder.

$^1$H-NMR (DMSO-d$_6$) δ: 2.65 (s, 3H), 2.82 (q, 1H, J=10 Hz), 3.05–3.08 (m, 1H), 3.22 (t, 1H, J=12 Hz), 3.54 (d, 1H, J=12 Hz), 3.62–3.67 (m, 1H), 3.86–3.98 (m, 5H), 4.08 (d, 1H, J=14 Hz), 4.29 (dd, 1H, J=11 Hz, 3 Hz), 4.39–4.41 (m, 2H), 4.58–4.64 (m, 1H), 6.12 (s, 1H), 6.22 (dt, 2H, J=16 Hz, 7 Hz), 6.49 (dt, 1H, J=8 Hz, 3 Hz), 6.74 (dd, 1H, J=9 Hz, 6 Hz), 6.78 (d, 1H, J=16 Hz), 6.88 (dd, 1H, J=12 Hz, 3 Hz), 8.11 (s, 1H), 11.60 (brs, 1H)

EXAMPLE 80

3-[3-[1-[2-Amino-6-(3-hydroxy-1-azetidinyl)-4-pyrimidinyl]-5-methyl-4-pyrazolyl]-2-trans-propen-1-yl]-9-fluoro-2,3,4,4a,5,6-hexahydro-1H-pyrazino[2,1-c]-1,4-benzoxazine hydrochloride (isomer B)

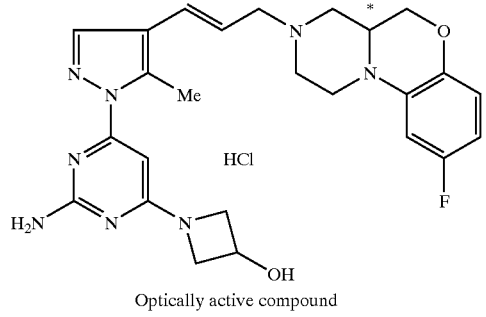

Optically active compound

Using 188 mg of the compound obtained in Example 78-(5), 136 mg of 3-hydroxyazetidine hydrochloride and 114 mg of potassium carbonate, the same reaction and after-treatment of Example 45 were carried out to obtain 209 mg of the title compound as a white powder.

$^1$H-NMR (DMSO-d$_6$) δ: 2.65 (s, 3H), 2.82 (q, 1H, J=10 Hz), 3.04–3.07 (m, 1H), 3.22 (t, 1H, J=12 Hz), 3.54 (d, 1H, J=12 Hz), 3.62–3.67 (m, 1H), 3.86–3.98 (m, 5H), 4.08 (d, 1H, J=14 Hz), 4.29 (dd, 1H, J=11 Hz, 3 Hz), 4.39–4.41 (m, 2H), 4.58–4.64 (m, 1H), 6.13 (s, 1H), 6.22 (dt, 2H, J=16 Hz, 7 Hz), 6.49 (dt, 1H, J=8 Hz, 3 Hz), 6.74 (dd, 1H, J=9 Hz, 6

Hz), 6.80 (d, 1H, J=16 Hz), 6. 88 (dd, 1H, J=11 Hz, 2 Hz), 8.11 (s, 1H), 11.67 (brs, 1H)

EXAMPLE 81

3-[3-[1-[4-Amino-6-(3-hydroxy-1-azetidinyl)-2-pyrimidinyl]-5-methyl-4-pyrazolyl]-2-trans-propen-1-yl]-9-fluoro-2,3,4,4a,5,6-hexahydro-1H-pyrazino[2,1-c]-1,4-benzoxazine hydrochloride (isomer A)

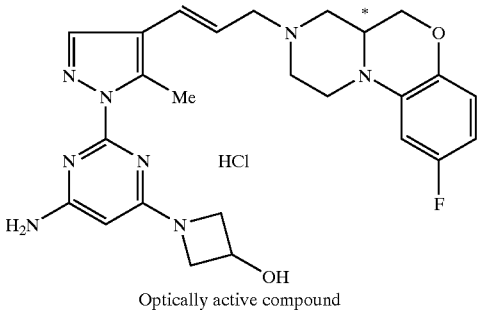

Optically active compound (1) 3-[3-[1-[4-Chloro-6-(4-methoxybenzylamino)-2-pyrimidinyl]-5-methyl-4-pyrazolyl]-2-trans-propen-1-yl]-9-fluoro-2,3,4,4a,5,6-hexahydro-1H-pyrazino[2,1-c]-1,4-benzoxazine (isomer A)

By dissolving 386 mg of the compound obtained in Example 77-(9) in 35 ml of ethanol and using 644 mg of 3-[1-(4-chloro-6-(4-methoxybenzylamino)-2-pyrimidinyl)-5-methyl-4-pyrazolyl]-2-trans-propenal and 480 μl of acetic acid, the same reaction and after-treatment of Example 77-(10) were carried out to obtain 897 mg of the title compound.

$^1$H-NMR (CDCl$_3$) δ: 1.88 (t, 1H, J=11 Hz), 2.22–2.31 (m, 1H), 2.64 (s, 3H), 2.88–2.93 (m, 2H), 3.09 (d, 1H, J=12 Hz), 3.19–3.27 (m, 3H), 3.58 (d, 1H, J=12 Hz), 3.81 (s, 3H), 3.96 (t, 1H, J=9 Hz), 4.18 (dd, 1H, J=11 Hz, 3 Hz), 4.43 (brs, 2H), 6.05 (dt, 1H, J=16 Hz, 7 Hz), 6.25 (s, 1H), 6.37–6.40 (m, 2H), 6.49 (dd, 1H, J=11 Hz, 3 Hz), 6.68 (dd, 1H, J=9 Hz, 6 Hz), 6.89 (d, 2H, J=9 Hz), 7.22 (d, 2H, J=9 Hz), 7.82 (s, 1H).

(2) 3-[3-[1-(6-Amino-4-chloro-2-pyrimidinyl)-5-methyl-4-pyrazolyl]-2-trans-propen-1-yl]-9-fluoro-2,3,4,4a,5,6-hexahydro-1H-pyrazino[2,1-c]-1,4-benzoxazine (isomer A)

Using 897 mg of the compound obtained in Example 81-(1), the same reaction and after-treatment of Example 31-(7) were carried out to obtain 495 mg of the title compound as a white solid.

$^1$H-NMR (CDCl$_3$) δ: 1.84 (t, 1H, J=11 Hz), 2.26–2.34 (m, 1H), 2.67 (s, 3H), 2.85–2.95 (m, 2H), 3.07 (d, 1H, J=11 Hz), 3.16–3.26 (m, 3H), 3.58 (d, 1H, J=12 Hz), 3.96 (dd, 1H, J=11 Hz, 9 Hz), 4.18 (dd, 1H, J=11 Hz, 3 Hz), 5.28 (brs, 1H), 6.07 (dt, 1H, J=16 Hz, 7 Hz), 6.34 (s, 1H), 6.35–6.41 (m, 2H), 6.49 (dd, 1H, J=11 Hz, 3 Hz), 6.68 (dd, 1H, J=9 Hz, 6 Hz), 7.84 (s, 1H).

(3) 3-[3-[1-[4-Amino-6-(3-hydroxy-1-azetidinyl)-2-pyrimidinyl]-5-methyl-4-pyrazolyl]-2-trans-propen-1-yl]-9-fluoro-2,3,4,4a,5,6-hexahydro-1H-pyrazino[2,1-c]-1,4-benzoxazine hydrochloride (isomer A)

Using 357 mg of the compound obtained in Example 81-(2), 357 mg of 3-hydroxyazetidine hydrochloride and 300 mg of potassium carbonate, the same reaction and after-treatment of Example 45 were carried out to obtain 390 mg of the title compound as a white powder.

$^1$H-NMR (DMSO-d$_6$) δ: 2.62 (s, 3H), 2.79–2.84 (m, 1H), 3.05–3.08 (m, 1H), 3.26 (t, 1H, J=12 Hz), 3.54 (d, 1H, J=11 Hz), 3.69–3.71 (m, 1H), 3.83–3.98 (m, 5H), 4.08 (d, 1H, J=13 Hz), 4.28–4.32 (m, 3H), 4.59–4.65 (m, 1H), 5.27 (s, 1H), 6.30 (dt, 2H, J=16 Hz, 7 Hz), 6.49 (dt, 1H, J=8 Hz, 3 Hz), 6.74 (dd, 1H, J=9 Hz, 6 Hz), 6.81 (d, 1H, J=16 Hz), 6.88 (dd, 1H, J=12 Hz, 3 Hz), 8.25 (s, 1H), 11.93 (brs, 1H)

EXAMPLE 82

3-[3-[1-[4-Amino-6-(3-hydroxy-1-azetidinyl)-2-pyrimidinyl]-5-methyl-4-pyrazolyl]-2-trans-propen-1-yl]-9-fluoro-2,3,4,4a,5,6-hexahydro-1H-pyrazino[2,1-c]-1,4-benzoxazine hydrochloride (isomer B)

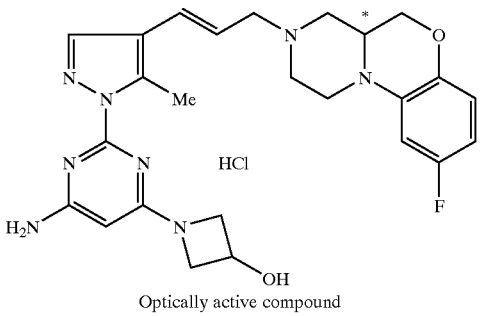

Optically active compound (1) 3-[3-[1-(4-Chloro-6-(4-methoxybenzylamino)-2-pyrimidinyl]-5-methyl-4-pyrazolyl]-2-trans-propen-1-yl]-9-fluoro-2,3,4,4a,5,6-hexahydro-1H-pyrazino[2,1-c]-1,4-benzoxazine (isomer B)

Using 487 mg of the compound obtained in Example 78-(4) and 813 mg of 3-[1-(4-chloro-6-(4-methoxybenzylamino)-2-pyrimidinyl)-5-methyl-4-pyrazolyl]-2-trans-propenal, the same reaction, after-treatment and purification of Example 81-(1) were carried out to obtain 588 mg of the title compound.

$^1$H-NMR (CDCl$_3$) δ: 1.90 (t, 1H, J=11 Hz), 2.25–2.32 (m, 1H), 2.63 (s, 3H), 2.90–3.00 (m, 2H), 3.12 (d, 1H, J=11 Hz), 3.20–3.31 (m, 3H), 3.58 (d, 1H, J=11 Hz), 3.81 (s, 3H), 3.96 (t, 1H, J=9 Hz), 4.18 (dd, 1H, J=11 Hz, 3 Hz), 4.48 (brs, 2H), 6.05 (dt, 1H, J=16 Hz, 7 Hz), 6.25 (s, 1H), 6.37–6.43 (m, 2H), 6.49 (dd, 1H, J=11 Hz, 3 Hz), 6.68 (dd, 1H, J=9 Hz, 6 Hz), 6.89 (d, 2H, J=9 Hz), 7.23 (d, 2H, J=9 Hz), 7.84 (s, 1H).

(2) 3-[3-[1-(6-Amino-4-chloro-2-pyrimidinyl)-5-methyl-4-pyrazolyl]-2-trans-propen-1-yl]-9-fluoro-2,3,4,4a,5,6-hexahydro-1H-pyrazino[2,1-c]-1,4-benzoxazine (isomer B)

Using 588 mg of the compound obtained in Example 82-(1), the same reaction, after-treatment and purification of Example 31-(7) were carried out to obtain 277 mg of the title compound as a white solid.

$^1$H-NMR (CDCl$_3$) δ: 1.84 (t, 1H, J=11 Hz), 2.26 (dt, 1H, J=12 Hz, 3 Hz), 2.67 (s, 3H), 2.84–2.95 (m, 2H), 3.07 (d, 1H, J=10 Hz), 3.13–3.26 (m, 3H), 3.57 (d, 1H, J=12 Hz), 3.96 (t, 1H, J=9 Hz), 4.18 (dd, 1H, J=10 Hz, 3 Hz), 5.33 (brs, 1H), 6.06 (dt, 1H, J=16 Hz, 7 Hz), 6.34 (s, 1H), 6.35–6.41 (m, 2H), 6.49 (dd, 1H, J=11 Hz, 3 Hz), 6.68 (dd, 1H, J=9 Hz, 6 Hz), 7.84 (s, 1H).

(3) 3-[3-[1-[4-Amino-6-(3-hydroxy-1-azetidinyl)-2-pyrimidinyl]-5-methyl-4-pyrazolyl]-2-trans-propen-1-yl]-9-fluoro-2,3,4,4a,5,6-hexahydro-1H-pyrazino[2,1-c]-1,4-benzoxazine hydrochloride (isomer B)

Using 277 mg of the compound obtained in Example 82-(2), 200 mg of 3-hydroxyazetidine hydrochloride and 170 mg of potassium carbonate, the same reaction and after-treatment of Example 45 were carried out to obtain 212 mg of the title compound as a white powder.

$^1$H-NMR (DMSO-d$_6$) δ: 2.62 (s, 3H), 2.79–2.84 (m, 1H), 3.05–3.08 (m, 1H), 3.26 (t, 1H, J=12 Hz), 3.54 (d, 1H, J=12

Hz), 3.68–3.71 (m, 1H), 3.84–3.98 (m, 5H), 4.08 (d, 1H, J=14 Hz), 4.28–4.32 (m, 3H), 4.59–4.62 (m, 1H), 5.27 (s, 1H), 6.30 (dt, 2H, J=16 Hz, 7 Hz), 6.49 (dt, 1H, J=8 Hz, 3 Hz), 6.74 (dd, 1H, J=9 Hz, 6 Hz), 6.81 (d, 1H, J=16 Hz), 6.88 (dd, 1H, J=12 Hz, 3 Hz), 8.25 (s, 1H), 12.00 (brs, 1H)

EXAMPLE 83

1-[1-[4-Amino-6-(3-hydroxyazetidino)-2-pyrimidinyl]-5-ethyl-4-pyrazolyl]-3-[4-(3,5-difluorophenyl)-1-piperazinyl]-1-trans-propene hydrochloride

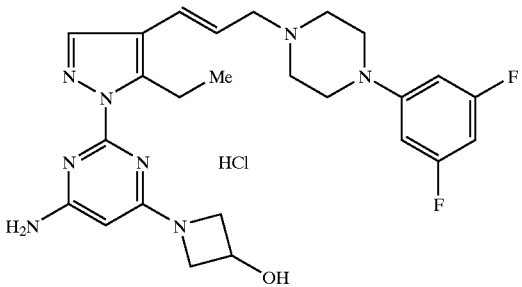

(1) Methyl 1-[4-chloro-6-(4-methoxybenzyl)amino-2-pyrimidinyl]-5-ethyl-4-pyrazolecarboxylate A 2.8 g portion of 4-chloro-2-hydrazino-6-(4-methoxybenzyl)aminopyrimidine was added to an ethanol solution (20 ml) of 1.72 g of methyl 2-(methoxymethylene)propionylacetate (methyl 2-methoxymethylene-3-oxopentanoate) at room temperature and stirred for 30 minutes, and then the mixture was heated under reflux for 3 hours. After concentration of the reaction solution under a reduced pressure, ether and hexane were added to the residue and the precipitate was collected by filtration to obtain 2.53 g of the title compound as a white solid.

$^1$H-NMR (CDCl$_3$) δ: 1.28 (t, 3H, J=7 Hz), 3.47 (q, 2H, J=7 Hz), 3.82 (s, 3H), 3.86 (s, 3H), 4.3–4.7 (brs, 2H), 6.34 (s, 1H), 6.90 (d, 2H, J=9 Hz), 7.24 (d, 2H, J=9 Hz), 8.05 (s,1H).

(2) 1-[4-Chloro-6-(4-methoxybenzyl)amino-2-pyrimidinyl]-5-ethyl-4-pyrazolecarbaldehyde Using 2.52 g of the compound obtained in Example 83-(1), the same reaction and after-treatment of Example 31-(3) were carried out to obtain 2.52 g of the title compound.

$^1$H-NMR (CDCl$_3$) δ: 1.32 (t, 3H, J=7 Hz), 3.45 (q, 2H, J=7 Hz), 3.82 (s, 3H), 4.35–4.80 (br, 2H), 6.36 (s, 1H), 6.90 (d, 2H, J=9 Hz), 7.24 (d, 2H, J=9 Hz), 8.09 (s, 1H), 10.00 (s, 1H).

(3) Ethyl 3-[1-[4-chloro-6-(4-methoxybenzyl)amino-2-pyrimidinyl]-5-ethyl-4-pyrazolyl]-2-trans-propenoate Using 2.52 g of the compound obtained in Example 83-(2) and 2.62 g of (carboethoxymethylene)triphenylphosphoran, the same reaction and after-treatment of Example 31-(4) were carried out to obtain 3.24 g of the title compound as a white solid.

$^1$H-NMR (CDCl$_3$) δ: 1.24 (t, 3H, J=7 Hz), 1.33 (t, 3H, J=7 Hz), 3.25 (q, 2H, J=7 Hz), 3.82 (s, 3H), 4.25 (q, 2H, J=7 Hz), 6.27 (d, 1H, J=16 Hz), 6.30 (s, 1H), 6.90 (d, 2H, J=9 Hz), 7.24 (d, 2H, J=9 Hz), 7.59 (d, 1H, J=16 Hz), 7.93 (s, 1H).

(4) 3-[1-[4-Chloro-6-(4-methoxybenzyl)amino-2-pyrimidinyl]-5-ethyl-4-pyrazolyl]-2-trans-propenal Using 3.24 g of the compound obtained in Example 83-(3), the same reaction and after-treatment of Example 31-(5) were carried out to obtain 1.78 g of the title compound.

$^1$H-NMR (CDCl$_3$) δ: 1.28 (t, 3H, J=7 Hz), 3.27 (q, 2H, J=7 Hz), 3.82 (s, 3H), 4.3–4.7 (br, 2H), 6.33 (s, 1H), 6.56 (dd, 1H, J=16 Hz, 8 Hz), 6.91 (d, 2H, J=9 Hz), 7.24 (d, 2H, J=9 Hz), 7.38 (d, 1H, J=16 Hz), 7.95 (s, 1H), 9.65 (d, 1H, J=8 Hz).

(5) 1-[1-[4-Chloro-6-(4-methoxybenzyl)amino-2-pyrimidinyl]-5-ethyl-4-pyrazolyl]-3-[4-(3,5-difluorophenyl)-1-piperazinyl]-1-trans-propene A 796 mg portion of the compound obtained in Example 83-(4) was dissolved in 20 ml of ethanol and mixed with 515 mg of 1-(3,5-difluorophenyl)-1-piperazine hydrochloride and then with 500 mg of sodium cyanoborohydride, and the mixture was stirred at room temperature for 24 hours. The reaction solution was mixed with water and saturated sodium bicarbonate aqueous solution and then extracted three times with chloroform. The organic layer was dried with anhydrous sodium sulfate, the solvent was evaporated, the thus obtained residue was applied to a silica gel chromatography and developed with a mixed solvent of chloroform-methanol (98.5:1.5), and then the fractions containing the compound of interest were concentrated to obtain 712 mg of the title compound as a white solid.

$^1$H-NMR (CDCl$_3$) δ: 1.22 (t, 3H, J=7 Hz), 2.63 (t, 4H, J=5 Hz), 3.10–3.25 (m, 8H), 3.82 (s, 3H), 4.30–4.70 (brs, 2H), 6.08 (dt, 1H, J=16 Hz, 7 Hz), 6.20–6.30 (m, 1H), 6.25 (s, 1H), 6.35–6.45 (m, 3H), 6.90 (d, 2H, J=9 Hz), 7.24 (d, 2H, J=9 Hz), 7.83 (s, 1H).

(6) 1-[1-(4-Amino-6-chloro-2-pyrimidinyl)-5-ethyl-4-pyrazolyl]-3-[4-(3,5-difluorophenyl)-1-piperazinyl]-1-trans-propene Using 58 mg of the compound obtained in Example 83-(5), the same reaction and after-treatment of Example 31-(7) were carried out to obtain 46 mg of the title compound.

$^1$H-NMR (CDCl$_3$) δ: 1.25 (t, 3H, J=7 Hz), 2.66 (t, 4H, J=5 Hz), 3.20 (q, 2H, J=7 Hz), 3.21 (d, 2H, J=7 Hz), 3.24 (t, 4H, J=5 Hz), 5.35 (brs, 2H), 6.09 (dt, 1H, J=16 Hz, 7 Hz), 6.25 (tt, 1H, J=9 Hz, 2 Hz), 6.36 (s, 1H), 6.35–6.42 (m, 2H), 6.40 (d, 1H, J=16 Hz), 6.90 (d, 2H, J=9 Hz), 7.83 (s, 1H).

(7) 1-[1-[4-Amino-6-(3-hydroxy-1-azetidinyl)-2-pyrimidinyl]-5-ethyl-4-pyrazolyl]-3-[4-(3,5-difluorophenyl)-1-piperazinyl]-1-trans-propene hydrochloride Using 46 mg of the compound obtained in Example 83-(6), 44 mg of 3-hydroxyazetidine hydrochloride and 55 mg of potassium carbonate, the same reaction and after-treatment of Example 45 were carried out to obtain 28 mg of the title compound as a white powder.

$^1$H-NMR (DMSO-d$_6$) δ: 1.18 (t, 3H, J=7 Hz), 3.00–3.30 (m, 6H), 3.50–3.60 (m, 2H), 3.70–3.80 (m, 2H), 3.90–4.05 (m, 4H), 4.21 (t, 2H, J=8 Hz), 4.55–4.65 (m, 1H), 5.24 (s, 1H), 6.20 (dt, 1H, J=16 Hz, 7 Hz), 6.58 (t, 1H, J=9 Hz), 6.73 (dd, 2H, J=11 Hz, 2 Hz), 6.78 (d, 1H, J=16 Hz), 8.02 (s, 1H), 10.98 (brs, 1H)

EXAMPLE 84

1-[1-[4- Amino-6-(3-hydroxy-1-azetidinyl)-2-pyrimidinyl]-5-propyl-4-pyrazolyl]-3-[4-(3,5-difluorophenyl)-1-piperazinyl]-1-trans-propene hydrochloride

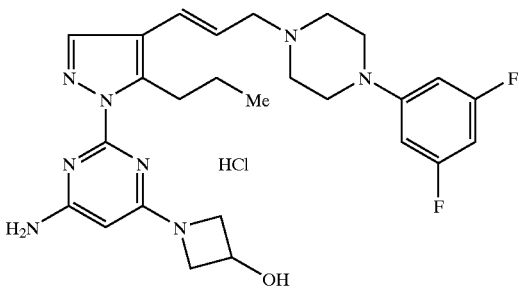

(1) Ethyl 1-[4-chloro-6-(4-methoxybenzyl)amino-2-pyrimidinyl]-5-propyl-4-pyrazolecarboxylate Using 1.11 g of ethyl 2-(ethoxymethylene)butyrylacetate (ethyl 2-ethoxymethylene-3-oxohexanoate) and 1.32 g of 4-chloro-2-hydrazino-6-(4-methoxybenzyl)aminopyrimidine, the same reaction and after-treatment of Example 83-(1) were carried out to obtain 1.57 g of the title compound as a milk white solid.

$^1$H-NMR (CDCl$_3$) δ: 0.97 (t, 3H, J=7 Hz), 1.37 (t, 3H, J=7 Hz), 1.70 (m, 2H), 3.45 (m, 2H), 3.81 (s, 3H), 4.32 (q, 2H, J=7 Hz), 4.3–4.7 (br, 2H), 6.32 (s, 1H), 6.90 (d, 2H, J=9 Hz), 7.24 (d, 2H, J=9 Hz), 8.05 (s, 1H).

(2) 1-[4-Chloro-6-(4-methoxybenzyl)amino-2-pyrimidinyl]-5-propyl-4-pyrazolecarbaldehyde Using 1.24 g of the compound obtained in Example 84-(1), the same reaction and after-treatment of Example 31-(3) were carried out to obtain 0.97 g of the title compound.

$^1$H-NMR (CDCl$_3$) δ: 0.95 (t, 3H, J=7 Hz), 1.73 (m, 2H), 3.42 (t, 2H, J=7 Hz), 3.82 (s, 3H), 4.35–4.70 (br, 2H), 6.35 (s, 1H), 6.90 (d, 2H, J=9 Hz), 7.24 (d, 2H, J=9 Hz), 8.10 (s, 1H), 9.99 (s, 1H).

(3) Ethyl 3-[1-[4-chloro-6-(4-methoxybenzyl)amino-2-pyrimidinyl]-5-propyl-4-pyrazolyl]-2-trans-propenoate Using 0.94 g of the compound obtained in Example 84-(2) and 1.11 g of (carboethoxymethylene)triphenylphosphoran, the same reaction and after-treatment of Example 31-(4) were carried out to obtain 1.10 g of the title compound as a white solid.

$^1$H-NMR (CDCl$_3$) δ: 0.96 (t, 3H, J=7 Hz), 1.33 (t, 3H, J=7 Hz), 1.65 (m, 2H), 3.21 (t, 2H, J=7 Hz), 3.81 (s, 3H), 4.25 (q, 2H, J=7 Hz), 4.35–4.70 (br, 2H), 6.27 (d, 1H, J=16 Hz), 6.29 (s, 1H), 6.90 (d, 2H, J=9 Hz), 7.24 (d, 2H, J=9 Hz), 7.58 (d, 1H, J=16 Hz), 7.93 (s, 1H).

(4) 3-[1-[4-Chloro-6-(4-methoxybenzyl)amino-2-pyrimidinyl]-5-propyl-4-pyrazolyl]-2-trans-propenal Using 1.10 g of the compound obtained in Example 84-(3), the same reaction and after-treatment of Example 31-(5) were carried out to obtain 0.76 g of the title compound.

$^1$H-NMR (CDCl$_3$) δ: 0.99 (t, 3H, J=7 Hz), 1.70 (m, 2H), 3.24 (t, 2H, J=7 Hz), 3.82 (s, 3H), 4.3–4.7 (br, 2H), 6.32 (s, 1H), 6.56 (dd, 1H, J=16 Hz, 8 Hz), 6.90 (d, 2H, J=9 Hz), 7.24 (d, 2H, J=9 Hz), 7.38 (d, 1H, J=16 Hz), 7.96 (s, 1H, 9.65 (d, 1H, J=8 Hz).

(5) 1-[1-[4-Chloro-6-(4-methoxybenzyl)amino-2-pyrimidinyl]-5-propyl-4-pyrazolyl]-3-[4-(3,5-difluorophenyl)-1-piperazinyl]-1-trans-propene Using 41 mg of the compound obtained in Example 84-(4) and 30 mg of 1-(3,5-difluorophenyl)-1-piperazine, the same reaction and after-treatment of Example 83-(5) were carried out to obtain 61 mg of the title compound.

$^1$H-NMR (CDCl$_3$) δ: 0.94 (t, 3H, J=7 Hz), 1.60–1.70 (m, 2H), 2.64 (t, 4H, J=5 Hz), 3.13 (t, 2H, J=7 Hz), 3.20 (d, 2H, J=7 Hz), 3.23 (t, 4H, J=5 Hz), 3.81 (s, 3H), 4.30–4.60 (brs, 2H), 6.07 (dt, 1H, J=16 Hz, 7 Hz), 6.20–6.30 (m, 1H), 6.24 (s, 1H), 6.35–6.40 (m, 2H), 6.38 (d, 1H, J=16 Hz), 6.89 (d, 2H, J=8 Hz), 7.23 (d, 2H, J=8 Hz), 7.84 (s, 1H).

(6) 1-[1-(4-Amino-6-chloro-2-pyrimidinyl)-5-propyl-4-pyrazolyl]-3-[4-(3,5-difluorophenyl)-1-piperazinyl]-1-trans-propene Using 61 mg of the compound obtained in Example 84-(5), the same reaction and after-treatment of Example 31-(7) were carried out to obtain 47 mg of the title compound.

$^1$H-NMR (CDCl$_3$) δ: 0.98 (t, 3H, J=7 Hz), 1.60–1.70 (m, 2H), 2.65 (t, 4H, J=5 Hz), 3.13 (t, 2H, J=7 Hz), 3.21 (d, 2H, J=7 Hz), 3.24 (t, 4H, J=5 Hz), 5.36 (brs, 2H), 6.08 (dt, 1H, J=16 Hz, 7 Hz), 6.25 (tt, 1H, J=9 Hz, 2 Hz), 6.35 (s, 1H), 6.35–6.40 (m, 2H), 6.39 (d, 1H, J=16 Hz), 7.84 (s, 1H).

(7) 1-[1-[4-Amino-6-(3-hydroxy-1-azetidinyl)-2-pyrimidinyl]-5-propyl-4-pyrazolyl]-3-[4-(3,5-difluorophenyl)-1-piperazinyl]-1-trans-propene hydrochloride Using 61 mg of the compound obtained in Example 84-(6), 44 mg of 3-hydroxyazetidine hydrochloride and 55 mg of potassium carbonate, the same reaction and after-treatment of Example 45 were carried out to obtain 29 mg of the title compound as a white powder.

$^1$H-NMR (DMSO-d$_6$) δ: 0.89 (t, 3H, J=7 Hz), 1.50–1.65 (m, 2H), 3.00–3.30 (m, 6H), 3.45–3.55 (m, 2H), 3.70–3.80 (m, 2H), 3.90–4.05 (m, 4H), 4.15–4.25 (m, 2H), 4.55–4.65 (m, 1H), 5.22 (s, 1H), 6.18 (dt, 1H, J=16 Hz, 7 Hz), 6.58 (t, 1H, J=9 Hz), 6.73 (d, 2H, J=10 Hz), 6.77 (d, 1H, J=16 Hz), 8.00 (s, 1H), 10.81 (brs, 1H)

EXAMPLE 85

1-[1-[4-Amino-6-(3-hydroxy-1-azetidinyl)-2-pyrimidinyl]-5-(2-propyl)-4-pyrazolyl]-3-[4-(3,5-difluorophenyl)-1-piperazinyl]-1-trans-propene hydrochloride

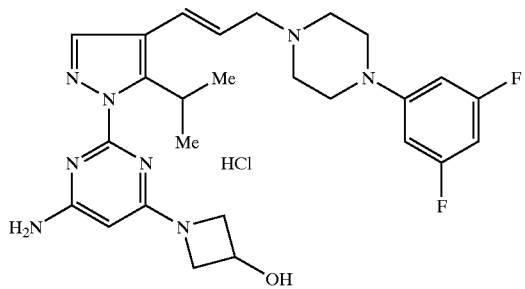

(1) Ethyl 1-[4-chloro-6-(4-methoxybenzyl)amino-2-pyrimidinyl]-5-(2-propyl)-4-pyrazolecarboxylate A 1.40 g portion of 4-chloro-2-hydrazino-6-(4-methoxybenzyl)aminopyrimidine was added at room temperature to an ethanol solution (10 ml) containing 1.07 g of ethyl 2-(ethoxymethylene)isobutyrylacetate (ethyl 2-ethoxymethylene-4-methyl-3-oxopentanoate), and the mixture was heated under reflux for 5 days. After concentration of the reaction solution under a reduced pressure, the residue was applied to a silica gel chromatography and developed with an ethyl acetate-hexane (3:7) mixed solvent, and then the fractions containing the compound of interest were concentrated to obtain 1.18 g of the title compound as a white solid.

$^1$H-NMR (CDCl$_3$) δ: 1.38 (t, 3H, J=7 Hz), 1.42 (d, 6H, J=7 Hz), 3.81 (s, 3H), 3.95 (quint., 1H, J=7 Hz), 4.31 (q, 2H, J=7 Hz), 4.3–4.7 (br, 2H), 6.37 (s, 1H), 6.90 (d, 2H, J=9 Hz), 7.23 (d, 2H, J=9 Hz), 8.03 (s, 1H).

(2) 1-[4-Chloro-6-(4-methoxybenzyl)amino-2-pyrimidinyl]-5-(2-propyl)-4-pyrazolecarbaldehyde Using 1.18 g of the compound obtained in Example 85-(1), the same reaction and after-treatment of Example 31-(3) were carried out to obtain 1.00 g of the title compound.

$^1$H-NMR (CDCl$_3$) δ: 1.45 (d, 6H, J=7 Hz), 3.82 (s, 3H), 3.99 (quint., 1H, J=7 Hz), 4.35–4.70 (br, 2H), 6.39 (s, 1H), 6.90 (d, 2H, J=9 Hz), 7.23 (d, 2H, J=9 Hz), 8.11 (s, 1H), 10.16 (s, 1H).

(3) Ethyl 3-[1-[4-chloro-6-(4-methoxybenzyl)amino-2-pyrimidinyl]-5-(2-propyl)-4-pyrazolyl]-2-trans-propenoate Using 1.00 g of the compound obtained in Example 85-(2), the same reaction and after-treatment of Example 31-(4) were carried out to obtain 1.10 g of the title compound as a white solid.

$^1$H-NMR (CDCl$_3$) δ: 1.33 (t, 3H, J=7 Hz), 1.41 (d, 6H, J=7 Hz), 3.82 (s, 3H), 3.98 (quint., 1H, J=7 Hz), 4.25 (q, 2H, J=7 Hz), 4.35–4.65 (br, 2H), 6.21 (d, 1H, J=16 Hz), 6.33 (s, 1H), 6.90 (d, 2H, J=9 Hz), 7.23 (d, 2H, J=9 Hz), 7.83 (d, 1H, J=16 Hz), 7.88 (s, 1H).

(4) 3-[1-[4-Chloro-6-(4-methoxybenzyl)amino-2-pyrimidinyl]-5-(2-propyl)-4-pyrazolyl]-2-trans-propenal Using 1.07 g of the compound obtained in Example 85-(3), the same reaction and after-treatment of Example 31-(5) were carried out to obtain 0.87 g of the title compound.

$^1$H-NMR (CDCl$_3$) δ: 1.44 (d, 6H, J=7 Hz), 3.81 (s, 3H), 4.02 (quint., 1H, J=7 Hz), 4.35–4.70 (br, 2H), 6.36 (s, 1H), 6.50 (dd, 1H, J=16 Hz, 8 Hz), 6.90 (d, 2H, J=9 Hz), 7.25 (d, 2H, J=9 Hz), 7.63 (d, 1H, J=16 Hz), 7.90 (s, 1H), 9.63 (d, 1H, J=8 Hz).

(5) 1-[1-[4-Chloro-6-(4-methoxybenzyl)amino-2-pyrimidinyl]-5-(2-propyl)-4-pyrazolyl]-3-[4-(3,5-difluorophenyl)-1-piperazinyl]-1-trans-propene Using 41 mg of the compound obtained in Example 85-(4) and 30 mg of 1-(3,5-difluorophenyl)piperazine, the same reaction and after-treatment of Example 83-(5) were carried out to obtain 62 mg of the title compound.

$^1$H-NMR (CDCl$_3$) δ: 1.36 (d, 6H, J=7 Hz), 2.64 (t, 4H, J=5 Hz), 3.19 (d, 2H, J=7 Hz), 3.24 (t, 4H, J=5 Hz), 3.81 (s, 3H), 3.98 (quint., 1H, J=7 Hz), 4.30–4.70 (brs, 2H), 6.00 (dt, 1H, J=16 Hz, 7 Hz), 6.25 (tt, 1H, J=9 Hz, 2 Hz), 6.29 (s, 1H), 6.36 (dd, 2H, J=11 Hz, 2 Hz), 6.62 (d, 1H, J=16 Hz), 6.89 (d, 2H, J=9 Hz), 7.22 (d, 2H, J=9 Hz), 7.77 (s, 1H).

(6) 1-[1-(4-Amino-6-chloro-2-pyrimidinyl)-5-(2-propyl)-4-pyrazolyl]-3-[4-(3,5-difluorophenyl)-1-piperazinyl]-1-trans-propene Using 62 mg of the compound obtained in Example 85-(5), the same reaction and after-treatment of Example 31-(7) were carried out to obtain 47 mg of the title compound.

$^1$H-NMR (CDCl$_3$) δ: 1.39 (d, 6H, J=7 Hz), 2.66 (t, 4H, J=5 Hz), 3.20 (d, 2H, J=7 Hz), 3.24 (t, 4H, J=5 Hz), 4.00 (quint., 1H, J=7 Hz), 5.45 (brs, 2H), 6.01 (dt, 1H, J=16 Hz, 7 Hz), 6.25 (tt, 1H, J=9 Hz, 2 Hz), 6.37 (dd, 2H, J=11 Hz, 2 Hz), 6.38 (s, 1H), 6.63 (d, 1H, J=16 Hz), 7.78 (s, 1H).

(7) 1-[1-[4-Amino-6-(3-hydroxy-1-azetidinyl)-2-pyrimidinyl]-5-(2-propyl)-4-pyrazolyl]-3-[4-(3,5-difluorophenyl)-1-piperazinyl]-1-trans-propene hydrochloride Using 47 mg of the compound obtained in Example 85-(6), 44 mg of 3-hydroxyazetidine hydrochloride and 55 mg of potassium carbonate, the same reaction and after-treatment of Example 45 were carried out to obtain 32 mg of the title compound as a white powder.

$^1$H-NMR (DMSO-d$_6$) δ: 1.32 (d, 6H, J=7 Hz), 3.00–3.30 (m, 4H), 3.45–3.60 (m, 2H), 3.65–3.85 (m, 3H), 3.90–4.05 (m, 4H), 4.10–4.25 (m, 2H), 4.55–4.65 (m, 1H), 5.25 (s, 1H), 6.11 (dt, 1H, J=16 Hz, 7 Hz), 6.57 (t, 1H, J=9 Hz), 6.74 (dd, 2H, J=11 Hz, 2 Hz), 6.97 (d, 1H, J=16 Hz), 7.91 (s, 1H), 10.90 (brs, 1H)

EXAMPLE 86

1-[1-[2-Amino-6-(3-hydroxy-3-methyl-1-azetidinyl)-4-pyrimidinyl]-5-(2-propyl)-4-pyrazolyl]-3-[(2R)-4-(3,5-difluorophenyl)-2-methyl-1-piperazinyl]-1-trans-propene hydrochloride

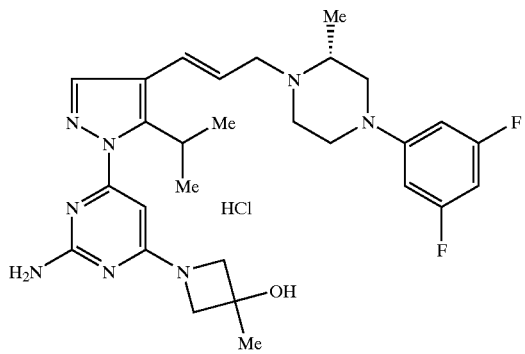

(1) Methyl 1-(2-amino-6-chloro-4-pyrimidinyl)-5-(2-propyl)-4-pyrazolecarboxylate After suspending 3.9 g of 2-amino-4-chloro-6-hydrazinopyrimidine in 50 ml of ethanol, 5.8 g of ethyl 2-(ethoxymethylene)isobutyrylacetate was added thereto and stirred at room temperature for 20 minutes and then at 80° C. for 48 hours. After cooling to room temperature, the reaction solution was mixed with 50 ml of hexane and again stirred for 24 hours. The precipitate was collected by filtration, washed with hexane and then dried to obtain 5.4 g of the title compound as a light brown solid.

$^1$H-NMR (CDCl$_3$) δ: 1.39 (t, 3H, J=7 Hz), 1.45 (d, 6H, J=7 Hz), 4.15–4.26 (m, 1H), 4.33 (q, 2H, J=7 Hz), 5.27 (brs, 2H), 7.17 (s, 1H), 8.02 (s, 1H).

(2) Ethyl 3-[1-(2-amino-6-chloro-4-pyrimidinyl)-5-(2-propyl)-4-pyrazolyl]-2-trans-propenoate Using 5.27 g of methyl 1-(2-amino-6-chloro-4-pyrimidinyl)-5-ethyl-4-pyrazolecarboxylate, the same reaction and after-treatment of Example 31-(3) were carried out to obtain 3.99 g of a white solid. Using this solid and 6.28 g of (carboethoxymethylene)triphenylphosphoran, the same reaction and after-treatment of Example 31-(4) were carried out to obtain 2.34 g of the title compound as a white solid.

$^1$H-NMR (CDCl$_3$) δ: 1.34 (t, 3H, J=7 Hz), 1.44 (d, 6H, J=7 Hz), 4.22–4.28 (m, 3H), 5.24 (br, 2H), 6.21 (d, 1H, J=16 Hz), 7.23 (s, 1H), 7.83 (d, 1H, J=16 Hz), 7.85 (s, 1H).

(3) 3-[1-(2-Amino-6-chloro-4-pyrimidinyl)-5-(2-propyl)-4-pyrazolyl]-2-trans-propenal Using 2.15 g of the compound obtained in Example 86-(2), the same reaction and after-treatment of Example 31-(5) were carried out to obtain 1.90 g of the title compound as a white solid.

$^1$H-NMR (CDCl$_3$) δ: 1.47 (d, 6H, J=7 Hz), 4.32 (quint., 1H, J=7 Hz), 5.22 (brs, 2H), 6.50 (dd, 1H, J=16 Hz, 8 Hz), 7.24 (s, 1H), 7.63 (d, 1H, J=16 Hz), 7.88 (s, 1H), 9.64 (d, 1H, J=8 Hz).

(4) 1-[1-(2-Amino-6-chloro-4-pyrimidinyl)-5-(2-propyl)-4-pyrazolyl]-3-[(2R)-4-(3,5-difluorophenyl)-2-methyl-1-piperazinyl]-1-trans-propene By dissolving 583 mg of the compound obtained in Example 86-(3) in 80 ml of ethanol and using 468 mg of the compound obtained in Example 72-(1) and 630 μl of acetic acid, the same reaction and after-treatment of Example 77-(10) were carried out to obtain 755 mg of the title compound as a white solid.

$^1$H-NMR (CDCl$_3$) δ: 1.19 (d, 3H, J=6 Hz), 1.39 (d, 6H, J=7 Hz), 2.41–2.46 (m, 1H), 2.57–2.72 (m, 2H), 2.94–3.08 (m, 3H), 3.38–3.50 (m, 2H), 3.60–3.65 (m, 1H), 4.25 (quint., 1H, J=7 Hz), 5.16 (brs, 2H), 6.02 (dt, 1H, J=16 Hz, 7 Hz), 6.21–6.26 (m, 1H), 6.35 (dd, 2H, J=11 Hz, 2 Hz), 6.61 (d, 1H, J=16 Hz), 7.23 (s, 1H), 7.74 (s, 1H).

(5) 1-[1-[2-Amino-6-(3-hydroxy-3-methyl-1-azetidinyl)-4-pyrimidinyl]-5-(2-propyl)-4-pyrazolyl]-3-[(2R)-4-(3,5-difluorophenyl)-2-methyl-1-piperazinyl]-1-trans-propene hydrochloride By suspending 377 mg of the compound obtained in Example 86-(4) in 30 ml of ethanol and using 150 mg of 3-methyl-3-hydroxyazetidine and 107 mg of potassium carbonate, the same reaction and after-treatment of Example 45 were carried out to obtain 155 mg of the title compound as a white powder.

$^1$H-NMR (DMSO-d$_6$) δ: 1.04 (d, 3H, J=6 Hz), 1.33 (d, 6H, J=7 Hz), 1.44 (s, 3H), 2.98–4.10 (m, 14H), 5.94 (s, 1H), 6.16 (dt, 1H, J=16 Hz, 7 Hz), 6.55 (t, 1H, J=9 Hz), 6.70–6.75 (m, 2H), 7.06 (d, 1H, J=16 Hz), 8.01 (s, 1H), 10.92 (brs, 1H)

EXAMPLE 87

1-[1-[2-Amino-6-(3-hydroxy-3-methyl-1-azetidinyl)-4-pyrimidinyl]-5-(2-propyl)-4-pyrazolyl]-3-[4-(3,5-difluorophenyl)-1-piperazinyl]-1-trans-propene hydrochloride

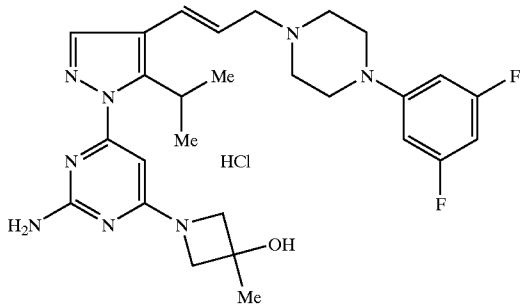

(1) 1-[1-(2-Amino-6-chloro-4-pyrimidinyl)-5-(2-propyl)-4-pyrazolyl]-3-[4-(3,5-difluorophenyl)-1-piperazinyl]-1-trans-propene Using 583 mg of the compound obtained in Example 86-(3) and 801 mg of 1-(3,5-difluorophenyl)piperazine, the same reaction and after-treatment of Example 77-(10) were carried out to obtain 1.35 g of the title compound as a white solid.

$^1$H-NMR (CDCl$_3$) δ: 1.39 (d, 6H, J=7 Hz), 2.63 (t, 4H, J=5 Hz), 3.18–3.25 (m, 6H), 4.25 (quint., 1H, J=7 Hz), 5.19 (brs, 2H), 6.01 (dt, 1H, J=16, 7 Hz), 6.25 (tt, 1H, J=9 Hz, 2 Hz), 6.37 (dd, 2H, J=11 Hz, 2 Hz), 6.61 (d, 1H, J=16 Hz), 7.23 (s, 1H), 7.75 (s, 1H).

(2) 1-[1-[2-Amino-6-(3-hydroxy-3-methyl-1-azetidinyl)-4-pyrimidinyl]-5-(2-propyl)-4-pyrazolyl]-3-[4-(3,5-difluorophenyl)-1-piperazinyl]-1-trans-propene hydrochloride Using 398 mg of the compound obtained in Example 87-(1), 150 mg of 3-methyl-3-hydroxyazetidine and 116 mg of potassium carbonate, the same reaction and after-treatment of Example 45 were carried out to obtain 231 mg of the title compound as a white powder.

$^1$H-NMR (DMSO-d$_6$) δ: 1.33 (d, 6H, J=7 Hz), 1.44 (s, 3H), 3.08–3.3 (m, 4H), 3.3–3.7 (m, 4H), 3.8–4.2 (m, 7H), 5.90 (s, 1H), 6.11 (dt, 1H, J=16 Hz, 7 Hz), 6.54–6.60 (m, 1H), 6.73 (dd, 2H, J=9 Hz, 2 Hz), 6.98 (d, 1H, J=16 Hz), 7.95 (s, 1H), 10.82 (brs, 1H)

EXAMPLE 88

1-[1-[2-Amino-6-(3-hydroxy-1-azetidinyl)-4-pyrimidinyl]-5-(2-propyl)-4-pyrazolyl]-3-[(2R)-4-(3,5-difluorophenyl)-2-methyl-1-piperazinyl]-1-trans-propene hydrochloride

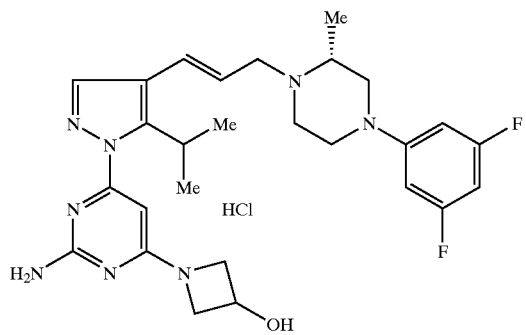

Using 377 mg of the compound obtained in Example 86-(4), 180 mg of 3-hydroxyazetidine hydrochloride and 226 mg of potassium carbonate, the same reaction and after-treatment of Example 45 were carried out to obtain 362 mg of the title compound as a white powder.

$^1$H-NMR (DMSO-d$_6$) δ: 1.33 (d, 6H, J=7 Hz), 1.44 (s, 3H), 3.08–3.3 (m, 4H), 3.3–3.7 (m, 4H), 3.8–4.2 (m, 7H), 5.90 (s, 1H), 6.11 (dt, 1H, J=16 Hz, 7 Hz), 6.54–6.60 (m, 1H), 6.73 (dd, 2H, J=9 Hz, 2 Hz), 6.98 (d, 1H, J=16 Hz), 7.95 (s, 1H), 10.82 (brs, 1H)

EXAMPLE 89

1-[1-[2-Amino-6-(3-hydroxy-1-azetidinyl)-4-pyrimidinyl]-5-(2-propyl)-4-pyrazolyl]-3-[4-(3,5-difluorophenyl)-1-piperazinyl]-1-trans-propene hydrochloride

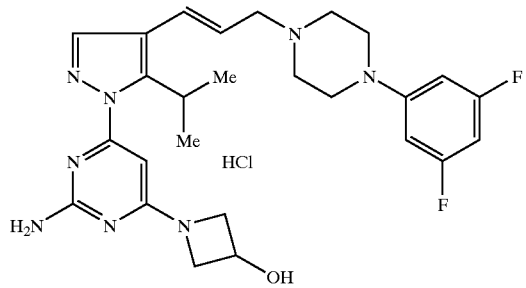

Using 474 mg of the compound obtained in Example 87-(1), 328 mg of 3-hydroxyazetidine hydrochloride and 276 mg of potassium carbonate, the same reaction and after-treatment of Example 35 were carried out to obtain 435 mg of the title compound as a white powder.

¹H-NMR (DMSO-d₆) δ: 1.34 (d, 6H, J=7 Hz), 3.0–3.2 (m, 2H), 3.2–3.3 (m, 2H), 3.45–3.60 (m, 2H), 3.8–4.2 (m, 7H), 4.3–4.5 (m, 2H), 4.55–4.70 (m, 1H), 6.01 (s, 1H), 6.16 (dt, 1H, J=16 Hz, 7 Hz), 6.57 (t, 1H, J=9 Hz), 6.73 (d, 2H, J=9 Hz), 7.00 (d, 1H, J=16 Hz), 8.03 (s, 1H), 11.07 (brs, 1H)

EXAMPLE 90

1-[1-[2-Amino-6-(3-hydroxy-3-methyl-1-azetidinyl)-4-pyrimidinyl]-5-ethyl-4-pyrazolyl]-3-[(2R)-4-(3,5-difluorophenyl)-2-methyl-1-piperazinyl]-1-trans-propene hydrochloride

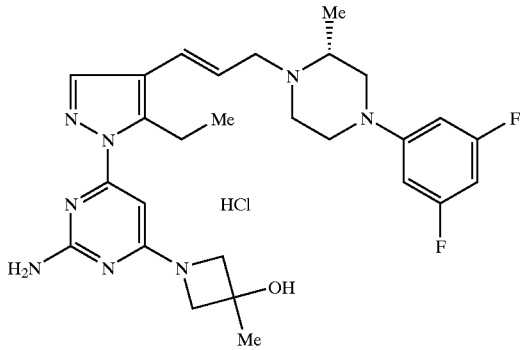

(1) Methyl 1-(2-amino-6-chloro-4-pyrimidinyl)-5-ethyl-4-pyrazolecarboxylate

After suspending 7.79 g portion of 2-amino-4-chloro-6-hydrazinopyrimidine in 100 ml of ethanol, 10.7 g of methyl methoxymethylenepropionylacetate was added thereto, and the mixture was stirred at room temperature for 20 minutes and then at 80° C. for 3 hours. After allowing the reaction solution to stand at 0° C. for 48 hours, the resulting precipitate was collected by filtration and dried to obtain 12.88 g of the title compound.

¹H-NMR (CDCl₃) δ: 1.30 (t, 3H, J=7 Hz), 3.55 (q, 2H, J=7 Hz), 3.87 (s, 3H), 5.22 (brs, 2H), 7.33 (s, 1H), 8.01 (s, 1H).

(2) 1-(2-Amino-6-chloro-4-pyrimidinyl)-5-ethyl-4-pyrazolecarbaldehyde

Using 4.0 g of the compound obtained in Example 90-(1), the same reaction and after-treatment of Example 31-(3) were carried out to obtain 3.0 g of the title compound as a white solid.

¹H-NMR (CDCl₃) δ: 1.36 (t, 3H, J=7 Hz), 3.53 (q, 2H, J=7 Hz), 5.30 (brs, 2H), 7.34 (s, 1H), 8.06 (s, 1H), 10.00 (s, 1H).

(3) Ethyl 3-[1-(2-amino-4-chloro-4-pyrimidinyl)-5-ethyl-4-pyrazolyl]-2-trans-propenoate Using 2.95 g of the compound obtained in Example 90-(2), the same reaction and after-treatment of Example 31-(4) were carried out to obtain 2.1 g of the title compound as a white solid.

¹H-NMR (CDCl₃) δ: 1.28 (t, 3H, J=7 Hz), 1.33 (t, 3H, J=7 Hz), 3.30 (q, 2H, J=7 Hz), 4.26 (q, 2H, J=7 Hz), 5.23 (brs, 2H), 6.27 (dd, 1H, J=16 Hz), 7.33 (s, 1H), 7.57 (d, 1H, J=16 Hz), 7.88 (s, 1H).

(4) 3-[1-(2-amino-6-chloro-4-pyrimidinyl)-5-ethyl-4-pyrazolyl]-2-trans-propenal

Using 2.1 g of the compound obtained in Example 90-(3), the same reaction and after-treatment of Example 31-(5) were carried out to obtain 1.6 g of the title compound as a white solid.

¹H-NMR (CDCl₃) δ: 1.32 (t, 3H, J=8 Hz), 3.33 (q, 2H, J=8 Hz), 5.25 (brs, 2H), 6.56 (dd, 1H, J=16 Hz, 9 Hz), 7.36 (s, 1H), 7.37 (d, 1H, J=16 Hz), 7.91 (s, 1H), 9.66 (d, 1H, J=9 Hz).

(5) 1-[1-[2-Amino-6-chloro-4-pyrimidinyl]-5-ethyl-4-pyrazolyl]-3-[(2R)-4-(3,5-difluorophenyl)-2-methyl-1-piperazinyl]-1-trans-propene Using the compound obtained in Example 90-(4), the same reaction and after-treatment of Example 77-(10) were carried out to obtain 860 mg of the title compound as a white powder.

¹H-NMR (CDCl₃) δ: 1.18 (d, 3H, J=6 Hz), 1.23 (t, 3H, J=7 Hz), 2.3–2.4 (m, 1H), 2.5–2.6 (m, 1H), 2.69 (dd, 1H, J=12 Hz, 10 Hz), 2.9–3.0 (m, 3H), 3.20 (q, 2H, J=7 Hz), 3.4–3.5 (m, 2H), 3.64 (dd, 1H, J=16 Hz, 6 Hz), 5.14 (brs, 2H), 6.10 (dt, 1H, J=16 Hz, 7 Hz), 6.23 (tt, 1H, J=9 Hz, 2 Hz), 6.35 (dd, 2H, J=9 Hz, 2 Hz), 6.37 (d, 1H, J=16 Hz), 7.31 (s, 1H), 7.78 (s, 1H).

(6) 1-[2-Amino-4-[4-[3-[(2R)-4-(3,5-difluorophenyl)-2-methylpiperazino]-1-propenyl]-5-ethyl-1H-1-pyrazolyl]-6-pyrimidinyl]-3-methyl-3-hydroxyazetidine hydrochloride Using 400 mg of the compound obtained in Example 90-(5), 0.15 g of 3-methyl-3-hydroxyazetidine and 0.1 ml of acetic acid, the same reaction, after-treatment and purification of Example 33 were carried out and then the product was recrystallized from ethanol to obtain 0.26 g of the title compound as a white powder.

¹H-NMR (DMSO-d₆) δ: 1.13 (t, 3H, J=7 Hz), 1.41 (s, 3H), 1.42 (d, 3H, J=6 Hz), 2.9–3.0 (m, 2H), 3.0–3.5 (m, 6H), 3.7–4.1 (m, 7H), 5.99 (s, 1H), 6.17 (dt, 1H, J=16 Hz, 7 Hz), 6.56 (t, 1H, J=10 Hz), 6.73 (d, 2H, J=10 Hz), 6.83 (d, 1H, J=16 Hz), 8.00 (s, 1H), 10.97 (brs, 1H)

EXAMPLE 91

1-[1-[2-Amino-6-(3-hydroxy-3-methyl-1-azetidinyl)-4-pyrimidinyl]-5-ethyl-4-pyrazolyl]-3-[4-(3,5-difluorophenyl)-1-piperazinyl]-1-trans-propene hydrochloride

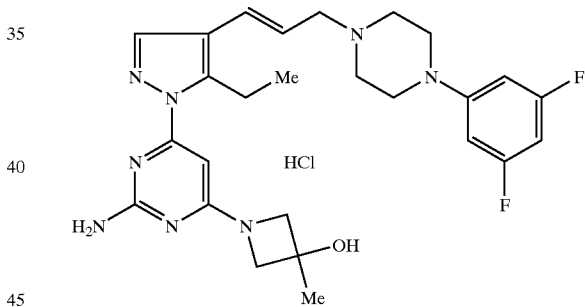

(1) 1-[1-(2-Amino-6-chloro-4-pyrimidinyl)-5-ethyl-4-pyrazolyl]-3-[4-(3,5-difluorophenyl)-1-piperazinyl]-1-trans-propene Using 800 mg of the compound obtained in Example 90-(4) and 630 mg of 1-(3,5-difluorophenyl)piperazine, the same reaction and after-treatment of Example 77-(10) were carried out to obtain 1.1 g of the title compound as a white powder.

¹H-NMR (CDCl₃) δ: 1.25 (t, 3H, J=7 Hz), 2.63 (t, 4H, J=5 Hz), 3.1–3.2 (m, 8H), 5.14 (brs, 2H), 6.11 (dt, 1H, J=16 Hz, 7 Hz), 6.25 (tt, 1H, J=9 Hz, 2 Hz), 6.36 (dd, 2H, J=9 Hz, 2 Hz), 6.39 (d, 1H, J=16 Hz), 7.32 (s, 1H), 7.79 (s, 1H).

(2) 1-[1-[2-Amino-6-(3-hydroxy-3-methyl-1-azetidinyl)-4-pyrimidinyl]-5-ethyl-4-pyrazolyl]-3-[4-(3,5-difluorophenyl)-1-piperazinyl]-1-trans-propene hydrochloride Using 400 mg of the compound obtained in Example 91-(1) and 150 mg of 3-methyl-3-hydroxyazetidine, the same reaction and after-treatment of Example 33 were carried out to obtain 210 mg of the title compound as a white powder.

¹H-NMR (DMSO-d₆) δ: 1.12 (t, 3H, J=7 Hz), 1.43 (s, 3H), 3.0–3.1 (m, 2H), 3.2–3.3 (m, 4H), 3.58 (d, 2H, J=7 Hz), 3.8–4.0 (m, 8H), 6.06 (s, 1H), 6.18 (dt, 1H, J=16 Hz, 7 Hz), 6.58 (tt, 1H, J=9 Hz, 2 Hz), 6.72 (dd, 2H, J=9 Hz, 2 Hz), 6.78 (d, 1H, J=16 Hz), 8.04 (s, 1H), 10.99 (brs, 1H)

EXAMPLE 92

1-[1-[2-Amino-6-(3-hydroxy-1-azetidinyl)-4-pyrimidinyl]-5-ethyl-4-pyrazolyl]-3-[(2R)-4-(3,5-difluorophenyl)-2-methyl-1-piperazinyl]-1-trans-propene hydrochloride

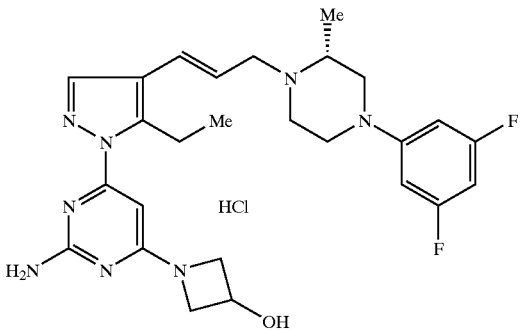

Using 400 mg of the compound obtained in Example 90-(5), 180 mg of 3-hydroxyazetidine hydrochloride and 0.12 g of potassium carbonate, the same reaction and after-treatment of Example 45 were carried out to obtain 300 mg of the title compound as a white powder.

¹H-NMR (DMSO-d₆) δ: 1.12 (t, 3H, J=7 Hz), 1.41 (d, 3H, J=6 Hz), 2.9–3.0 (m, 2H), 3.1–3.5 (m, 8H), 3.73 (dd, 2H, J=9 Hz, 4 Hz), 3.8–4.1 (m, 3H), 4.20 (t, 2H, J=9 Hz), 4.5–4.6 (m, 1H), 5.95 (s, 1H), 6.18 (dt, 1H, J=16 Hz, 7 Hz), 6.42 (brs, 2H), 6.56 (t, 1H, J=10 Hz), 6.73 (d, 2H, J=10 Hz), 6.83 (d, 1H, J=16 Hz), 8.00 (s, 1H), 10.99 (brs, 1H)

EXAMPLE 93

1-[1-[2-Amino-6-(3-hydroxy-1-azetidinyl)-4-pyrimidinyl]-5-ethyl-4-pyrazolyl]-3-[4-(3,5-difluorophenyl)-1-piperazinyl]-1-trans-propene hydrochloride

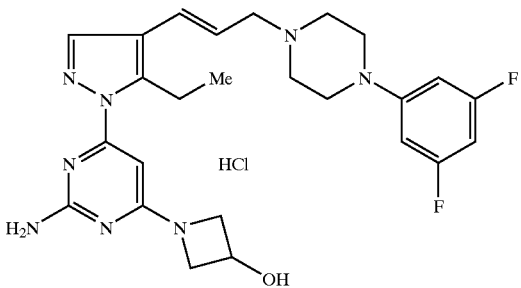

Using 400 mg of the compound obtained in Example 91-(1), 180 mg of 3-hydroxyazetidine hydrochloride and 0.12 g of potassium carbonate, the same reaction and after-treatment of Example 45 were carried out to obtain 260 mg of the title compound as a white powder.

¹H-NMR (DMSO-d₆) δ: 1.12 (t, 3H, J=7 Hz), 2.9–3.0 (m, 2H), 3.1–3.3 (m, 6H), 3.51 (d, 2H, J=7 Hz), 3.72 (dd, 2H, J=9 Hz, 4 Hz), 3.8–4.0 (m, 4H), 4.18 (t, 2H, J=9 Hz), 4.5–4.6 (m, 1H), 5.94 (s, 1H), 6.14 (dt, 1H, J=16 Hz, 7 Hz), 6.40 (brs, 2H), 6.58 (t, 1H, J=10 Hz), 6.72 (d, 2H, J=10 Hz), 6.75 (d, 1H, J=16 Hz), 7.96 (s, 1H), 10.55 (brs, 1H)

What is claimed is:

1. A compound represented by formula (I):

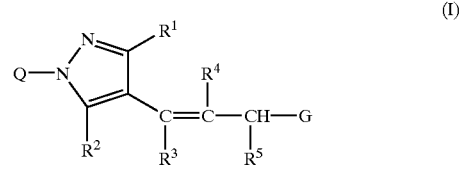

wherein $R^1$ represents a hydrogen atom, a halogen atom, a hydroxyl group, an alkoxyl group, an amino group, an alkylamino group, an aryl group or an alkyl group, wherein the alkyl group may have a substituent selected from a halogen atom, an amino group, an alkylamino group, a hydroxyl group, an alkoxyl group, a mercapto group and an alkylthio group;

$R^2$ represents a hydrogen atom, a halogen atom, a hydroxyl group, an alkoxyl group, an amino group, an alkylamino group, an aryl group, or an alkyl group, wherein the alkyl group may have a substituent selected from a halogen atom, an amino group, an alkylamino group, a hydroxyl group, an alkoxyl group, a mercapto group and an alkylthio group;

$R^3$ represents a hydrogen atom, a halogen atom, an alkoxyl group, an amino group, an alkylamino group, an aryl group or an alkyl group, wherein the alkyl group may have a substituent selected from a halogen atom, an amino group, an alkylamino group, a hydroxyl group, an alkoxyl group, a mercapto group and an alkylthio group;

$R^4$ represents a hydrogen atom, a halogen atom, an alkoxyl group, an amino group, an alkylamino group, an aryl group or an alkyl group, wherein the alkyl group may have a substituent selected from a halogen atom, an amino group, an alkylamino group, a hydroxyl group, an alkoxyl group, a mercapto group and an alkylthio group;

$R^5$ represents a hydrogen atom, an alkyl group, an alkenyl group, an alkynyl group, an aryl group or an arylalkyl group, wherein the alkyl group may have a substituent selected from a halogen atom, an amino group, an alkylamino group, a hydroxyl group, an alkoxyl group, a mercapto group and an alkylthio group;

Q represents an amidino group, a phenyl group or a monocyclic heterocyclic ring group, wherein said monocyclic heterocyclic ring group is a five- or six-membered ring, the heteroatoms of the heterocyclic ring are selected from the group consisting of O, N and S, and said heterocyclic ring may be saturated or unsaturated, and wherein the amidino group, phenyl group and monocyclic heterocyclic ring group may have one or more substituents selected from the group consisting of an alkyl group (which may be substituted by a halogen atom, an amino group, an alkylamino group, a hydroxyl group, an alkoxyl group, a mercapto group or an alkylthio group), a halogen atom, a hydroxyl group, an alkoxyl group, an alkoxylalkoxyl group, an amino group, an alkylamino group, an acylamino group, an alkylaminoalkylamino group, a nitro group, a cyano group, a carbamoyl group, a mercapto group, an alkylthio group, an arylthio group, an alkylsulfinyl group, an arylsulfinyl group, an alkylsulfonyl group, an arylsulfonyl group, an aminosulfonyl group, an alkylaminosulfonyl group, an arylaminosulfonyl group and an aryl group; and G represents a condensed tricyclic heterocyclic ring, wherein said condensed tricyclic heterocyclic ring comprises at least one heterocyclic ring, each of the rings of the condensed tricyclic heterocyclic ring is independently a five- to seven-membered ring, the heteroatoms of the heterocyclic ring are selected from the group consisting of O, S, and N, and each of the rings of the condensed tricyclic heterocyclic ring is independently saturated or unsaturated, and wherein the condensed tricyclic heterocyclic ring may have one or more substituents selected from the group consisting of an alkyl group (which may be substituted by a halogen atom, an amino group, an alkylamino group, a hydroxyl group, an alkoxyl group, a mercapto group or an alkylthio group), a halogen atom, a hydroxyl group, an alkoxyl group, a mercapto group, an alkylthio group, an amino group, an alkylamino group, an acylamino group, a nitro group, a cyano group, a carbamoyl group and an aryl group, the condensed tricyclic heterocyclic ring may have an epoxy group and the condensed tricyclic heterocyclic ring may also have a carbonyl group as a constituent element of the ring or a salt thereof, with the proviso that, in said compound and a salt thereof, a compound in which G is a condensed tricyclic heterocyclic ring, and a saturated or unsaturated hydrocarbon ring or heterocyclic ring of the condensed ring can be represented by a saturated hydrocarbon ring or saturated heterocyclic ring having no substituent, (excluding a case in which Q is a pyrimidinyl group and binds at the 2-position), and a salt thereof are excluded.

2. The compound or a salt thereof according to claim 1, wherein the condensed tricyclic heterocyclic ring is composed of a nitrogen-containing heterocyclic ring, a saturated or unsaturated hydrocarbon ring or heterocyclic ring, and a benzene ring.

3. A compound represented by a formula (Ia):

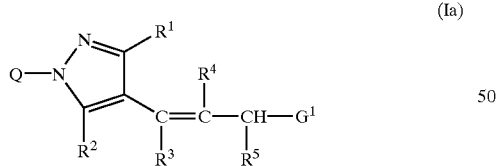

wherein, $R^1$ represents a hydrogen atom, a halogen atom, a hydroxyl group, an alkoxyl group, an amino group, an alkylamino group, an aryl group or an alkyl group, wherein the alkyl group may have a substituent selected from a halogen atom, an amino group, an alkylamino group, a hydroxyl group, an alkoxyl group, a mercapto group and an alkylthio group;

$R^2$ represents a hydrogen atom, a halogen atom, a hydroxyl group, an alkoxyl group, an amino group, an alkylamino group, an aryl group, or an alkyl group, wherein the alkyl group may have a substituent selected from a halogen atom, an amino group, an alkylamino group, a hydroxyl group, an alkoxyl group, a mercapto group and an alkylthio group;

$R^3$ represents a hydrogen atom, a halogen atom, an alkoxyl group, an amino group, an alkylamino group, an aryl group or an alkyl group, wherein the alkyl group may have a substituent selected from a halogen atom, an amino group, an alkylamino group, a hydroxyl group, an alkoxyl group, a mercapto group and an alkylthio group;

$R^4$ represents a hydrogen atom, a halogen atom, an alkoxyl group, an amino group, an alkylamino group, an aryl group or an alkyl group, wherein the alkyl group may have a substituent selected from a halogen atom, an amino group, an alkylamino group, a hydroxyl group, an alkoxyl group, a mercapto group and an alkylthio group;

$R^5$ represents a hydrogen atom, an alkyl group, an alkenyl group, an alkynyl group, an aryl group or an arylalkyl group, wherein the alkyl group may have a substituent selected from a halogen atom, an amino group, an alkylamino group, a hydroxyl group, an alkoxyl group, a mercapto group and an alkylthio group;

Q represents an amidino group, a phenyl group or a monocyclic heterocyclic ring group, wherein said monocyclic heterocyclic ring group is a five- or six-membered ring, the heteroatoms of the heterocyclic ring are selected from the group consisting of O, N and S, and said heterocyclic ring may be saturated or unsaturated, and wherein the amidino group, phenyl group and monocyclic heterocyclic ring group may have one or more substituents selected from the group consisting of an alkyl group (which may be substituted by a halogen atom, an amino group, an alkylamino group, a hydroxyl group, an alkoxyl group, a mercapto group or an alkylthio group), a halogen atom, a hydroxyl group, an alkoxyl group, an alkoxylalkoxyl group, an amino group, an alkylamino group, an acylamino group, an alkylaminoalkylamino group, a nitro group, a cyano group, a carbamoyl group, a mercapto group, an alkylthio group, an arylthio group, an alkylsulfinyl group, an arylsulfinyl group, an alkylsulfonyl group, an arylsulfonyl group, an aminosulfonyl group, an alkylaminosulfonyl group, an arylaminosulfonyl group and an aryl group; and $G^1$ represents a condensed tricyclic heterocyclic group, wherein said condensed tricyclic heterocyclic ring comprises at least one heterocyclic ring, each of the rings of the condensed tricyclic heterocyclic ring is independently a five- to seven-membered ring, the heteroatoms of the heterocyclic ring are selected from the group consisting of O, S, and N, and each of the rings of the condensed tricyclic heterocyclic ring is independently saturated or unsaturated, and wherein the condensed tricyclic heterocyclic group comprises:

a nitrogen-containing heterocyclic ring, a saturated or unsaturated hydrocarbon ring or heterocyclic ring, and a benzene ring, wherein the nitrogen-containing heterocyclic ring constituting the condensed tricyclic heterocyclic ring may have one or more substituents selected from the group consisting of an alkyl group (which may be substituted by a halogen atom, an amino group, an alkylamino group, a hydroxyl group, an alkoxyl group, a mercapto group or an alkylthio group), a halogen atom, a hydroxyl group, an alkoxyl group, a mercapto group, an alkylthio group, an amino group, an alkylamino group, an acylamino group, a nitro group, a cyano group, a carbamoyl group and an aryl group, and the nitrogen-containing heterocyclic ring may contain a carbonyl group as a constituent element of the ring, the saturated or unsaturated hydrocarbon ring or heterocyclic ring constituting the condensed tricyclic heterocyclic ring may have one or more substituents selected from the group consisting of an alkyl group (which may be substituted by a halogen atom, an amino group, an alkylamino group, a hydroxyl group, an alkoxyl group, a mercapto group or an alkylthio group), an halogen atom, a hydroxyl group, an alkoxyl group, a mercapto group, an alkylthio group, an amino group, an alkylamino group, an acylamino group, a nitro group, a cyano group, a carbamoyl group and an aryl group, it may have an epoxy group between ring-forming two atoms, and the saturated or unsaturated hydrocarbon ring or heterocyclic ring may contain a carbonyl group as a constituent element of the ring, and the benzene ring constituting the condensed tricyclic heterocyclic ring may have one or more substituents selected from the group consisting of an alkyl group (which may be substituted by a halogen atom, an amino group, an alkylamino group, a hydroxyl group, an alkoxyl group, a mercapto group or an alkylthio group), a halogen atom, a hydroxyl group, an alkoxyl group, a mercapto group, an alkylthio group, an amino group, an alkylamino group, an acylamino group, a nitro group, a cyano group, a carbamoyl group and an aryl group or a salt thereof, with the proviso that, in said compound and a salt thereof, a compound in which $G^1$ is a condensed tricyclic heterocyclic ring, and a saturated or unsaturated hydrocarbon ring or heterocyclic ring of the condensed ring can be represented by a saturated hydrocarbon ring or saturated heterocyclic ring having no substituent (excluding a case in which Q is a pyrimidinyl group and binds at the 2-position), and a salt thereof are excluded.

4. The compound or a salt thereof according to claim 2 or 3, wherein Q is a pyrimidinyl group and binds to the pyrazole ring at the 2-position.

5. The compound or a salt thereof according to claim 2 or 3, wherein the saturated or unsaturated hydrocarbon ring or heterocyclic ring which constitutes the condensed tricyclic heterocyclic ring has a substituent.

6. A compound represented by a formula (Ib):

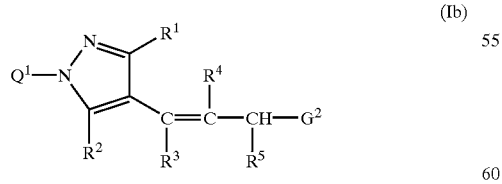

(Ib)

wherein, $R^1$ represents a hydrogen atom, a halogen atom, a hydroxyl group, an alkoxyl group, an amino group, an alkylamino group, an aryl group or an alkyl group, wherein the alkyl group may have a substituent selected from a halogen atom, an amino group, an alkylamino group, a hydroxyl group, an alkoxyl group, a mercapto group and an alkylthio group;

$R^2$ represents a hydrogen atom, a halogen atom, a hydroxyl group, an alkoxyl group, an amino group, an alkylamino group, an aryl group, or an alkyl group, wherein the alkyl group may have a substituent selected from a halogen atom, an amino group, an alkylamino group, a hydroxyl group, an alkoxyl group, a mercapto group and an alkylthio group;

$R^3$ represents a hydrogen atom, a halogen atom, an alkoxyl group, an amino group, an alkylamino group, an aryl group or an alkyl group, wherein the alkyl group may have a substituent selected from a halogen atom, an amino group, an alkylamino group, a hydroxyl group, an alkoxyl group, a mercapto group and an alkylthio group;

$R^4$ represents a hydrogen atom, a halogen atom, an alkoxyl group, an amino group, an alkylamino group, an aryl group or an alkyl group, wherein the alkyl group may have a substituent selected from a halogen atom, an amino group, an alkylamino group, a hydroxyl group, an alkoxyl group, a mercapto group and an alkylthio group;

$R^5$ represents a hydrogen atom, an alkyl group, an alkenyl group, an alkynyl group, an aryl group or an arylalkyl group, wherein the alkyl group may have a substituent selected from a halogen atom, an amino group, an alkylamino group, a hydroxyl group, an alkoxyl group, a mercapto group and an alkylthio group;

$G^2$ represents a group —$Z^1$—$Z^2$, wherein $Z^1$ represents a nitrogen-containing saturated heterocyclic ring structure represented by

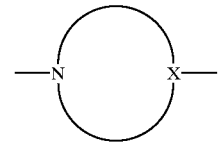

wherein said nitrogen-containing saturated heterocyclic ring structure comprises a five- to six-membered ring and X is a nitrogen atom or CH, which may contain a ketone moiety, and the ring may have one or more groups as substituents selected from the group consisting of an alkyl group (which may be substituted by a halogen atom, an amino group, an alkylamino group, a hydroxyl group, an alkoxyl group, a mercapto group or an alkylthio group), a halogen atom, a hydroxyl group, an alkoxyl group, an amino group, an alkylamino group and an aryl group, and $Z^2$ represent a phenyl group or a heterocyclic ring group, and these phenyl group and heterocyclic ring group may have one or more substituents selected from the group consisting of an alkyl group (which may be substituted by a halogen atom, an amino group, an alkylamino group, a hydroxyl group, an alkoxyl group, a mercapto group or an alkylthio group), a halogen atom, a hydroxyl group, an alkoxyl group, a mercapto group, an alkylthio group, an amino group, an alkylamino group, an acylamino group, a nitro group, a cyano group, a carbamoyl group and an aryl group, or $G^2$ represents a condensed tricyclic heterocyclic ring group, wherein said condensed tricyclic heterocyclic ring comprises at least one heterocyclic ring, each of the rings of the condensed tricyclic heterocyclic ring is independently a five- to seven-membered ring, the heteroatoms of the heterocyclic ring are selected from the group consisting of O, S, and N, and each of the rings of the condensed tricyclic heterocyclic ring is independently saturated or unsaturated, and wherein the condensed tricyclic heterocyclic ring group may have one or more substituents selected from the group consisting of an alkyl group (which may be substituted by a halogen atom, an amino group, an alkylamino group, a hydroxyl group, an alkoxyl group, a mercapto group or an alkylthio group), a halogen atom, a hydroxyl group, an alkoxyl group, a mercapto group, an alkylthio group, an amino group, an alkylamino group, an acylamino group, a nitro group, a cyano group, a carbamoyl group and an aryl group, the condensed tricyclic heterocyclic ring group may have an epoxy group, and the condensed tricyclic heterocyclic ring may contain a carbonyl group as a constituent element of the ring, and $Q^1$ represents a phenyl group or a monocyclic heterocyclic ring group, wherein said monocyclic heterocyclic ring group is a five- or six-membered ring, the heteroatoms of the heterocyclic ring are selected from the group consisting of O, N and S, and said heterocyclic ring may be saturated or unsaturated, and the phenyl group and monocyclic heterocyclic ring group have at least one group selected from the following (A) and may further have one or more groups selected from (B) as substituents, (A): an alkyl group having a substituent selected from the group consisting of a trialkylammonio group, a cyano group, an ureido group, an alkylureido group, an amidino group, a guanidino group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group and an arylsulfamoyl group, and it may further have at least one group selected from these groups, a group —$R^{71}$—$R^7$, wherein $R^7$ represents a monocyclic nitrogen-containing heterocyclic ring group, $R^{71}$ represents single bond or an alkylene group having from 1 to 3 carbon atoms, and $R^7$ and $R^{71}$ (excluding the case of single bond) may each independently have one or more substituents selected from the group consisting of an alkyl group (which may have one or more substituents selected from the group consisting of a halogen atom, a hydroxyl group, an amino group, an alkylamino group, a trialkylammonio group, a cyano group, an ureido group, an alkylureido group, an amidino group, a guanidino group, an alkoxyl group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a mercapto group and an alkylthio group), a halogen atom, a hydroxyl group, an amino group, an alkylamino group, a trialkylammonio group, a cyano group, an ureido group, an alkylureido group, an amidino group, a guanidino group, an alkoxyl group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a mercapto group and an alkylthio group, a group —$R^{72}$—$R^{74}$—$R^7$, wherein $R^7$ represents a monocyclic nitrogen-containing heterocyclic ring group, each of $R^{72}$ and $R^{73}$—$R^{74}$ independently represents single bond or an alkylene group having from 1 to 3 carbon atoms, $R^{73}$ represents an oxygen atom or a sulfur atom, and $R^7$, $R^{72}$ (excluding the case of single bond) and $R^{74}$ (excluding the case of single bond) may each independently have one or more substituents selected from the group consisting of an alkyl group (which may have one or more substituents selected from the group consisting of a halogen atom, a hydroxyl group, an amino group, an alkylamino group, a trialkylammonio group, a cyano group, an ureido group, an alkylureido group, an amidino group, a guanidino group, an alkoxyl group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a mercapto group and an alkylthio group), a halogen atom, a hydroxyl group, an amino group, an alkylamino group, a trialkylammonio group, a cyano group, an ureido group, an alkylureido group, an amidino group, a guanidino group, an alkoxyl group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a mercapto group and an alkylthio group, a group —$R^{72}$—$NR^{75}$—$R^{74}$—$R^8$, wherein $R^{72}$ and $R^{74}$ each independently represents single bond or an alkylene group having from 1 to 3 carbon atoms, $R^{75}$ represents an alkyl group (which may have one or more substituents selected from the group consisting of a halogen atom, a hydroxyl group, an amino group, an alkylamino group, a trialkylammonio group, a cyano group, an ureido group, an alkylureido group, an amidino group, a guanidino group, an alkoxyl group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a mercapto group and an alkylthio group), a hydrogen atom, a hydroxyl group, an alkoxyl group or —$R^{74}$—$R^8$, and $R^8$ represents an alkylsulfonyl group, an arylsulfonyl group, a monocyclic nitrogen-containing heterocyclic ring group, wherein $R^8$ (excluding the case of alkylsulfonyl group and arylsulfonyl group), $R^{72}$ (excluding the case of single bond) and $R^{74}$ (excluding the case of single bond) may each independently have one or more substituents selected from the group consisting of an alkyl group (which may have one or more substituents selected from the group consisting of a halogen atom, a hydroxyl group, an amino group, an alkylamino group, a trialkylammonio group, a cyano group, an ureido group, an alkylureido group, an amidino group, a guanidino group, an alkoxy group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a mercapto group and an alkylthio group), a halogen atom, a hydroxyl group, an amino group, an alkylamino group, a trialkylammonio group, a cyano group, an ureido group, an alkylureido group, an amidino group, a guanidino group, an alkoxyl group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a mercapto group and an alkylthio group, a group $—R^{81}—R^{82}—R^9$, wherein $R^{81}$ represents single bond or an alkylene group having from 1 to 3 carbon atoms, $R^{82}$ represents an oxygen atom or a sulfur atom, wherein $R^{81}$ (excluding the case of single bond) may have one or more substituents selected from the group consisting of alkyl group (which may have one or more substituents selected from the group consisting of a halogen atom, a hydroxyl group, an amino group, an alkylamino group, a trialkylammonio group, a cyano group, an ureido group, an alkylureido group, an amidino group, a guanidino group, an alkoxyl group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a mercapto group and an alkylthio group), a halogen atom, a hydroxyl group, an amino group, an alkylamino group, a trialkylammonio group, a cyano group, an ureido group, an alkylureido group, an amidino group, a guanidino group, an alkoxyl group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a mercapto group and an alkylthio group, and $R^9$ represents an alkyl group having a substituent, wherein the substituent of alkyl group is selected from the group consisting of a halogen atom, a hydroxyl group, an amino group, an alkylamino group, a trialkylammonio group, a cyano group, an ureido group, an alkylureido group, an amidino group, a guanidino group, an alkoxyl group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a mercapto group and an alkylthio group, and it may further have at least one group selected from these groups, or a group $—R^{81}—NR^{83}—R^9$, wherein $R^{81}$ represents single bond or an alkylene group having from 1 to 3 carbon atoms, wherein $R^{81}$ (excluding the case of single bond) may have one or more substituents selected from the group consisting of an alkyl group (which may have one or more substituents selected from the group consisting of a halogen atom, a hydroxyl group, an amino group, an alkylamino group, a trialkylammonio group, a cyano group, an ureido group, an alkylureido group, an amidino group, a guanidino group, an alkoxyl group, a hydroxyalkoxyl group, an alkoxylalkoxyl group, an aminoalkoxy group, a hydroxyalkylamino group, an aminoalkylamino group, a carboxyl group, a carbamoyl group, a sulfamoyl group, an alkylsulfamoyl group, an arylsulfamoyl group, a mercapto group and an alkylthio group), a halogen atom, a hydroxyl group, an amino group, an alkylamino group, a trialkylammonio group, a cyano group, an ureido group, an alkylureido group, an amidino group, a guanidino group, an alkoxyl group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a mercapto group and an alkylthio group, $R^{83}$ represents an alkyl group (which may have one or more substituents selected from the group consisting of a halogen atom, a hydroxyl group, an amino group, an alkylamino group, a trialkylammonio group, a cyano group, an ureido group, an alkylureido group, an amidino group, a guanidino group, an alkoxyl group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a mercapto group and an alkylthio group), a hydrogen atom, a hydroxyl group or an alkoxyl group, and $R^9$ represents an alkyl group having a substituent, wherein the substituent of alkyl group is selected from the group consisting of a halogen atom, a hydroxyl group, an amino group, an alkylamino group, a trialkylammonio group, a cyano group, an ureido group, an alkylureido group, an amidino group, a guanidino group, an alkoxyl group, a hydroxyalkoxyl group, an alkoxylalkoxyl group, an aminoalkoxyl group, a hydroxyalkylamino group, an aminoalkylamino group, a carboxyl group, a carbamoyl group, a sulfamoyl group, an alkylsulfamoyl group, an arylsulfamoyl group, a mercapto group and an alkylthio group, and it may further have at least one group selected from these groups (with the proviso that a case in which $R^{81}$ is single bond, $R^{83}$ is a hydrogen atom and $R^9$ is an alkylamino group is excluded), (B): alkyl group (which may be substituted by a halogen atom, an amino group, an alkylamino group, a hydroxyl group, an alkoxyl group, a mercapto group or an alkylthio group), a halogen atom, a hydroxyl group, an alkoxyl group, an alkoxylalkoxyl group, an amino group, an alkylamino group, an acylamino group, an alkylaminoalkylamino group, a nitro group, a cyano group, a carbamoyl group, a mercapto group, an alkylthio group, an arylthio group, an alkylsulfinyl group, an arylsulfinyl group, an alkylsulfonyl group, an arylsulfonyl group, an aminosulfonyl group, an alkylaminosulfonyl group, an arylaminosulfonyl group or an aryl group, or a salt thereof.

7. The compound or a salt thereof according to claim 6, wherein the condensed tricyclic heterocyclic group of $G^2$ is composed of a nitrogen-containing heterocyclic ring, a saturated or unsaturated hydrocarbon ring or heterocyclic ring, and a benzene ring.

8. The compound or a salt thereof according to claim 2, wherein G has a nitrogen atom, as a free valency, of the nitrogen-containing heterocyclic ring which constitutes the condensed tricyclic heterocyclic ring.

9. The compound or a salt thereof according to claim 2, wherein the nitrogen-containing heterocyclic ring which constitutes the condensed tricyclic heterocyclic group of G has a size of six-membered ring.

10. The compound or a salt thereof according to claim 2, wherein the nitrogen-containing heterocyclic ring which constitutes the condensed tricyclic heterocyclic a group of G is piperazine, piperidine or tetrahydropyridine.

11. The compound or a salt thereof according to claim 2, wherein the saturated or unsaturated hydrocarbon ring or heterocyclic ring which constitutes the condensed tricyclic heterocyclic group of G has a size of from five- to seven-membered ring.

12. The compound or a salt thereof according to claim 2, wherein the condensed tricyclic heterocyclic ring of G is

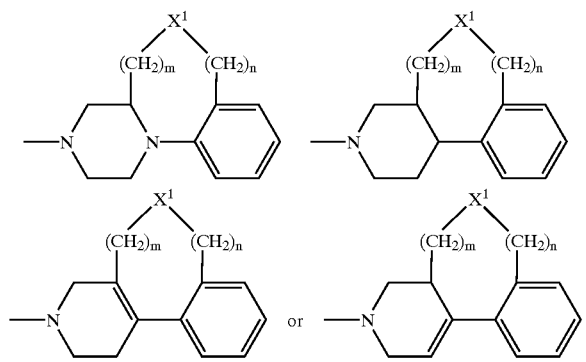

wherein $X^1$ represents an oxygen atom, a sulfur atom, NH, $CH_2$ or C=O, each of m and n independently represents 0 or an integer of 1 or 2, and the partial structure represented by

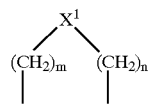

may form an unsaturated ring by including a double bond.

13. The compound or a salt thereof according to claim 2, wherein Q is a monocyclic heterocyclic group.

14. The compound or a salt thereof according to claim 2, wherein the monocyclic heterocyclic group of Q is a nitrogen-containing heterocyclic group.

15. The compound or a salt thereof according to claim 2, wherein the monocyclic heterocyclic group of Q is a nitrogen-containing heterocyclic group of five- or six-membered ring.

16. The compound or a salt thereof according to claim 2, wherein the monocyclic heterocyclic group of Q is an unsaturated nitrogen-containing heterocyclic group of five- or six-membered ring.

17. The compound or a salt thereof according to claim 2, wherein the monocyclic heterocyclic group of Q is derived from pyridine, piperazine, pyridazine, pyrazine or triazine.

18. The compound or a salt thereof according to claim 6, wherein $Z^1$ is piperazine or piperidine.

19. The compound or a salt thereof according to claim 6, wherein $Z^2$ is a phenyl group and has one or more substituents selected from the group consisting of an alkyl group (which may be substituted by a halogen atom, an amino group, an alkylamino group, a hydroxyl group, an alkoxyl group, a mercapto group or an alkylthio group), a halogen atom, a hydroxyl group, an alkoxyl group, a mercapto group, an alkylthio group, an amino group, an alkylamino group, an acylamino group, a nitro group, a cyano group, a carbamoyl group and an aryl group.

20. The compound or a salt thereof according to claim 6, wherein $Z^2$ is phenyl group and has the same or different two substituents selected from the group consisting of a halogen atom, a hydroxyl group, a cyano group and an alkyl group (which may be substituted by a halogen atom, an amino group, an alkylamino group, a hydroxyl group, an alkoxyl group, a mercapto group or an alkylthio group).

21. The compound or a salt thereof according to claim 3, wherein $G^1$ has a nitrogen atom, as a free valency, of the nitrogen-containing heterocyclic ring which constitutes the condensed tricyclic heterocyclic ring.

22. The compound or a salt thereof according to claim 6, wherein $G^2$ has a nitrogen atom, as a free valency, of the nitrogen-containing heterocyclic ring which constitutes the condensed tricyclic heterocyclic ring.

23. The compound or a salt thereof according to claim 3, wherein the nitrogen-containing heterocyclic ring which constitutes the condensed tricyclic heterocyclic group of $G^1$ has a size of six-membered ring.

24. The compound or a salt thereof according to claim 6, wherein the nitrogen-containing heterocyclic ring which constitutes the condensed tricyclic heterocyclic group of $G^2$ has a size of six-membered ring.

25. The compound or a salt thereof according claim 3, wherein the nitrogen-containing heterocyclic ring which constitutes the condensed tricyclic heterocyclic group of $G^1$ is piperazine, piperidine or tetrahydropyridine.

26. The compound or a salt thereof according to claim 6, wherein the nitrogen-containing heterocyclic ring which constitutes the condensed tricyclic heterocyclic group of $G^2$ is piperazine, piperidine or tetrahydropyridine.

27. The compound or a salt thereof according to claim 3, wherein the saturated or unsaturated hydrocarbon ring or heterocyclic ring which constitutes the condensed tricyclic heterocyclic group of $G^1$ has a size of from five- to seven-membered ring.

28. The compound or a salt thereof according to claim 6, wherein the saturated or unsaturated hydrocarbon ring or heterocyclic ring which constitutes the condensed tricyclic heterocyclic group of $G^2$ has a size of from five- to seven-membered ring.

29. The compound or a salt thereof according to claim 3, wherein the condensed tricyclic heterocyclic ring of $G^1$ is

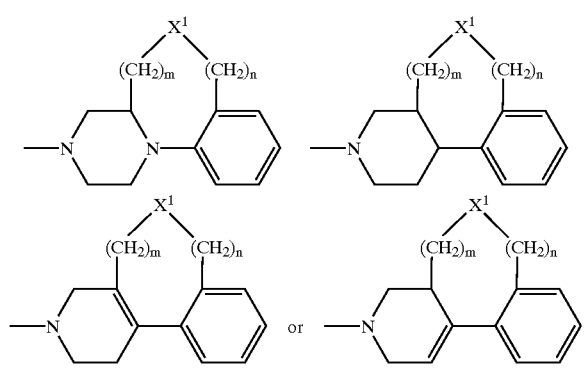

wherein $X^1$ represents an oxygen atom, a sulfur atom, NH, $CH_2$ or C=O, each of m and n independently represents 0 or an integer of 1 or 2, and the partial structure represented by

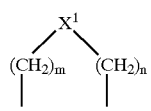

may form an unsaturated ring by including a double bond.

30. The compound or a salt thereof according to claim 6, wherein the condensed tricyclic heterocyclic ring of $G^2$ is

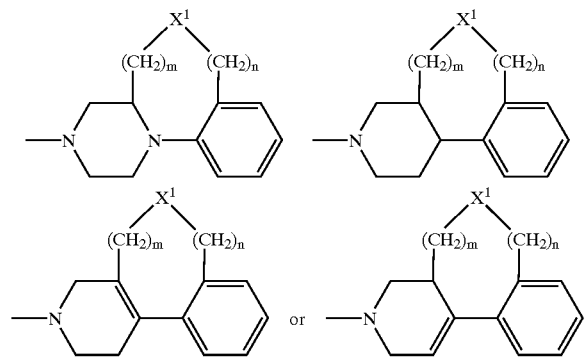

wherein $X^1$ represents an oxygen atom, a sulfur atom, NH, $CH_2$ or C=O, each of m and n independently represents 0 or an integer of 1 or 2, and the partial structure represented by

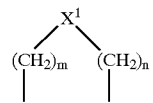

may form an unsaturated ring by including a double bond.

31. The compound or a salt thereof according to claim 6, wherein $Q^1$ is a monocyclic heterocyclic group.

32. The compound or a salt thereof according to claim 6, wherein the monocyclic heterocyclic group of $Q^1$ is a nitrogen-containing heterocyclic group.

33. The compound or a salt thereof according to claim 6, wherein the monocyclic heterocyclic group of $Q^1$ is a nitrogen-containing heterocyclic group of five- or six-membered ring.

34. The compound or a salt thereof according to claim 6, wherein the monocyclic heterocyclic group of $Q^1$ is an unsaturated nitrogen-containing heterocyclic group of five- or six-membered ring.

35. The compound or a salt thereof according to claim 6, wherein the monocyclic heterocyclic group of $Q^1$ is derived from pyridine, piperazine, pyridazine, pyrazine or triazine.

* * * * *